United States Patent
Lachance et al.

(10) Patent No.: US 9,168,248 B2
(45) Date of Patent: Oct. 27, 2015

(54) SPIRO COMPOUNDS USEFUL AS INHIBITORS OF STEAROYL-COENZYME A DELTA-9 DESATURASE

(75) Inventors: Nicolas Lachance, Pierrefonds (CA); Jean-Philippe Leclerc, Laval (CA); Chun Sing Li, Dollard-Des-Ormeaux (CA); Oscar Miguel Moradei, Kirkland (CA)

(73) Assignee: Merck Canada Inc., Quebec (CA)

( * ) Notice: Subject to any disclaimer, the term of this patent is extended or adjusted under 35 U.S.C. 154(b) by 1083 days.

(21) Appl. No.: 13/148,985

(22) PCT Filed: Feb. 16, 2010

(86) PCT No.: PCT/CA2010/000218
§ 371 (c)(1),
(2), (4) Date: Aug. 11, 2011

(87) PCT Pub. No.: WO2010/094120
PCT Pub. Date: Aug. 26, 2010

(65) Prior Publication Data
US 2011/0312952 A1  Dec. 22, 2011

Related U.S. Application Data

(60) Provisional application No. 61/207,784, filed on Feb. 17, 2009, provisional application No. 61/249,284, filed on Oct. 7, 2009.

(51) Int. Cl.
| | |
|---|---|
| *C07D 471/00* | (2006.01) |
| *C07D 491/10* | (2006.01) |
| *A61K 31/44* | (2006.01) |
| *A61K 31/438* | (2006.01) |
| *C07D 491/107* | (2006.01) |

(52) U.S. Cl.
CPC .......... *A61K 31/438* (2013.01); *C07D 491/107* (2013.01)

(58) Field of Classification Search
CPC ............. A61K 31/438; C07D 491/107; C07D 491/113
USPC ............ 544/70; 546/17; 514/230.5, 278, 183, 514/212.01
See application file for complete search history.

(56) References Cited

U.S. PATENT DOCUMENTS

| | | | |
|---|---|---|---|
| 7,365,079 B2 * | 4/2008 | Otake et al. .................... | 514/278 |
| 2008/0182838 A1 | 7/2008 | Leblanc et al. | |
| 2009/0325956 A1 | 12/2009 | Taniguchi et al. | |
| 2010/0069351 A1 | 3/2010 | Taniguchi et al. | |
| 2011/0092529 A1 * | 4/2011 | Brown et al. .................. | 514/278 |

FOREIGN PATENT DOCUMENTS

| | | |
|---|---|---|
| WO | 2005/011653 A2 | 2/2005 |
| WO | 2005/011654 A2 | 2/2005 |
| WO | 2005/011655 A2 | 2/2005 |
| WO | 2005/011656 A2 | 2/2005 |
| WO | 2005/011657 A2 | 2/2005 |
| WO | 2006/014168 A1 | 2/2006 |
| WO | 2006/034279 A1 | 3/2006 |
| WO | 2006/034312 A1 | 3/2006 |
| WO | 2006/034315 A2 | 3/2006 |
| WO | 2006/034338 A1 | 3/2006 |
| WO | 2006/034440 A2 | 3/2006 |
| WO | 2006/034441 A1 | 3/2006 |
| WO | 2006/034446 A2 | 3/2006 |
| WO | 2006/034341 A2 | 6/2006 |
| WO | 2006/086445 A2 | 8/2006 |
| WO | 2006/086447 A2 | 8/2006 |
| WO | 2006/101521 A2 | 9/2006 |
| WO | 2006/125178 A2 | 11/2006 |
| WO | 2006/125179 A1 | 11/2006 |
| WO | 2006/125180 A1 | 11/2006 |
| WO | 2006/125181 A2 | 11/2006 |
| WO | 2006/125194 A2 | 11/2006 |
| WO | 2006/130986 A1 | 12/2006 |
| WO | 2007/009236 A1 | 1/2007 |
| WO | 2007/044085 A2 | 4/2007 |

(Continued)

OTHER PUBLICATIONS

B. Behrouzian et al., "Mechanism of fatty acid desaturation: a biorganic perspective", Prostaglandins, Leukotrienes and Essential Fatty Acids, vol. 68, pp. 107-112 (2003).
A. Dobrzyn et al., "Stearoyl-CoA desaturase as a new drug target for obesity treatment", Obesity Reviews, vol. 6, pp. 169-174 (2005).
G. Jiang et al., "Prevetion of obesity in mice by antisense oligonmucleotide inhibitors of stearoyl-CoA desaturase-1", J. Clinical Investigation, vol. 115, No. 4, pp. 1030-1038 (2005).
G. Liu et al., "Discovery of Potent, Selective, Orally Bioavailable Stearoyl-CoA Desaturase 1 Inhibitors", J. Med. Chem., vol. 50, pp. 3086-3100 (2007).
I. Marques-Lopes, et al., c"Postprandial de novo liopgenesis and metabolic changes induced by a high-carbohydrate, low-fat meal in lean and overweight men", Am. J. Clin. Nutr., vol. 73, pp. 253-261 (2001).
M. Miyazaki et al., "Identification and Characterization of Murine SCD4, a Novel Heart-specific Stearoyl-CoA Desaturase Isoform Regulated by Leptin and Dietary Factors", J. of Biological Chemistry, vol. 278, No. 36, pp. 33904-33911 (2003).

(Continued)

*Primary Examiner* — Shobha Kantamneni
(74) *Attorney, Agent, or Firm* — Eric A. Meade; Catherine D. Fitch

(57) ABSTRACT

Heteroaromatic compounds of structural formula (I) are selective inhibitors of stearoyl-coenzyme A delta-9 desaturase (SCD1) relative to other known stearoyl-coenzyme A desaturases. The compounds of the present invention are useful for the prevention and treatment of conditions related to abnormal lipid synthesis and metabolism, including cardiovascular disease, such as atherosclerosis; obesity; diabetes; neurological disease; metabolic syndrome; insulin resistance; and liver steatosis.

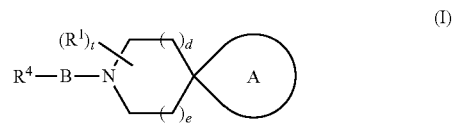

(I)

13 Claims, No Drawings

(56) References Cited

FOREIGN PATENT DOCUMENTS

| WO | 2007/046867 A2 | 4/2007 |
| WO | 2007/046868 A2 | 4/2007 |
| WO | 2007/050124 A1 | 5/2007 |
| WO | 2007/056846 A1 | 5/2007 |
| WO | 2007/071023 A1 | 6/2007 |
| WO | 2007/130075 A1 | 11/2007 |
| WO | 2007/134457 A1 | 11/2007 |
| WO | 2007/136746 A2 | 11/2007 |
| WO | 2007/143823 A1 | 12/2007 |
| WO | 2007/143824 A1 | 12/2007 |
| WO | 2008/003753 A1 | 1/2008 |
| WO | 2008/017161 A1 | 2/2008 |
| WO | 2008/024390 A2 | 2/2008 |
| WO | 2008/029266 A1 | 3/2008 |
| WO | 2008/036715 A1 | 3/2008 |
| WO | 2008/044767 A1 | 4/2008 |
| WO | 2008/046226 A1 | 4/2008 |
| WO | 2008/056687 A1 | 5/2008 |
| WO | 2008/062276 A2 | 5/2008 |
| WO | 2008/064474 A1 | 6/2008 |
| WO | 2008/074824 A2 | 6/2008 |
| WO | 2008/074835 A1 | 6/2008 |
| WO | 2008/096746 A1 | 8/2008 |
| WO | 2008/127349 A2 | 10/2008 |

OTHER PUBLICATIONS

J. Ntambi et al., "Loss of stearoyl-CoA desaturase-1 function protects mice against adiposity", PNAS, vol. 99, No. 17, pp. 11482-11486 (2002).

N. Oshino, "The Dynamic Behavior during Dietary Induction of the Terminal Ensyme (Cyanide-Sensitive Factor) of the stearoyl CoA Desaturation System of Rat Liver Microsomes", Archives of Biochemistry & Biophysics, vol. 149, pp. 378-387 (1972).

Y. Park et al., "Inhibition of hepatic stearoyl-CoA desaturase activity by trans-10, cis-12 conjugated linoleic acid and its derivatives", Biochemica et Biophysica Acta, vol. 1486, pp. 285-292 (2000).

R. K. Raju et al., "Inhibition of Fatty Acyl Desaturase by Cyclopropene Fatty Acids", J. Biol. Chem., vol. 242, No. 3, pp. 379-384 (1967).

N. Scaglia et al., "Stearoyl-CoA Desaturase is Involved in the Control of Proliferatin, Anchorage-independent Growth, and Survival in Human Transformed Cells", J. Biol. Chem., vol. 280 No. 27, pp. 25339-25349 (2005).

P. Sjogran et al., "Fatty acid desaturases in human adipose tissue: relationships between gene expression, desaturation indexes and insulin resistance", Diabetologia, vol. 51, pp. 328-335 (2008).

P. Stritmatter et al., "Purfication and Properties of Rat Liver Micosomal Stearyl Coenzyme A Desaturase", Proc. Nat. Acad Sci. USA, vol. 71, No. 11, pp. 4565-4569 (1974).

M. Thiede et al., "Construction and Sequence of cDNA for Rat Liver Stearyl Coenzyme A Desaturase", J. Biol. Chem., vol. 261, No. 28, pp. 13230-13235 (1986).

Z. Xin et al., "Discovery of piperdine-aryl urea-based stearoyl-CoA desaturase 1 inhibitors", Biorganic & Medicinal Chem. Letters, vol. 18, pp. 4298-4302 (2008).

L. Zhang et al., "Human stearoyl-CoA desaturase: alternative transcripts generated from a single gene by usage of tandem polyadenylation sites", Biochem. J., vol. 340, pp. 255-264 (1999).

S. Zhang et al., "Characterization of human SCD2, an oligomeric desaturase with improved stability and enzyme activity by crosslinking in intact cells", Biochem. J., vol. 388, pp. 135-142 (2005).

H. Zhao et al., "Discovery of 1-(4-phenoxypiperidin-1-yl)-2-arylaminoethanone stearoyl-CoA desaturase 1 inhibitors", Bioorganic & Med. Chem. Letters, vol. 17, pp. 3388-3391 (2007).

Y. Zheng et al., "SCD1 is expressed in sebaceous glands and is disrupted in the asebia mouse", Nature Genetics, vol. 23, pp. 268-270 (1999).

K. Mihara, "Structure and Regulation of Rat Liver Microsomal Stearoyl-CoA Desaturase Gene", J. Biochem., vol. 108, p. 1022 (1990)—abstract.

* cited by examiner

SPIRO COMPOUNDS USEFUL AS INHIBITORS OF STEAROYL-COENZYME A DELTA-9 DESATURASE

CROSS-REFERENCE TO RELATED APPLICATIONS

This application is a U.S. National Phase application under 35 U.S.C. §371 of PCT Application No. PCT/CA2010/000218, filed Feb. 16, 2010, which claims priority from and the benefit of U.S. Provisional Application No. 61/207,784, filed Feb. 17, 2009, and U.S. Provisional Application No. 61/249,284, filed Oct. 7, 2009.

FIELD OF THE INVENTION

The present invention relates to heteroaromatic compounds which are inhibitors of stearoyl-coenzyme A delta-9 desaturase (SCD) and the use of such compounds to control, prevent and/or treat conditions or diseases mediated by SCD activity. The compounds of the present invention are useful for the control, prevention and treatment of conditions and diseases related to abnormal lipid synthesis and metabolism, including cardiovascular disease, such as atherosclerosis; obesity; diabetes; neurological disease; metabolic syndrome; insulin resistance; cancer; and hepatic steatosis.

BACKGROUND OF THE INVENTION

At least three classes of fatty acyl-coenzyme A (CoA) desaturases (delta-5, delta-6 and delta-9 desaturases) are responsible for the formation of double bonds in mono- and polyunsaturated fatty acyl-CoAs derived from either dietary sources or de novo synthesis in mammals. The delta-9 specific stearoyl-CoA desaturases (SCDs) catalyze the rate-limiting formation of the cis-double bond at the C9-C10 position in monounsaturated fatty acyl-CoAs. The preferred substrates are stearoyl-CoA and palmitoyl-CoA, with the resulting oleoyl and palmitoleoyl-CoA as the main components in the biosynthesis of phospholipids, triglycerides, cholesterol esters and wax esters (Dobrzyn and Natami, *Obesity Reviews*, 6: 169-174 (2005)).

The rat liver microsomal SCD protein was first isolated and characterized in 1974 (Strittmatter et al., *PNAS*, 71: 4565-4569 (1974)). A number of mammalian SCD genes have since been cloned and studied from various species. For example, two genes have been identified from rat (SCD1 and SCD2, Thiede et al., *J. Biol. Chem.*, 261, 13230-13235 (1986)), Mihara, K., *J. Biochem.* (Tokyo), 108: 1022-1029 (1990)); four genes from mouse (SCD1, SCD2, SCD3 and SCD4) (Miyazaki et al., *J. Biol. Chem.*, 278: 33904-33911 (2003)); and two genes from human (SCD1 and ACOD4 (SCD2)), (Zhang, et al., *Biochem. J.*, 340: 255-264 (1991); Beiraghi, et al., *Gene*, 309: 11-21 (2003); Zhang et al., *Biochem. J.*, 388: 135-142 (2005)). The involvement of SCDs in fatty acid metabolism has been known in rats and mice since the 1970's (Oshino, N., *Arch. Biochem. Biophys.*, 149: 378-387 (1972)). This has been further supported by the biological studies of a) Asebia mice that carry the natural mutation in the SCD1 gene (Zheng et al., *Nature Genetics*, 23: 268-270 (1999)), b) SCD1-null mice from targeted gene deletion (Ntambi, et al., *PNAS*, 99: 11482-11486 (2002), and c) the suppression of SCD1 expression during leptin-induced weight loss (Cohen et al., *Science*, 297: 240-243 (2002)). The potential benefits of pharmacological inhibition of SCD activity has been demonstrated with anti-sense oligonucleotide inhibitors (ASO) in mice (Jiang, et al., *J. Clin. Invest.*, 115: 1030-1038 (2005)). ASO inhibition of SCD activity reduced fatty acid synthesis and increased fatty acid oxidation in primary mouse hepatocytes. Treatment of mice with SCD-ASOs resulted in the prevention of diet-induced obesity, reduced body adiposity, hepatomegaly, steatosis, postprandial plasma insulin and glucose levels, reduced de novo fatty acid synthesis, decreased the expression of lipogenic genes, and increased the expression of genes promoting energy expenditure in liver and adipose tissues. Thus, SCD inhibition represents a novel therapeutic strategy in the treatment of obesity and related metabolic disorders.

There is compelling evidence to support that elevated SCD activity in humans is directly implicated in several common disease processes. For example, there is an elevated hepatic lipogenesis to triglyceride secretion in non-alcoholic fatty liver disease patients (Diraison, et al., *Diabetes Metabolism*, 29: 478-485 (2003)); Donnelly, et al., *J. Clin. Invest.*, 115: 1343-1351 (2005)). Elevated SCD activity in adipose tissue is closely coupled to the development of insulin resistance (Sjogren, et al., *Diabetologia*, 51(2): 328-35 (2007)). The postprandial de novo lipogenesis is significantly elevated in obese subjects (Marques-Lopes, et al., *American Journal of Clinical Nutrition*, 73: 252-261 (2001)). Knockout of the SCD gene ameliorates Metabolic Syndrome by reducing plasma triglycerides, reducing weight gain, increasing insulin sensitivity, and reduces hepatic lipid accumulation (MacDonald, et al., *Journal of Lipid Research*, 49(1): 217-29 (2007)). There is a significant correlation between a high SCD activity and an increased cardiovascular risk profile including elevated plasma triglycerides, a high body mass index and reduced plasma HDL (Attie, et al., *J. Lipid Res.*, 43: 1899-1907 (2002)). SCD activity plays a key role in controlling the proliferation and survival of human transformed cells (Scaglia and Igal, *J. Biol. Chem.*, (2005)). RNA interference of SCD-1 reduces human tumor cell survival (Morgan-Lappe, et al., *Cancer Research*, 67(9): 4390-4398 (2007)).

Other than the above mentioned anti-sense oligonucleotides, inhibitors of SCD activity include non-selective thia-fatty acid substrate analogs [B. Behrouzian and P. H. Buist, *Prostaglandins, Leukotrienes, and Essential Fatty Acids*, 68: 107-112 (2003)], cyclopropenoid fatty acids (Raju and Reiser, *J. Biol. Chem.*, 242: 379-384 (1967)), certain conjugated long-chain fatty acid isomers (Park, et al., *Biochim. Biophys. Acta*, 1486: 285-292 (2000)), and a series of heterocyclic derivatives disclosed in published international patent application publications WO 2005/011653, WO 2005/011654, WO 2005/011655, WO 2005/011656, WO 2005/011657, WO 2006/014168, WO 2006/034279, WO 2006/034312, WO 2006/034315, WO 2006/034338, WO 2006/034341, WO 2006/034440, WO 2006/034441, WO 2006/034446, WO 2006/086445; WO 2006/086447; WO 2006/101521; WO 2006/125178; WO 2006/125179; WO 2006/125180; WO 2006/125181; WO 2006/125194; WO 2007/044085; WO 2007/046867; WO 2007/046868; WO 2007/050124; WO 2007/130075; WO 2007/136746; and WO 2008/074835, all assigned to Xenon Pharmaceuticals, Inc. SCD inhibitors are also disclosed in the following published international patent application publications: WO 2008/074835; WO 2008/074824; WO 2008/036715; WO 2008/044767; WO 2008/029266; WO 2008/062276; and WO 2008/127349.

A number of international patent applications assigned to Merck Frosst Canada Ltd. that disclose SCD inhibitors useful for the treatment of obesity and Type 2 diabetes have also published: WO 2006/130986 (14 Dec. 2006); WO 2007/009236 (25 Jan. 2007); WO 2007/056846 (24 May 2007); WO 2007/071023 (28 Jun. 2007); WO 2007/134457 (29 Nov.

2007); WO 2007/143823 (21 Dec. 2007); WO 2007/143824 (21 Dec. 2007); WO 2008/017161 (14 Feb. 2008); WO 2008/046226 (24 Apr. 2008); WO 2008/064474 (5 Jun. 2008); and US 2008/0182838 (31 Jul. 2008).

WO 2008/003753 (assigned to Novartis) discloses a series of pyrazolo[1,5-a]pyrimidine analogs as SCD inhibitors; WO 2007/143697 and WO 2008/024390 (assigned to Novartis and Xenon Pharmaceuticals) disclose heterocyclic derivatives as SCD inhibitors; and WO 2008/096746 (assigned to Takeda Pharmaceutical) and WO 2008/056687 (assigned to Daiichi) disclose spiro compounds as SCD inhibitors.

Small molecule SCD inhibitors have also been described by (a) G. Liu, et al., "Discovery of Potent, Selective, Orally Bioavailable SCD1 Inhibitors," in *J. Med. Chem.*, 50: 3086-3100 (2007); (b) H. Zhao, et al., "Discovery of 1-(4-phenoxypiperidin-1-yl)-2-arylaminoethanone SCD1 inhibitors," *Bioorg. Med. Chem. Lett.*, 17: 3388-3391 (2007); (c) Z. Xin, et al., "Discovery of piperidine-aryl urea-based stearoyl-CoA desaturase 1 inhibitors," *Bioorg. Med. Chem. Lett.*, 18: 4298-4302 (2008); and (d) C. S. Li, et al., "Thiazole analog as stearoyl-CoA desaturase 1 inhibitor," *Bioorg. Med. Chem. Lett.*, 19: 5214-5217 (2009) and references therein.

The present invention is concerned with novel heteroaromatic compounds as inhibitors of stearoyl-CoA delta-9 desaturase which are useful in the treatment and/or prevention of various conditions and diseases mediated by SCD activity including those related, but not limited, to elevated lipid levels, as exemplified in non-alcoholic fatty liver disease, cardiovascular disease, obesity, diabetes, metabolic syndrome, and insulin resistance.

The role of stearoyl-coenzyme A desaturase in lipid metabolism has been described by M. Miyazaki and J. M. Ntambi, *Prostaglandins, Leukotrienes, and Essential Fatty Acids*, 68: 113-121 (2003). The therapeutic potential of the pharmacological manipulation of SCD activity has been described by A. Dobrzyn and J. M. Ntambi, in "Stearoyl-CoA desaturase as a new drug target for obesity treatment," *Obesity Reviews*, 6: 169-174 (2005).

SUMMARY OF THE INVENTION

The present invention relates to heteroaromatic compounds of structural formula I:

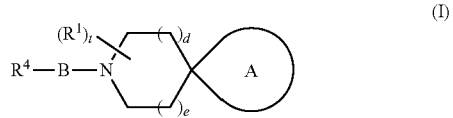

These heteroaromatic compounds are effective as inhibitors of SCD. They are therefore useful for the treatment, control or prevention of disorders responsive to the inhibition of SCD, such as diabetes, insulin resistance, lipid disorders, obesity, atherosclerosis, metabolic syndrome, and cancer.

The present invention also relates to pharmaceutical compositions comprising the compounds of the present invention and a pharmaceutically acceptable carrier.

The present invention also relates to methods for the treatment, control, or prevention of disorders, diseases, or conditions responsive to inhibition of SCD in a subject in need thereof by administering the compounds and pharmaceutical compositions of the present invention.

The present invention also relates to methods for the treatment, control, or prevention of Type 2 diabetes, insulin resistance, obesity, lipid disorders, atherosclerosis, metabolic syndrome, and cancer by administering the compounds and pharmaceutical compositions of the present invention.

The present invention also relates to methods for the treatment, control, or prevention of obesity by administering the compounds of the present invention in combination with a therapeutically effective amount of another agent known to be useful to treat the condition.

The present invention also relates to methods for the treatment, control, or prevention of Type 2 diabetes by administering the compounds of the present invention in combination with a therapeutically effective amount of another agent known to be useful to treat the condition.

The present invention also relates to methods for the treatment, control, or prevention of insulin resistance by administering the compounds of the present invention in combination with a therapeutically effective amount of another agent known to be useful to treat the condition.

The present invention also relates to methods for the treatment, control, or prevention of atherosclerosis by administering the compounds of the present invention in combination with a therapeutically effective amount of another agent known to be useful to treat the condition.

The present invention also relates to methods for the treatment, control, or prevention of lipid disorders by administering the compounds of the present invention in combination with a therapeutically effective amount of another agent known to be useful to treat the condition.

The present invention also relates to methods for the treatment, control, or prevention of metabolic syndrome by administering the compounds of the present invention in combination with a therapeutically effective amount of another agent known to be useful to treat the condition.

The present invention also relates to methods for the treatment, control, or prevention of cancer by administering the compounds of the present invention in combination with a therapeutically effective amount of another agent known to be useful to treat the condition.

DETAILED DESCRIPTION OF THE INVENTION

The present invention is concerned with heteroaromatic compounds useful as inhibitors of SCD. Compounds of the present invention are described by structural formula I:

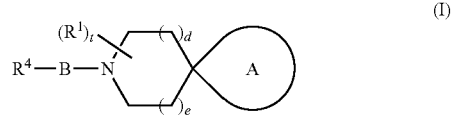

or a pharmaceutically acceptable salt thereof; wherein A is selected from the group consisting of:

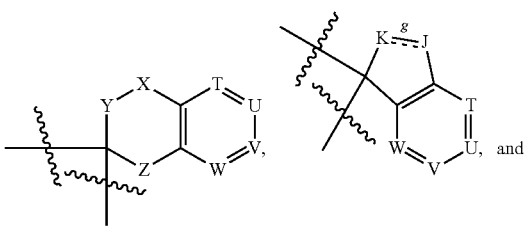

-continued

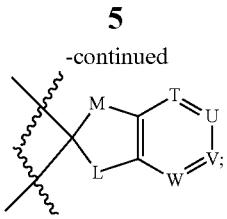

g is a single bond or a double bond;
J and K are each independently selected from the group consisting of: S, O, NH, CH and $CH_2$, wherein each NH is unsubstituted or substituted with $R^g$, and wherein each CH and $CH_2$ is unsubstituted or substituted with $R^2$, provided that when g is a single bond at least one of J and K is $CH_2$ unsubstituted or substituted with $R^2$, and further provided that when g is a double bond then both J and K are CH;
L and M are each independently selected from the group consisting of: S, O, NH and $CH_2$, wherein each NH is unsubstituted or substituted with $R^g$, and wherein each $CH_2$ is unsubstituted or substituted with $R^2$;
T, U, V and W are each independently selected from N and CH, wherein each CH is unsubstituted or substituted with $R^3$, provided that at least two of T, U, V and W are CH;
X is $CH_2$, wherein $CH_2$ is unsubstituted or substituted with $R^2$;
Y is independently selected from the group consisting of: O, NH and $CH_2$, wherein each NH is unsubstituted or substituted with $R^g$, and wherein each $CH_2$ is unsubstituted or substituted with $R^2$;
Z is independently selected from the group consisting of: S, S(O), $S(O)_2$, O, NH and $CH_2$, wherein each NH is unsubstituted or substituted with $R^g$, and wherein each $CH_2$ is unsubstituted or substituted with $R^2$;
B is a 5 membered heteroaryl ring containing 1, 2 or 3 heteroatoms selected from NH, O and S, wherein any CH is unsubstituted or substituted with one substituent selected from $R^a$, and wherein any NH is unsubstituted or substituted with one substituent selected from $R^b$;
each $R^1$ is independently selected from the group consisting of: hydrogen, halogen, and $C_{1-3}$ alkyl, wherein alkyl is unsubstituted or substituted with one to three substituents independently selected from halogen and hydroxy;
each $R^2$ is independently selected from the group consisting of:
(1) hydrogen,
(2) halogen,
(3) oxo,
(4) $C_{1-6}$ alkyl,
(5) $(CH_2)_nOR^e$,
(6) $(CH_2)_nN(R^e)_2$,
(7) $(CH_2)_nC \equiv N$,
(8) $(CH_2)_nCOR^e$, and
(9) $(CH_2)_nS(O)_qR^e$,
wherein alkyl is unsubstituted or substituted with hydroxy or one to three halogens, and wherein any $CH_2$ in $R^2$ is unsubstituted or substituted with one to two groups independently selected from halogen, hydroxy, and $C_{1-4}$ alkyl unsubstituted or substituted with one to five fluorines;
each $R^3$ is independently selected from the group consisting of:
(1) hydrogen,
(2) halogen,
(3) —$C_{1-6}$ alkyl,
(4) —$C_{1-6}$ alkenyl,
(5) —$OC_{1-6}$ alkyl,
(6) $(CH_2)_nOR^e$,
(7) $(CH_2)_nN(R^e)_2$,
(8) $(CH_2)_nC \equiv N$,
(9) $(CH_2)_nCOR^e$, and
(10) $(CH_2)_nS(O)_qR^e$,
wherein alkyl is unsubstituted or substituted with one to three substituents selected from: hydroxy, halogen, $C_{1-4}$ alkyl, $C_{3-6}$ cycloalkyl, $C_{2-5}$ cycloheteroalkyl, aryl, and heteroaryl wherein alkyl, cycloalkyl, cycloheteroalkyl, aryl and heteroaryl are unsubstituted or substituted with one to three substituents selected from: halogen, hydroxy, and $C_{1-4}$ alkyl unsubstituted or substituted with one to five fluorines, and wherein any $CH_2$ in $R^3$ is unsubstituted or substituted with one to two groups independently selected from halogen, hydroxy, and $C_{1-4}$ alkyl unsubstituted or substituted with one to five fluorines;

$R^4$ is selected from the group consisting of:

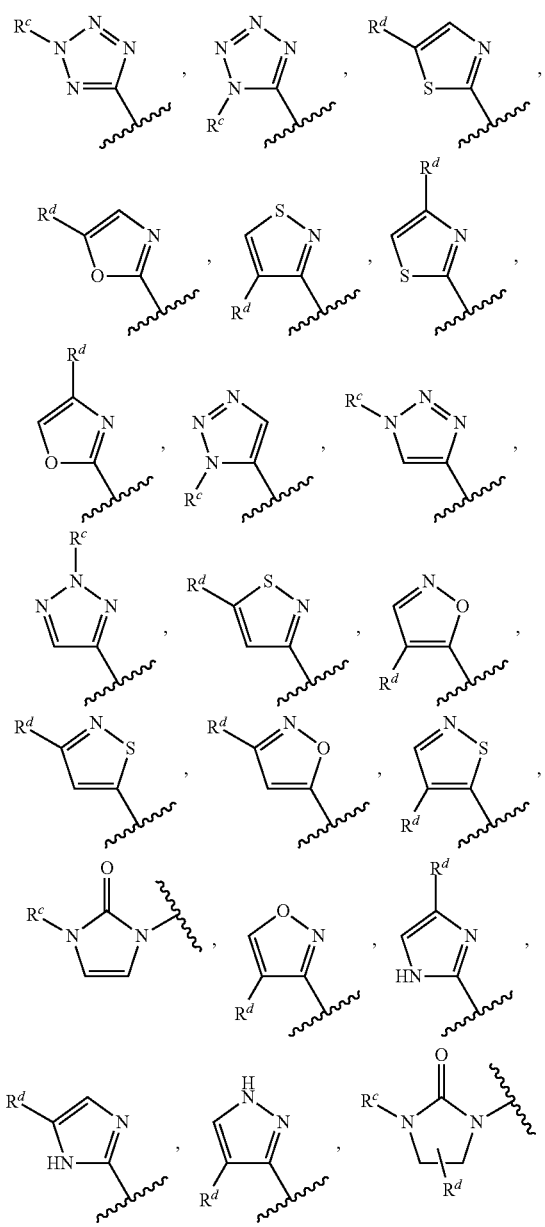

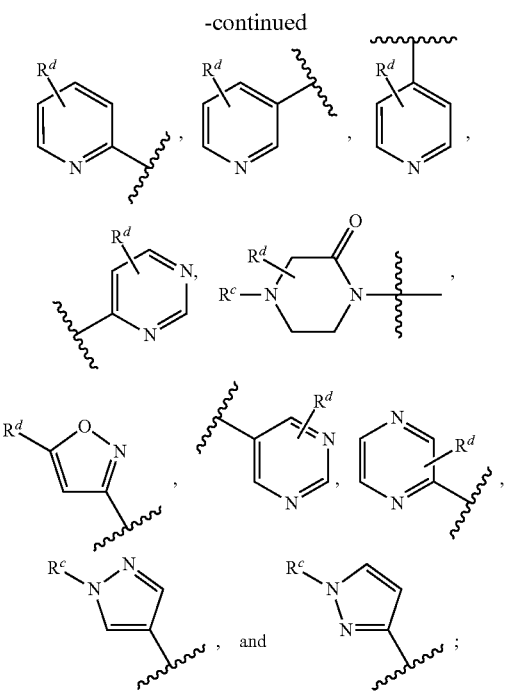

each $R^a$ is independently selected from the group consisting of:
(1) hydrogen,
(2) halogen,
(3) cyano,
(4) $C_{1-4}$ alkyl, unsubstituted or substituted with one to five fluorines,
(5) $C_{1-4}$ alkoxy, unsubstituted or substituted with one to five fluorines,
(6) $C_{1-4}$ alkylthio, unsubstituted or substituted with one to five fluorines,
(7) $C_{1-4}$ alkylsulfonyl,
(8) —$CO_2H$,
(9) $C_{1-4}$ alkyloxycarbonyl, and
(10) $C_{1-4}$ alkylcarbonyl;

each $R^b$ is independently selected from the group consisting of:
(1) hydrogen, and
(2) $C_{1-4}$ alkyl,
wherein alkyl is unsubstituted or substituted with one to five fluorines;

each $R^c$ is independently selected from the group consisting of:
(1) —$(CH_2)_m CO_2H$,
(2) —$(CH_2)_m CO_2 C_{1-3}$ alkyl,
(3) —$(CH_2)_m$—$NR^b$—$(CH_2)_p CO_2H$,
(4) —$(CH_2)_m$—$NR^b$—$(CH_2)_p CO_2 C_{1-3}$ alkyl,
(5) —$(CH_2)_m$—O—$(CH_2)_p CO_2H$,
(6) —$(CH_2)_m$—O—$(CH_2)_p CO_2 C_{1-3}$ alkyl,
(7) —$(CH_2)_m$—S—$(CH_2)_p CO_2H$, and
(8) —$(CH_2)_m$—S—$(CH_2)_p CO_2 C_{1-3}$ alkyl,
wherein any $CH_2$ in $R^c$ is unsubstituted or substituted with one to two groups independently selected from halogen, hydroxy, and $C_{1-4}$ alkyl unsubstituted or substituted with one to five fluorines;

each $R^d$ is independently selected from the group consisting of:
(1) —$(CH_2)_n CO_2H$,
(2) —$(CH_2)_n CO_2 C_{1-3}$ alkyl,
(3) —$(CH_2)_n$—$NR^b$—$(CH_2)_p CO_2H$,
(4) —$(CH_2)_n$—$NR^b$—$(CH_2)_p CO_2 C_{1-3}$ alkyl,
(5) —$(CH_2)_n$—O—$(CH_2)_p CO_2H$,
(6) —$(CH_2)_n$—O—$(CH_2)_p CO_2 C_{1-3}$ alkyl,
(7) —$(CH_2)_n$—S—$(CH_2)_p CO_2H$, and
(8) —$(CH_2)_n$—S—$(CH_2)_p CO_2 C_{1-3}$ alkyl,
wherein any $CH_2$ in $R^d$ is unsubstituted or substituted with one to two groups independently selected from the group consisting of: halogen, hydroxy, and $C_{1-4}$ alkyl unsubstituted or substituted with one to five fluorines;

each $R^e$ is independently selected from the group consisting of:
(1) hydrogen, and
(2) $C_{1-6}$ alkyl,
wherein alkyl is unsubstituted or substituted with one to three substituents independently selected from the group consisting of: halogen, cyano, —$C_{1-4}$ alkoxy, —$C_{1-4}$ alkylthio, —$C_{1-4}$ alkylsulfonyl, —$CO_2H$, and —$CO_2 C_{1-4}$ alkyl;

each $R^g$ is independently selected from the group consisting of:
(1) hydrogen, and
(2) $C_{1-6}$ alkyl;

m is an integer from 1 to 3;
n is an integer from 0 to 3;
p is an integer from 1 to 3;
q is an integer from 1 to 2;
t is an integer from 0 to 8;
d is an integer from 0 to 2; and
e is an integer from 0 to 2,
provided that d+e is 2.

In one embodiment of the present invention, A is selected from the group consisting of:

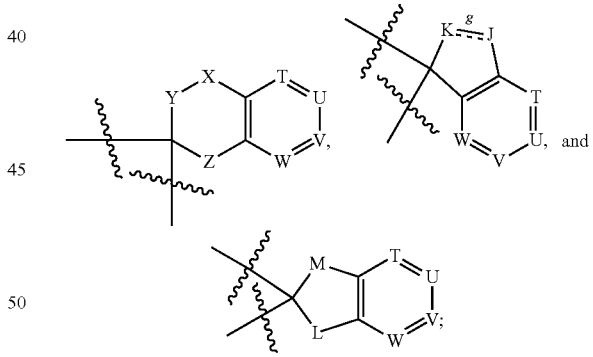

In a class of this embodiment, A is selected from the group consisting of:

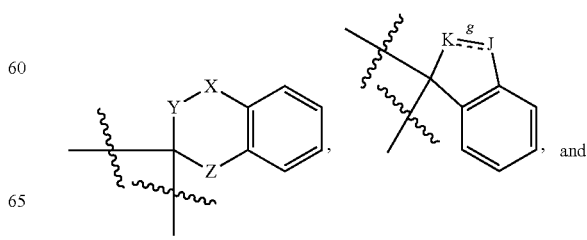

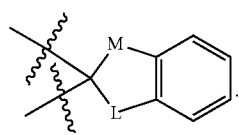
In another class of this embodiment, A is selected from the group consisting of:
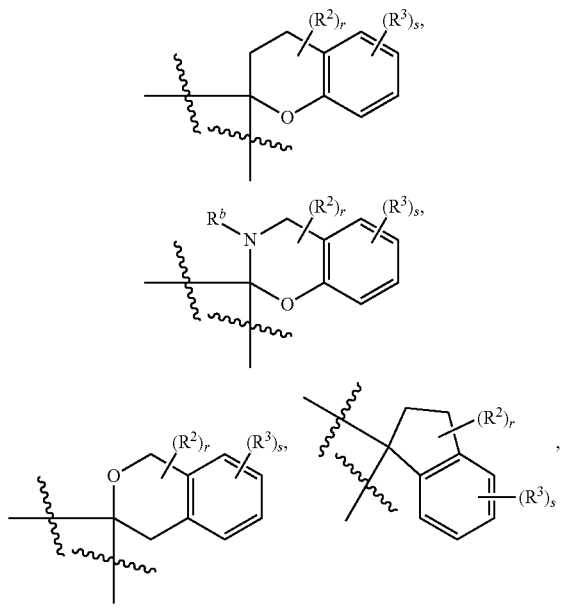
In another class of this embodiment, A is selected from the group consisting of:
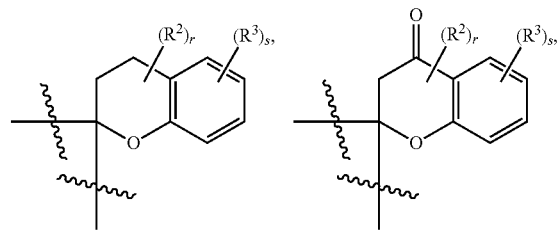
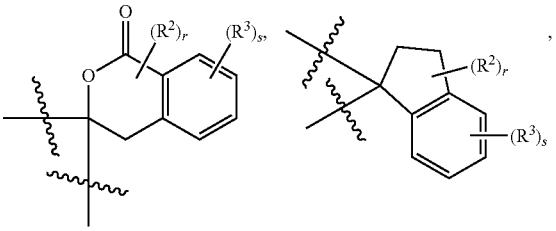
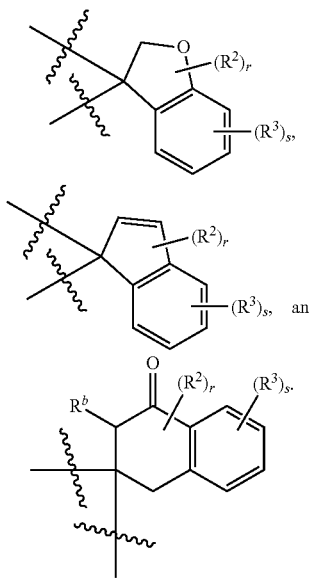
In another class of this embodiment, A is selected from the group consisting of:
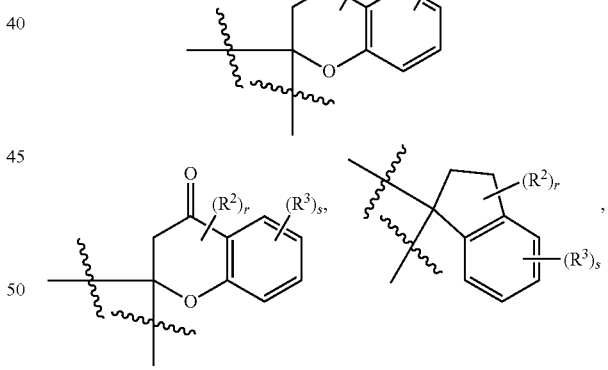

In another class of this embodiment, A is selected from the group consisting of:

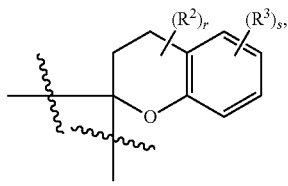

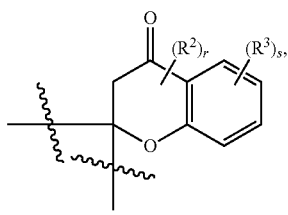

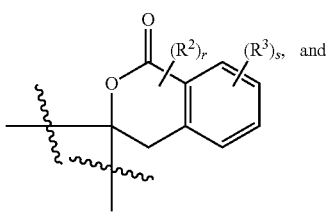

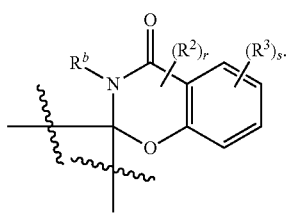

In another class of this embodiment, A is selected from the group consisting of:

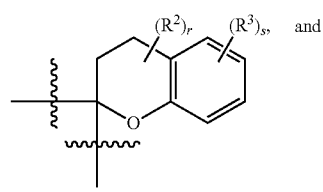

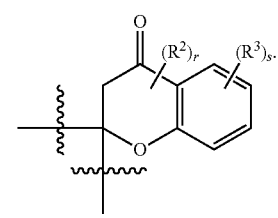

In another class of this embodiment, A is selected from the group consisting of:

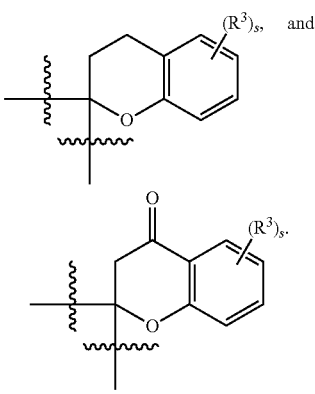

In another class of this embodiment, A is:

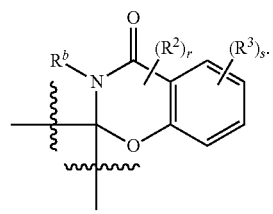

In another class of this embodiment, A is:

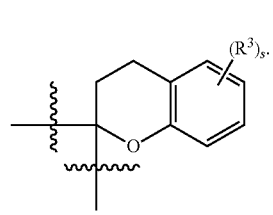

In another class of this embodiment, A is:

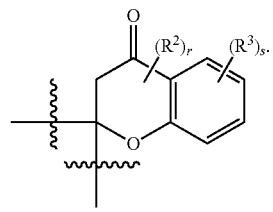

In another class of this embodiment, A is:

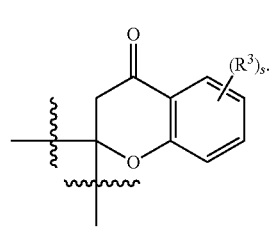

In another class of this embodiment, A is:

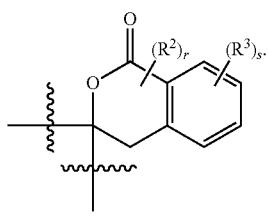

In another class of this embodiment, A is selected from the group consisting of:

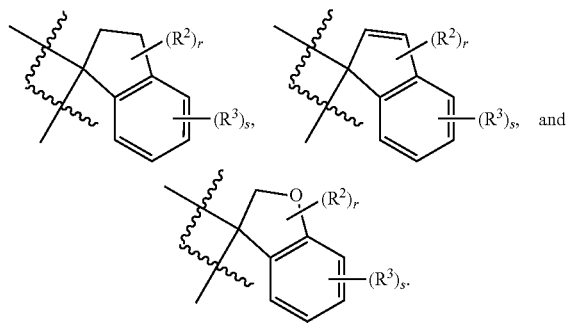

In another embodiment of the present invention, B is a 5-membered heteroaryl ring containing 1, 2 or 3 heteroatoms selected from NH, O and S, wherein any CH is unsubstituted or substituted with one substituent selected from $R^a$, and wherein any NH is unsubstituted or substituted with one substituent selected from $R^b$.

In another class of this embodiment B is a 5-membered heteroaryl ring containing 2 or 3 heteroatoms selected from NH, O and S, wherein any CH is unsubstituted or substituted with one substituent selected from $R^a$, and wherein NH is unsubstituted or substituted with one substituent selected from $R^b$.

In another class of this embodiment, B is selected from the group consisting of:

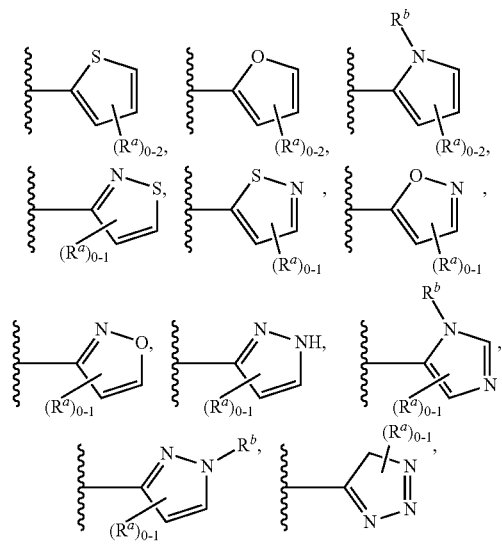

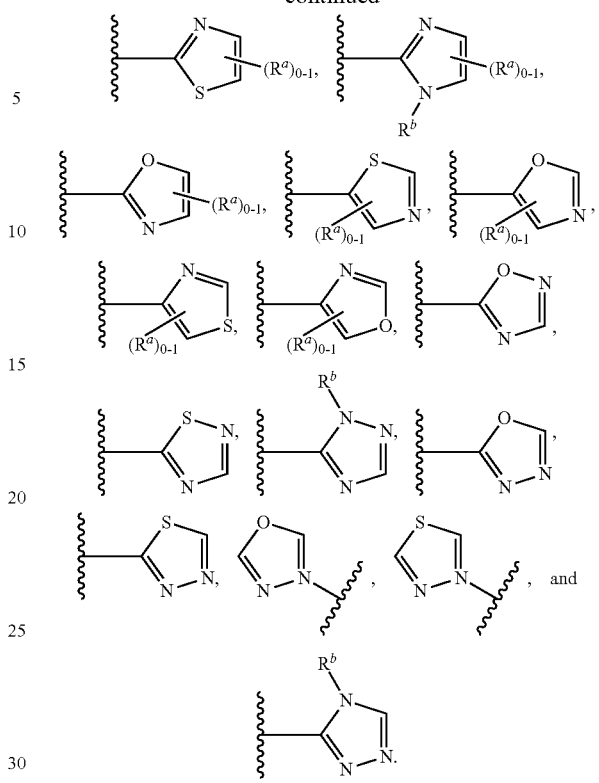

In another class of this embodiment, B is selected from the group consisting of:

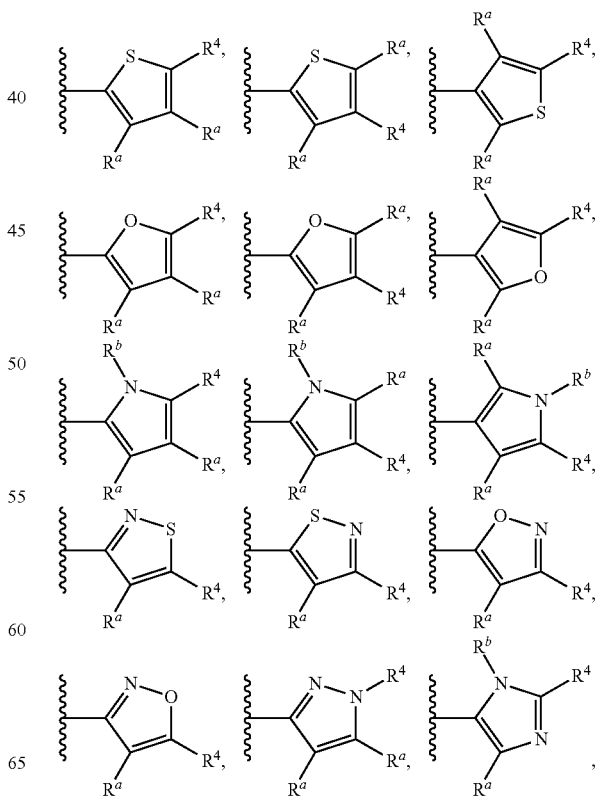

-continued

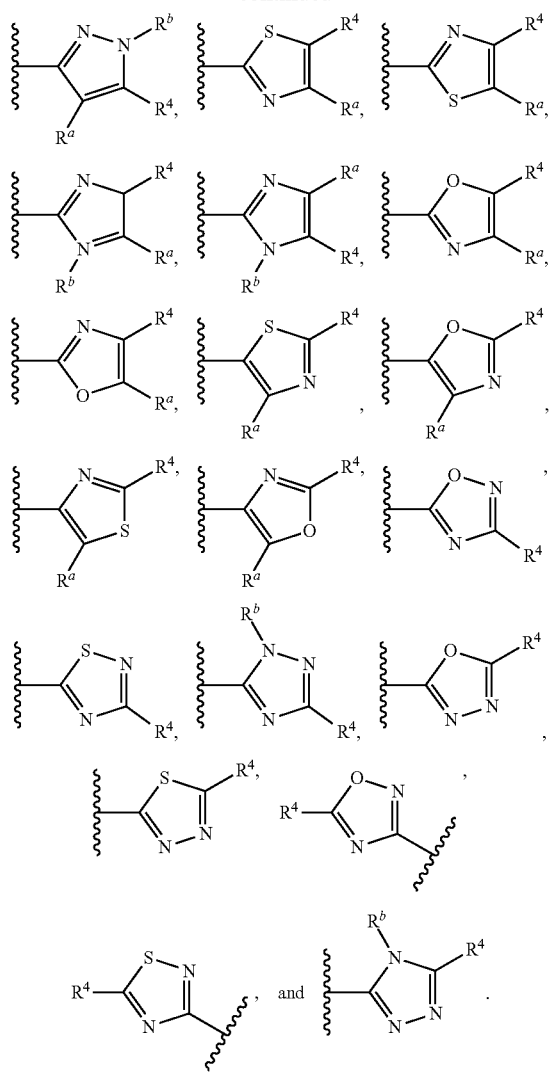

In another class of this embodiment, B is selected from the group consisting of:

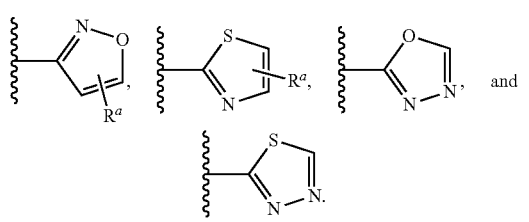

In another class of this embodiment, B is selected from the group consisting of:

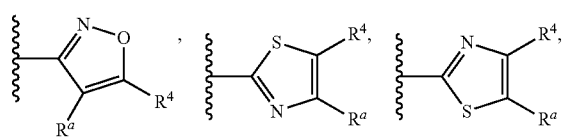

-continued

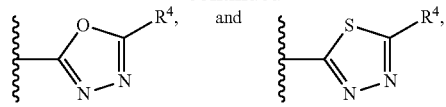

In another class of this embodiment, B is selected from the group consisting of:

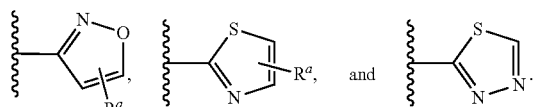

In another class of this embodiment, B is selected from the group consisting of:

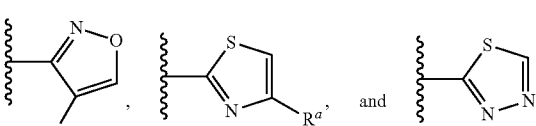

In another embodiment of the present invention, B-$R^4$ is selected from the group consisting of:

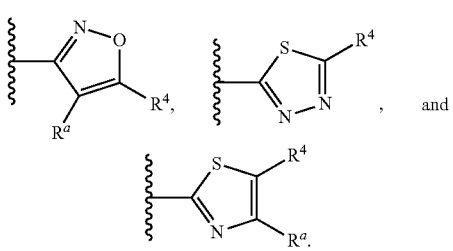

In a class of this embodiment, B-$R^4$ is

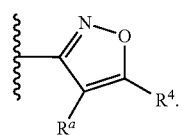

In another class of this embodiment, B-$R^4$ is

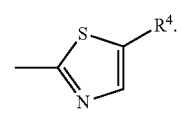

In yet another class of this embodiment, B-$R^4$ is

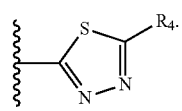

In another embodiment of the present invention, B-R$^4$ is selected from the group consisting of:

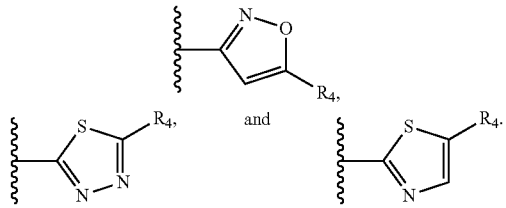

In a class of this embodiment, B-R$^4$ is

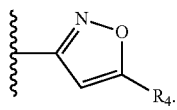

In another embodiment of the present invention, J and K are each independently selected from the group consisting of: S, O, NH, CH and CH$_2$, wherein each NH is unsubstituted or substituted with R$^g$, and wherein each CH and CH$_2$ is unsubstituted or substituted with R$^2$, provided that when g is a single bond at least one of J and K is CH$_2$ unsubstituted or substituted with R$^2$, and further provided that when g is a double bond then both J and K are CH. In a class of this embodiment, J and K are each independently selected from the group consisting of: O, NH, CH and CH$_2$, wherein each NH is unsubstituted or substituted with R$^g$, and wherein each CH and CH$_2$ is unsubstituted or substituted with R$^2$, provided that when g is a single bond at least one of J and K is CH$_2$ unsubstituted or substituted with R$^2$, and further provided that when g is a double bond then both J and K are CH. In another class of this embodiment, g is a single bond, J is O and K is CH$_2$, wherein CH$_2$ is unsubstituted or substituted with R$^2$. In another class of this embodiment, g is a single bond, J is O and K is C=O. In another class of this embodiment, g is a single bond, J is CH$_2$ and K is O, wherein CH$_2$ is unsubstituted or substituted with R$^2$. In another class of this embodiment, g is a single bond, J is CH$_2$ and K is O. In another class of this embodiment, g is a single bond, J is CH$_2$ and K is O, wherein CH$_2$ is unsubstituted or substituted with R$^2$. In another class of this embodiment, g is a single bond, J is C=O and K is O. In another class of this embodiment, g is a single bond, J and K are CH$_2$, wherein CH$_2$ is unsubstituted or substituted with R$^2$. In another class of this embodiment, g is a single bond, J is C=O and K is CH$_2$. In another class of this embodiment, g is a single bond, J is CH$_2$ and K is C=O.

In another class of this embodiment, g is a double bond, J and K are selected from N and CH, wherein each NH is unsubstituted or substituted with R$^g$, and wherein each CH is unsubstituted or substituted with R$^2$. In another class of this embodiment, g is a double bond, J and K are CH, wherein each CH is unsubstituted or substituted with R$^2$. In another class of this embodiment, g is a double bond, J and K are CH.

In another embodiment of the present invention, L and M are each independently selected from the group consisting of: S, O, NH and CH$_2$, wherein each NH is unsubstituted or substituted with R$^g$, and wherein each CH$_2$ is unsubstituted or substituted with R$^2$. In class of this embodiment, M and L are each independently selected from the group consisting of: S, O, NH and CH$_2$, wherein each NH is unsubstituted or substituted with R$^g$, and wherein CH$_2$ is unsubstituted or substituted with R$^2$. In another class of this embodiment, M and L are each independently selected from the group consisting of: O, NH and CH$_2$, wherein NH is unsubstituted or substituted with R$^g$, and wherein CH$_2$ is unsubstituted or substituted with R$^2$. In another class of this embodiment, g is a single bond, M and L ure CH$_2$, wherein CH$_2$ is unsubstituted or substituted with R$^2$. In another class of this embodiment, g is a single bond, M is C=O and L is CH$_2$.

In another embodiment of the present invention, T, U, V and W are each independently selected from N and CH, wherein CH is unsubstituted or substituted with R$^3$. In a class of this embodiment, T, U, V and W are each CH, wherein CH is unsubstituted or substituted with R$^3$. In another class of this embodiment, T, U, V and W are each independently selected from N and CH, wherein CH is unsubstituted or substituted with R$^3$, provided that at least one of T, U, V and W is N. In another class of this embodiment, T, U, V and W are each independently selected from N and CH, wherein CH is unsubstituted or substituted with R$^3$, provided that one of T or W is N. In another class of this embodiment, T is N and U, V and W are CH, wherein CH is unsubstituted or substituted with R$^3$. In another class of this embodiment, T, U, V are CH and W is N, wherein CH is unsubstituted or substituted with R$^3$.

In another embodiment of the present invention, X is CH$_2$, wherein CH$_2$ is unsubstituted or substituted with one or two substituents selected from R$^2$. In a class of this embodiment of the present invention, X is CH$_2$.

In another embodiment of the present invention, Y is independently selected from the group consisting of: O, NH and CH$_2$, wherein each NH is unsubstituted or substituted with R$^g$, and wherein each CH$_2$ is unsubstituted or substituted with one or two substituents selected from R$^2$. In a class of this embodiment, Y is CH$_2$, wherein CH$_2$ is unsubstituted or substituted with R$^2$. In another class of this embodiment, Y is CH$_2$.

In another embodiment of the present invention, Z is independently selected from the group consisting of: S, S(O), S(O)$_2$, O, NH and CH$_2$, wherein each NH is unsubstituted or substituted with R$^g$, and wherein each CH$_2$ is unsubstituted or substituted with R$^2$. In a class of this embodiment, Z is independently selected from the group consisting of: S, O, NH and CH$_2$, wherein each NH is unsubstituted or substituted with R$^g$, and wherein each CH$_2$ is unsubstituted or substituted with R$^2$. In another class of this embodiment, Z is independently selected from the group consisting of: O, NH and CH$_2$, wherein each NH is unsubstituted or substituted with R$^g$, and wherein each CH$_2$ is unsubstituted or substituted with R$^2$. In another class of this embodiment, Z is independently selected from the group consisting of: O and CH$_2$, wherein CH$_2$ is unsubstituted or substituted with R$^2$. In another class of this embodiment, Z is independently selected from the group consisting of: O and CH$_2$. In another class of this embodiment, Z is CH$_2$, wherein CH$_2$ is unsubstituted or substituted with R$^2$. In another class of this embodiment, Z is O.

In another class of this embodiment, X and Y are CH$_2$ and Z is O, wherein each CH$_2$ is unsubstituted or substituted with R$^2$. In another class of this embodiment, X and Y are CH$_2$ and Z is O. In another class of this embodiment, X is C=O, Y is CH$_2$ and Z is O, wherein CH$_2$ is unsubstituted or substituted with R$^2$. In another class of this embodiment, X is C=O, Y is CH$_2$ and Z is O. In another class of this embodiment, X is C—OH, Y is CH$_2$ and Z is O. In another class of this embodiment, X is CH—F, Y is CH$_2$ and Z is O. In another class of this embodiment, X is CH$_2$, Y is —CH—CH$_3$ and Z is O.

In another class of this embodiment, X is CH$_2$, Y is NH and Z is O, wherein NH is unsubstituted or substituted with R$^g$, and wherein CH$_2$ is unsubstituted or substituted with R$^2$. In another class of this embodiment, X is C=O, Y is NH and Z is O, wherein NH is unsubstituted or substituted with $R^g$. In another class of this embodiment, X is C=O, Y is NH and Z is O. In another class of this embodiment, X and Z are $CH_2$, and Y is NH, wherein NH is unsubstituted or substituted with $R^g$, and wherein each $CH_2$ is unsubstituted or substituted with $R^2$. In another class of this embodiment, X is C=O, Y is NH and Z is $CH_2$, wherein NH is unsubstituted or substituted with $R^g$, and wherein $CH_2$ is unsubstituted or substituted with $R^2$. In another class of this embodiment, X is C=O, Y is NH and Z is $CH_2$.

In another class of this embodiment, Y is O, and X and Z are $CH_2$, wherein each $CH_2$ is unsubstituted or substituted with $R^2$. In another class of this embodiment, X is C=O, Y is O and Z is $CH_2$, wherein each $CH_2$ is unsubstituted or substituted with $R^2$. In another class of this embodiment, X is C=O, Y is O and Z is $CH_2$. In another class of this embodiment, X and Y are $CH_2$ and Z is S, wherein each $CH_2$ is unsubstituted or substituted with $R^2$. In another class of this embodiment, X is C=O, Y is $CH_2$ and Z is S, wherein each $CH_2$ is unsubstituted or substituted with $R^2$. In another class of this embodiment, X is C=O, Y is $CH_2$ and Z is S.

In another embodiment of the present invention, each $R^1$ is independently selected from the group consisting of: hydrogen, halogen, and $C_{1-3}$ alkyl, wherein alkyl is unsubstituted or substituted with one to three substituents independently selected from halogen and hydroxy. In a class of this embodiment, each $R^1$ is independently selected from the group consisting of: hydrogen, halogen, or $C_{1-3}$ alkyl. In another class of this embodiment, each $R^1$ is hydrogen.

In another embodiment of the present invention, each $R^2$ is independently selected from the group consisting of: hydrogen, halogen, oxo, —$C_{1-6}$ alkyl, —$OC_{1-6}$ alkyl, $(CH_2)_nOR^e$, $(CH_2)_nN(R^e)_2$, $(CH_2)_nC\equiv N$, $(CH_2)_nCOR^e$, and $(CH_2)_nS(O)_qR^e$,
wherein alkyl is unsubstituted or substituted with hydroxy or one to three halogens; and wherein any $CH_2$ in $R^2$ is unsubstituted or substituted with one to two groups independently selected from halogen, hydroxy, and $C_{1-4}$ alkyl unsubstituted or substituted with one to five fluorines. In a class of this embodiment, each $R^2$ is independently selected from the group consisting of: hydrogen, halogen, oxo, —$C_{1-6}$ alkyl, —$OC_{1-6}$ alkyl, $(CH_2)_nOR^e$, $(CH_2)_nN(R^e)_2$, $(CH_2)_nC\equiv N$, and $(CH_2)_nCOR^e$, wherein alkyl is unsubstituted or substituted with hydroxy or one to three halogens; and wherein any $CH_2$ in $R^2$ is unsubstituted or substituted with one to two groups independently selected from halogen, hydroxy, and $C_{1-4}$ alkyl unsubstituted or substituted with one to five fluorines. In a subclass of this class, each $R^2$ is independently selected from the group consisting of: hydrogen, halogen, and oxo. In another subclass of this class, each $R^2$ is independently selected from the group consisting of: hydrogen, bromo, chloro, fluoro, and oxo. In another subclass of this class, each $R^2$ is independently selected from the group consisting of: hydrogen, and oxo. In another subclass of this class, each $R^2$ is hydrogen. In another subclass of this class, each $R^2$ is oxo. In another class of this embodiment, each $R^2$ is independently selected from the group consisting of: hydrogen, deuterium, halogen, oxo, —$C_{1-6}$ alkyl, and —$OR^e$, wherein alkyl is unsubstituted or substituted with hydroxy or one to three halogens. In a subclass of this class, each $R^2$ is independently selected from the group consisting of: hydrogen, deuterium, halogen, oxo, —$C_{1-6}$ alkyl, and —OH. In another subclass of this class, each $R^2$ is independently selected from the group consisting of: hydrogen, deuterium, fluoro, oxo, —$CH_3$, and —OH.

In another embodiment of the present invention, each $R^3$ is independently selected from the group consisting of: hydrogen, halogen, —$C_{1-6}$ alkyl, —$C_{1-6}$ alkenyl, —$OC_{1-6}$ alkyl, —$(CH_2)_nOR^e$, —$(CH_2)_nN(R^e)_2$, —$(CH_2)_nC\equiv N$, —$(CH_2)_nCOR^e$, and —$(CH_2)_nS(O)_qR^e$, wherein alkyl is unsubstituted or substituted with one to three substituents selected from: hydroxy, halogen, $C_{1-4}$ alkyl, $C_{3-6}$ cycloalkyl, $C_{2-5}$ cycloheteroalkyl, aryl, and heteroaryl wherein alkyl, cycloalkyl, cycloheteroalkyl, aryl and heteroaryl are unsubstituted or substituted with one to three substituents selected from: halogen, hydroxy, and $C_{1-4}$ alkyl unsubstituted or substituted with one to five fluorines, and wherein any $CH_2$ in $R^3$ is unsubstituted or substituted with one to two groups independently selected from halogen, hydroxy, and $C_{1-4}$ alkyl unsubstituted or substituted with one to five fluorines. In a class of this embodiment, Broader: each $R^3$ is independently selected from the group consisting of: hydrogen, halogen, —$C_{1-6}$ alkyl, —$C_{1-6}$ alkenyl, —$OC_{1-6}$ alkyl, and $(CH_2)_nOR^e$, wherein alkyl is unsubstituted or substituted with one to three substituents selected from: hydroxy, halogen, $C_{1-4}$ alkyl, $C_{3-6}$ cycloalkyl, $C_{2-5}$ cycloheteroalkyl, aryl, and heteroaryl wherein alkyl, cycloalkyl, cycloheteroalkyl, aryl and heteroaryl are unsubstituted or substituted with one to three substituents selected from: halogen, hydroxy, and $C_{1-4}$ alkyl unsubstituted or substituted with one to five fluorines. In another class of this embodiment, each $R^3$ is independently selected from the group consisting of: hydrogen, halogen, —$C_{1-6}$ alkyl, —$C_{1-6}$ alkenyl, —$OC_{1-6}$ alkyl, and $(CH_2)_nOR^e$, wherein alkyl is unsubstituted or substituted with one to three substituents selected from: hydroxy, halogen, $C_{1-4}$ alkyl, $C_{3-6}$ cycloalkyl, and phenyl, wherein alkyl, cycloalkyl, and phenyl are unsubstituted or substituted with one to three substituents selected from: halogen, hydroxy, and $C_{1-4}$ alkyl unsubstituted or substituted with one to five fluorines. In another class of this embodiment, each $R^3$ is independently selected from the group consisting of: hydrogen, halogen, —$C_{1-6}$ alkyl, —$C_{1-6}$ alkenyl, —$OC_{1-6}$ alkyl, and $(CH_2)_nOR^e$, wherein alkyl is unsubstituted or substituted with one to three substituents selected from: hydroxy, halogen, $C_{1-4}$ alkyl, cyclopropyl and difluoro phenyl. In another class of this embodiment, each $R^3$ is independently selected from the group consisting of: hydrogen, Cl, Br, F, I, —$CH_3$, —$CF_3$, —$CH_2CH_3$, —CH=$CH_2$, —$OCH_3$, —$OCF_3$, —$OCH_2CH_3$, —$OCH_2CH_2F$, —$O(CH_2)_2CH_3$, O—$CH_2$-cyclopropyl, O—$CH_2$-difluorophenyl, and —OH. In another class of this embodiment, each $R^3$ is independently selected from the group consisting of: Cl, Br, F, I, —$CH_3$, —$CF_3$, —$CH_2CH_3$, —CH=$CH_2$, —$OCH_3$, —$OCF_3$, —$OCH_2CH_3$, —$OCH_2CH_2F$, —$O(CH_2)_2CH_3$, O—$CH_2$-cyclopropyl, O—$CH_2$-difluorophenyl, and —OH.

In another embodiment of the present invention, each $R^3$ is independently selected from the group consisting of: hydrogen, Cl, Br, —$CH_3$, —$CF_3$, and —$OCF_3$. In a class of this embodiment, each $R^3$ is independently selected from the group consisting of: Cl, Br, —$CH_3$, —$CF_3$, and —$OCF_3$.

In another embodiment of the present invention, $R^3$ is independently selected from the group consisting of: hydrogen, halogen, —$C_{1-6}$ alkyl, —$OC_{1-6}$ alkyl, $(CH_2)_nOR^e$, $(CH_2)_nN(R^e)_2$, $(CH_2)_nC\equiv N$, $(CH_2)_nCOR^e$, and $(CH_2)_nS(O)_qR^e$, wherein alkyl is unsubstituted or substituted with hydroxy or one to three halogens; and wherein any $CH_2$ in $R^3$ is unsubstituted or substituted with one to two groups independently selected from halogen, hydroxy, and $C_{1-4}$ alkyl unsubstituted or substituted with one to five fluorines. In a class of this embodiment, $R^3$ is independently selected from the group consisting of: hydrogen, halogen, —$C_{1-6}$ alkyl, —$OC_{1-6}$ alkyl, $(CH_2)_nOR^e$, $(CH_2)_nN(R^e)_2$, $(CH_2)_nC\equiv N$, and $(CH_2)_n$ COR$^e$, wherein alkyl is unsubstituted or substituted with hydroxy or one to three halogens; and wherein any CH$_2$ in R$^3$ is unsubstituted or substituted with one to two groups independently selected from halogen, hydroxy, and C$_{1-4}$ alkyl unsubstituted or substituted with one to five fluorines. In a class of this embodiment, R$^3$ is independently selected from the group consisting of: hydrogen, halogen, —C$_{1-6}$ alkyl, —OH, and —OC$_{1-6}$ alkyl, wherein alkyl is unsubstituted or substituted with hydroxy or one to three halogens; and wherein any CH$_2$ in R$^3$ is unsubstituted or substituted with one to two groups independently selected from halogen, hydroxy, and C$_{1-4}$ alkyl unsubstituted or substituted with one to five fluorines. In a subclass of this class, R$^3$ is independently selected from the group consisting of: hydrogen, halogen, —C$_{1-6}$ alkyl, —OH, and —OC$_{1-6}$ alkyl. In another subclass of this class, R$^3$ is independently selected from the group consisting of: hydrogen, halogen, —OH, and —OC$_{1-6}$ alkyl, wherein alkyl is unsubstituted or substituted with hydroxy or one to three halogens, and wherein any CH$_2$ in R$^3$ is unsubstituted or substituted with one to two groups independently selected from halogen, hydroxy, —OH, and C$_{1-4}$ alkyl unsubstituted or substituted with one to five fluorines. In another subclass of this class, R$^3$ is independently selected from the group consisting of: hydrogen, halogen, —OH, and —OC$_{1-6}$ alkyl. In another subclass of this class, R$^3$ is independently selected from the group consisting of: hydrogen, halogen, —OH and OCH$_3$. In another subclass of this class, R$^3$ is independently selected from the group consisting of: —OH and OCH$_3$. In another subclass of this class, R$^3$ is independently selected from the group consisting of: hydrogen, and halogen. In another subclass of this class, R$^3$ is independently selected from the group consisting of: hydrogen, bromo, chloro and fluoro. In another subclass of this class, R$^3$ is independently selected from the group consisting of: hydrogen, chloro and fluoro. In another subclass of this class, R$^3$ is independently selected from the group consisting of: hydrogen, and chloro. In another subclass of this class, R$^3$ is chloro. In another subclass of this class, R$^3$ is halogen. In another subclass of this class, R$^3$ is independently selected from the group consisting of: bromo, chloro and fluoro. In another subclass of this class, R$^3$ is independently selected from the group consisting of: chloro and fluoro. In another class of this embodiment, R$^3$ is chloro.

In a class of this embodiment, R$^3$ is independently selected from the group consisting of: hydrogen, halogen, —C$_{1-6}$ alkyl, —OC$_{1-6}$ alkyl, (CH$_2$)$_n$OR$^e$, (CH$_2$)$_n$N(R$^e$)$_2$, (CH$_2$)$_n$C≡N, and (CH$_2$)$_n$COR$^e$, wherein alkyl is unsubstituted or substituted with hydroxy or one to three halogens; and wherein any CH$_2$ in R$^3$ is unsubstituted or substituted with one to two groups independently selected from halogen, hydroxy, and C$_{1-4}$ alkyl unsubstituted or substituted with one to five fluorines. In a class of this embodiment, R$^3$ is independently selected from the group consisting of: hydrogen, halogen, —C$_{1-6}$ alkyl, —OH, and —OC$_{1-6}$ alkyl, wherein alkyl is unsubstituted or substituted with hydroxy or one to three halogens; and wherein any CH$_2$ in R$^3$ is unsubstituted or substituted with one to two groups independently selected from halogen, hydroxy, and C$_{1-4}$ alkyl unsubstituted or substituted with one to five fluorines.

In another embodiment of the present invention, R$^4$ is selected from the group consisting of: heteroaryl, and cycloheteroalkyl, wherein any NH group is unsubstituted or substituted with R$^c$, and wherein any CH or CH$_2$ group is unsubstituted or substituted with 1 to 2 substituents selected from R$^d$. In a class of this embodiment, R$^4$ is heteroaryl, wherein any NH group is unsubstituted or substituted with R$^c$, and wherein any CH or CH$_2$ group is unsubstituted or substituted with one substituent selected from R$^d$. In a class of this embodiment, R$^4$ is heteroaryl, wherein any NH group is unsubstituted or substituted with R$^c$, and wherein any CH group is unsubstituted or substituted with one substituent selected from R$^d$. In another class of this embodiment, R$^4$ is cycloheteroalkyl, wherein any NH group is unsubstituted or substituted with R$^c$, and wherein any CH or CH$_2$ group is unsubstituted or substituted with one substituent selected from R$^d$. In another class of this embodiment, R$^4$ is cycloheteroalkyl, wherein any NH group is unsubstituted or substituted with R$^c$, and wherein any CH$_2$ group is unsubstituted or substituted with one to two substituents selected from R$^d$.

In another embodiment of the present invention, R$^4$ is selected from the group consisting of:

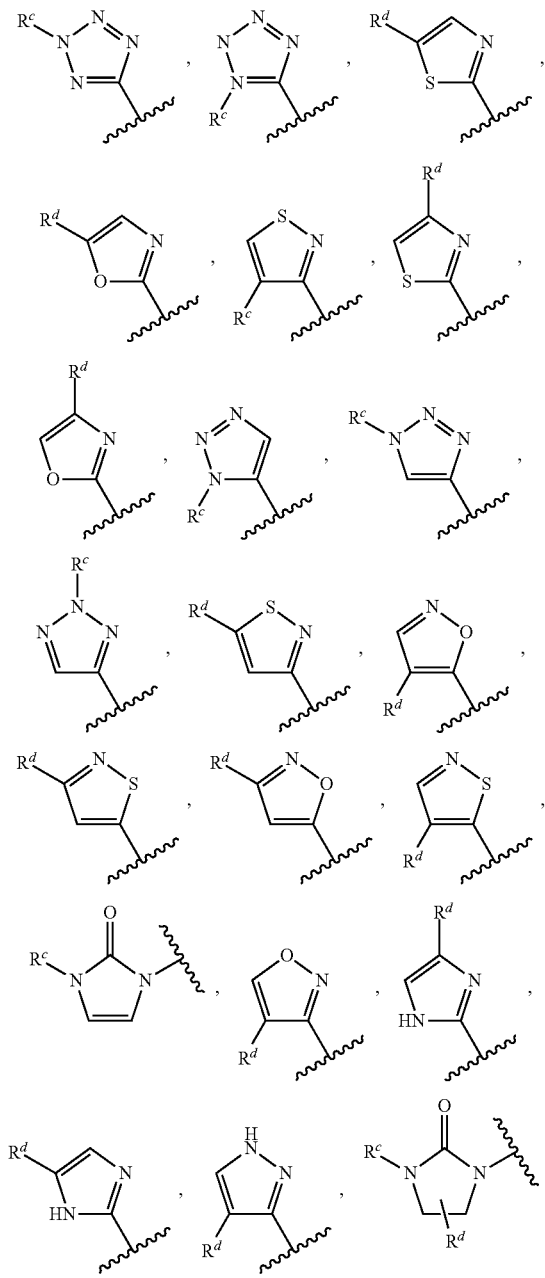

-continued
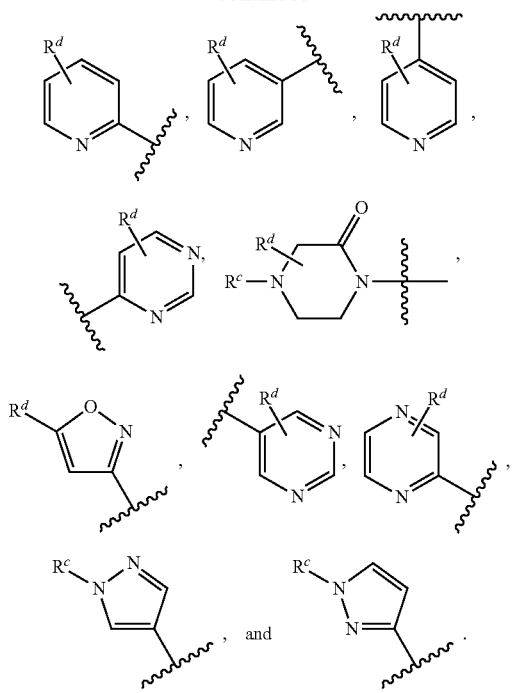
In a class of this embodiment, $R^4$ is selected from the group consisting of:
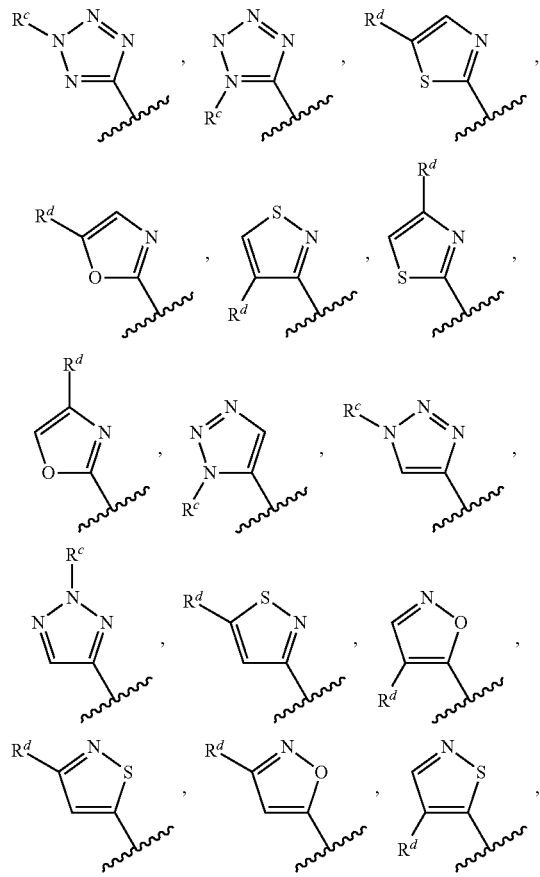
-continued
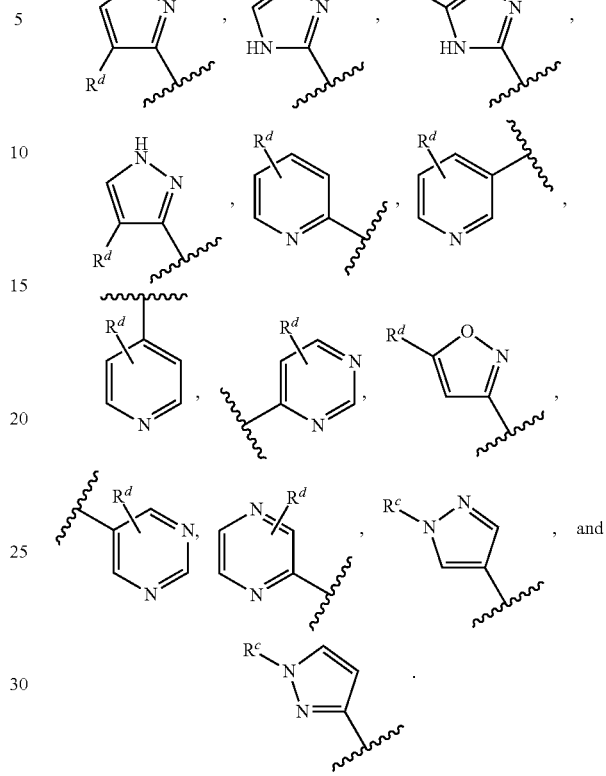
In a class of this embodiment, $R^4$ is selected from the group consisting of:
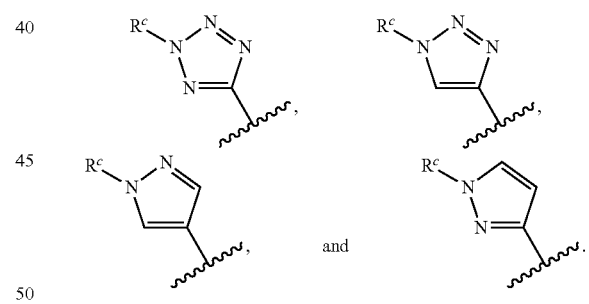
In another class of this embodiment, $R^4$ is selected from the group consisting of:
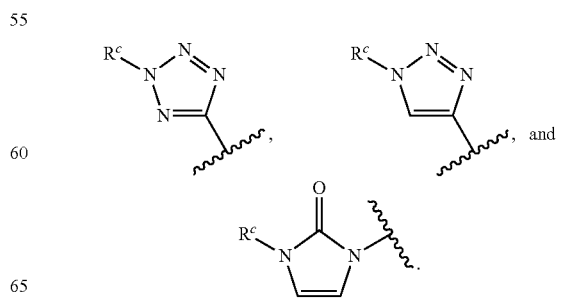

In another class of this embodiment, $R^4$ is selected from the group consisting of:

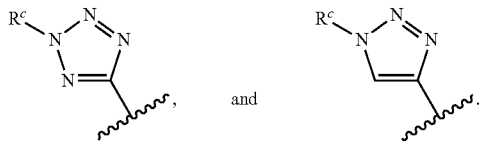
and

In another class of this embodiment, $R^4$ is:

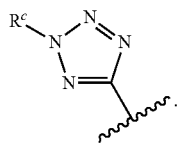

In another class of this embodiment, $R^4$ is selected from the group consisting of:

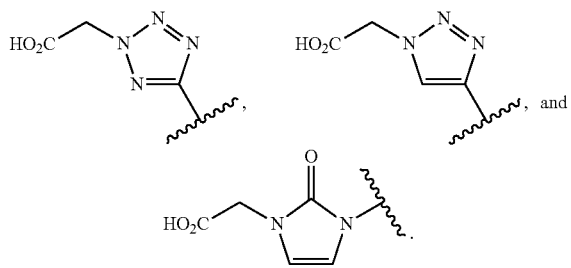
and

In another class of this embodiment, $R^4$ is:

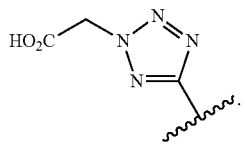

In another embodiment of the present invention, each $R^a$ is independently selected from the group consisting of: hydrogen, halogen, cyano, $C_{1-4}$ alkyl, unsubstituted or substituted with one to five fluorines, $C_{1-4}$ alkoxy, unsubstituted or substituted with one to five fluorines, $C_{1-4}$ alkylthio, unsubstituted or substituted with one to five fluorines, $C_{1-4}$ alkylsulfonyl, $-CO_2H$, $C_{1-4}$ alkyloxycarbonyl, and $C_{1-4}$ alkylcarbonyl. In a class of this embodiment, $R^a$ is independently selected from the group consisting of: hydrogen, halogen, cyano, and $C_{1-4}$ alkyl, unsubstituted or substituted with one to five fluorines. In another class of this embodiment, $R^a$ is independently selected from the group consisting of: hydrogen, and $C_{1-4}$ alkyl, unsubstituted or substituted with one to five fluorines. In another class of this embodiment, $R^a$ is hydrogen. In another class of this embodiment, $R^a$ is $C_{1-4}$ alkyl, unsubstituted or substituted with one to five fluorines. In another class of this embodiment, $R^a$ is $C_{1-4}$ alkyl.

In another embodiment of the present invention, each $R^b$ is independently selected from the group consisting of: hydrogen, and $C_{1-4}$ alkyl, wherein alkyl is unsubstituted or substituted with one to five fluorines. In a class of this embodiment, $R^b$ is hydrogen. In another class of this embodiment, $R^b$ is $C_{1-4}$ alkyl, wherein alkyl is unsubstituted or substituted with one to five fluorines. In another class of this embodiment, $R^b$ is $C_{1-4}$ alkyl.

In another embodiment of the present invention, each $R^c$ is independently selected from the group consisting of: $-(CH_2)_mCO_2H$, $-(CH_2)_mCO_2C_{1-3}$ alkyl, $-(CH_2)_m-NR^b-(CH_2)_pCO_2H$, $-(CH_2)_m-NR^b-(CH_2)_pCO_2C_{1-3}$ alkyl, $-(CH_2)_m-O-(CH_2)_pCO_2H$, $-(CH_2)_m-O-(CH_2)_pCO_2C_{1-3}$ alkyl, $-(CH_2)_m-S-(CH_2)_pCO_2H$, and $-(CH_2)_m-S-(CH_2)_pCO_2C_{1-3}$ alkyl, wherein any $CH_2$ in $R^c$ is unsubstituted or substituted with one to two groups independently selected from halogen, hydroxy, and $C_{1-4}$ alkyl unsubstituted or substituted with one to five fluorines. In another class of this embodiment, $R^e$ is selected from the group consisting of: $-(CH_2)_mCO_2H$, $-(CH_2)_mCO_2C_{1-3}$ alkyl, $-(CH_2)_mOCOH$, $-(CH_2)_mOCOC_{1-3}$ alkyl, $-(CH_2)_mCOH$, $-(CH_2)_mCOC_{1-3}$ alkyl, $-(CH_2)_m-NR^b-(CH_2)_pCO_2H$, $-(CH_2)_m-NR^b-(CH_2)_pCO_2C_{1-3}$ alkyl, $-(CH_2)_m-O-(CH_2)_pCO_2H$, and $-(CH_2)_m-O-(CH_2)_pCO_2C_{1-3}$ alkyl, wherein any $CH_2$ in $R^c$ is unsubstituted or substituted with one to two groups independently selected from halogen, hydroxy, and $C_{1-4}$ alkyl unsubstituted or substituted with one to five fluorines. In another class of this embodiment, $R^c$ is selected from the group consisting of: $-(CH_2)_mCO_2H$, $-(CH_2)_mCO_2C_{1-3}$ alkyl, $-(CH_2)_mOCOH$, $-(CH_2)_mO-COC_{1-3}$ alkyl, $-(CH_2)_mCOH$, and $-(CH_2)_mCOC_{1-3}$ alkyl, wherein any $CH_2$ in $R^c$ is unsubstituted or substituted with one to two groups independently selected from halogen, hydroxy, and $C_{1-4}$ alkyl unsubstituted or substituted with one to five fluorines. In another class of this embodiment, $R^c$ is selected from the group consisting of: $-(CH_2)_mCO_2H$, $-(CH_2)_mCO_2C_{1-3}$ alkyl, $-(CH_2)_mOCOH$, $-(CH_2)_mO-COC_{1-3}$ alkyl, $-(CH_2)_mCOH$, $-(CH_2)_mCOC_{1-3}$ alkyl, $-(CH_2)_m-NR^b-(CH_2)_pCO_2H$, $-(CH_2)_m-NR^b-(CH_2)_pCO_2C_{1-3}$ alkyl, wherein any $CH_2$ in $R^c$ is unsubstituted or substituted with one to two groups independently selected from halogen, hydroxy, and $C_{1-4}$ alkyl unsubstituted or substituted with one to five fluorines. In another class of this embodiment, $R^c$ is selected from the group consisting of: $-(CH_2)_mCO_2H$, and $-(CH_2)_mCO_2C_{1-3}$ alkyl, wherein any $CH_2$ in $R^c$ is unsubstituted or substituted with one to two groups independently selected from halogen, hydroxy, and $C_{1-4}$ alkyl unsubstituted or substituted with one to five fluorines. In another class of this embodiment, $R^c$ is $-(CH_2)_mCO_2H$. In another class of this embodiment, $R^c$ is $-(CH_2)_qCO_2C_{1-3}$ alkyl.

In another embodiment of the present invention, each $R^d$ is independently selected from the group consisting of: $-(CH_2)_nCO_2H$, $-(CH_2)_nCO_2C_{1-3}$ alkyl, $-(CH_2)_n-NR^b-(CH_2)_pCO_2H$, $-(CH_2)_n-NR^b-(CH_2)_pCO_2C_{1-3}$ alkyl, $-(CH_2)_n-O-(CH_2)_pCO_2H$, $-(CH_2)_n-O-(CH_2)_pCO_2C_{1-3}$ alkyl, $-(CH_2)_n-S-(CH_2)_pCO_2H$, and $-(CH_2)_n-S-(CH_2)_pCO_2C_{1-3}$ alkyl, wherein any $CH_2$ in $R^d$ is unsubstituted or substituted with one to two groups independently selected from the group consisting of: halogen, hydroxy, and $C_{1-4}$ alkyl unsubstituted or substituted with one to five fluorines. In another class of this embodiment, each $R^d$ is independently selected from the group consisting of: $-(CH_2)_nCO_2H$, $-(CH_2)_nCO_2C_{1-3}$ alkyl, $-(CH_2)_n-NR^b-(CH_2)_pCO_2H$, $-(CH_2)_n-NR^b-(CH_2)_pCO_2C_{1-3}$ alkyl, $-(CH_2)_n-O-(CH_2)_pCO_2H$, and $-(CH_2)_n-O-(CH_2)_pCO_2C_{1-3}$ alkyl, wherein any $CH_2$ in $R^d$ is unsubstituted or substituted with one to two groups independently selected from the group consisting of: halogen, hydroxy, and $C_{1-4}$ alkyl unsubstituted or substituted with one to five fluorines. In another class of this embodiment, $R^d$ is selected from the group consisting of: $-(CH_2)_nCO_2H$, $-(CH_2)_nCO_2C_{1-3}$ alkyl, —(CH$_2$)$_n$—NR$^b$—(CH$_2$)$_p$CO$_2$H, and —(CH$_2$)$_n$—NR$^b$—(CH$_2$)$_p$CO$_2$C$_{1-3}$ alkyl, wherein any CH$_2$ in R$^d$ is unsubstituted or substituted with one to two groups independently selected from halogen, hydroxy, and C$_{1-4}$ alkyl unsubstituted or substituted with one to five fluorines. In another class of this embodiment, R$^d$ is selected from the group consisting of: —(CH$_2$)$_n$CO$_2$H, and —(CH$_2$)$_n$—NR$^b$—(CH$_2$)$_p$CO$_2$H, wherein any CH$_2$ in R$^d$ is unsubstituted or substituted with one to two groups independently selected from halogen, hydroxy, and C$_{1-4}$ alkyl unsubstituted or substituted with one to five fluorines. In another class of this embodiment, R$^d$ is selected from the group consisting of: —CH$_2$CO$_2$H, and —NH—CH$_2$CO$_2$H. In another class of this embodiment, R$^d$ is —CH$_2$CO$_2$H. In another class of this embodiment, R$^d$ is —NH—CH$_2$CO$_2$H.

In another embodiment of the present invention, each R$^e$ is independently selected from the group consisting of: hydrogen, and C$_{1-6}$ alkyl, wherein alkyl is unsubstituted or substituted with one to three substituents independently selected from the group consisting of halogen, cyano, —C$_{1-4}$ alkoxy, —C$_{1-4}$ alkylthio, —C$_{1-4}$ alkylsulfonyl, —CO$_2$H, and —CO$_2$C$_{1-4}$ alkyl. In a class of this embodiment, R$^e$ is hydrogen. In another class of this embodiment, R$^e$ is C$_{1-6}$ alkyl, wherein alkyl is unsubstituted or substituted with one to three substituents independently selected from the group consisting of: halogen, cyano, —C$_{1-4}$ alkoxy, alkylthio, —C$_{1-4}$ alkylsulfonyl, —CO$_2$H, and —CO$_2$C$_{1-4}$ alkyl. In another class of this embodiment, R$^e$ is C$_{1-6}$ alkyl.

In another embodiment of the present invention, each R$^g$ is independently selected from the group consisting of: hydrogen, and C$_{1-6}$ alkyl. In a class of this embodiment, R$^g$ is hydrogen. In another class of this embodiment, R$^g$ is C$_{1-6}$ alkyl.

In another embodiment of the present invention, g is a single bond or a double bond. In a class of this embodiment, g is a single bond. In another class of this embodiment, g is a double bond.

In another embodiment of the present invention, m is 1, 2, or 3. In a class of this embodiment, s is 1 or 2. In another class of this embodiment, m is 2 or 3. In another class of this embodiment, m is 1 or 3. In another class of this embodiment, m is 1. In another class of this embodiment, m is 2. In another class of this embodiment, m is 3.

In another embodiment of the present invention, n is 0, 1, 2 or 3. In a class of this embodiment, n is 0, 1 or 2. In another class of this embodiment, n is 0 or 1. In another class of this embodiment, n is 1 or 2. In another class of this embodiment, n is 0 or 2. In another class of this embodiment, n is 0. In another class of this embodiment, n is 1. In another class of this embodiment, n is 2. In another class of this embodiment, n is 3.

In another embodiment of the present invention, p is 1, 2, or 3. In a class of this embodiment, p is 1 or 2. In another class of this embodiment, p is 2 or 3. In another class of this embodiment, p is 1 or 3. In another class of this embodiment, p is 1. In another class of this embodiment, p is 2. In another class of this embodiment, p is 3.

In another embodiment of the present invention, q is 1 or 2. In another class of this embodiment, q is 1. In another class of this embodiment, q is 2.

In another embodiment of the present invention, r is 0, 1, 2 or 3. In a class of this embodiment, r is 0, 1 or 2. In another class of this embodiment, r is 0 or 1. In another class of this embodiment, r is 1 or 2. In another class of this embodiment, r is 0 or 2. In another class of this embodiment, r is 0. In another class of this embodiment, r is 1. In another class of this embodiment, r is 2. In another class of this embodiment, r is 3.

In another embodiment of the present invention, s is 0, 1, 2, 3 or 4. In a class of this embodiment, s is 0, 1, 2 or 3. In a class of this embodiment, s is 0, 1 or 2. In another class of this embodiment, s is 0 or 1. In another class of this embodiment, s is 1 or 2. In another class of this embodiment, s is 0 or 2. In another class of this embodiment, s is 0. In another class of this embodiment, s is 1. In another class of this embodiment, s is 2. In another class of this embodiment, s is 3.

In another embodiment of the present invention, t is 0, 1, 2, 3, 4, 5, 6, 7 or 8. In a class of this embodiment, t is 0, 1, 2, 3 or 4. In a class of this embodiment, t is 0, 1, 2 or 3. In a class of this embodiment, t is 0, 1 or 2. In another class of this embodiment, t is 0 or 1. In another class of this embodiment, t is 1 or 2. In another class of this embodiment, t is 0 or 2. In another class of this embodiment, t is 0. In another class of this embodiment, t is 1. In another class of this embodiment, t is 2. In another class of this embodiment, t is 3. In another class of this embodiment, t is 4. In another class of this embodiment, t is 5. In another class of this embodiment, t is 6. In another class of this embodiment, t is 7. In another class of this embodiment, t is 8.

In another embodiment of the present invention, d is 0, 1 or 2. In a class of this embodiment, d is 0. In another class of this embodiment, d is 1. In another class of this embodiment, d is 2.

In another embodiment of the present invention, e is 0, 1 or 2. In a class of this embodiment, e is 0. In another class of this embodiment, e is 1. In another class of this embodiment, e is 2.

In another embodiment of the present invention, d is 0, and e is 2. In another embodiment of the present invention, d is 1 and e is 1. In another embodiment of the present invention, d is 2 and e is 0.

In another embodiment of the present invention, the invention relates to compounds of structural formula I, wherein:

A is selected from the group consisting of:

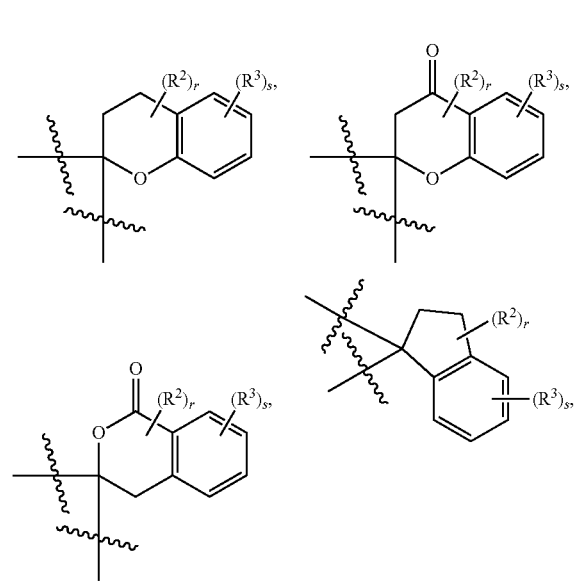

-continued

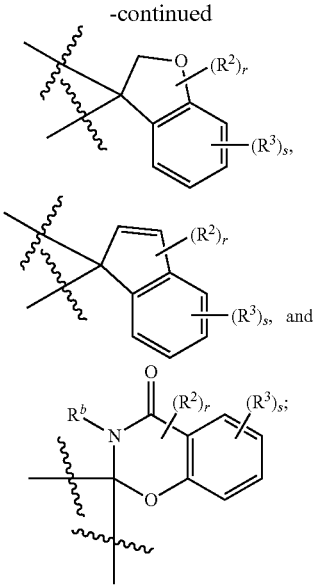

B is selected from the group consisting of:

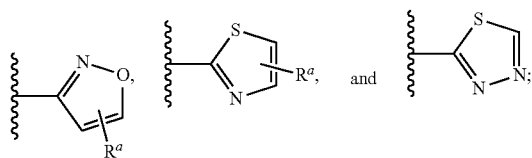

$R^2$ is independently selected from the group consisting of: hydrogen, deuterium, halogen, oxo, —$C_{1-6}$ alkyl, and —$OR^e$, wherein alkyl is unsubstituted or substituted with hydroxy or one to three halogens;

each $R^3$ is independently selected from the group consisting of: hydrogen, halogen, —$C_{1-6}$ alkyl, —$C_{1-6}$ alkenyl, —$OC_{1-6}$ alkyl, and —$(CH_2)_nOR^e$, wherein alkyl is unsubstituted or substituted with one to three substituents selected from: hydroxy, halogen, $C_{1-4}$ alkyl, $C_{3-6}$ cycloalkyl, $C_{2-5}$ cycloheteroalkyl, aryl, and heteroaryl wherein alkyl, cycloalkyl, cycloheteroalkyl, aryl and heteroaryl are unsubstituted or substituted with one to three substituents selected from: halogen, hydroxy, and $C_{1-4}$ alkyl unsubstituted or substituted with one to five fluorines, and wherein any $CH_2$ in $R^3$ is unsubstituted or substituted with one to two groups independently selected from halogen, hydroxy, and $C_{1-4}$ alkyl unsubstituted or substituted with one to five fluorines;

$R^4$ is selected from the group consisting of:

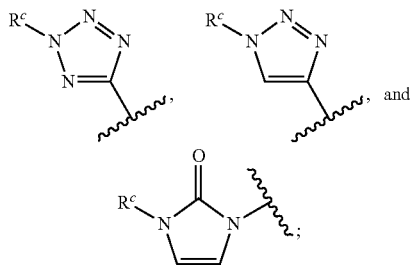

s is 0 or 1; and r is 0 or 1; or a pharmaceutically acceptable salt thereof. In a class of this embodiment, each $R^2$ is independently selected from the group consisting of: $R^2$ is independently selected from the group consisting of: hydrogen, deuterium, halogen, oxo, —$C_{1-6}$ alkyl, and —OH; and each $R^3$ is independently selected from the group consisting of: Cl, Br, F, I, —$CH_3$, —$CF_3$, —$CH_2CH_3$, —$CH=CH_2$, —$OCH_3$, —$OCF_3$, —$OCH_2CH_3$, —$OCH_2CH_2F$, —$O(CH_2)_2CH_3$, and —OH.

In another embodiment of the present invention, the invention relates to compounds of structural formula I, wherein:
A is selected from the group consisting of:

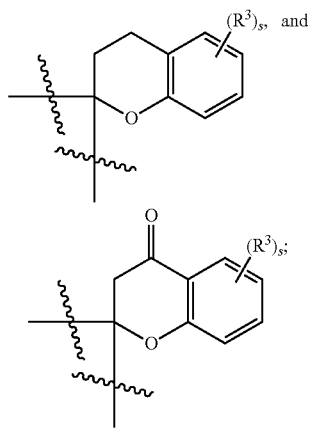

B is selected from the group consisting of:

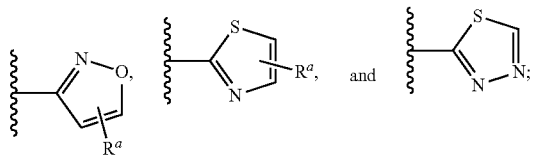

$R^4$ is

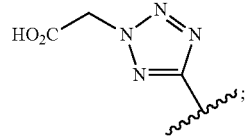

$R^3$ is independently selected from the group consisting of: hydrogen, halogen and —$OCH_3$; and s is 0 or 1; or a pharmaceutically acceptable salt thereof.

In another embodiment of the present invention, the invention relates to compounds of structural formula I, wherein:
A is:

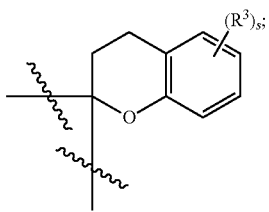

B-R⁴ is selected from the group consisting of:

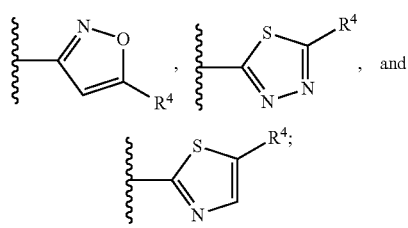

each R³ is independently selected from the group consisting of: Cl, Br, —CH₃, —CF₃, and —OCF₃;

R⁴ is:

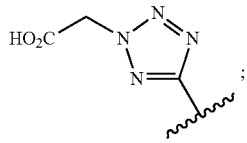 [SMILES: *c1nnn(CC(=O)O)n1]

and s is 1; or a pharmaceutically acceptable salt thereof.

In another embodiment of the present invention, the invention relates to compounds of structural formula Ia:

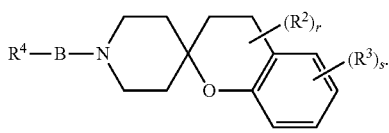

Ia

In another embodiment of the present invention, the invention relates to compounds of structural formula Ib:

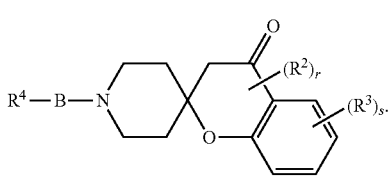

Ib

In another embodiment of the present invention, the invention relates to compounds of structural formula Ic:

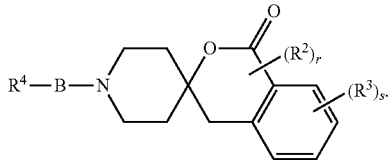

Ic

In another embodiment of the present invention, the invention relates to compounds of structural formula Id:

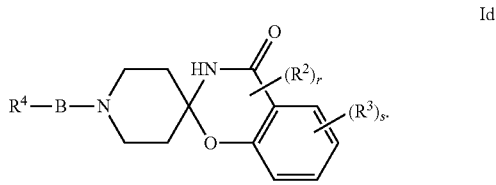

Id

In another embodiment of the present invention, the invention relates to compounds of structural formula Ie:

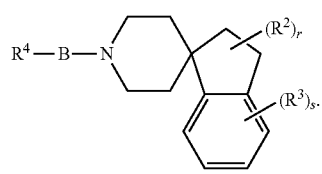

Ie

In another embodiment of the present invention, the invention relates to compounds of structural formula If:

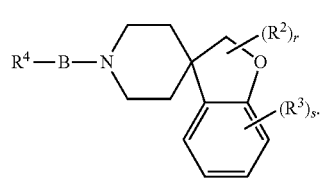

If

In another embodiment of the present invention, the invention relates to compounds of structural formula Ig:

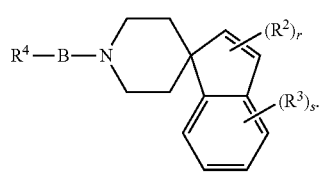

Ig

In another embodiment of the present invention, the invention relates to compounds of structural formula Ih:

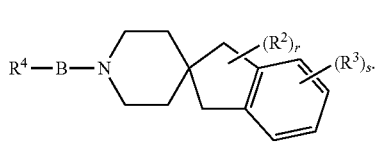

Ih

In another embodiment of the present invention, the invention relates to compounds of structural formula Ii:

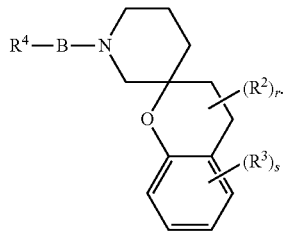

Ii

In another embodiment of the present invention, the invention relates to compounds of structural formula Ij:

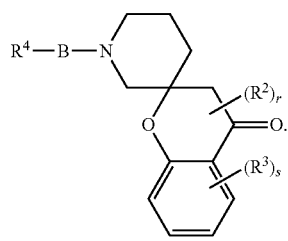

Ij

Illustrative, but nonlimiting, examples of compounds of the present invention that are useful as inhibitors of SCD are the following:

| Example | Structure | IC$_{50}$ hSCD-1 |
|---|---|---|
| 1 | 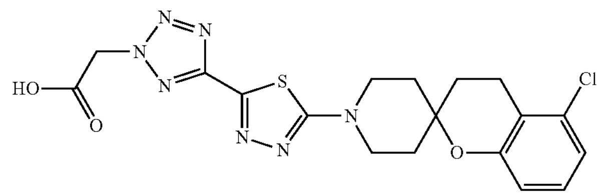 [SMILES: O=C(O)Cn1nnc(-c2nnc(N3CCC4(CCc5c(Cl)cccc5O4)CC3)s2)n1] | 12 nM |
| 2 | 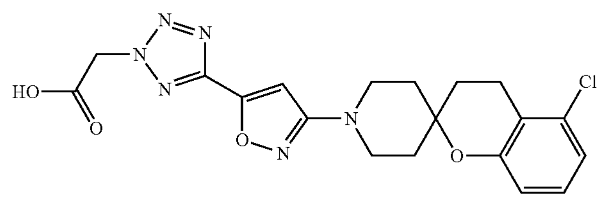 [SMILES: O=C(O)Cn1nnc(-c2cc(N3CCC4(CCc5c(Cl)cccc5O4)CC3)no2)n1] | 11 nM |
| 3 | 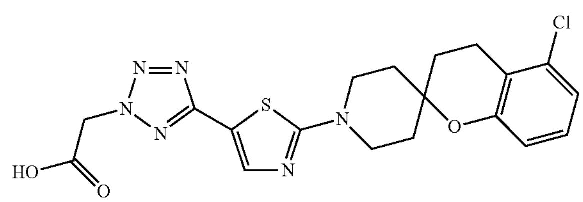 [SMILES: O=C(O)Cn1nnc(-c2cnc(N3CCC4(CCc5c(Cl)cccc5O4)CC3)s2)n1] | 13 nM |
| 4 | 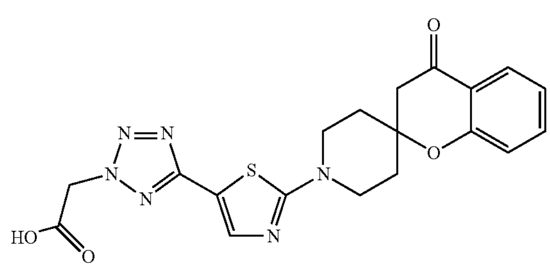 [SMILES: O=C(O)Cn1nnc(-c2cnc(N3CCC4(CC3)CC(=O)c3ccccc3O4)s2)n1] | 41 nM |
| 5 | 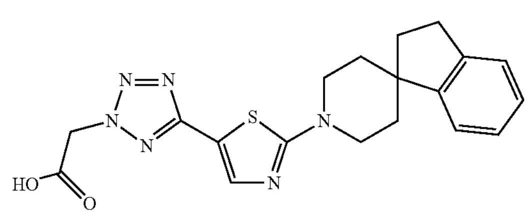 [SMILES: O=C(O)Cn1nnc(-c2cnc(N3CCC4(CCc5ccccc54)CC3)s2)n1] | 49 nM |

-continued
| Example | Structure | IC$_{50}$ hSCD-1 |
|---|---|---|
| 6 | 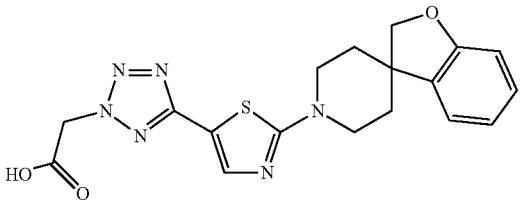 [SMILES: O=C(O)Cn1nnc(-c2cnc(N3CCC4(CC3)COc3ccccc34)s2)n1] | 65 nM |
| 7 | 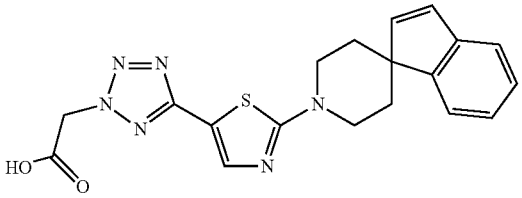 [SMILES: O=C(O)Cn1nnc(-c2cnc(N3CCC4(C=Cc5ccccc54)CC3)s2)n1] | 244 nM |
| 8 | 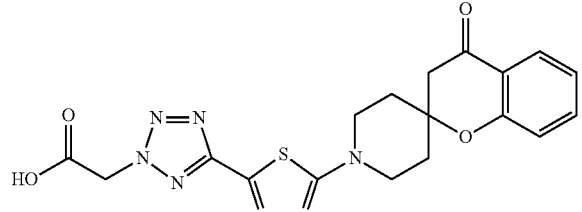 | 708 nM |
| 9 | 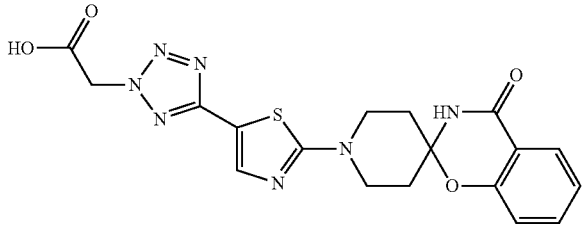 [SMILES: O=C(O)Cn1nnc(-c2cnc(N3CCC4(CC3)NC(=O)c3ccccc3O4)s2)n1] | 181 nM |
| 10 | 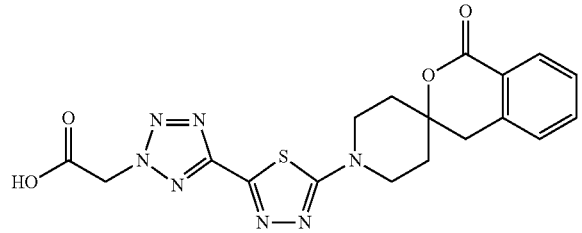 [SMILES: O=C(O)Cn1nnc(-c2nnc(N3CCC4(CC3)Cc3ccccc3C(=O)O4)s2)n1] | 338 nM |
| 11 | 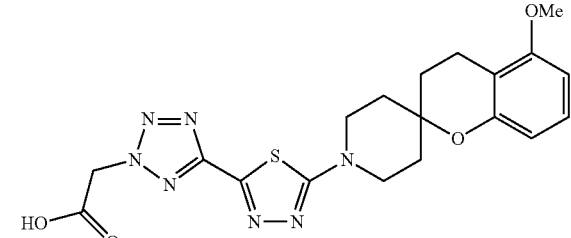 | 13 nM |

-continued
| Example | Structure | IC$_{50}$ hSCD-1 |
|---|---|---|
| 12 | 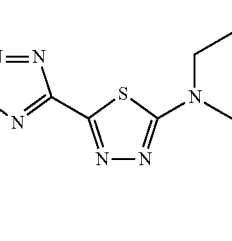 | 366 nM |
| 13 | 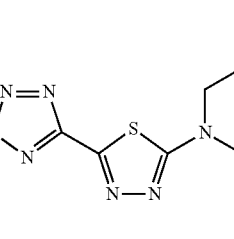 | 24 nM |
| 14 | 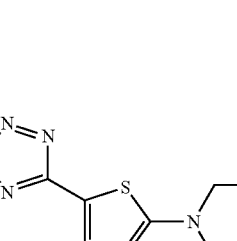 | 12 nM |
| 15 | 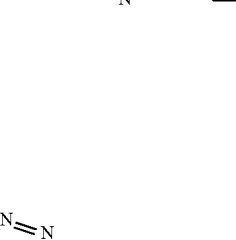 | 17 nM |
| 16 | 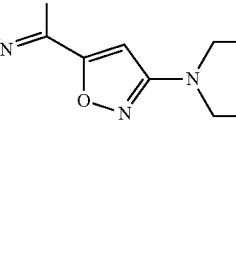 | 1 nM |

-continued
| Example | Structure | IC$_{50}$ hSCD-1 |
|---------|-----------|------------------|
| 17 | 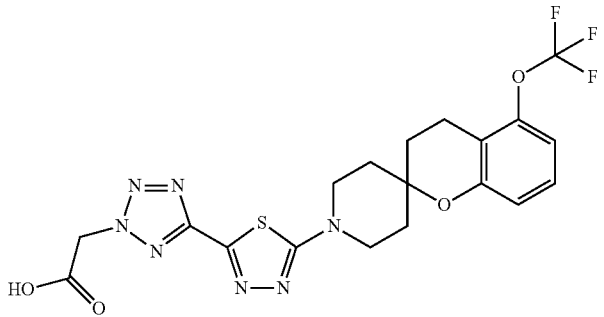 | 1 nM |
| 18 | 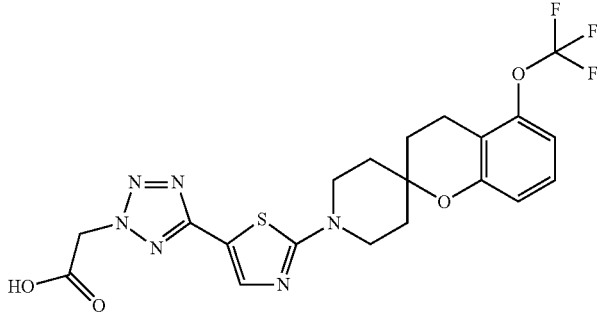 [SMILES: O=C(O)Cn1nnc(-c2cnc(N3CCC4(CCc5c(OC(F)(F)F)cccc5O4)CC3)s2)n1] | 1 nM |
| 22 | 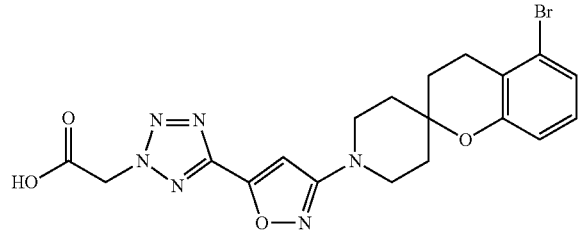 [SMILES: O=C(O)Cn1nnc(-c2cc(N3CCC4(CCc5c(Br)cccc5O4)CC3)no2)n1] | 1 nM |
| 28 | 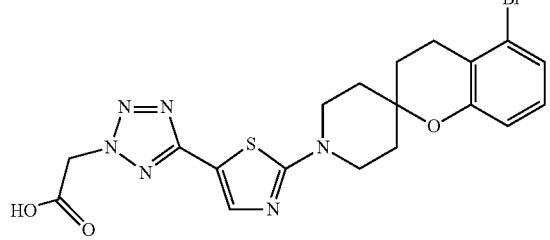 | 1 nM |
| 42 | 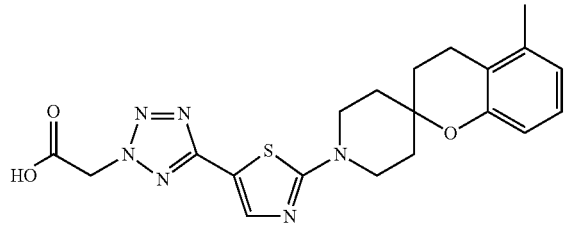 [SMILES: Cc1cccc2c1CCC1(CCN(c3ncc(-c4nnn(CC(=O)O)n4)s3)CC1)O2] | 1 nM |

| Example | Structure | IC$_{50}$ hSCD-1 |
|---|---|---|
| 46 | 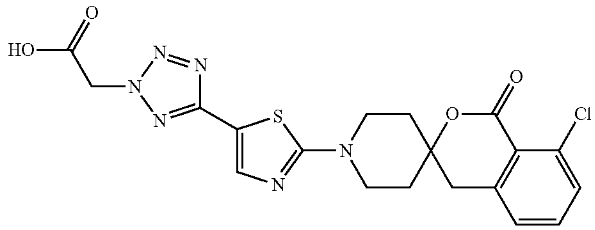 [SMILES: O=C(O)Cn1nnc(-c2cnc(N3CCC4(CC3)Cc3cccc(Cl)c3C(=O)O4)s2)n1] | 21 nM |
| 54 | 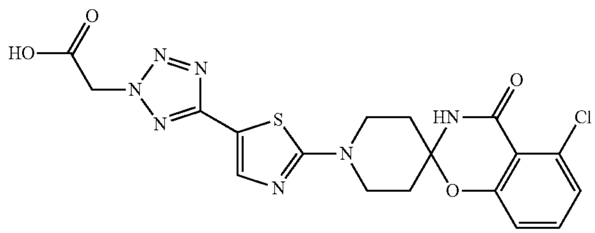 [SMILES: O=C(O)Cn1nnc(-c2cnc(N3CCC4(CC3)NC(=O)c3c(Cl)cccc3O4)s2)n1] | 62 nM |
| 68 | 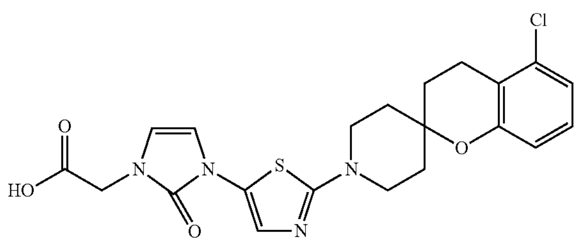 [SMILES: O=C(O)Cn1ccn(-c2cnc(N3CCC4(CCc5c(Cl)cccc5O4)CC3)s2)c1=O] | 3 nM |
| 72 | 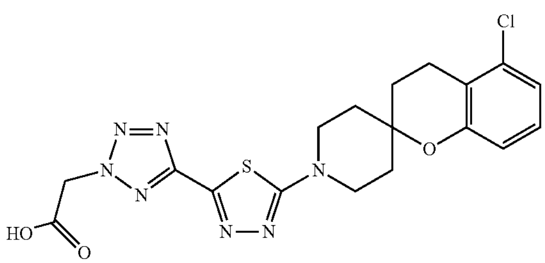 | 3 nM |
| 75 | 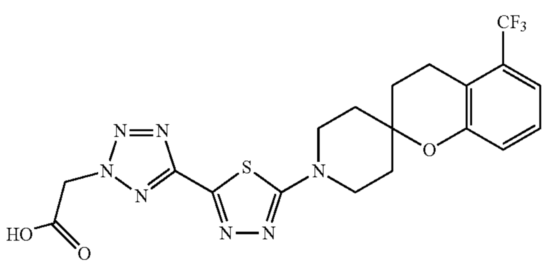 [SMILES: O=C(O)Cn1nnc(-c2nnc(N3CCC4(CCc5c(cccc5C(F)(F)F)O4)CC3)s2)n1] | 1 nM |
| 76 | | 1 nM | and pharmaceutically acceptable salts thereof.

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. When no number of carbon atoms is specified, $C_{1-6}$ is intended.

The term "alkenyl" shall mean straight or branched-chain alkenes having the specified number of carbon atoms. Examples of alkenyl include vinyl, 1-propenyl, 1-butenyl, 2-butenyl, and the like.

The term "alkynyl" refers to straight or branched-chain alkynes having the specified number of carbon atoms. Examples of alkynyl include ethynyl, propynyl, butynyl, pentynyl, and the like.

The term "alkoxy" refers to straight or branched chain alkoxides of the number of carbon atoms specified (e.g., $C_{1-6}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-6}$ alkylthio), or any number within this range [i.e., methylthio (MeS—), ethylthio, isopropylthio, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl ($MeSO_2$—), ethylsulfonyl, isopropylsulfonyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

"Cycloalkyl" means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

"Cycloheteroalkyl" means nonaromatic, mono- or bicyclic or bridged saturated carbocyclic rings, each having from 2 to 14 carbon atoms and containing 1, 2, 3, 4 or 5 heteroatoms selected from N, NH, O and S. Examples of cycloheteroalkyl include tetrahydrofuranyl, azetidinyl, perhydroazepinyl, dihydrofuranyl, dioxanyl, oxanyl, morpholinyl, 1,4-dithianyl, piperazinyl, piperidinyl, 1,3-dioxolanyl, imidazolidinyl, imidazolinyl, pyrrolinyl, pyrrolidinyl, pyranyl, tetrahydropyranyl, dihydropyranyl, oxathiolanyl, dithiolanyl, 1,3-dithianyl, oxathianyl, thiomorpholinyl, dioxidoisothiazolidinyl, azacycloheptyl, diazobicyclo[3.2.1]-octane, and hexahydroindazolyl. The cycloheteroalkyl ring may be substituted on the ring carbons and/or the ring nitrogens. In one embodiment of the present invention, cycloheteroalkyl is substituted or unsubstituted piperazine.

"Heteroaryl" means an aromatic or partially aromatic heterocycle that contains at least one ring heteroatom selected from O, S and N. Heteroaryls thus includes heteroaryls fused to other kinds of rings, such as aryls, cycloalkyls and heterocycles that are not aromatic. Examples of heteroaryl groups include: pyrrolyl, isoxazolyl, isothiazolyl, pyrazolyl, pyridyl, oxazolyl, oxadiazolyl (in particular, 1,3,4-oxadiazol-2-yl and 1,2,4-oxadiazol-3-yl), thiadiazolyl, thiazolyl, imidazolyl, triazolyl, tetrazolyl, furyl, triazinyl, thienyl, pyrimidyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, and the like. For heterocycloalkyl and heteroaryl groups, rings and ring systems containing from 3-15 atoms are included, forming 1-3 rings.

The term "5 membered heteroaryl ring" means an aromatic or partially aromatic heterocycle that contains at least one ring heteroatom selected from O, S and N. Examples of 5 membered heteroaryl rings include: pyrrolyl, isoxazolyl, isothiazolyl, pyrazolyl, pyridyl, oxazolyl, oxadiazolyl (in particular, 1,3,4-oxadiazol-2-yl and 1,2,4-oxadiazol-3-yl), thiadiazolyl, thiazolyl, imidazolyl, triazolyl, tetrazolyl, furyl, triazinyl, thienyl, and the like.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

The term "compounds of structural formula I" includes the compounds of structural formula I, Ia, Ib, Ic, Id, Ie, If, Ig, Ih and Ii, and pharmaceutically acceptable salts thereof.

Compounds of structural formula I may contain one or more asymmetric centers and can thus occur as racemates and racemic mixtures, single enantiomers, diastereomeric mixtures and individual diastereomers. The present invention is meant to comprehend all such isomeric forms of the compounds of structural formula I.

Compounds of structural formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general structural formula I may be obtained by stereospecific synthesis using optically pure starting materials or reagents of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts.

For example, a ketone and its enol form are keto-enol tautomers. The individual tautomers as well as mixtures thereof are encompassed with compounds of the present invention.

In the compounds of structural formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetyl, pivaloyl, benzoyl, and aminoacyl, can be employed. Included are those esters and acyl groups known in the art for modifying the solubility or hydrolysis characteristics for use as sustained-release or prodrug formulations.

Solvates, in particular hydrates, of the compounds of structural formula I are included in the present invention as well.

The subject compounds are useful in a method of inhibiting the stearoyl-coenzyme A delta-9 desaturase enzyme (SCD) in a patient such as a mammal in need of such inhibition comprising the administration of an effective amount of the compound. The compounds of the present invention are therefore useful to control, prevent, and/or treat conditions and diseases mediated by high or abnormal SCD enzyme activity.

As defined herein, a condition or disease mediated by high or abnormal SCD enzyme activity is defined as any disease or condition in which the activity of SCD is elevated and/or where inhibition of SCD can be demonstrated to bring about symptomatic improvements for the individual so treated. As defined herein, a condition or disease mediated by high or abnormal SCD enzyme activity includes, but is not limited to cardiovascular disease, dyslipidemias, (including but not limiting to disorders of serum levels of triglycerides, hypertriglyceridemia, VLDL, HDL, LDL, cholesterol, and total cholesterol, hypercholesterolemia, as well as cholesterol disorders), familial combined hyperlipidemia, coronary artery disease, atherosclerosis, heart disease, cerebrovascular disease (including but not limited to stroke, ischemic stroke, and transient ischemic attack), peripheral vascular disease, and ischemic retinopathy.

A condition or disease mediated by high or abnormal SCD enzyme activity also includes metabolic syndrome (including but not limited to dyslipidemia, obesity and insulin resistance, hypertension, microalbuminemia, hyperuricaemia, and hypercoagulability), Syndrome X, diabetes, insulin resistance, decreased glucose tolerance, non-insulin-dependent diabetes mellitus, Type II diabetes, Type I diabetes, diabetic complications, body weight disorders (including but not limited to obesity, overweight, cacahexia, and anorexia), weight loss, body mass index and leptin-related diseases.

A condition or disease mediated by high or abnormal SCD enzyme activity also includes fatty liver, hepatic steatosis, hepatitis, non-alcoholic hepatitis, non-alcoholic steatohepatitis, alcoholic hepatitis, acute fatty liver, fatty liver of pregnancy, drug-induced hepatitis, erythrohepatic protporphyria, iron overload disorders, hereditary hemochromatosis, hepatic fibrosis, hepatic cirrhosis, hepatoma and conditions related thereto.

Thus, one aspect of the present invention concerns a method of treating hyperglycemia, diabetes or insulin resistance in a mammalian patient in need of such treatment, which comprises administering to said patient an effective amount of a compound in accordance with structural formula I or a pharmaceutically salt or solvate thereof.

A second aspect of the present invention concerns a method of treating non-insulin dependent diabetes mellitus (Type 2 diabetes) in a mammalian patient in need of such treatment comprising administering to the patient an antidiabetic effective amount of a compound in accordance with structural formula I.

A third aspect of the present invention concerns a method of treating obesity in a mammalian patient in need of such treatment comprising administering to said patient a compound in accordance with structural formula I in an amount that is effective to treat obesity.

A fourth aspect of the invention concerns a method of treating metabolic syndrome and its sequelae in a mammalian patient in need of such treatment comprising administering to said patient a compound in accordance with structural formula I in an amount that is effective to treat metabolic syndrome and its sequelae. The sequelae of the metabolic syndrome include hypertension, elevated blood glucose levels, high triglycerides, and low levels of HDL cholesterol.

A fifth aspect of the invention concerns a method of treating a lipid disorder selected from the group consisting of dyslipidemia, hyperlipidemia, hypertriglyceridemia, hypercholesterolemia, low HDL and high LDL in a mammalian patient in need of such treatment comprising administering to said patient a compound in accordance with structural formula I in an amount that is effective to treat said lipid disorder.

A sixth aspect of the invention concerns a method of treating atherosclerosis in a mammalian patient in need of such treatment comprising administering to said patient a compound in accordance with structural formula I in an amount effective to treat atherosclerosis.

A seventh aspect of the invention concerns a method of treating cancer in a mammalian patient in need of such treatment comprising administering to said patient a compound in accordance with structural formula I in an amount effective to treat cancer.

A further aspect of the invention concerns a method of treating a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) fatty liver disease, (21) polycystic ovary syndrome, (22) sleep-disordered breathing, (23) metabolic syndrome, and (24) other conditions and disorders where insulin resistance is a component, in a mammalian patient in need of such treatment comprising administering to the patient a compound in accordance with structural formula I in an amount that is effective to treat said condition.

Yet a further aspect of the invention concerns a method of delaying the onset of a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) fatty liver disease, (21) polycystic ovary syndrome, (22) sleep-disordered breathing, (23) metabolic syndrome, and (24) other conditions and disorders where insulin resistance is a component, and other conditions and disorders where insulin resistance is a component, in a mammalian patient in need of such treatment comprising administering to the patient a compound in accordance with structural formula I in an amount that is effective to delay the onset of said condition.

Yet a further aspect of the invention concerns a method of reducing the risk of developing a condition selected from the group consisting of (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) fatty liver disease, (21) polycystic ovary syndrome, (22) sleep-disordered breathing, (23) metabolic syndrome, and (24) other conditions and disorders where insulin resistance is a component, in a mammalian patient in need of such treatment comprising administering to the patient a compound in accordance with structural formula I in an amount that is effective to reduce the risk of developing said condition.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent, such as a mouse, species can be treated. However, the method can also be practiced in other species, such as avian species (e.g., chickens).

The present invention is further directed to a method for the manufacture of a medicament for inhibiting stearoyl-coenzyme A delta-9 desaturase enzyme activity in humans and animals comprising combining a compound of the present invention with a pharmaceutically acceptable carrier or diluent. More particularly, the present invention is directed to the use of a compound of structural formula I in the manufacture of a medicament for use in treating a condition selected from the group consisting of hyperglycemia, Type 2 diabetes, insulin resistance, obesity, and a lipid disorder in a mammal, wherein the lipid disorder is selected from the group consisting of dyslipidemia, hyperlipidemia, hypertriglyceridemia, hypercholesterolemia, low HDL, and high LDL.

The subject treated in the present methods is generally a mammal, preferably a human being, male or female, in whom inhibition of stearoyl-coenzyme A delta-9 desaturase enzyme activity is desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibitors of stearoyl-coenzyme A delta-9 desaturase (SCD) enzyme activity may be demonstrated by the following microsomal and whole-cell based assays:

I. SCD Enzyme Activity Assay:

The potency of compounds of formula I against the stearoyl-CoA desaturase was determined by measuring the conversion of radiolabeled stearoyl-CoA to oleoyl-CoA using rat liver microsome or human SCD1 following previously published procedures with some modifications (Joshi, et al., *J. Lipid Res.*, 18: 32-36 (1977); Talamo, et al., *Anal. Biochem*, 29: 300-304 (1969)). Liver microsome was prepared from male Wistar or Sprague Dawley rats on a high carbohydrate diet for 3 days (LabDiet #5803, Purina). The livers were homogenized (1:10 w/v) in a buffer containing 250 mM sucrose, 1 mM EDTA, 5 mM DTT and 50 mM Tris-HCl (pH 7.5). After a 100,000×g centrifugation for 60 min, the liver microsome pellet was suspended in a buffer containing 100 mM sodium phosphate, 20% glycerol, 2 mM DTT, and stored at −78° C. Human SCD1 desaturase system was reconstituted using human SCD1 from a baculovirus/Sf9 expression system, cytochrome B5 and cytochrome B5 reductase. Typically, test compound in 2 μL DMSO was incubated for 15 mM at room temperature with 180 μL of the SCD enzyme in a buffer containing 100 mM Tris-HCl (pH 7.5), ATP (5 mM), Coenzyme-A (0.1 mM), Triton X-100 (0.5 mM) and NADH (2 mM). The reaction was initiated by the addition of 20 μL of [$^3$H]-stearoyl-CoA (final concentration=2 μM, radioactivity concentration=1 μCi/mL). After 10 mM, the reaction mixture (80 μL) was mixed with a calcium chloride/charcoal aqueous suspension (100 μL charcoal (10% w/v) plus 25 μL CaCl$_2$ (2N). After centrifugation to precipitate the radioactive fatty acid species, tritiated water released from 9,10-[$^3$H]-stearoyl-CoA by the SCD enzyme was quantified on a scintillation counter.

II. Whole Cell-based SCD (Delta-9), Delta-5 and Delta-6 Desaturase Assays:

Human HepG2 cells were grown on 24-well plates in MEM media (Gibco cat#11095-072) supplemented with 10% heat-inactivated fetal bovine serum at 37° C. under 5% CO$_2$ in a humidified incubator. Test compound dissolved in the media was incubated with the subconfluent cells for 15 mM at 37° C. [1-$^{14}$C]-stearic acid was added to each well to a final concentration of 0.05 μCi/mL to detect SCD-catalyzed [$^{14}$C]-oleic acid formation. 0.05 μCi/mL of [1-$^{14}$C]-eicosatrienoic acid or [1-$^{14}$C]-linolenic acid plus 10 μM of 2-amino-N-(3-chlorophenyl)benzamide (a delta-5 desaturase inhibitor) was used to index the delta-5 and delta-6 desaturase activities, respectively. After 4 h incubation at 37° C., the culture media was removed and the labeled cells were washed with PBS (3×1 mL) at room temperature. The labeled cellular lipids were hydrolyzed under nitrogen at 65° C. for 1 h using 400 μL of 2N sodium hydroxide plus 50 μl of L-α-phosphatidylcholine (2 mg/mL in isopropanol, Sigma #P-3556). After acidification with phosphoric acid (60 μL), the radioactive species were extracted with 300 μL of acetonitrile and quantified on a HPLC that was equipped with a C-18 reverse phase column and a Packard Flow Scintillation Analyzer. The levels of [$^{14}$C]-oleic acid over [$^{14}$C]-stearic acid, [$^{14}$C]-arachidonic acid over [$^{14}$C]-eicosatrienoic acid, and [$^{14}$C]-eicosatetraenoic acid (8, 11, 14, 17) over [$^{14}$C]-linolenic acid were used as the corresponding activity indices of SCD, delta-5 and delta-6 desaturase, respectively.

The compounds of the present invention, including the compounds of Examples 1 to 81, exhibit an SCD inhibition constant IC$_{50}$ of less than 1 μM. Preferred compounds of the present invention were found to exhibit an SCD inhibition constant IC$_{50}$ of less than 0.1 μM.

In Vivo Efficacy of Compounds of the Present Invention:

The in vivo efficacy of compounds of formula I was determined by following the conversion of [1-$^{14}$C]-stearic acid to [1-$^{14}$C]oleic acid in animals as exemplified below. Mice were dosed with a compound of formula I and one hour later the radioactive tracer, [1-$^{14}$C]-stearic acid, was dosed at 20 μCi/kg IV. At 3 h post dosing of the compound, the liver was harvested and then hydrolyzed in 10 N sodium hydroxide for 24 h at 80° C., to obtain the total liver fatty acid pool. After phosphoric acid acidification of the extract, the amount of [1-$^{14}$C]-stearic acid and [1-$^{14}$C]-oleic acid was quantified on a HPLC that was equipped with a C-18 reverse phase column and a Packard Flow Scintillation Analyzer.

The subject compounds are further useful in a method for the prevention or treatment of the aforementioned diseases, disorders and conditions in combination with other agents.

The compounds of the present invention may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

The compounds of the present invention may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of formula I, and either administered separately or in the same pharmaceutical composition, include, but are not limited to:

(a) dipeptidyl peptidase-IV (DPP-4) inhibitors;

(b) insulin sensitizers including (i) PPARγ agonists, such as the glitazones (e.g. troglitazone, pioglitazone, englitazone, MCC-555, rosiglitazone, balaglitazone, and the like) and other PPAR ligands, including PPARα/γ dual agonists, such as KRP-297, muraglitazar, naveglitazar, Galida, TAK-559, PPARα agonists, such as fenofibric acid derivatives (gemfibrozil, clofibrate, fenofibrate and bezafibrate), and selective PPARγ modulators (SPPARγM's), such as disclosed in WO 02/060388, WO 02/08188, WO 2004/019869, WO 2004/020409, WO 2004/020408, and WO 2004/066963; (ii) biguanides such as metformin and phenformin, and (iii) protein tyrosine phosphatase-1B (PTP-1B) inhibitors;

(c) insulin or insulin mimetics;

(d) sulfonylureas and other insulin secretagogues, such as tolbutamide, glyburide, glipizide, glimepiride, and meglitinides, such as nateglinide and repaglinide;

(e) α-glucosidase inhibitors (such as acarbose and miglitol);

(f) glucagon receptor antagonists, such as those disclosed in WO 98/04528, WO 99/01423, WO 00/39088, and WO 00/69810;

(g) GLP-1, GLP-1 analogues or mimetics, and GLP-1 receptor agonists, such as exendin-4 (exenatide), liraglutide (N,N-2211), CJC-1131, LY-307161, and those disclosed in WO 00/42026 and WO 00/59887;

(h) GIP and GIP mimetics, such as those disclosed in WO 00/58360, and GIP receptor agonists;

(i) PACAP, PACAP mimetics, and PACAP receptor agonists such as those disclosed in WO 01/23420;

(j) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as naveglitazar and muraglitazar, (vi) inhibitors of cholesterol absorption, such as beta-sitosterol and ezetimibe, (vii) acyl CoA:cholesterol acyltransferase inhibitors, such as avasimibe, and (viii) antioxidants, such as probucol;

(k) PPARδ agonists, such as those disclosed in WO 97/28149;

(l) antiobesity compounds, such as fenfluramine, dexfenfluramine, phentermine, sibutramine, orlistat, neuropeptide $Y_1$ or $Y_5$ antagonists, CB1 receptor inverse agonists and antagonists, $β_3$ adrenergic receptor agonists, melanocortin-receptor agonists, in particular melanocortin-4 receptor agonists, ghrelin antagonists, bombesin receptor agonists (such as bombesin receptor subtype-3 agonists), and melanin-concentrating hormone (MCH) receptor antagonists;

(m) ileal bile acid transporter inhibitors;

(n) agents intended for use in inflammatory conditions such as aspirin, non-steroidal anti-inflammatory drugs (NSAIDs), glucocorticoids, azulfidine, and selective cyclooxygenase-2 (COX-2) inhibitors;

(o) antihypertensive agents, such as ACE inhibitors (enalapril, lisinopril, captopril, quinapril, tandolapril), A-II receptor blockers (losartan, candesartan, irbesartan, valsartan, telmisartan, and eprosartan), beta blockers and calcium channel blockers;

(p) glucokinase activators (GKAs), such as those disclosed in WO 03/015774; WO 04/076420; and WO 04/081001;

(q) inhibitors of 11β-hydroxysteroid dehydrogenase type 1, such as those disclosed in U.S. Pat. No. 6,730,690; WO 03/104207; and WO 04/058741;

(r) inhibitors of cholesteryl ester transfer protein (CETP), such as torcetrapib;

(s) inhibitors of fructose 1,6-bisphosphatase, such as those disclosed in U.S. Pat. Nos. 6,054,587; 6,110,903; 6,284,748; 6,399,782; and 6,489,476;

(t) acetyl CoA carboxylase-1 and/or -2 inhibitors;

(u) AMPK activators; and (v) agonists of GPR-119.

Dipeptidyl peptidase-IV inhibitors that can be combined with compounds of structural formula I include those disclosed in U.S. Pat. No. 6,699,871; WO 02/076450 (3 Oct. 2002); WO 03/004498 (16 Jan. 2003); WO 03/004496 (16 Jan. 2003); EP 1 258 476 (20 Nov. 2002); WO 02/083128 (24 Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); WO 03/082817 (9 Oct. 2003); WO 03/000181 (3 Jan. 2003); WO 04/007468 (22 Jan. 2004); WO 04/032836 (24 Apr. 2004); WO 04/037169 (6 May 2004); and WO 04/043940 (27 May 2004). Specific DPP-IV inhibitor compounds include sitagliptin (MK-0431); vildagliptin (LAF 237); denagliptin; P93/01; saxagliptin (BMS 477118); RO0730699; MP513; SYR-322: ABT-279; PHX1149; GRC-8200; and TS021.

Antiobesity compounds that can be combined with compounds of structural formula I include fenfluramine, dexfenfluramine, phentermine, sibutramine, orlistat, neuropeptide $Y_1$ or $Y_5$ antagonists, cannabinoid CB1 receptor antagonists or inverse agonists, melanocortin receptor agonists, in particular, melanocortin-4 receptor agonists, ghrelin antagonists, bombesin receptor agonists, and melanin-concentrating hormone (MCH) receptor antagonists. For a review of antiobesity compounds that can be combined with compounds of structural formula I, see S. Chaki et al., "Recent advances in feeding suppressing agents: potential therapeutic strategy for the treatment of obesity," *Expert Opin. Ther. Patents*, 11: 1677-1692 (2001); D. Spanswick and K. Lee, "Emerging antiobesity drugs," *Expert Opin. Emerging Drugs*, 8: 217-237 (2003); and J. A. Fernandez-Lopez, et al., "Pharmacological Approaches for the Treatment of Obesity," *Drugs*, 62: 915-944 (2002).

Neuropeptide Y5 antagonists that can be combined with compounds of structural formula I include those disclosed in U.S. Pat. No. 6,335,345 (1 Jan. 2002) and WO 01/14376 (1 Mar. 2001); and specific compounds identified as GW 59884A; GW 569180A; LY366377; and CGP-71683A.

Cannabinoid CB1 receptor antagonists that can be combined with compounds of formula I include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. Nos. 5,532,237; 5,292,736; PCT Publication WO 03/086288; PCT Publication WO 03/087037; PCT Publication WO 04/048317; PCT Publication WO 03/007887; PCT Publication WO 03/063781; PCT Publication WO 03/075660; PCT Publication WO 03/077847; PCT Publication WO 03/082190; PCT Publication WO 03/082191; PCT Publication WO 03/087037; PCT Publication WO 03/086288; PCT Publication WO 04/012671; PCT Publication WO 04/029204; PCT Publication WO 04/040040; PCT Publication WO 01/64632; PCT Publication WO 01/64633; and PCT Publication WO 01/64634.

Melanocortin-4 receptor (MC4R) agonists useful in the present invention include, but are not limited to, those disclosed in U.S. Pat. Nos. 6,294,534, 6,350,760, 6,376,509, 6,410,548, 6,458,790, 6,472,398, 5,837,521, 6,699,873, which are hereby incorporated by reference in their entirety; in US Patent Application Publication Nos. US 2002/0004512, US2002/0019523, US2002/0137664, US2003/0236262, US2003/0225060, US2003/0092732, US2003/109556, US 2002/0177151, US 2002/187932, US 2003/0113263, which are hereby incorporated by reference in their entirety; and in WO 99/64002, WO 00/74679, WO 02/15909, WO 01/70708, WO 01/70337, WO 01/91752, WO 02/068387, WO 02/068388, WO 02/067869, WO 03/007949, WO 2004/024720, WO 2004/089307, WO 2004/078716, WO 2004/078717, WO 2004/037797, WO 01/58891, WO 02/070511, WO 02/079146, WO 03/009847, WO 03/057671, WO 03/068738, WO 03/092690, WO 02/059095, WO 02/059107, WO 02/059108, WO 02/059117, WO 02/085925, WO 03/004480, WO 03/009850, WO 03/013571, WO 03/031410, WO 03/053927, WO 03/061660, WO 03/066597, WO 03/094918, WO 03/099818, WO 04/037797, WO 04/048345, WO 02/018327, WO 02/080896, WO 02/081443, WO 03/066587, WO 03/066597, WO 03/099818, WO 02/062766, WO 03/000663, WO 03/000666, WO 03/003977, WO 03/040107, WO 03/040117, WO 03/040118, WO 03/013509, WO 03/057671, WO 02/079753, WO 02/092566, WO 03/-093234, WO 03/095474, and WO 03/104761.

One particular aspect of combination therapy concerns a method of treating a condition selected from the group consisting of hypercholesterolemia, atherosclerosis, low HDL levels, high LDL levels, hyperlipidemia, hypertriglyceridemia, and dyslipidemia, in a mammalian patient in need of such treatment comprising administering to the patient a therapeutically effective amount of a compound of structural formula I and an HMG-CoA reductase inhibitor.

More particularly, this aspect of combination therapy concerns a method of treating a condition selected from the group consisting of hypercholesterolemia, atherosclerosis, low HDL levels, high LDL levels, hyperlipidemia, hypertriglyceridemia and dyslipidemia in a mammalian patient in need of such treatment wherein the HMG-CoA reductase inhibitor is a statin selected from the group consisting of lovastatin, simvastatin, pravastatin, cerivastatin, fluvastatin, atorvastatin, and rosuvastatin.

In another aspect of the invention, a method of reducing the risk of developing a condition selected from the group consisting of hypercholesterolemia, atherosclerosis, low HDL levels, high LDL levels, hyperlipidemia, hypertriglyceridemia and dyslipidemia, and the sequelae of such conditions is disclosed comprising administering to a mammalian patient in need of such treatment a therapeutically effective amount of a compound of structural formula I and an HMG-CoA reductase inhibitor.

In another aspect of the invention, a method for delaying the onset or reducing the risk of developing atherosclerosis in a human patient in need of such treatment is disclosed comprising administering to said patient an effective amount of a compound of structural formula I and an HMG-CoA reductase inhibitor.

More particularly, a method for delaying the onset or reducing the risk of developing atherosclerosis in a human patient in need of such treatment is disclosed, wherein the HMG-CoA reductase inhibitor is a statin selected from the group consisting of: lovastatin, simvastatin, pravastatin, cerivastatin, fluvastatin, atorvastatin, and rosuvastatin.

In another aspect of the invention, a method for delaying the onset or reducing the risk of developing atherosclerosis in a human patient in need of such treatment is disclosed, wherein the HMG-Co A reductase inhibitor is a statin and further comprising administering a cholesterol absorption inhibitor.

More particularly, in another aspect of the invention, a method for delaying the onset or reducing the risk of developing atherosclerosis in a human patient in need of such treatment is disclosed, wherein the HMG-Co A reductase inhibitor is a statin and the cholesterol absorption inhibitor is ezetimibe.

In another aspect of the invention, a pharmaceutical composition is disclosed which comprises:
(1) a compound of structural formula I;
(2) a compound selected from the group consisting of:
  (a) dipeptidyl peptidase IV (DPP-IV) inhibitors;
  (b) insulin sensitizers including (i) PPARγ agonists, such as the glitazones (e.g. troglitazone, pioglitazone, englitazone, MCC-555, rosiglitazone, balaglitazone, and the like) and other PPAR ligands, including PPARα/γ dual agonists, such as KRP-297, muraglitazar, naveglitazar, Galida, TAK-559, PPARα agonists, such as fenofibric acid derivatives (gemfibrozil, clofibrate, fenofibrate and bezafibrate), and selective PPARγ modulators (SPPARγM's), such as disclosed in WO 02/060388, WO 02/08188, WO 2004/019869, WO 2004/020409, WO 2004/020408, and WO 2004/066963; (ii) biguanides such as metformin and phenformin, and (iii) protein tyrosine phosphatase-1B (PTP-1B) inhibitors;
  (c) insulin or insulin mimetics;
  (d) sulfonylureas and other insulin secretagogues, such as tolbutamide, glyburide, glipizide, glimepiride, and meglitinides, such as nateglinide and repaglinide;
  (e) α-glucosidase inhibitors (such as acarbose and miglitol);
  (f) glucagon receptor antagonists, such as those disclosed in WO 98/04528, WO 99/01423, WO 00/39088, and WO 00/69810;
  (g) GLP-1, GLP-1 analogues or mimetics, and GLP-1 receptor agonists, such as exendin-4 (exenatide), liraglutide (N,N-2211), CJC-1131, LY-307161, and those disclosed in WO 00/42026 and WO 00/59887;
  (h) GIP and GIP mimetics, such as those disclosed in WO 00/58360, and GIP receptor agonists;
  (i) PACAP, PACAP mimetics, and PACAP receptor agonists such as those disclosed in WO 01/23420;
  (j) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as naveglitazar and muraglitazar, (vi) inhibitors of cholesterol absorption, such as beta-sitosterol and ezetimibe, (vii) acyl CoA:cholesterol acyltransferase inhibitors, such as avasimibe, and (viii) antioxidants, such as probucol;
  (k) PPARδ agonists, such as those disclosed in WO 97/28149;
  (l) antiobesity compounds, such as fenfluramine, dexfenfluramine, phentermine, sibutramine, orlistat, neuropeptide $Y_1$ or $Y_5$ antagonists, CB1 receptor inverse agonists and antagonists, $\beta_3$ adrenergic receptor agonists, melanocortin-receptor agonists, in particular melanocortin-4 receptor agonists, ghrelin antagonists, bombesin receptor agonists (such as bombesin receptor subtype-3 agonists), and melanin-concentrating hormone (MCH) receptor antagonists;

(m) ileal bile acid transporter inhibitors;

(n) agents intended for use in inflammatory conditions such as aspirin, non-steroidal anti-inflammatory drugs (NSAIDs), glucocorticoids, azulfidine, and selective cyclooxygenase-2 (COX-2) inhibitors;

(o) antihypertensive agents, such as ACE inhibitors (enalapril, lisinopril, captopril, quinapril, tandolapril), A-II receptor blockers (losartan, candesartan, irbesartan, valsartan, telmisartan, and eprosartan), beta blockers and calcium channel blockers;

(p) glucokinase activators (GKAs), such as those disclosed in WO 03/015774; WO 04/076420; and WO 04/081001;

(q) inhibitors of 11β-hydroxysteroid dehydrogenase type 1, such as those disclosed in U.S. Pat. No. 6,730,690; WO 03/104207; and WO 04/058741;

(r) inhibitors of cholesteryl ester transfer protein (CETP), such as torcetrapib;

(s) inhibitors of fructose 1,6-bisphosphatase, such as those disclosed in U.S. Pat. Nos. 6,054,587; 6,110,903; 6,284,748; 6,399,782; and 6,489,476;

(t) acetyl CoA carboxylase-1 and/or -2 inhibitors;

(u) AMPK activators; and (v) agonists of GPR 119; and (3) a pharmaceutically acceptable carrier.

When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl or n-propyl p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require inhibition of stearoyl-CoA delta-9 desaturase enzyme activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.
Preparation of Compounds of the Invention:

The compounds of structural formula I can be prepared according to the procedures of the following Schemes and Examples, using appropriate materials and are further exemplified by the following specific example. The compound illustrated in the example is not, however, to be construed as forming the only genus that is considered as the invention. The Example further illustrates details for the preparation of the compounds of the present invention. Those skilled in the art will readily understand that known variations of the conditions and processes of the following preparative procedures can be used to prepare these compounds. All temperatures are degrees Celsius unless otherwise noted. Mass spectra (MS) were measured by electrospray ion-mass spectroscopy (ESMS).

List of Abbreviations: ACN is acetonitrile; $Ac_2O$ is acetic anhydride; AcOH is acetic acid; aq is aqueous; Boc is tert-butyloxycarbonyl; n-BuLi is n-butyl lithium; t-BuOH is tert-butanol; t-BuLi is tert-butyl lithium; t-BuONO is tert-butyl nitrite; CAN is ceric ammonium nitrate; Celite™ is diatomaceous earth; $CuSO_4$ is copper sulfate; DAST is (diethylamino)sulfur trifluoride; DBU is 1,8-diazabicyclo-[5.4.0]undec-7-ene; DCM is dichloromethane; DEAD: diethyl azodicarboxylate; DIPEA or DIEA is N,N-diisopropyl ethyl amine (Hunig's base); DME is 1,2-dimethoxyethane; DMAP is 4-dimethyl amino pyridine; DMF is N,N-dimethylformamide; DMSO is dimethyl sulfoxide; DPPA is diphenyl phosphoryl azide; dppf is 1,1'-bis(diphenylphosphino)ferrocene; EA is ethyl acetate; equiv is equivalent(s); ESI is electrospray ionization; Et$_3$N is triethylamine; Et$_3$SiH is triethylsilane; EtOAc is ethyl acetate; EtOH is ethyl alcohol; Et$_2$O is diethyl ether; g is gram(s); h is hour(s); HATU is (2-(7-Aza-1H-benzotriazole-1-yl)-1,1,3,3-tetramethyluronium hexafluorophosphate); HCl is hydrochloric acid; HMPA is hexamethylphosphoramide; in vacuo is rotary evaporation under diminished pressure; i-PrOH or IPA is isopropanol; K$_2$CO$_3$ is potassium carbonate; LC is liquid chromatography; LC/MS is liquid chromatography/mass spectroscopy; L is liter(s); LiHMDS is lithium hexamethyldisilazide; ml and mL is milliliter; M is molar; mmol is millimole(s); MeOH is methyl alcohol; MgSO$_4$ is magnesium sulfate; min is minute(s); MS is mass spectrum; MOMCl is chloromethyl methyl ether; MTBE is methyl tert-butyl ether; NaOH is sodium hydroxide; NaN$_3$ is sodium azide; NaOAC is sodium acetate; NMP is N-methyl-2-pyrrolidinone; NMR is nuclear magnetic resonance spectroscopy; PE is petroleum ether; Ph is phenyl; PPh$_3$ is triphenyl phosphine; sat. and sat is saturated; SiO$_2$ is silicon dioxide; rt and RT is room temperature; TEA is triethyl amine; TFA is trifluoroacetic acid; TFAA is trifluoroacetic anhydride; THF is tetrahydrofuran; TMP is 2,2,6,6-tetramethylpiperidine; and wt % is weight percent.

Method A

The spiro moieties can be prepared according to the procedures described by L. Yang., et. al., Bioorg. Med. Chem. Lett., 8, 107-112 (1998). Here is an illustration with A-5. An appropriately substituted 2'-hydroxyacetophenone A-1 is reacted with an appropriately substituted cyclic ketone intermediate A-2 in the presence of a base, such as pyrrolidine, in a solvent, such as methanol, to give the spiro-intermediate A-3.

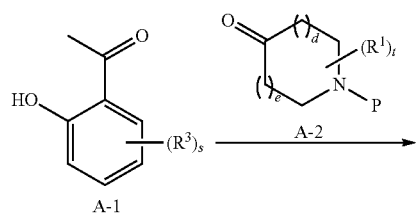

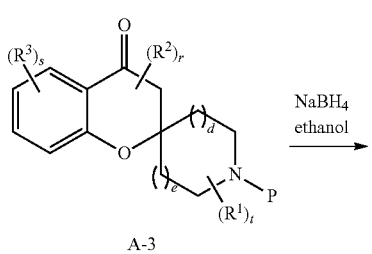

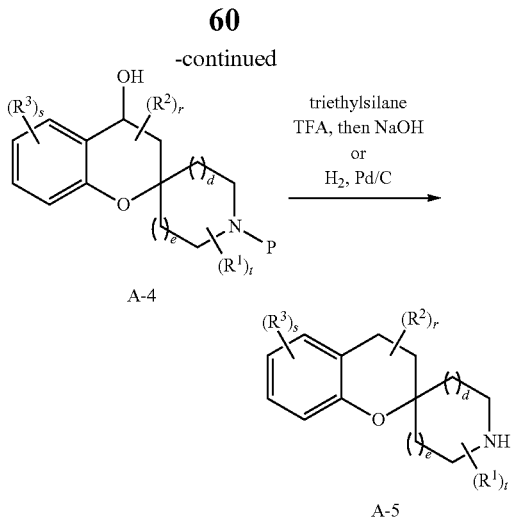

P = Boc, Cbz

The carbonyl of intermediate A-3 is then reduced in a 2-step sequence via alcohol A-4 to give the spiro-cyclic amine intermediate A-5 for further coupling reaction. The spiro intermediate A-5 is either isolated as a free base or a salt with an acid such as HCl or TFA. For R$^3$=OH in A-4, it can be further react with an alkyl or benzyl group to provide the corresponding alkylated analog.

Method B

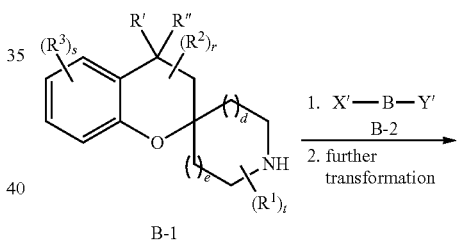

3: R', R'' = H
4: R' = H, R'' = OH
5: R', R'' = O

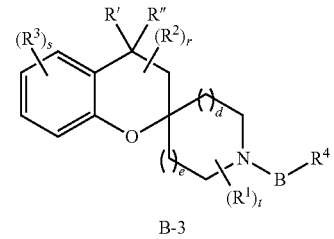

7: R', R'' = H
8: R' = H, R'' = OH
9: R', R'' = O

An appropriately substituted spiro intermediate B-1, prepared according the Method A, is reacted with an appropriately halo-substituted (X'=Cl, Br) heteroaryl B-2, wherein heteroaryl ring B is as previously defined, and Y' is a functional group such as halogen (Cl, Br, I), ester, amide, nitrile or heterocycle which is suitable for the transformation to substituent R$^4$ as previously defined. The functional group Y' is then converted by typical standard transformations to substituent R$^4$ to give the desired moiety for final product B-3.

For R³=OH in B-1, it can be further transformed to the corresponding alkylated analog after coupling reaction with B-2 at an appropriate step. Other spiro moieties can be used to couple with B-2 to obtain the corresponding analogs.

INTERMEDIATE 1

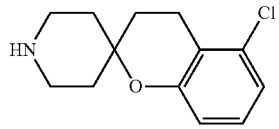

5-Chloro-3,4-dihydrospiro[chromene-2,4'-piperidine]hydrochloride salt

Step 1: 1-(2-Chloro-6-hydroxyphenyl)ethanone. To a solution of 3-chlorophenol (50 g, 390.62 mmol, 1.00 equiv) in DCM (500 mL) was added DIEA (554 g, 4.29 mol, 11.00 equiv), followed by chloro(methoxy)methane (380 g, 10.00 equiv) at 20° C. The resulting mixture was allowed to react, with stirring, for 4 h at 20° C. The reaction mixture was then quenched with water. The separated organic phase was washed with water (2×), dried over Na₂SO₄ and then concentrated under vacuum to give 1-chloro-3-(methoxymethoxy)benzene as a white oil.

To a solution of 1-chloro-3-(methoxymethoxy)benzene (24 g, 136.74 mmol, 1.00 equiv, 98%) in THF (240 mL) was added TMP (21 g, 150.00 mmol, 1.10 equiv). To the above solution was added n-BuLi (61 mL, 1.10 equiv, 2.5 mol/L) dropwise with stirring at −75° C. over 30 min. After stirring for 2 h at −75° C., the resulting mixture was reacted with Ac₂O (15.5 g, 148.92 mmol, 1.10 equiv, 98%) via dropwise addition with stirring at −75° C. over 30 min. The mixture was stirred for additional 30 min at room temperature, and then quenched by adding water. The resulting mixture was extracted with 2×300 mL of ethyl acetate. The combined organic layers was washed with H₂O, dried over Na₂SO₄ and concentrated under vacuum to give 1-(2-chloro-6-(methoxymethoxy)phenyl)-ethanone as a yellow oil.

To a solution of 1-(2-chloro-6-(methoxymethoxy)phenyl) ethanone (38 g, 177.03 mmol, 1.00 equiv) in THF (380 mL) was added HCl (aq. 35 g, 2.00 equiv, 36%). The resulting mixture was allowed to react, with stirring, for 3 h at 65° C. The resulting mixture was extracted with ethyl acetate. The organic phase was separated, dried and concentrated under vacuum to give the crude title compound.

Step 2: tert-Butyl 5-chloro-4-oxo-3,4-dihydro-1'H-spiro [chromene-2,4'-piperidine]-1'-carboxylate. A mixture of tert-butyl 4-oxopiperidine-1-carboxylate (14 g, 70.35 mmol, 1.00 equiv), pyrrolidine (7 g, 98.59 mmol, 1.40 equiv) and 1-(2-chloro-6-hydroxyphenyl)ethanone (12 g, 70.59 mmol, 1.00 equiv) in MeOH (150 mL) was reacted at 65° C. for 20 min. The reaction mixture was cooled to room temperature and concentrated. To the residue was added 500 mL of ethyl acetate. The mixture was then washed with water (2×). The organic phase was dried over anhydrous sodium sulfate and concentrated under vacuum to give the title compound as a white solid.

Step 3: tert-Butyl 5-chloro-4-hydroxy-3,4-dihydro-1'H-spiro[chromene-2,4'-piperidine]-1'-carboxylate. To a solution of tert-butyl 5-chloro-4-oxo-3,4-dihydro-1'H-spiro [chromene-2,4'-piperidine]-1'-carboxylate (30 g, 85.27 mmol, 1.00 equiv) in EtOH (300 mL) was added portionwise NaBH₄ (3.3 g, 87.23 mmol, 1.02 equiv) at 25° C. over 30 min. The resulting mixture was allowed to react, with stirring, for 1 h at room temperature. The reaction was then quenched with water and extracted with ethyl acetate. The organic layers were combined, washed with H₂O (2×), dried over anhydrous sodium sulfate and concentrated under vacuum to give the title compound as a white solid.

Step 4: 5-Chloro-3,4-dihydrospiro[chromene-2,4'-piperidine]hydrochloride salt. To a mixture of tert-butyl 5-chloro-4-hydroxy-3,4-dihydro-1'H-spiro[chromene-2,4'-piperidine]-1'-carboxylate (12.4 g, 35.04 mmol, 1.00 equiv) in trifluoroacetic acid (130 mL) was added triethylsilane (16.8 g, 144.48 mmol, 4.12 equiv). The resulting mixture was allowed to react, with stirring, for 5 h while the temperature was maintained at 80° C. to reflux. The resulting mixture was concentrated under vacuum. To the resulting residue were added 200 mL of Et₂O. The resulting solids were collected by filtration to give the TFA salt as a white solid. The TFA salt was converted to the free base by the treatment with aqueous NaOH. The free base was then dissolved in Et₂O and reacted with HCl gas to give the title compound as a white solid.

INTERMEDIATE 2

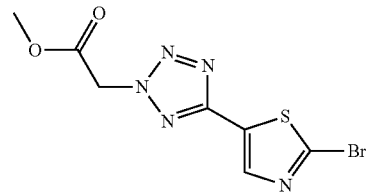 [SMILES: COC(=O)Cn1nnc(-c2cnc(Br)s2)n1]

Ethyl[5-(2-bromo-1,3-thiazol-5-yl)-2H-tetrazol-2-yl] acetate

Step 1: 2-Bromo-1,3-thiazole-5-carboxamide Into a 2 L round-bottom flask was added ethyl 2-bromothiazole-5-carboxylate (50.0 g, 212 mmol), THF (500 mL) and MeOH (250 mL). To this was added concentrated ammonium hydroxide in water (590 mL) and the reaction mixture was stirred at room temperature for 4 h. The solvents were removed under reduced pressure, and the crude mixture poured into a separatory funnel containing brine (1 L). The aqueous layer was extracted with EtOAc (4×500 mL) and the combined organic layers were washed with brine, dried over Na₂SO₄, filtered and concentrated under reduced pressure to give the title compound.

Step 2: 2-Bromo-1,3-thiazole-5-carbonitrile Into a 2 L round-bottom flask containing 2-bromo-1,3-thiazole-5-carboxamide (41.5 g, 201 mmol) in CH₂Cl₂ (1.3 L) was added triethylamine (70 mL, 502 mmol). The resulting solution was cooled to 0° C. and trifluoroacetic anhydride (34 mL, 241 mmol) was added slowly over 15 minutes. The reaction mixture was allowed to warm to room temperature and stirred for 2 h. The reaction mixture was poured into a 3 L separatory funnel containing saturated aqueous NaHCO₃ solution (500 mL). The aqueous layer was extracted with dichloromethane (2×1.2 L) and the combined organic layers were washed with brine, dried over Na₂SO₄, filtered and concentrated under reduced pressure. The resulting crude reaction mixture was filtered through a short plug of silica gel on a sintered glass funnel, washing with copious quantities of EtOAc. The filtrate was concentrated under reduced pressure to provide the title compound.

Step 3: 5-(2-Bromo-1,3-thiazol-5-yl)-2H-tetrazole A solution of 2-bromo-1,3-thiazole-5-carbonitrile (5.00 g, 26.5 mmol) in 2-propanol (75 mL) and water (38 mL) was treated with ZnBr$_2$ (5.96 g, 26.5 mmol) and sodium azide (2.58 g, 39.7 mmol). The reaction mixture was heated at 120° C. for 5 h. The cooled reaction mixture was diluted with water (50 mL) and acidified to pH=3 using aqueous 1 M HCl solution (approximately 20 mL). The mixture was poured into a 500 mL separatory funnel and the aqueous layer was extracted with EtOAc (4×100 mL). The combined organic layers were washed with brine, dried over Na$_2$SO$_4$, filtered and concentrated under reduced pressure to provide the title compound.

Step 4: Ethyl[5-(2-bromo-1,3-thiazol-5-yl)-2H-tetrazol-2-yl]acetate Into a 250 mL round-bottom flask containing 5-(2-bromo-1,3-thiazol-5-yl)-2H-tetrazole (5.43 g, 22.5 mmol) in THF (81 mL) was added triethylamine (7.2 mL, 52 mmol) and ethyl bromoacetate (3.8 mL, 34 mmol). The resulting mixture was heated at 80° C. for 1 h, and then cooled to room temperature. The reaction mixture was poured into a separatory funnel containing water (80 mL) and the aqueous layer was extracted with EtOAc (2×160 mL). The combined organic layers were washed with brine, dried over Na$_2$SO$_4$, filtered and concentrated under reduced pressure. Purification by column chromatography through silica gel, eluting with 100% hexanes to 50:50 hexanes:EtOAc as a gradient provided the title compound as a single regioisomer. $^1$H NMR (d$_6$-DMSO, 400 MHz) 8.39 (1H, s), 5.93 (2H, s), 4.21 (2H, q, J=7.0 Hz), 1.22 (3H, t, J=7.0 Hz).

INTERMEDIATE 3

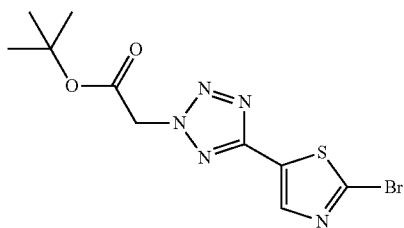 [SMILES: CC(C)(C)OC(=O)Cn1nnc(-c2cnc(Br)s2)n1]

tert-Butyl[5-(2-bromo-1,3-thiazol-5-yl)-2H-tetrazol-2-yl]acetate

This compound was synthesized in a similar manner as described for ethyl[5-(2-bromo-1,3-thiazol-5-yl)-2H-tetrazol-2-yl]acetate (INTERMEDIATE 2) using tert-butyl bromoacetate in place of ethyl bromoacetate in step 4. $^1$H NMR (CDCl$_3$, 400 MHz) 8.22 (1H, s), 5.32 (2H, s), 1.47 (9H, s). MS (ESI, Q$^+$) m/z 346, 348 (M+1, $^{79}$Br, $^{81}$Br).

INTERMEDIATE 4

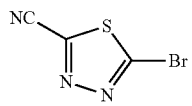

5-Bromo-1,3,4-thiadiazole-2-carbonitrile

Step 1: Ethyl 5-bromo-1,3,4-thiadiazole-2-carboxylate To a suspension of ethyl 5-amino-1,3,4-thiadiazole-2-carboxylate in CH$_3$CN (0.32 M) was added CuBr$_2$ (2 equiv). The mixture turned dark green and was stirred for 15 min at room temperature. t-BuONO, 90% (2 equiv) was added dropwise over 15-20 min. The mixture became slightly warm and gas evolved after about 5 min and then throughout the addition. After completion of the addition and after gas evolution subsided, the mixture was heated at 60° C. for 30 min. Solvent was then evaporated in vacuo. Water and EtOAc were added and the mixture was stirred until the dark green color disappeared. The organic phase became light brown and the aqueous phase was green with insoluble material. The entire mixture was filtered through Celite™ and washed with EtOAc. The EtOAc layer was separated, washed with diluted brine, dried (Na$_2$SO$_4$) and concentrated to give the title compound. $^1$H NMR (400 MHz, acetone-d$_6$): δ 4.52 (q, 2H), 1.43 (t, 3H).

Step 2: 5-Bromo-1,3,4-thiadiazole-2-carboxamide To a solution of ethyl 5-bromo-1,3,4-thiadiazole-2-carboxylate in THF (1.1 M) at room temperature was added concentrated NH$_4$OH (2.9 equiv). The mixture was stirred at room temperature overnight and a precipitate appeared in the aqueous layer. Volatile solvent was removed in vacuo. The mixture was diluted with water and the precipitate was collected, washed with water and dried under vacuum to give the title compound. $^1$H NMR (400 MHz, acetone-d$_6$): δ 7.99 (s, 1H), 7.55 (s, 1H).

Step 3: 5-Bromo-1,3,4-thiadiazole-2-carbonitrile To a solution of 5-bromo-1,3,4-thiadiazole-2-carboxamide and Et$_3$N (2.3 equiv) in THF (0.5 M) at 0° C. was added TFAA (1.1 equiv). The mixture was then warmed to room temperature and stirred for 30 min. Solvent was evaporated in vacuo. The resulting residue was diluted with water. The precipitate was collected, washed with water, and dried to give the title compound.

INTERMEDIATE 5

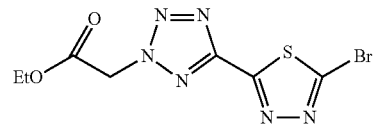 [SMILES: CCOC(=O)Cn1nnc(-c2nnc(Br)s2)n1]

Ethyl[5-(5-bromo-1,3,4-thiadiazol-2-yl)-2H-tetrazol-2-yl]acetate

To a suspension of 5-bromo-1,3,4-thiadiazole-2-carbonitrile (1 g, 5 mmol) and ZnBr$_2$ (1.1 g, 5 mmol) in i-PrOH (10 mL) and H$_2$O (5 mL) was added NaN$_3$ (0.65 g, 10 mmol) in a sealed tube. The mixture was stirred at 120° C. overnight and then cooled to room temperature. The mixture was adjusted to pH=4 with HCl (2 M) and extracted with EtOAc (50 mL×3). The combined organic layers was dried over Na$_2$SO$_4$, filtered and concentrated in vacuum to afford the crude 5-(5-bromo-1,3,4-thiadiazol-2-yl)-1H-tetrazole. $^{13}$C NMR (DMSO, 300 MHz): δ 159.12, 150.65, 142.84.

To a solution of 5-(5-bromo-1,3,4-thiadiazol-2-yl)-1H-tetrazole (1 g, 4.3 mmol) in DMF (20 mL) was added Cs$_2$CO$_3$ (2.1 g, 6.45 mmol) and ethyl bromoacetate (0.95 mL, 8.6 mmol). The resulting solution was stirred at 90° C. for 1 hour.

The mixture was partitioned between EtOAc (100 mL) and water (200 mL). The combined organic layers were dried over anhydrous Na$_2$SO$_4$, filtered and evaporated in vacuo. Chromatography over silica afforded the title compound as a white solid, contaminated with the 1-alkylated isomer ethyl[5-(5-bromo-1,3,4-thiadiazol-2-yl)-1H-tetrazol-1-yl]acetate. $^1$HNMR (CDCl$_3$, 300 MHz): δ 5.70 (s, 2H), 4.26 (q, J=7 Hz, 2H), 1.28 (t, J=7 Hz, 3H).

INTERMEDIATE 6

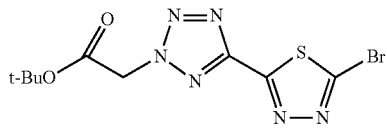 [SMILES: CC(C)(C)OC(=O)Cn1nnc(-c2nnc(Br)s2)n1]

tert-Butyl[5-(5-bromo-1,3,4-thiadiazol-2-yl)-2H-tetrazol-2-yl]acetate

The title compound was prepared in a similar manner as described for Intermediate 5 from 5-(5-bromo-1,3,4-thiadiazol-2-yl)-1H-tetrazole and tert-butyl bromoacetate. The isolated title compound was contaminated with ~20% of tert-butyl[5-(5-bromo-1,3,4-thiadiazol-2-yl)-1H-tetrazol-1-yl]acetate. $^1$HNMR (CDCl$_3$ 300 MHz): δ 5.43 (s, 2H), 1.47 (s, 9H).

INTERMEDIATE 7

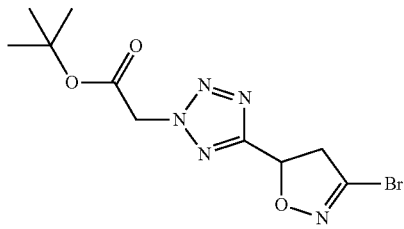 [SMILES: CC(C)(C)OC(=O)Cn1nnc(C2CC(Br)=NO2)n1]

tert-Butyl[5-(3-bromo-4,5-dihydroisoxazol-5-yl)-2H-tetrazol-2-yl]acetate

Step 1: Ethyl 3-bromo-4,5-dihydroisoxazole-5-carboxylate To a round-bottom flask containing hydroxycarbonimidic dibromide (100 g, 490 mmol) was slowly added DMF (300 mL) followed by ethyl acrylate (59 g, 590 mmol). The mixture was cooled to −10° C. and then a solution of KHCO$_3$ (99 g, 990 mmol) in water (400 mL) was added dropwise over 90 min, at a rate which maintained the internal temperature below 0° C. Stirring was continued at 0° C. for 1.5 h. The reaction mixture was poured into a 4 L separatory funnel containing water (500 mL) and the aqueous layer was extracted with MTBE (3×500 mL). The combined organic layers were washed with brine, dried over MgSO$_4$, filtered and concentrated under reduced pressure to give a yellow oil which was used directly in Step 2.

Step 2: 3-Bromo-4,5-dihydroisoxazole-5-carboxamide Ethyl 3-bromo-4,5-dihydroisoxazole-5-carboxylate (109 g, 490 mmol) was added to a 1 L round-bottom flask containing 2.0 M NH$_3$ in MeOH (295 mL). The reaction mixture was heated at 50° C. for 2.5 h and then cooled to room temperature and stirred overnight for 16 h. The resulting slurry was diluted with 500 mL of diethyl ether and stirred in an ice-bath for 1 h. The product was isolated by filtration under vacuum, affording the title compound as a tan solid. $^1$H NMR (CDCl$_3$, 400 MHz): δ 6.70 (1H, bs), 5.92 (1H, bs), 5.06 (1H, dd, J=11.0, 6.5 Hz), 3.64-3.51 (2H, m). MS (ESI, Q$^+$) m/z 193, 195 (M+1, $^{79}$Br, $^{81}$Br).

Step 3: 3-Bromo-4,5-dihydroisoxazole-5-carbonitrile To a solution of 3-bromo-4,5-dihydroisoxazole-5-carboxamide (30.0 g, 155 mmol) in THF (360 mL) was added triethylamine (43.0 mL, 311 mmol). The solution was cooled to 0° C. and TFAA (33.0 mL, 233 mmol) was added slowly over 20 min, at a rate which maintained the internal temperature below 15° C. The reaction mixture was stirred at 0° C. for 1 h. The reaction mixture was poured into a 2 L separatory funnel containing water (500 mL) and the aqueous layer was extracted with MTBE (3×500 mL). The combined organic layers were washed with a saturated aqueous NaHCO$_3$ solution (2×250 mL) and brine, dried over MgSO$_4$, filtered and concentrated under reduced pressure to afford the title compound.

Step 4: 5-(3-Bromo-4,5-dihydroisoxazol-5-yl)-2H-tetrazole To a 2 L round-bottom flask equipped with a reflux condenser, heating mantle and under N$_2$, was added 3-bromo-4,5-dihydroisoxazole-5-carbonitrile (39.4 g, 225 mmol), zinc oxide (1.8 g, 23 mmol), THF (40 mL) and water (200 mL). To this solution was added in slowly a solution of sodium azide (16 g, 250 mmol) in water (10 mL) over 5 min and the mixture was warmed to 75° C. for 16 h. Heating was applied at a rate in where the internal temperature of the reaction mixture did not exceed 80° C. The reaction mixture was cooled to 0° C. and acidified to pH 3-4 with slow addition of 2 N aqueous HCl solution. During the acidification, the internal temperature was maintained below 5° C. The reaction mixture was poured into a 2 L separatory funnel and the aqueous layer was extracted with EtOAc (3×500 mL). The combined organic layers were washed with brine, dried over MgSO$_4$, filtered and concentrated under reduced pressure to afford the title compound.

Step 5: tert-Butyl[5-(3-bromo-4,5-dihydroisoxazol-5-yl)-2H-tetrazol-2-yl]acetate To a 2 L round-bottom flask equipped with a reflux condenser, heating mantle and under N$_2$ was added 5-(3-bromo-4,5-dihydroisoxazol-5-yl)-2H-tetrazole (49 g, 225 mmol) and THF (500 mL). Triethylamine (53 mL, 383 mmol) was added to the mixture and the solution was heated to 55° C. while tert-butyl bromoacetate (66 g, 338 mmol) was added. The mixture was heated at 55° C. for 1 h and then cooled to room temperature. The reaction mixture was poured into a 2 L separatory funnel containing 1 N aqueous HCl solution (500 mL) and the aqueous layer was extracted with EtOAc (3×500 mL). The combined organic layers were washed with brine, dried over MgSO$_4$, filtered and concentrated under reduced pressure. Purification by column chromatography through Iatrobead™ silica gel, eluting with 75:15:5 hexanes/EtOAc/CH$_2$Cl$_2$, afforded the title product in a greater than 10:1 regioisomeric purity. $^1$H NMR (CDCl$_3$, 400 MHz): δ 5.98 (1H, dd, J=11.0, 7.5 Hz), 5.35 (2H, s), 3.87 (1H, dd, J=17.5, 7.5 Hz), 3.70 (1H, dd, J=17.5, 11.0 Hz), 1.50 (9H, s). MS (ESI, Q$^+$) m/z 332, 334 (M+1, $^{79}$Br, $^{81}$Br).

INTERMEDIATE 8

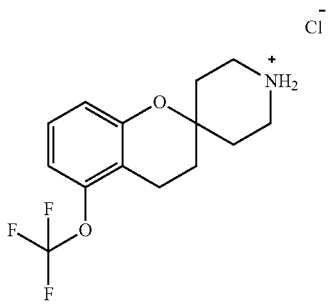 [SMILES: [Cl-] ; FC(F)(F)Oc1cccc2c1CCC1(CC[NH2+]CC1)O2]

5-(Trifluoromethoxy)-3,4-dihydrospiro[chromene-2,
4'-piperidinium]chloride

Step 1: 1-Bromo-2-(methoxymethyl)-4-(trifluoromethoxy)benzene To a cold solution of 2-bromo-5-(trifluoromethoxy)phenol (50 g, 195 mmol) and Hunig's base (120 mL, 687 mmol) in $CH_2Cl_2$ (100 mL) at −78° C. (frozen as a white cake) was added MOM-Cl (35 mL, 461 mmol). The white cake was warmed to room temperature and stirred overnight. The mixture was diluted with water (150 mL), the mixture was stirred for 15 min and extracted with $CH_2Cl_2$ (2×). The $CH_2Cl_2$ extracts were combined, washed with brine, dried ($Na_2SO_4$), filtered and concentrated. The resulting residue was purified by column chromatography on $SiO_2$ (isocratic 10% EtOAc/hexanes) to afford the title product as a colorless oil. $^1$H NMR (400 MHz, acetone-$d_6$): δ 7.74 (d, 1 H), 7.22 (d, 1 H), 6.99 (dd, 1 H), 5.40 (s, 2 H), 3.52 (s, 3 H).

Step 2: 1-[2-(Methoxymethoxy)-6-(trifluoromethoxy)phenyl]ethanone A solution of 1-bromo-2-(methoxymethoxy)-4-(trifluoromethoxy)benzene (60 g, 198 mmol) in THF (500 mL) at −100° C. was treated by a slow addition of t-BuLi in pentane (1.7M) (1.3 equiv) over 45 min by keeping internal temperature between −97° C. to −102°. After 1 h at −100° C., following the end of the addition of t-BuLi, diisopropylamine (0.1 equiv) was added at −100° C. and the mixture was allowed to warm up and then stirred for 3 h at −90° C. The reaction mixture was cooled back to −100° C., then acetic anhydride (24 mL, 254 mmol) was added drop wise keeping the internal temperature below −95° C. The final suspension was warmed to 0° C. The mixture was poured into water (300 mL) and the volatiles were evaporated under reduced pressure. More water (50 mL) was added and the aqueous media was extracted with EtOAc (350 mL), and washed with brine. The aqueous phases were back extracted with EtOAc. The organic layers were combined, dried ($MgSO_4$), filtered and evaporated under reduced pressure. The resulting material was purified on chromatography column on $SiO_2$ (gradient 0 to 20% EtOAc/hexanes) to afford the title compound as an colorless oil. $^1$H NMR (500 MHz, acetone-$d_6$): δ 7.51 (t, 1H), 7.26 (d, 1 H), 7.07 (d, 1 H), 5.33 (s, 2 H), 3.48 (s, 3 H), 2.51 (s, 3 H).

Step 3: 1-[2-Hydroxy-6-(trifluoromethoxy)phenyl]ethanone To a solution of 1-[2-(methoxymethoxy)-6-(trifluoromethoxy)phenyl]ethanone (48 g, 181 mmol) in i-PrOH (60 mL) was added aq HCl 37% (8 mL, 97 mmol). The reaction mixture was heated to 50° C. for 2 h, and then poured into water. The reaction mixture was cooled to 0° C., pentane was added (400 mL) and the mixture was poured into 0.5 N HCl (500 mL). The organic layer was separated, washed with 0.5 N HCl (4×250 mL) and brine. The aqueous phases were back extracted with pentane (400 mL). The organic layers were combined, dried ($MgSO_4$), filtered, cooled to 0° C. and evaporated under reduced pressure by keeping the water bath at 0° C. to give the title compound as a yellow oil containing some i-PrOH. The crude material was used such as in the next step. $^1$H NMR (400 MHz, acetone-$d_6$): δ 12.08 (br s, 1 H), 7.60 (t, 1 H), 7.02 (d, 1 H), 6.97 (d, 1 H), 2.70 (s, 3 H).

Step 4: tert-Butyl 4-oxo-5-(trifluoromethoxy)-3,4-dihydro-1'H-spiro[chromene-2,4'-piperidine]-1'-carboxylate A mixture of 75% in weight of 1-[2-hydroxy-6-(trifluoromethoxy)phenyl]ethanone (50 g, 170 mmol), 1-BOC-4-piperidone (32 g, 161 mmol) in xylene (50 mL), was treated with pyrrolidine (2.6 mL, 32.1 mmol). The mixture was heated to 105° C. for 14 h by removing water and volatile solvents. The crude reaction was purified by column chromatography on $SiO_2$ (isocratic 100% hexanes and then a slow gradient from 5 to 20% EtOAc/hexanes). After evaporation of the solvents, the resulting material was triturated with hexanes at −78° C. The cold suspension was filtered and trituration was repeated to afford the title compound as a white solid. $^1$H NMR (400 MHz, acetone-$d_6$): δ 7.67 (t, 1 H), 7.19 (dd, 1H), 7.01 (d, 1 H), 3.89 (br d, 2 H), 3.24 (br s, 2 H), 2.87 (s, 2 H), 2.06-1.95 (m, 2 H), 1.79-1.69 (m, 2 H), 1.46 (s, 9 H).

Step 5: tert-Butyl 4-hydroxy-5-(trifluoromethoxy)-3,4-dihydro-1'H-spiro[chromene-2,4'-piperidine]-P-carboxylate Into a 500 mL flask, a mixture of tert-butyl 4-oxo-5-(trifluoromethoxy)-3,4-dihydro-1'H-spiro[chromene-2,4'-piperidine]-1'-carboxylate (15 g, 37.4 mmol) in THF (50 mL) and MeOH (50 mL) was treated with $NaBH_4$ (2.1 g, 56.1 mmol) at −78° C., then warmed and stirred for 1 h at 0° C. Acetone was added to quench the excess hydride and the volatiles were evaporated under reduced pressure. Water and aq $NaHCO_3$ were added, and the aqueous media was extracted with EtOAc. The organic layer was washed with aq $NaHCO_3$ (2×), and brine. The aqueous phases were back extracted with EtOAc. The organic layers were combined, dried ($MgSO_4$), filtered and concentrated to afford the title compound as an off-white solid. The crude material was used such as in the next step. $^1$H NMR (400 MHz, acetone-$d_6$): δ 7.33 (t, 1 H), 6.92 (d, 2 H), 5.09-5.05 (m, 1 H), 4.50 (d, 1 H), 3.85 (d, 1 H), 3.76 (d, 1 H), 3.36 (br s, 1 H), 3.16 (br s, 1 H), 2.25-2.16 (m, 2 H), 2.04 (dd, 1 H), 1.78-1.69 (m, 3 H), 1.47 (s, 9 H).

Step 6: 5-(Trifluoromethoxy)-3,4-dihydrospiro[chromene-2,4'-piperidinium]chloride Into a 1 L flask, a cold (−78° C.) solution of tert-butyl 4-hydroxy-5-(trifluoromethoxy)-3,4-dihydro-1'H-spiro[chromene-2,4'-piperidine]-1'-carboxylate (15 g, 37.2 mmol) in $CH_2Cl_2$ (80 mL) was treated with $Et_3SiH$ (24 mL, 150 mmol) followed by TFA (40 mL). The final mixture was warmed to room temperature and heated to reflux (oil bath at 50° C.) for 24 h. The resulting mixture was concentrated under vacuum. To the resulting residue was added 4 M HCl in dioxane (30 mL) and the solution was concentrated. This treatment with HCl was repeated three times. The resulting residue was triturated with $Et_2O$, and the white solid was collected by filtration and dried to afford the title compound. The supernatant was concentrated and treated again with 4 M HCl as described above to afford more of the title compound as a white solid after trituration with $Et_2O$/heptane. Alternatively, the title compound may be synthesized according to the following procedure: To a solution of tert-butyl 4-hydroxy-5-(trifluoromethoxy)-3,4-dihydro-1'H-spiro[chromene-2,4'-piperidine]-1'-carboxylate (23.6 g, 58.5 mmol) in degassed EtOAc (234 mL) were added dropwise $Pd(OH)_2$ catalyst (4.72 g, 6.72 mmol) and MsOH (22.49 g, 234 mmol). The reaction was shaken on a Parr shaker under 50 psi of $H_2$ overnight. The mixture was then filtered over Solka Flok™ under a flow of N₂ and rinsed with 600 mL of EtOAc. The resulting filtrate was washed with 2 N NaOH (2×), dried over MgSO₄ and concentrated under reduced pressure to give the title compound. LC-MS: m/z=288.1 (MH+). ¹H NMR (400 MHz, DMSO-d₆): δ 9.12 (br s, 1 H), 9.01 (br s, 1 H), 7.23 (t, 1 H), 6.92-6.86 (m, 2 H), 3.23-3.12 (m, 2 H), 3.11-2.91 (m, 2H), 2.70 (t, 2 H), 1.87-1.78 (m, 6 H).

INTERMEDIATE 9

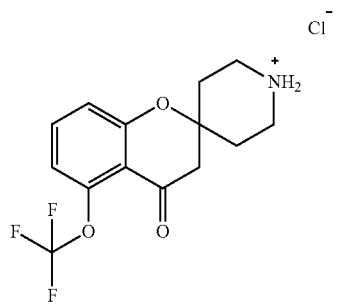 [SMILES: [Cl-] ; O=C1CC2(CC[NH2+]CC2)Oc2cccc(OC(F)(F)F)c21]

4-Oxo-5-(trifluoromethoxy)-3,4-dihydrospiro [chromene-2,4'-piperidinium]chloride A mixture of tert-butyl 4-oxo-5-(trifluoromethoxy)-3,4-dihydro-1'H-spiro[chromene-2,4'-piperidine]-F-carboxylate (1.0 g, 2.491 mmol) (from Intermediate 8, Step 4) in 1,4-dioxane (25 mL) was treated with 4 M HCl in dioxane (25 mL, 100 mmol). The suspension was heated for 30-60 min before the mixture was evaporated to dryness. The residue was triturated with Et₂O/heptane, filtered and dried to afford the title compound as a beige solid. ¹H NMR (500 MHz, DMSO-d₆): δ 8.96 (br s, 1 H), 8.72 (br s, 1 H), 7.70 (t, 1 H), 7.23 (d, 1 H), 7.05 (d, 1 H), 3.26-3.17 (m, 2 H), 3.17-3.04 (m, 2 H), 2.96 (s, 2 H), 2.11 (d, 2 H), 1.97-1.86 (m, 2 H).

INTERMEDIATE 10

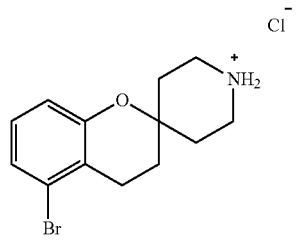 [SMILES: [Cl-] ; Brc1cccc2c1CCC1(CC[NH2+]CC1)O2]

5-Bromo-3,4-dihydrospiro[chromene-2,4'-piperidinium]chloride

Step 1: 1-Bromo-3-(methoxymethoxy)benzene To a solution of 3-bromophenol (10 g, 57.8 mmol) and Hunig's base (35.7 mL, 205 mmol) in CH₂Cl₂ (30 mL) at −78° C., was added MOM-Cl (10.98 mL, 145 mmol). The mixture was warmed to room temperature and stirred overnight. The mixture was diluted with water (150 mL), stirred for 15 min and extracted with CH₂Cl₂ (2×). The CH₂Cl₂ extract was washed with brine, dried (Na₂SO₄), filtered and concentrated to give a yellow oil. The material was purified by column chromatography on SiO₂ (gradient from 0 to 20% EtOAc/hexanes) to give the title compound as a colorless oil.

Step 2: 1-[2-Bromo-6-(methoxymethoxy)phenyl]ethanone To a solution of diisopropylamine (9.85 mL, 69.1 mmol) in THF (100 mL) at −78° C. was slowly added 2.5 M n-BuLi (29.9 mL, 74.9 mmol). The solution was warmed and stirred 20 min at 0° C., cooled to −100° C. before the slow addition of the cold THF (40 mL) solution of 1-bromo-3-(methoxymethoxy)benzene (12.5 g, 57.6 mmol) via a cannula. The mixture was stirred for 2 h at −100° C., keeping the internal temperature kept between −94° C. and 101° C. Then acetic anhydride (10.00 mL, 106 mmol) was added drop wise to the reaction mixture and internal temperature was kept below −95° C. The final white suspension was warmed to room temperature. Then water (100 mL) was added and the volatile materials were evaporated under reduced pressure. More water was added and the aqueous media was extracted with EtOAc, and washed with brine. The aqueous phases were back extracted with EtOAc. The organic layers were combined, dried (Na₂SO₄), filtered and evaporated under reduced pressure. The residue was purified on chromatography column on SiO₂ (120 g, gradient 0 to 15% EtOAc/hexanes) to afford the title compound as a colorless oil.

Step 3: 1-(2-Bromo-6-hydroxyphenyl)ethanone To a solution of 1-[2-bromo-6-(methoxymethoxy)phenyl]ethanone (12.6 g, 48.6 mmol) in 2-propanol (100 mL) was added aq HCl (37%, 20 mL, 244 mmol). The solution was heated to 65° C. for 4 h. Then, the volatiles were evaporated under reduced pressure. Water was added and the aqueous media was extracted with EtOAc, and washed with brine. The aqueous phases were back extracted with EtOAc. The organic layers were combined, dried (Na₂SO₄), filtered and evaporated under reduced pressure. The resulting residue was purified by trituration with heptane to afford the title compound as a beige solid.

Step 4: tert-Butyl 5-bromo-4-oxo-3,4-dihydro-1'H-spiro[chromene-2,4'-piperidine]-1'-carboxylate A mixture of 1-(2-bromo-6-hydroxyphenyl)ethanone (8.81 g, 41.0 mmol), 1-boc-4-piperidone (8.82 g, 44.2 mmol) and pyrrolidine (0.847 mL, 10.24 mmol) in xylene (70 mL) was heated to 100° C. for 16 h by removing water. The residue was purified by column chromatography on SiO₂ (gradient from 0 to 30% EtOAc/hexanes), followed by a co-evaporation with Et₂O/heptane to give the title compound as a beige solid. LC-MS: m/z=418.0, 420.0 (M+Na).

Step 5: tert-Butyl 5-bromo-4-hydroxy-3,4-dihydro-1'H-spiro[chromene-2,4'-piperidine]-1'-carboxylate A mixture of tert-butyl 5-bromo-4-oxo-3,4-dihydro-1'H-spiro[chromene-2,4'-piperidine]-1'-carboxylate (2.04 g, 5.15 mmol) in THF (20 mL) and MeOH (20 mL) was treated with NaBH₄ (0.390 g, 10.30 mmol) at 0° C. The suspension was warmed to room temperature and stirred for 1 h. Acetone was added to quench the excess of hydride and the volatiles were evaporated under reduced pressure. Water was added and the aqueous media was extracted with EtOAc. The organic layer was washed with water, aq NaHCO₃, and brine. The aqueous phases were back extracted with EtOAc and the organic layers were combined, dried (Na₂SO₄), filtered and concentrated to give the title compound as an off-white solid.

Step 6: 5-Bromo-3,4-dihydrospiro[chromene-2,4'-piperidinium]chloride A cold solution of tert-butyl 5-bromo-4-hydroxy-3,4-dihydro-1'H-spiro[chromene-2,4'-piperidine]-1'-carboxylate (514 mg, 1.291 mmol) in CH₂Cl₂ (8 mL) was treated with triethylsilane (1.649 mL, 10.32 mmol), followed by TFA (4 mL). The final mixture was warmed to room temperature and then heated to 80° C. for 5.5 h. The resulting mixture was concentrated under vacuum. To the resulting residue was added 4 M HCl in dioxane (4 mL) and the solution was concentrated (repeated twice). Then, to the residue was added Et₂O and a white solid precipitate was observed. The suspension was triturated under ultrasound, filtered and dried to give the title compound as a white solid. LC-MS: m/z=284.0, 282.0 (MH+). ¹H NMR (500 MHz, DMSO-d₆): δ 8.76 (br s, 2 H), 7.19 (d, 1H), 7.09 (t, 1 H), 6.90 (d, 1 H), 3.24-3.16 (m, 2 H), 3.07 (td, 2 H), 2.70 (t, 2 H), 1.92-1.77 (m, 6H).

INTERMEDIATE 11

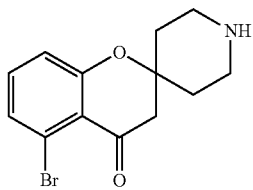 [SMILES: O=C1CC2(CCNCC2)Oc2cccc(Br)c21]

5-Bromospiro[chromene-2,4'-piperidin]-4(3H)-one A mixture of tert-butyl 5-bromo-4-oxo-3,4-dihydro-1'H-spiro[chromene-2,4'-piperidine]-1'-carboxylate (4.6 g, 10.45 mmol) (Intermediate 10, Step 4) in 1,4-dioxane (7 mL) was treated with 4 M HCl in dioxane (50 mL, 200 mmol). The suspension was heated with a heat gun for 5-10 min before the mixture was evaporated to dryness. The HCl salt was neutralized with 1 N NaOH and the aqueous phase was extracted with MTBE. The organic layer was washed with water, brine. The aqueous phases were back extracted with MTBE. The organic layers were combined, dried (MgSO₄), filtered and concentrated. The residue was triturated with heptane, filtered and dried to afford the title compound as a pink solid. LC-MS: m/z=296.0, 298.0 (MH+). ¹H NMR (500 MHz, DMSO-d₆): δ 7.40 (t, 1 H), 7.28 (d, 1 H), 7.08 (d, 1 H), 2.84 (s, 2 H), 2.85-2.75 (m, 2 H), 2.68 (dt, 2 H), 1.80-1.71 (m, 2 H), 1.63-1.55 (m, 2 H).

INTERMEDIATE 12

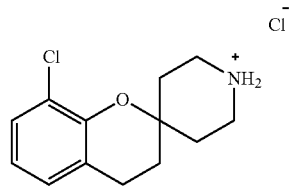 [SMILES: [Cl-] ; Clc1cccc2c1OC1(CC[NH2+]CC1)CC2]

8-Chloro-3,4-dihydrospiro[chromene-2,4'-piperidinium]chloride

Step 1: tert-Butyl 8-chloro-4-oxo-3,4-dihydro-1'H-spiro[chromene-2,4'-piperidine]-1'-carboxylate A mixture of 1-(3-chloro-2-hydroxyphenyl)ethanone (500 mg, 2.93 mmol), 1-boc-4-piperidone (584 mg, 2.93 mmol) and pyrrolidine (61 pt, 0.738 mmol) in Xylene (4 mL) was heated to 100° C. for 20 h. The reaction mixture was purified by column chromatography on SiO₂ (40 g, gradient from 0 to 40% EtOAc/hexanes) to afford the title compound as a white solid. LC-MS: m/z=376.1, 374.1 (M+Na).

Step 2: tert-Butyl 8-chloro-4-hydroxy-3,4-dihydro-1'H-spiro[chromene-2,4'-piperidine]-1'-carboxylate A mixture of tert-butyl 8-chloro-4-oxo-3,4-dihydro-1'H-spiro[chromene-2,4'-piperidine]-1'-carboxylate (910 mg, 2.59 mmol) in THF (10 mL) and MeOH (10 mL) was treated with NaBH₄ (196 mg, 5.17 mmol) at 0° C. The suspension was warmed to room temperature and stirred for 1 h. Acetone was added to quench the excess of hydride and the volatile evaporated under reduced pressure. Water was added and the aqueous media was extracted with EtOAc. The organic layer was washed with water, aq NaHCO₃, and brine. The aqueous phases were back extracted with EtOAc and the organic layers were combined, dried (Na₂SO₄), filtered and concentrated to give the title compound as a foamy white solid. LC-MS: m/z=376.1, 378.1 (M+Na).

Step 3: 8-Chloro-3,4-dihydrospiro[chromene-2,4'-piperidinium]chloride TFA (10 mL) was added to tert-butyl 8-chloro-4-hydroxy-3,4-dihydro-1'H-spiro[chromene-2,4'-piperidine]-1'-carboxylate (905 mg, 2.56 mmol) and an exotherm was observed. Due to the exotherm, the solution was cooled rapidly to 0° C. and it was treated with triethylsilane (1.634 mL, 10.23 mmol). The mixture was heated to 80° C. for 1.5 h. The resulting mixture was concentrated under vacuum. To the residue was added 4 M HCl in dioxane (4 mL) and the solution was concentrated (this was repeated twice). Then, to the residue was added Et₂O and the white solid was triturated under ultrasound, filtered and dried to give the title compound. LC-MS: m/z=238.1, 240.1 (MH+). ¹H NMR (500 MHz, DMSO-d₆): δ 8.82 (br s, 2 H), 7.27 (d, 1 H), 7.11 (d, 1 H), 6.88 (t, 1 H), 3.29-3.22 (m, 2 H), 3.05 (td, 2 H), 2.81 (t, 2 H), 1.95-1.79 (m, 6 H).

INTERMEDIATE 13

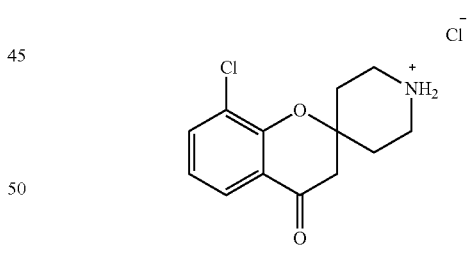

8-Chloro-4-oxo-3,4-dihydrospiro[chromene-2,4'-piperidinium]chloride A mixture of tert-butyl 8-chloro-4-oxo-3,4-dihydro-1'H-spiro[chromene-2,4'-piperidine]-1'-carboxylate (877 mg, 2.493 mmol) (Intermediate 12, Step 1) in 1,4-dioxane (4 mL) was treated with 4 M HCl in dioxane (6 mL, 24.00 mmol). The suspension was heated with heat gun for 5-10 min before the mixture was evaporated to dryness. The residue was triturated with Et₂O, filtered and dried to give the title compound as a white solid. LC-MS: m/z=252.0, 254.0 (MH+). ¹H NMR (400 MHz, DMSO-d₆): δ 8.98 (br s, 2 H), 7.82 (d, 1 H), 7.75 (d, 1 H), 7.14 (t, 1 H), 3.27 (d, 2 H), 3.10-2.99 (m, 4 H), 2.16 (d, 2 H), 2.02-1.89 (m, 2 H).

INTERMEDIATE 14

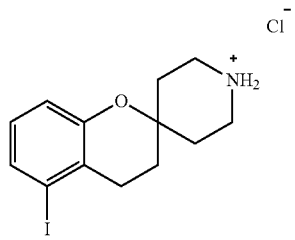 [SMILES: [Cl-] ; Ic1cccc2c1CCC1(CC[NH2+]CC1)O2]

5-Iodo-3,4-dihydrospiro[chromene-2,4'-piperidinium]chloride

Step 1: tert-Butyl 5-iodo-4-oxo-3,4-dihydro-1'H-spiro[chromene-2,4'-piperidine]-1'-carboxylate Following literature reference *J. Am. Chem. Soc.* 2002, 124, 14844-14845, dioxane (30 mL) was added to a mixture of tert-butyl 5-bromo-4-oxo-3,4-dihydro-1'H-spiro[chromene-2,4'-piperidine]-1'-carboxylate (2.4 g, 6.06 mmol) (Intermediate 10, Step 4), NaI (1.952 g, 13.02 mmol), CuI (0.173 g, 0.908 mmol) and (R,R)-(−)-N,N'-dimethyl-1,2-cyclohexanediamine (0.258 g, 1.817 mmol). The reaction mixture was heated to 120° C. for 24 h, diluted with EtOAc and the resulting suspension was filtered through a pad of SiO$_2$ by eluting with 100% EtOAc. After concentration, the residue was purified by flash chromatography on SiO$_2$ (50 g, gradient from 0% to 50% EtOAc/hexanes) to afford the title compound as a yellow oil. LC-MS: m/z=466.1 (M+Na)

Step 2: tert-Butyl 4-hydroxy-5-iodo-3,4-dihydro-1'H-spiro[chromene-2,4'-piperidine]-1'-carboxylate A mixture of tert-butyl 5-iodo-4-oxo-3,4-dihydro-1'H-spiro[chromene-2,4'-piperidine]-1'-carboxylate (800 mg, 1.805 mmol) in THF (8 mL) and MeOH (8.00 mL) was treated with NaBH$_4$ (137 mg, 3.61 mmol) at 0° C. The suspension was warmed to room temperature and stirred for 1 h. Then acetone was added to quench the excess of hydride and the volatiles were evaporated under reduced pressure. Water was added to the residue and the aqueous media was extracted with EtOAc. The organic layer was washed with water, aq NaHCO$_3$, and brine. The aqueous phases were back extracted with EtOAc and the organic layers were combined, dried (Na$_2$SO$_4$), filtered and concentrated to give the title compound as an off-white solid. LC-MS: m/z=468.0 (M+Na).

Step 3: 5-Iodo-3,4-dihydrospiro[chromene-2,4'-piperidinium]chloride A cold solution of tert-butyl 4-hydroxy-5-iodo-3,4-dihydro-1'H-spiro[chromene-2,4'-piperidine]-1'-carboxylate (800 mg, 1.797 mmol) in CH$_2$Cl$_2$ (10 mL) was treated with triethylsilane (2.296 mL, 14.37 mmol) followed by TFA (5 mL). The final mixture was warmed to room temperature, then heated to 80° C. for 10 h and concentrated under vacuum. To the residue was added 4 M HCl in dioxane (10-15 mL) and the solution was concentrated again (this was repeated three times). To the resulting residue was added Et$_2$O and the white solid was triturated under ultrasound, filtered and dried to afford the title compound as a white solid. (LC-MS: m/z=330.0 (MH+)). $^1$H NMR (500 MHz, DMSO-d$_6$): δ 8.61 (br s, 2 H), 7.44 (dd, 1 H), 6.94-6.88 (m, 2 H), 3.24-3.16 (m, 2 H), 3.07 (td, 2 H), 2.61 (t, 2 H), 1.92-1.74 (m, 6 H).

INTERMEDIATE 15

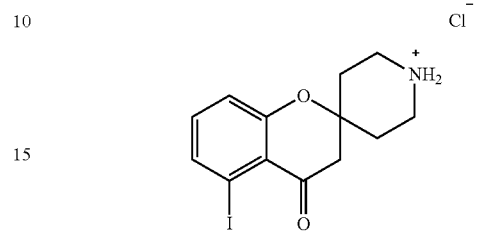

5-Iodo-4-oxo-3,4-dihydrospiro[chromene-2,4'-piperidinium]chloride A mixture of tert-butyl 5-iodo-4-oxo-3,4-dihydro-1'H-spiro[chromene-2,4'-piperidine]-1'-carboxylate (718 mg, 1.296 mmol; Intermediate 14, Step 1) in 1,4-dioxane (4 mL) was treated with 4 M HCl in dioxane (8 mL, 32 mmol). The suspension was heated with heat gun for 20-30 min before the mixture was evaporated to dryness. The residue was triturated with 1,4-dioxane, filtered and dried to give the title compound as an off-white solid. LC-MS: m/z=344.0 (MH+). $^1$H NMR (500 MHz, DMSO-d$_6$): δ 8.84 (br s, 1 H), 8.67 (br s, 1 H), 7.62 (dd, 1 H), 7.18 (t, 1 H), 7.11 (dd, 1 H), 3.16-3.09 (m, 2 H), 3.08-2.97 (m, 2 H), 2.92 (s, 2 H), 2.01 (d, 2 H), 1.88-1.77 (m, 2 H).

INTERMEDIATE 16

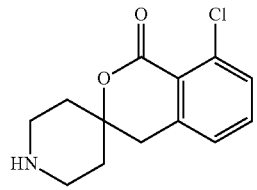 [SMILES: O=C1OC2(CCNCC2)Cc2cccc(Cl)c21]

8-Chlorospiro[isochromene-3,4'-piperidin]-1(4H)-one To a solution of 2-bromo-6-chloro-benzoic acid (1.50 g, 6.37 mmol) in THF (25 mL) at −78 C was added n-butyl lithium (2.5 M in hexanes, 5.35 mL, 13.38 mmol) dropwise. The solution was stirred for 1 h before 1-oxa-6-aza-spiro[2.5]octane-6-carboxylic acid tert-butyl ester (1.63 g, 7.64 mmol; prepared as described in literature procedure Sabbani, S. et al., Bioorg. Med. Chem. Lett. 2008, 18, 5804-5808) in THF (8.5 mL) was added to the mixture. The stirring was continued for 5 h at −78 C, then left overnight and warmed to room temperature. The reaction mixture was quenched with NaOH (1 N, 30 mL). The volatiles were removed under reduced pressure. The resulting aqueous layer was washed with MTBE (15 mL) and acidified with 6N HCl (30 mL). The lactonization and deprotection were achieved by heating to 60° C. for 3 h. The resulting mixture was cooled in an ice bath to keep the temperature below 20° C. as it was basified with 10 N NaOH to pH 10-12. The aqueous layer was extracted with IPA (2×60 mL). The combined organic layers were washed with brine, dried over anhydrous MgSO$_4$ and concentrated under reduced pressure. The residue was purified by Combiflash™ chromatography (amine column, elution with 0-10% MeOH/DCM) to afford the title compound as solid. ¹H NMR (CDCl₃, 400 MHz) 7.45-7.40 (2H, m), 7.19-7.14 (1H, m), 4.36 (1H, br), 3.17-3.09 (2H, m), 3.05 (2H, s), 2.94 (2H, ddd), 1.96-1.88 (2H, m), 1.74 (2H, ddd). MS (ESI, Q⁺) m/z 252.0, 254.0 (M+1, ³⁵Cl, ³⁷Cl).

INTERMEDIATE 17

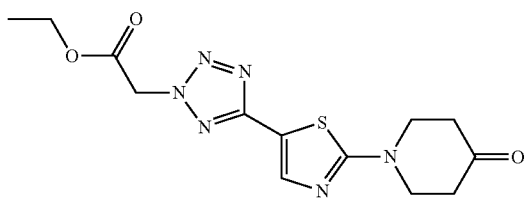 [SMILES: CCOC(=O)Cn1nnc(-c2cnc(N3CCC(=O)CC3)s2)n1]

Ethyl{5-[2-(4-oxopiperidin-1-yl)-1,3-thiazol-5-yl]-2H-tetrazol-2-yl}acetate

Step 1: Ethyl{5-[2-(1,4-dioxa-8-azaspiro[4.5]dec-8-yl)-1,3-thiazol-5-yl]-2H-tetrazol-2-yl}acetate. The title compound was prepared in a similar manner as that described for Example 13 (step 1) from Intermediate 2 and 1,4-dioxa-8-azaspiro[4.5]decane.

Step 2: Ethyl{5-[2-(4-oxopiperidin-1-yl)-1,3-thiazol-5-yl]-2H-tetrazol-2-yl}acetate. To a solution of ethyl{5-[2-(1,4-dioxa-8-azaspiro[4.5]dec-8-yl)-1,3-thiazol-5-yl]-2H-tetrazol-2-yl}acetate (377 mg, 0.99 mmol) in THF (4.95 mL) was added 1N HCl (1.09 mL, 1.09 mmol). The reaction mixture was heated to 65° C. for 3 h. The volatiles were evaporated under reduced pressure. The mixture was diluted with water (20 mL) and extracted with EtOAc (3×5 mL). The combined organic fractions were dried over MgSO₄, filtered and evaporated under reduced pressure. The residue was purified by Combiflash™ chromatography (SiO₂, 12 g, elution with 10-70% EtOAc/hexanes over 40 min) to afford the title compound as solid. ¹H NMR (500 MHz, DMSO-d₆): δ 7.92 (s, 1 H), 5.85 (s, 2 H), 4.22 (q, 2 H), 3.90 (t, 4 H), 2.57 (t, 4 H), 1.23 (t, 3 H). MS (+ESI): m/z 337.1 (MH+).

INTERMEDIATE 18

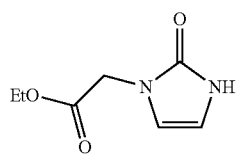

Ethyl (2-oxo-2,3-dihydro-1H-imidazol-1-yl)acetate

Step 1: Ethyl N-{[(2,2-dimethoxyethyl)amino]carbonyl}glycinate To a solution of ethyl isocyanatoacetate (8.84 mL, 77 mmol) in CH₂Cl₂ (100 mL) at 0° C. was added aminoacetaldehyde dimethyl acetal (8.86 mL, 81 mmol) over a period of 10 min. The mixture was further stirred for 30 min, quenched with water. The CH₂Cl₂ layer was separated, washed with water, dried (Na₂SO₄) and concentrated to give the crude title compound as an oil.

Step 2: Ethyl (2-oxo-2,3-dihydro-1H-imidazol-1-yl)acetate To a solution of ethyl N-{[(2,2-dimethoxyethyl)amino]carbonyl}glycinate (16 g, 68.3 mmol) in acetic acid (20 mL) was added 80% aqueous formic acid (80 mL, 1669 mmol). The mixture was stirred at 65° C. for 1 h. Most volatile materials were removed in vacuo. The residue was diluted with small amount of water (~10 to 20 mL) and extracted with EtOAc (3×50 mL). The combined EtOAc extracts were concentrated and dried in vacuo. The residue was swished with Et₂O, filtered and dried to give the title compound as a pale yellow solid. ¹H NMR (500 MHz, acetone-d₆): δ 9.49 (s, 1 H), 6.45 (d, 1 H), 6.40 (d, 1 H), 4.39 (s, 2 H), 4.23-4.14 (q, 2 H), 1.29-1.23 (t, 3 H).

INTERMEDIATE 19

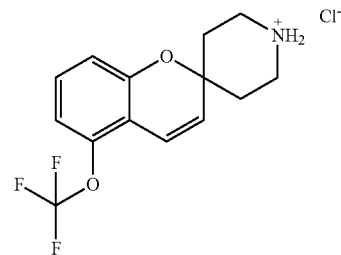 [SMILES: FC(F)(F)Oc1cccc2c1C=CC1(CCNCC1)O2 ; [Cl-]]

5-(Trifluoromethoxy)spiro[chromene-2,4'-piperidinium] chloride A mixture of tert-butyl 4-hydroxy-5-(trifluoromethoxy)-3,4-dihydro-1'H-spiro[chromene-2,4'-piperidine]-1'-carboxylate (0.92 g, 2.29 mmol; Intermediate 8, Step 5) was diluted with 4 M HCl in dioxane (60 mL, 240 mmol) and heated to 120° C. for 3-4 days. The suspension was concentrated under vacuum. The residue was diluted with MTBE and the salt was treated with 1 N NaOH. The organic layer was separated and washed twice with water and brine. The aqueous phases were back extracted with MTBE. The organic layers were combined, dried (MgSO₄), treated with active charcoal, filtered through a Celite™ pad, concentrated and treated with 4 M HCl in dioxane, and evaporated to dryness. The residue was triturated with Et₂O/heptane, filtered and dried to afford the title compound as a beige solid. LC-MS: m/z=286.2 (MH+). ¹H NMR (400 MHz, DMSO-d₆): δ 9.11 (br s, 1 H), 8.99 (br s, 1 H), 7.32 (t, 1 H), 7.02 (d, 1 H), 6.98 (d, 1 H), 6.68 (d, 1 H), 6.03 (d, 1 H), 3.30-3.10 (m, 4 H), 2.13-2.01 (m, 2 H), 2.03-1.88 (m, 2 H).

INTERMEDIATE 20

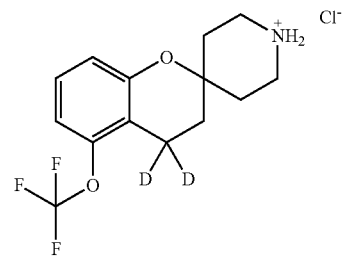 [SMILES: [2H]C1([2H])CC2(CCNCC2)Oc2cccc(OC(F)(F)F)c21 ; [Cl-]]

5-(Trifluoromethoxy)-3,4-dihydrospiro[chromene-2,4'-piperidinium]chloride-d₂

Step 1: tert-Butyl 4-hydroxy-5-(trifluoromethoxy)-3,4-dihydro-1'H-spiro[chromene-2,4'-piperidine]-1'-carboxylate-d₁ The title compound was prepared, as a tan solid, starting from tert-butyl 4-oxo-5-(trifluoromethoxy)-3,4-dihydro-1'H-spiro[chromene-2,4'-piperidine]-1'-carboxylate (600 mg, 1.50 mmol; Intermediate 8, Step 4) through 2 synthetic steps in the same manner as described for Intermediate 8, but using deuterated reagents (NaBD₄, MeOD, Et₃SiD, TFA-d) for Steps 5 and 6. LC-MS: m/z=290.1 (MH+). ¹H NMR (400 MHz, DMSO-d₆): δ 8.94 (br s, 1 H), 8.81 (br s, 1 H), 7.27 (t, 1 H), 6.95-6.89 (m, 2 H), 3.25-3.16 (m, 2 H), 3.16-3.03 (m, 2H), 1.95-1.78 (m, 6 H).

EXAMPLE 1

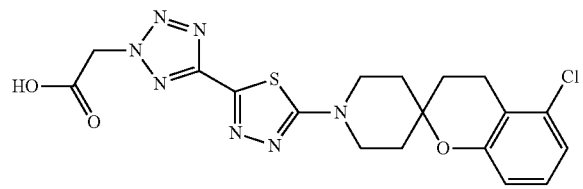 [SMILES: O=C(O)Cn1nnc(-c2nnc(N3CCC4(CCc5c(Cl)cccc5O4)CC3)s2)n1]

{5-[5-(5-Chloro-3,4-dihydro-1'H-spiro[chromene-2,4'-piperidin]-1'-yl)-1,3,4-thiadiazol-2-yl]-2H-tetrazol-2-yl}acetic acid Step 1: 5-(5-Chloro-3,4-dihydro-1'H-spiro[chromene-2,4'-piperidin]-1'-yl)-1,3,4-thiadiazole-2-carbonitrile. To a mixture of 5-bromo-1,3,4-thiadiazole-2-carbonitrile (200 mg, 1.053 mmol), piperidine, 5-chloro-3,4-dihydrospiro[chromene-2,4'-piperidine]hydrochloride salt (346 mg, 1.263 mmol) in dioxane (5 mL) was added DIPEA (0.551 mL, 3.16 mmol). The mixture was stirred at room temperature for 2 h. After dilution with water, the mixture was extracted with EtOAc. The EtOAc extract was washed with 0.5M HCl (2×), brine, dried (Na₂SO₄) and concentrated. Combi-Flash® (40 g, 20-50% EtOAc in hexanes for 20 min, 35 mL/min, 18 mL/fraction) gave the title compound as yellow foam. ¹H NMR (500 MHz, acetone-d₆): δ 7.16 (t, 1 H), 7.00 (d, 1 H), 6.89 (d, 1 H), 3.98 (d, 2 H), 3.78-3.71 (m, 2 H), 2.83 (t, 2 H), 2.02-1.89 (m, 6 H).

Step 2: 5-Chloro-1'-[5-(1H-tetrazol-5-yl)-1,3,4-thiadiazol-2-yl]-3,4-dihydrospiro[chromene-2,4'-piperidine]. A mixture of 5-(5-chloro-3,4-dihydro-1'H-spiro[chromene-2,4'-piperidin]-1'-yl)-1,3,4-thiadiazole-2-carbonitrile (340 mg, 0.980 mmol), ammonium chloride (157 mg, 2.94 mmol) and sodium azide (127 mg, 1.961 mmol) in DMF (5 mL) was heated at 110° C. for 3 h. After cooling, the mixture was diluted with water, and acidified with 1N HCl (1 mL). The precipitate was collected, washed with water and dried to give the title compound as a white solid. MS: m/z 390 (MH+).

Step 3: Ethyl{5-[5-(5-chloro-3,4-dihydro-1'H-spiro[chromene-2,4'-piperidin]-1'-yl)-1,3,4-thiadiazol-2-yl]-2H-tetrazol-2-yl}acetate. A mixture of -chloro-1'-[5-(1H-tetrazol-5-yl)-1,3,4-thiadiazol-2-yl]-3,4-dihydrospiro[chromene-2,4'-piperidine] (275 mg, 0.705 mmol), ethyl bromoacetate (120 µL, 1.078 mmol) and triethylamine (250 µL, 1.794 mmol) in THF (10 mL) was refluxed for 3 h. After cooling, the mixture was diluted with water and extracted with EtOAc. The EtOAc extract was washed with water (2×), dried (Na₂SO₄) and concentrated. Combi-Flash® (40 g, 20-60% EtOAc in hexanes for 20 min, 35 mL/min, 20 mL/fraction) to give the less polar ethyl{5-[5-(5-chloro-3,4-dihydro-1'H-spiro[chromene-2,4'-piperidin]-1'-yl)-1,3,4-thiadiazol-2-yl]-1H-tetrazol-1-yl}acetate as a white foam and the more polar title compound as a white foam. ¹H NMR (500 MHz, acetone-d₆): δ 7.16 (t, 1 H), 7.01 (d, 1 H), 6.90 (d, 1 H), 5.80 (s, 2 H), 4.30 (q, 2 H), 3.96 (d, 2 H), 3.73-3.64 (m, 2 H), 2.84 (m, 2 H), 2.03-1.90 (m, 6 H), 1.26 (t, 3 H).

Step 4: {5-[5-(5-Chloro-3,4-dihydro-1'H-spiro[chromene-2,4'-piperidin]-1'-yl)-1,3,4-thiadiazol-2-yl]-2H-tetrazol-2-yl}acetic acid A mixture of ethyl{5-[5-(5-chloro-3,4-dihydro-1'H-spiro[chromene-2,4'-piperidin]-1'-yl)-1,3,4-thiadiazol-2-yl]-2H-tetrazol-2-yl}acetate (200 mg, 0.420 mmol) and 1M NaOH (1 mL, 1.0 mmol) in THF (5 mL) and MeOH (1 mL) was stirred at room temperature for 2 h. The mixture was then diluted with water and acidified with 1M HCl. White precipitate appeared and the mixture was extracted with EtOAc. The EtOAc extract was washed with water, dried (Na₂SO₄) and concentrated. The resulting residue was swished with Et₂O and a small amount of EtOAc, filtered and dried to give the title compound as a white powder. ¹H NMR (500 MHz, acetone-d₆): δ 7.16 (t, 1 H), 7.00 (d, 1 H), 6.90 (d, 1 H), 5.79 (s, 2 H), 3.96 (d, 2 H), 3.73-3.65 (m, 2 H), 2.84 (t, 2 H), 2.04-1.90 (m, 6 H). MS: m/z 448 (MH+).

EXAMPLE 2

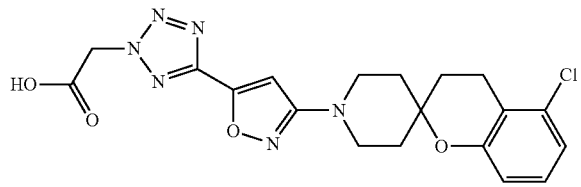 [SMILES: O=C(O)Cn1nnc(-c2cc(N3CCC4(CCc5c(Cl)cccc5O4)CC3)no2)n1]

{5-[3-(5-Chloro-3,4-dihydro-1'H-spiro[chromene-2,4'-piperidin]-1'-yl)isoxazol-5-yl]-2H-tetrazol-2-yl}acetic acid Step 1: Ethyl 3-bromo-4,5-dihydroisoxazole-5-carboxylate. To a vigorously stirred mixture of hydroxycarbonimidic dibromide (15.5 g, 76.4 mmol) and ethyl acrylate (15.3 g, 153 mmol) in DMF (200 mL) was added a solution of 15 wt % aqueous KHCO₃ (102 mL, 153 mmol). The mixture was stirred at room temperature overnight. Water was added and the mixture was extracted twice with methyl tert-butyl ether. The combined organic extracts were washed with brine, dried (Na₂SO₄) and concentrated in vacuo to give the title compound.

Step 2: 3-Bromo-4,5-dihydroisoxazole-5-carboxamide. A mixture of ethyl 3-bromo-4,5-dihydroisoxazole-5-carboxylate (6.2 g, 28 mmol) and a solution of 2 M ammonia in MeOH (56 mL) was stirred at room temperature for 1 to 2 hours. Volatile materials were removed in vacuo to give the crude title compound as a white solid.

Step 3: 3-(5-Chloro-3,4-dihydro-1'H-spiro[chromene-2,4'-piperidin]-1'-yl)-4,5-dihydroisoxazole-5-carboxamide. A mixture of 3-bromo-4,5-dihydroisoxazole-5-carboxamide (500 mg, 2.59 mmol), 5-chloro-3,4-dihydrospiro[chromene-2,4'-piperidine]hydrochloride salt (800 mg, 2.92 mmol) and DIPEA (1.357 mL, 7.77 mmol) in ethanol (5 mL) was refluxed for 6 h. After cooling, volatile materials were removed in vacuo. The resulting residue was diluted with water, acidified with 1N HCl and extracted with EtOAc. The EtOAc extract was washed sucessively with 0.5M HCl, water (2×), dried (Na₂SO₄) and concentrated to give the title compound as a light brown powder.

Step 4: 3-(5-Chloro-3,4-dihydro-1'H-spiro[chromene-2,4'-piperidin]-1'-yl)isoxazole-5-carboxamide. To a stirred suspension of 3-(5-chloro-3,4-dihydro-1'H-spiro[chromene-2,4'-piperidin]-1'-yl)-4,5-dihydroisoxazole-5-carboxamide (420 mg, 1.2 mmol) and sodium acetate (295 mg, 3.6 mmol) in chlorobenzene (5 mL) was added iodine (350 mg, 1.4 mmol). The mixture was heated at reflux temperature for 3 h. After cooling, a solution of Na₂S₂O₃, water and EtOAc were added. The mixture was stirred for 5 min and filtered through Celite™ to remove the insoluble material. The organic layer was then separated, washed with brine, dried (Na₂SO₄) and concentrated. The resulting residue was triturated with Et₂O, filtered and dried to give the title compound as a light brown powder. MS: m/z 348 (MH+).

Step 5: 3-(5-Chloro-3,4-dihydro-1'H-spiro[chromene-2,4'-piperidin]-1'-yl)isoxazole-5-carbonitrile. To a suspension of 3-(5-chloro-3,4-dihydro-1'H-spiro[chromene-2,4'-piperidin]-1'-yl)isoxazole-5-carboxamide (280 mg, 0.805 mmol) and TEA (0.337 mL, 2.415 mmol) in CH₂Cl₂ (8 mL) at room temperature was added TFAA (0.171 mL, 1.208 mmol). The mixture became homogeneous almost immediately. After further stirring for 30 min, the mixture was quenched with saturated NaHCO₃ and extracted with CH₂Cl₂. The CH₂Cl₂ extract was washed with brine, dried (Na₂SO₄) and concentrated. Combi-Flash® (12 g, 20-50% EtOAc in hexanes for 20 min, 25 mL/min, 20 mL/fraction) gave the title compound as a pale yellow oil, which solidifed on standing. ¹H NMR (500 MHz, acetone-d₆): δ 7.32 (d, 1 H), 7.15 (td, 1 H), 6.99 (dd, 1 H), 6.86 (dd, 1 H), 3.65 (dd, 2 H), 3.44-3.34 (m, 2 H), 2.83-2.79 (m, 2 H), 2.01-1.79 (m, 6 H). MS: m/z 330 (MH+).

Step 6: {5-[3-(5-Chloro-3,4-dihydro-1'H-spiro[chromene-2,4'-piperidin]-1'-yl)isoxazol-5-yl]-2H-tetrazol-2-yl}acetic acid The title compound was prepared in a similar manner as described for Example 1, Steps 2 to 4 starting from 3-(5-chloro-3,4-dihydro-1'H-spiro[chromene-2,4'-piperidin]-1'-yl)isoxazole-5-carbonitrile. ¹H NMR (500 MHz, acetone-d₆): δ 7.15 (t, 1 H), 7.01-6.96 (m, 2 H), 6.88 (d, 1 H), 5.80 (s, 2 H), 3.71 (m, 2 H), 3.42-3.35 (m, 2 H), 2.83 (m, 2 H), 1.97-1.81 (m, 6 H). MS: m/z 431 (MH+).

EXAMPLE 3

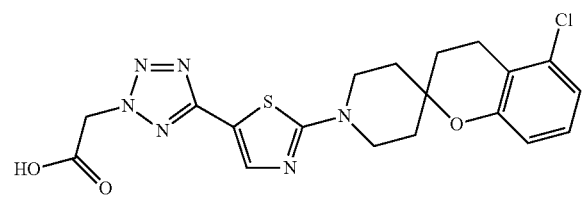 [SMILES: O=C(O)Cn1nnc(-c2cnc(N3CCC4(CCc5c(Cl)cccc5O4)CC3)s2)n1]

{5-[2-(5-Chloro-3,4-dihydro-1'H-spiro[chromene-2,4'-piperidin]-1'-yl)-1,3-thiazol-5-yl]-2H-tetrazol-2-yl}acetic acid Step 1: tert-Butyl{5-[2-(5-chloro-3,4-dihydro-1'H-spiro[chromene-2,4'-piperidin]-1'-yl)-1,3-thiazol-5-yl]-2H-tetrazol-2-yl}acetate. To a solution of tert-butyl[5-(2-bromo-1,3-thiazol-5-yl)-2H-tetrazol-2-yl]acetate (80 mg, 0.23 mmol) and 5-chloro-3,4-dihydrospiro[chromene-2,4'-piperidinium] chloride (82 mg, 0.30 mmol) in NMP (1.25 mL) was added DBU (91 µL, 0.60 mmol). The tube was sealed and immersed into a preheated oil bath at 130° C., and stirred at this temperature for 20 min. The reaction was then diluted with EtOAc, poured into 0.5 N HCl, extracted with EtOAc, washed with water (3×) and brine, dried (Na₂SO₄), filtered and concentrated. After evaporation of solvents, the residue was purified twice by flash chromatography on SiO₂ (10 g; gradient from 0 to 60% EtOAc/hexanes) to afford the title product as a white solid. LC-MS: m/z=503.1, 505.1 (MH+). ¹H NMR (400 MHz, acetone-d₆): δ 7.85 (s, 1 H), 7.17 (t, 1 H), 7.01 (dd, 1 H), 6.91 (dd, 1 H), 5.57 (s, 2 H), 3.96 (dt, 2 H), 3.61-3.53 (m, 2 H), 2.87-2.82 (m, 2 H), 2.02-1.83 (m, 6 H), 1.51 (s, 9 H).

Step 2: {5-[2-(5-Chloro-3,4-dihydro-1'H-spiro[chromene-2,4'-piperidin]-1'-yl)-1,3-thiazol-5-yl]-2H-tetrazol-2-yl}acetic acid. Water (0.4 mL) and formic acid (1.6 mL, 42 mmol) were added to tert-butyl{5-[2-(5-chloro-3,4-dihydro-1'H-spiro[chromene-2,4'-piperidin]-1'-yl)-1,3-thiazol-5-yl]-2H-tetrazol-2-yl}acetate (65 mg, 0.13 mmol) and the resulting solution was immersed into a preheated oil bath at 100° C. for 1 h. The reaction was poured into water, extracted with EtOAc, washed with water (3×) and brine, dried (Na₂SO₄), filtered and concentrated. After evaporation of solvent, the residue was dissolved into EtOAc and filtered through a pad of Celite™. The solvent was removed under vacuum and the resulting material was triturated with Et₂O/heptane, filtered and dried to afford the title product as a white solid. LC-MS: m/z=449.0, 447.0 (MH+). ¹H NMR (500 MHz, DMSO-d₆): δ 13.77 (br s, 1 H), 7.88 (s, 1 H), 7.15 (t, 1 H), 7.01 (d, 1 H), 6.86 (d, 1 H), 5.69 (s, 2 H), 3.86-3.78 (m, 2 H), 3.53-3.43 (m, 2 H), 2.74 (t, 2 H), 1.92 (t, 2 H), 1.87-1.74 (m, 4 H).

EXAMPLE 4

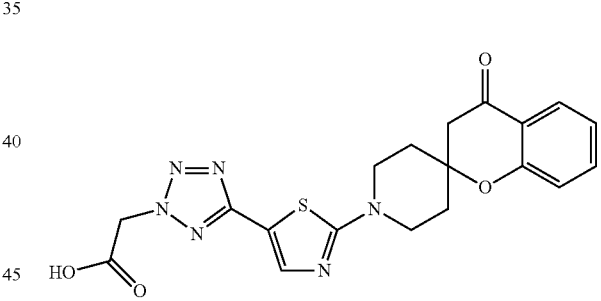

{5-[2-(4-Oxo-3,4-dihydro-1'H-spiro[chromene-2,4'-piperidin]-1'-yl)-1,3-thiazol-5-yl]-2H-tetrazol-2-yl}acetic acid Step 1: tert-Butyl{5-[2-(4-oxo-3,4-dihydro-1'H-spiro[chromene-2,4'-piperidin]-1'-yl)-1,3-thiazol-5-yl]-2H-tetrazol-2-yl}acetate. To a solution of tert-butyl[5-(2-bromo-1,3-thiazol-5-yl)-2H-tetrazol-2-yl]acetate (80 mg, 0.23 mmol) and spiro[chromene-2,4'-piperidin]-4(3H)-one (68 mg, 0.31 mmol) in NMP (1.25 mL) was added DBU (49 µL, 0.33 mmol). The tube was sealed and immersed into a preheated oil bath at 130° C., and stirred at this temperature for 20 min. The reaction was diluted with EtOAc, poured into 0.5 N HCl, extracted with EtOAc, washed with water (3×) and brine, dried (Na₂SO₄), filtered and concentrated. After evaporation of the solvent, the residue was purified by flash chromatography on SiO₂ (12 g; gradient from 0 to 60% EtOAc/hexanes) to afford the title product as a pink solid. LC-MS: m/z=483.1 (MH+). ¹H NMR (400 MHz, acetone-d₆): δ 7.85-7.82 (m, 2

H), 7.63 (ddd, 1 H), 7.17 (d, 1 H), 7.13-7.08 (m, 1 H), 5.58 (s, 2 H), 4.01-3.95 (m, 2 H), 3.61 (td, 2 H), 2.91 (s, 2 H), 2.25-2.19 (m, 2 H), 2.03-1.92 (m, 2 H), 1.51 (s, 9 H).

Step 2: {5-[2-(4-Oxo-3,4-dihydro-1'H-spiro[chromene-2, 4'-piperidin]-1'-yl)-1,3-thiazol-5-yl]-2H-tetrazol-2-yl}acetic acid. Water (0.4 mL) and formic acid (1.6 mL, 41.7 mmol) were added to tert-butyl{5-[2-(4-oxo-3,4-dihydro-1'H-spiro[chromene-2,4'-piperidin]-1'-yl)-1,3-thiazol-5-yl]-2H-tetrazol-2-yl}acetate (54 mg, 0.112 mmol) and the resulting solution was immersed into a preheated oil bath at 100° C. for 1 h. The reaction was poured into water, extracted with EtOAc, washed with water (3×) and brine, dried ($Na_2SO_4$), filtered and concentrated. The solvent was removed under vacuum and the resulting material was triturated with $Et_2O$/heptane, filtered and dried to afford the title product as a pink solid. LC-MS: m/z=427.1 (MH+). $^1$H NMR (400 MHz, DMSO-$d_6$): δ 13.78 (br s, 1 H), 7.88 (s, 1 H), 7.77 (dd, 1 H), 7.64-7.59 (m, 1 H), 7.15 (d, 1 H), 7.09 (t, 1 H), 5.69 (s, 2 H), 3.91-3.81 (m, 2 H), 3.54-3.43 (m, 2 H), 2.93 (s, 2 H), 2.06 (d, 2 H), 1.94-1.84 (m, 2 H).

EXAMPLE 5

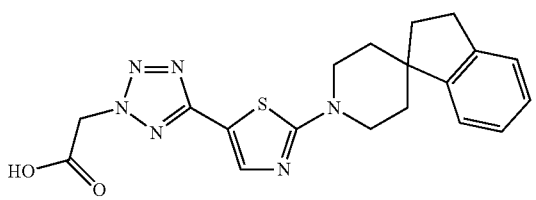 [SMILES: O=C(O)Cn1nnc(-c2cnc(N3CCC4(CCc5ccccc54)CC3)s2)n1]

{5-[2-(2,3-Dihydro-1'H-spiro[indene-1,4'-piperidin]-1'-yl)-1,3-thiazol-5-yl]-2H-tetrazol-2-yl}acetic acid Step 1: tert-Butyl{5-[2-(2,3-dihydro-1'H-spiro[indene-1,4'-piperidin]-1'-yl)-1,3-thiazol-5-yl]-2H-tetrazol-2-yl}acetate To a solution of tert-butyl[5-(2-bromo-1,3-thiazol-5-yl)-2H-tetrazol-2-yl]acetate (80 mg, 0.231 mmol) and 2,3-dihydrospiro[indene-1,4'-piperidinium]chloride (69.8 mg, 0.312 mmol) in NMP (1.25 mL) was added DBU (87 µL, 0.577 mmol). The tube was sealed and immersed into a preheated oil bath at 130° C., and stirred at this temperature for 20 min. The reaction was diluted with EtOAc, poured into 0.5 N HCl, extracted with EtOAc, washed with water (3×) and brine, dried ($Na_2SO_4$), filtered and concentrated. After evaporation of the solvents, the residue was purified by flash chromatography on $SiO_2$ (12 g) (gradient from 0 to 60% EtOAc/hexanes) to afford the title product as a white solid. LC-MS: m/z=453.2 (MH+).

Step 2: {5-[2-(2,3-Dihydro-1'H-spiro[indene-1,4'-piperidin]-1'-yl)-1,3-thiazol-5-yl]-2H-tetrazol-2-yl}acetic acid Water (0.4 mL) and formic acid (1.6 mL, 41.7 mmol) were added to tert-butyl {5-[2-(2,3-dihydro-1'H-spiro[indene-1,4'-piperidin]-1'-yl)-1,3-thiazol-5-yl]-2H-tetrazol-2-yl}acetate (43 mg, 0.095 mmol) and the solution was immersed into a preheated oil bath at 100° C. for 1 h. The reaction was poured into water, extracted with EtOAc, washed with water (3×) and brine, dried ($Na_2SO_4$), filtered and concentrated. Solvents were removed under vacuum and the material was triturated with $Et_2O$/heptane, filtered and dried to afford the title product as a white solid. $^1$H NMR (400 MHz, DMSO-$d_6$): δ 13.78 (br s, 1 H), 7.90 (s, 1 H), 7.27-7.22 (m, 2 H), 7.21-7.15 (m, 2 H), 5.69 (s, 2 H), 4.01 (d, 2 H), 3.42-3.35 (m, 2 H), 2.92 (t, 2 H), 2.13 (t, 2 H), 1.94 (td, 2 H), 1.62 (d, 2 H). LC-MS: m/z=397.1 (MH+).

EXAMPLE 6

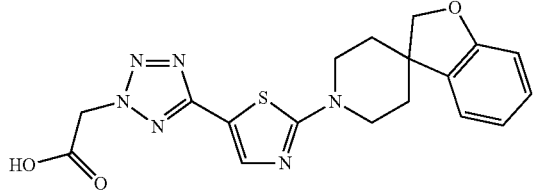 [SMILES: O=C(O)Cn1nnc(-c2cnc(N3CCC4(CC3)COc3ccccc34)s2)n1]

{5-[2-(1'H-Spiro[1-benzofuran-3,4'-piperidin]-1'-yl)-1,3-thiazol-5-yl]-2H-tetrazol-2-yl}acetic acid Step 1: tert-Butyl{5-[2-(1'H-spiro[1-benzofuran-3,4'-piperidin]-1'-yl)-1,3-thiazol-5-yl]-2H-tetrazol-2-yl}acetate To a solution of tert-butyl[5-(2-bromo-1,3-thiazol-5-yl)-2H-tetrazol-2-yl]acetate (80 mg, 0.231 mmol) and spiro[1-benzofuran-3,4'-piperidine] (74.3 mg, 0.393 mmol) in NMP (1.25 mL) was added DBU (70 µL, 0.464 mmol). The tube was sealed and immersed into a preheated oil bath at 130° C., and stirred at this temperature for 20 min. The reaction was diluted with EtOAc, poured into 0.5 N HCl, extracted with EtOAc, washed with water (3×) and brine, dried ($Na_2SO_4$), filtered and concentrated. After evaporation of the solvents, the residue was purified by flash chromatography on $SiO_2$ (12 g) (gradient 0 to 60% EtOAc/hexanes) to afford the title product as an off-white solid. LC-MS: m/z=455.1 (MH+).

Step 2: {5-[2-(1'H-Spiro[1-benzofuran-3,4'-piperidin]-1'-yl)-1,3-thiazol-5-yl]-2H-tetrazol-2-yl}acetic acid Water (0.4 mL) and formic acid (1.6 mL, 41.7 mmol) were added to tert-butyl{5-[2-(1'H-spiro[1-benzofuran-3,4'-piperidin]-1'-yl)-1,3-thiazol-5-yl]-2H-tetrazol-2-yl}acetate (57 mg, 0.125 mmol) and the solution was immersed into a preheated oil bath at 100° C. for 1 h. The reaction was poured into water, extracted with EtOAc, washed with water (3×) and brine, dried ($Na_2SO_4$), filtered and concentrated. Solvents were removed under vacuum and the material was triturated with $Et_2O$/heptane, filtered and dried to afford the title product as a white solid. LC-MS: m/z=399.1 (MH+). $^1$H NMR (400 MHz, DMSO-$d_6$): δ 13.79 (br s, 1 H), 7.90 (s, 1 H), 7.30 (d, 1 H), 7.15 (t, 1 H), 6.87 (t, 1 H), 6.82 (d, 1 H), 5.70 (s, 2 H), 4.52 (s, 2 H), 4.00 (d, 2 H), 3.39-3.28 (m, 2 H), 2.01 (td, 2 H), 1.81 (d, 2 H).

EXAMPLE 7

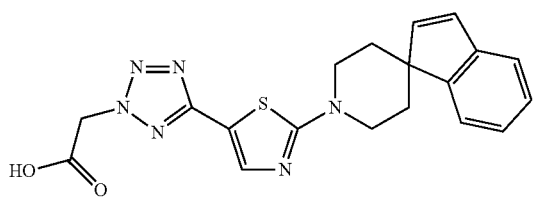 [SMILES: O=C(O)Cn1nnc(-c2cnc(N3CCC4(C=Cc5ccccc54)CC3)s2)n1]

{5-[2-(1'H-Spiro[indene-1,4'-piperidin]-1'-yl)-1,3-thia-
zol-5-yl]-2H-tetrazol-2-yl}acetic acid Step 1: tert-Butyl{5-[2-(1'H-spiro[indene-1,4'-piperidin]-1'-yl)-1,3-thiazol-5-yl]-2H-tetrazol-2-yl}acetate To a solution of tert-butyl[5-(2-bromo-1,3-thiazol-5-yl)-2H-tetrazol-2-yl]acetate (80 mg, 0.231 mmol) and spiro[indene-1,4'-piperidinium]chloride (87 mg, 0.393 mmol) in NMP (1.25 mL) was added DBU (87 µL, 0.577 mmol). The tube was sealed and immersed into a preheated oil bath at 130° C., and stirred at this temperature for 20 min. The reaction was diluted with EtOAc, poured into 0.5 N HCl, extracted with EtOAc, washed with water (3×) and brine, dried ($Na_2SO_4$), filtered and concentrated. After evaporation of the solvents, the residue was purified by flash chromatography on $SiO_2$ (12 g) (gradient 0 to 60% EtOAc/hexanes) to afford the title product as a white solid. LC-MS: m/z=451.1 (MH+).

Step 2: {5-[2-(1'H-Spiro[indene-1,4'-piperidin]-1'-yl)-1,3-thiazol-5-yl]-2H-tetrazol-2-yl}acetic acid Water (0.4 mL) and formic acid (1.6 mL, 41.7 mmol) were added to tert-butyl{5-[2-(1'H-spiro[indene-1,4'-piperidin]-1'-yl)-1,3-thiazol-5-yl]-2H-tetrazol-2-yl}acetate (61 mg, 0.135 mmol) and the solution was immersed into a preheated oil bath at 100° C. for 1 h. The reaction was poured into water, extracted with EtOAc, washed with water (3×) and brine, dried ($Na_2SO_4$), filtered and concentrated. Solvents were removed under vacuum and the material was triturated with $Et_2O$/heptane, filtered and dried to afford the title product as a white solid. LC-MS: m/z=395.0 (MH+). $^1$H NMR (400 MHz, DMSO-$d_6$): δ 13.80 (br s, 1 H), 7.93 (s, 1 H), 7.50 (d, 1 H), 7.38 (d, 1 H), 7.26 (t, 1 H), 7.23-7.17 (m, 2 H), 6.89 (d, 1 H), 5.71 (s, 2 H), 4.12 (d, 2 H), 3.57 (td, 2 H), 2.23 (td, 2 H), 1.35 (d, 2 H).

EXAMPLE 8

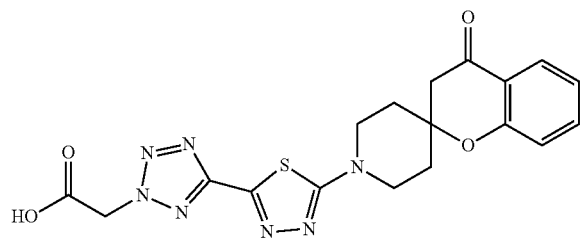 [SMILES: O=C(O)Cn1nnc(-c2nnc(N3CCC4(CC3)CC(=O)c3ccccc3O4)s2)n1]

{5-[5-(4-Oxo-3,4-dihydro-1'H-spiro[chromene-2,4'-piperidin]-1'-yl)-1,3,4-thiadiazol-2-yl]-2H-tetrazol-2-yl}acetic acid Step 1: tert-Butyl{5-[5-(4-oxo-3,4-dihydro-1'H-spiro[chromene-2,4'-piperidin]-1'-yl)-1,3,4-thiadiazol-2-yl]-2H-tetrazol-2-yl}acetate The title compound was prepared in a similar manner as that described for Example 5 (step 1) from tert-butyl[5-(2-bromo-1,3-thiazol-5-yl)-2H-tetrazol-2-yl]acetate and spiro[chromene-2,4'-piperidin]-4(3H)-one hydrochloride.

Step 2: {5-[5-(4-Oxo-3,4-dihydro-1'H-spiro[chromene-2,4'-piperidin]-1'-yl)-1,3,4-thiadiazol-2-yl]-2H-tetrazol-2-yl}acetic acid. To a solution of tert-butyl{5-[5-(4-oxo-3,4-dihydro-1'H-spiro[chromene-2,4'-piperidin]-1'-yl)-1,3,4-thiadiazol-2-yl]-2H-tetrazol-2-yl}acetate (30 mg, 0.062 mmol) in dichloromethane (0.5 mL) was added TFA (200 uL). The reaction was stirred at room temperature overnight. The reaction mixture was co-evaporated several times with $CH_2Cl_2$, ether and hexanes until residue became solid. The residue was purified by trituration in ether/hexanes (1:10) to afford the title compound as a solid. $^1$H NMR (500 MHz, DMSO-$d_6$): δ 7.78-7.75 (m, 1 H), 7.62 (d, 1 H), 7.16-7.12 (m, 1 H), 7.11-7.07 (m, 1 H), 5.83 (s, 2 H), 3.89-3.84 (m, 2 H), 3.65-3.57 (m, 2 H), 2.92 (s, 2 H), 2.11-2.03 (m, 2 H), 1.96-1.89 (m, 2 H). MS (+ESI): m/z 428 (MH+).

EXAMPLE 9

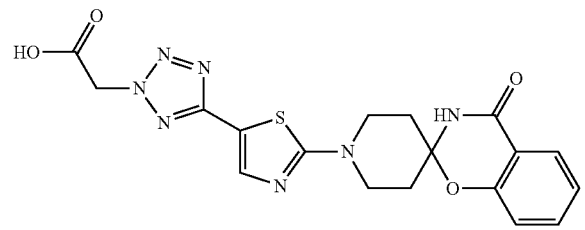 [SMILES: O=C(O)Cn1nnc(-c2cnc(N3CCC4(CC3)NC(=O)c3ccccc3O4)s2)n1]

{5-[2-(4-Oxo-3,4-dihydro-1'H-spiro[1,3-benzoxazine-2,4'-piperidin]-1'-yl)-1,3-thiazol-5-yl]-2H-tetrazol-2-yl}acetic acid Step 1: tert-Butyl{5-[2-(4-oxo-3,4-dihydro-1'H-spiro[1,3-benzoxazine-2,4'-piperidin]-1'-yl)-1,3-thiazol-5-yl]-2H-tetrazol-2-yl}acetate The title compound was prepared in a similar manner as that described for Example 5 (step 1) from tert-butyl[5-(2-bromo-1,3-thiazol-5-yl)-2H-tetrazol-2-yl]acetate and spiro[1,3-benzoxazine-2,4'-piperidin]-4(3H)-one.

Step 2: 2-Methoxyethyl{[5-(5-chloro-3,4-dihydro-1'H-spiro[chromene-2,4'-piperidin]-1'-yl)[1,3]thiazolo[5,4-d]pyrimidin-2-yl]amino}acetate The title compound was prepared from tert-butyl{5-[2-(4-oxo-3,4-dihydro-1'H-spiro[1,3-benzoxazine-2,4'-piperidin]-1'-yl)-1,3-thiazol-5-yl]-2H-tetrazol-2-yl}acetate and LiOH in THF—$H_2O$ at 0° C. HOAc was used to acidify in the work-up. $^1$H NMR (500 MHz, acetone-$d_6$): δ 7.88 (d, 1 H), 7.82 (s, 1 H), 7.58 (t, 1 H), 7.19-7.13 (m, 2 H), 5.38 (s, 2 H), 4.03 (d, 2 H), 3.58 (t, 2 H), 2.34 (d, 2 H), 2.15-2.05 (m, 2 H). MS (+ESI): m/z 428 (MH+).

EXAMPLE 10

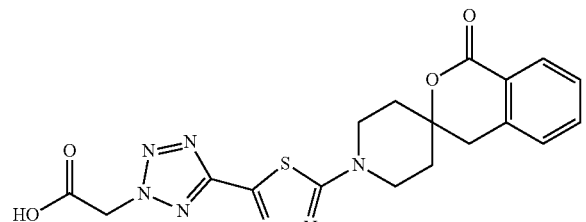

{5-[5-(1-Oxo-1,4-dihydro-1'H-spiro[isochromene-3,4'-piperidin]-1'-yl)-1,3,4-thiadiazol-2-yl]-2H-tetrazol-2-yl}acetic acid Step 1: tert-Butyl{5-[5-(1-oxo-1,4-dihydro-1'H-spiro[isochromene-3,4'-piperidin]-1'-yl)-1,3,4-thiadiazol-2-yl]-2H-tetrazol-2-yl}acetate The title compound was prepared in a similar manner as that described for Example 5 (step 1) from tert-butyl[5-(2-bromo-1,3-thiazol-5-yl)-2H-tetrazol-2-yl]acetate and spiro[isochromene-3,4'-piperidin]-1(4H)-one hydrochloride.

Step 2: {5-[5-(1-Oxo-1,4-dihydro-1'H-spiro[isochromene-3,4'-piperidin]-1'-yl)-1,3,4-thiadiazol-2-yl]-2H-tetrazol-2-yl}acetic acid The title compound was prepared in a similar manner as that described for Example 8 (step 2) from tert-butyl{5-[5-(1-oxo-1,4-dihydro-1'H-spiro[isochromene-3,4'-piperidin]-1'-yl)-1,3,4-thiadiazol-2-yl]-2H-tetrazol-2-yl}acetate and TFA. $^1$H NMR (500 MHz, DMSO-$d_6$): δ 7.97-7.94 (m, 1 H), 7.70-7.66 (m, 1 H), 7.49-7.45 (m, 1 H), 7.41-7.38 (m, 1 H), 5.83 (s, 2 H), 3.88-3.82 (m, 2 H), 3.62-3.57 (m, 2 H), 3.23 (s, 2 H), 2.03-1.89 (m, 4 H). MS (+ESI): m/z 428 (MH$^+$).

EXAMPLE 11

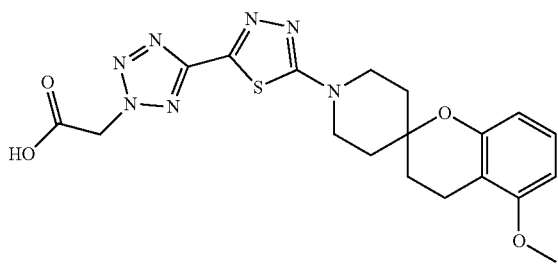 [SMILES: COc1cccc2c1CCC1(CCN(c3nnc(-c4nnn(CC(=O)O)n4)s3)CC1)O2]

{5-[5-(5-Methoxy-3,4-dihydro-1'H-spiro[chromene-2,4'-piperidin]-1'-yl)-1,3,4-thiadiazol-2-yl]-2H-tetrazol-2-yl}acetic acid Step 1: Benzyl 5-methoxy-4-oxo-3,4-dihydro-1'H-spiro[chromene-2,4'-piperidine]-1'-carboxylate. To a solution of benzyl 4-oxopiperidine-1-carboxylate (2.354 g, 10.09 mmol) in methanol (21 ml), freshly distilled pyrrolidine (1.2 ml, 14.51 mmol) followed by 1-(2-hydroxy-6-methoxyphenyl)ethanone (1.92 g, 11.55 mmol) was added and the mixture stirred under external temperature of +73° C. for 90 min, cooled down to room temperature, diluted with EtOAc and successively washed with aqueous 5% KHSO$_4$, 2M NaOH in water and water, dried over MgSO$_4$, filtered and concentrated. The oily residue was submitted to chromatographic column of silicagel eluted with 30% to 90% EtOAc in hexane to give the title product as white foam. MS: m/z=382.2 (MH+). $^1$H NMR (500 MHz, DMSO-$d_6$): δ 7.49 (t, 1 H), 7.36 (m, 5H), 6.65 (t, 2H), 5.10 (s, 2 H), 3.8 (m, overlapped with singulet at 3.79 ppm); 3.79 (s, 3H); 3.22 (bs, 2H), 2.72 (bs, 2H); 1.85 (d, 2H); 1.63 (m, 2H).

Step 2: Benzyl-4-hydroxy-5-methoxy-3,4-dihydro-1'H-spiro[chromene-2,4'-piperidine]-1'-carboxylate. A solution of benzyl 5-methoxy-4-oxo-3,4-dihydro-1'H-spiro[chromene-2,4'-piperidine]-1'-carboxylate (629.5 mg, 1.650 mmol) in THF (1.5 ml) and MeOH (3.00 ml) stirred at 0° C., was treated with solid sodium borohydride (190 mg, 5.02 mmol) slowly added portion wise. After the addition was completed, the final mixture was further stirred at the same temperature for 2 h, quenched at 0° C. by addition of acetone, diluted with EtOAc. The mixture was washed with saturated NaHCO$_3$, dried over Na$_2$SO$_4$, filtered and concentrated to give the title compound as a beige solid, which was used in the next step without further purification. MS: m/z=406.2 (MNa+).

Step 3: 5-methoxy-3,4-dihydrospiro[chromene-2,4'-piperidine] A degassed solution of benzyl4-hydroxy-5-methoxy-3,4-dihydro-1'H-spiro[chromene-2,4'-piperidine]-1'-carboxylate (576 mg, 1.502 mmol) in ethyl acetate (25 ml) was treated with solid 10% Pd on carbon (223 mg, 14 mol %), and then MeOH (150 ml) was added. After stirring under vacuum for 3 min, a balloon filled with H$_2$ was adapted and the final suspension stirred at room temperature for 6 h. Then 10 M HCl was added (3 mL) and stirring continued under H$_2$ overnight. The reaction was filtered through a pad of Celite™ and concentrated, then diluted with dichloromethane, washed with 2M NaOH in brine, dried over MgSO$_4$, filtered and concentrated to give the title compound as a colorless oil. MS: m/z=234.2 (MH+). $^1$H NMR (500 MHz, DMSO-$d_6$): δ 7.02 (t, 1 H), 6.45 (d, 1 H), 6.37 (d, 1 H), 4.10 (bs, 1 H), 3.75 (s, 3H); 2.70 (m, 2H), 2.54 (m, overlapped with signal of solvent); 2.65 (m, 2H), 1.72 (t, 2H), 1.58 (m, 2H), 1.46 (m, 2H).

Step 4: Ethyl{5-[5-(5-methoxy-3,4-dihydro-1'H-spiro[chromene-2,4'-piperidin]-1'-yl)-1,3,4-thiadiazol-2-yl]-2H-tetrazol-2-yl}acetate. A mixture of 5-methoxy-3,4-dihydrospiro[chromene-2,4'-piperidine] (201 mg, 1.0 mmol), ethyl[5-(5-bromo-1,3,4-thiadiazol-2-yl)-2H-tetrazol-2-yl]acetate (322 mg, 1.009 mmol) and K$_2$CO$_3$ (438 mg, 3.17 mmol) was suspended in dry DME (7 mL), the containing vial sealed and the mixture stirred under N$_2$ at external temperature of +80° C. for 80 minutes. The reaction was diluted with EtOAc, and washed with saturated NaHCO$_3$, then water, dried over MgSO$_4$, filtered and concentrated. The resulting brown oily residue was submitted to chromatographic column of silica gel and eluted with 40% to 80% EtOAc in hexane to give the title compound as a yellow foam. MS: m/z=472.2 (MH+). $^1$H NMR (500 MHz, DMSO-$d_6$): δ 7.08 (t, 1H), 6.52 (d, 1 H), 6.48 (d, 1 H), 5.95 (s, 2 H), 4.24 (q, 2H), 3.84 (m, 2H); 3.77 (s, 3H); 3.57 (m, 2H); 2.58 (m, 2H), 1.85-1.75 (m, 6H), 1.25 (t, 3H).

Step 5: {5-[5-(5-Methoxy-3,4-dihydro-1'H-spiro[chromene-2,4'-piperidin]-1'-yl)-1,3,4-thiadiazol-2-yl]-2H-tetrazol-2-yl}acetic acid. A solution of ethyl{5-[5-(5-methoxy-3,4-dihydro-1'H-spiro[chromene-2,4'-piperidin]-1'-yl)-1,3,4-thiadiazol-2-yl]-2H-tetrazol-2-yl}acetate (220 mg, 0.467 mmol) in THF (8 mL) and ethanol (3 mL), was treated with a solution of NaOH (303 mg, 7.58 mmol) in water (4.0 mL). The resulting suspension stirred at room temperature for 1.5 h, and then diluted with DCM, washed with a 5% KHSO$_4$ in water (final pH=1.5), dried over MgSO$_4$, filtered and concentrated. The resulting residue was triturated with Et$_2$O, filtered and stored under vacuum to the title compound as a pale yellow solid. MS: m/z=444.1 (MH+). $^1$H NMR (500 MHz, DMSO-$d_6$): δ 13.9 (bs, 1H); 7.05 (t, 1 H), 6.52 (d, 1 H), 6.48 (d, 1 H), 5.80 (s, 2 H), 3.85 (m, 2H); 3.76 (s, 3H); 3.55 (m, 2H); 2.58 (m, 2H), 1.85-1.75 (m, 6H).

EXAMPLE 12

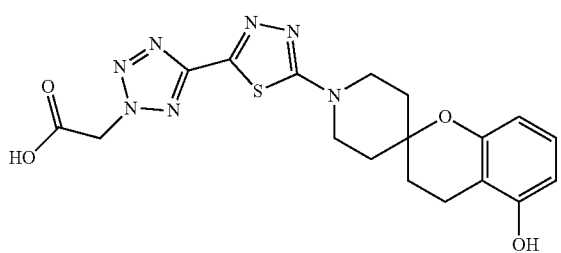 [SMILES: O=C(O)Cn1nnc(-c2nnc(N3CCC4(CCc5c(O)cccc5O4)CC3)s2)n1]

{5-[5-(5-Hydroxy-3,4-dihydro-1'H-spiro[chromene-2,4'-piperidin]-1'-yl)-1,3,4-thiadiazol-2-yl]-2H-tetrazol-2-yl}acetic acid The title compound was prepared through 5 synthetic steps in the same manner as described for example 13, but using 1-(2,6-dihydroxyphenyl)ethanone instead 1-(2-hydroxy-6-methoxyphenyl)ethanone in the step 1 the give the title compound as a white solid. MS: m/z=430.1 (MH+). $^1$H NMR (500 MHz, DMSO-$d_6$): δ 13.9 (bs, 1H); 9.40 (s, 1H); 6.90 (t, 1 H), 6.38 (d, 1 H), 6.30 (d, 1 H), 5.80 (s, 2 H), 3.85 (d, 2H); 3.56 (t, 2H); 2.55 (m, 2H, partially overlapped with signal of solvent), 1.85-1.75 (m, 6H).

EXAMPLE 13

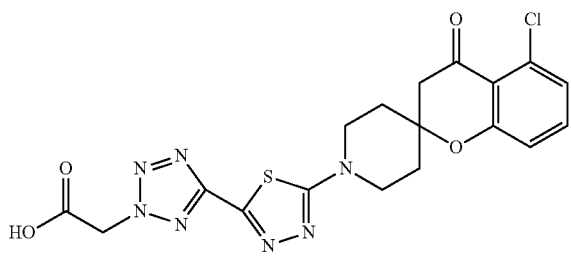 [SMILES: O=C(O)Cn1nnc(-c2nnc(N3CCC4(CC3)CC(=O)c3c(Cl)cccc3O4)s2)n1]

{5-[5-(5-Chloro-4-oxo-3,4-dihydro-1'H-spiro[chromene-2,4'-piperidin]-1'-yl)-1,3,4-thiadiazol-2-yl]-2H-tetrazol-2-yl}acetic acid Step 1: Ethyl{5-[5-(5-chloro-4-oxo-3,4-dihydro-1'H-spiro[chromene-2,4'-piperidin]-1'-yl)-1,3,4-thiadiazol-2-yl]-2H-tetrazol-2-yl}acetate. To a solution of Intermediate 5 (100 mg, 0.313 mmol) and 5-chlorospiro[chromene-2,4'-piperidin]-4(3H)-one hydrochloride (99 mg, 0.345 mmol) in THF (1.6 mL) was added TEA (131 µl, 0.94 mmol). The reaction mixture was warmed to 80° C. for 24 h. The solvent was evaporated under reduced pressure and the residue was purified by Combiflash™, eluting with a gradient of 40-80% EtOAc/hexanes to afford the title compound.

Step 2: {5-[5-(5-Chloro-4-oxo-3,4-dihydro-1'H-spiro[chromene-2,4'-piperidin]-1'-yl)-1,3,4-thiadiazol-2-yl]-2H-tetrazol-2-yl}acetic acid. The title compound was prepared in a similar manner as that described for Example 9 Step 2 from ethyl{5-[5-(5-chloro-4-oxo-3,4-dihydro-1'H-spiro[chromene-2,4'-piperidin]-1'-yl)-1,3,4-thiadiazol-2-yl]-2H-tetrazol-2-yl}acetate and LiOH at 0° C. $^1$H NMR (500 MHz, DMSO-$d_6$): δ 7.53 (t, 1 H), 7.14-7.11 (m, 2 H), 5.81 (s, 2 H), 3.89 (d, 2 H), 5.61 (t, 2 H), 2.99 (s, 2 H), 2.19 (d, 2 H), 1.95 (d, 2 H). MS (+ESI): m/z 463 (MH$^+$).

EXAMPLE 14

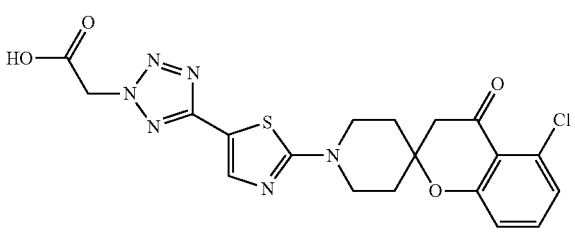

{5-[2-(5-Chloro-4-oxo-3,4-dihydro-1'H-spiro[chromene-2,4'-piperidin]-1'-yl)-1,3-thiazol-5-yl]-2H-tetrazol-2-yl}acetic acid Step 1: tert-Butyl{5-[2-(5-chloro-4-oxo-3,4-dihydro-1'H-spiro[chromene-2,4'-piperidin]-1'-yl)-1,3-thiazol-5-yl]-2H-tetrazol-2-yl}acetate. The title compound was prepared in a similar manner as that described for Example 5 Step 1 from Intermediate 3 and 5-chlorospiro[chromene-2,4'-piperidin]-4(3H)-one hydrochloride.

Step 2: {5-[2-(5-Chloro-4-oxo-3,4-dihydro-1'H-spiro[chromene-2,4'-piperidin]-1'-yl)-1,3-thiazol-5-yl]-2H-tetrazol-2-yl}acetic acid The title compound was prepared in a similar manner as that described for Example 9 Step 2 from tert-butyl{5-[2-(5-chloro-4-oxo-3,4-dihydro-1'H-spiro[chromene-2,4'-piperidin]-1'-yl)-1,3-thiazol-5-yl]-2H-tetrazol-2-yl}acetate and LiOH at 0° C. $^1$H NMR (400 MHz, DMSO-$d_6$): δ 7.90 (s, 1 H), 7.57 (t, 1 H), 7.18-7.11 (m, 2 H), 5.71 (s, 2 H), 3.85 (d, 2 H), 3.49 (t, 2 H), 2.95 (s, 2 H), 2.03 (d, 2 H), 1.89 (t, 2 H). MS (+ESI): m/z 462 (MH$^+$).

EXAMPLE 15

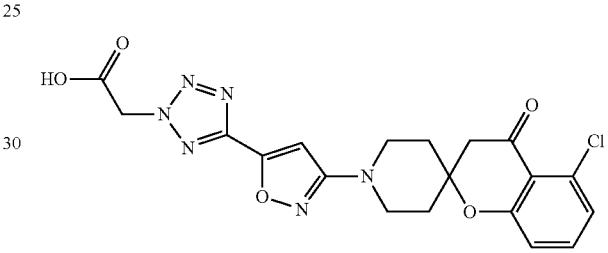

{5-[3-(5-Chloro-4-oxo-3,4-dihydro-1'H-spiro[chromene-2,4'-piperidin]-1'-yl)isoxazol-5-yl]-2H-tetrazol-2-yl}acetic acid Step 1: tert-Butyl{5-[3-(5-chloro-4-oxo-3,4-dihydro-1'H-spiro[chromene-2,4'-piperidin]-1'-yl)-4,5-dihydroisoxazol-5-yl]-2H-tetrazol-2-yl}acetate. To a solution of tert-butyl[5-(3-bromo-4,5-dihydroisoxazol-5-yl)-2H tetrazol-2-yl]acetate (200 mg, 0.602 mmol) and 5-chlorospiro[chromene-2,4'-piperidin]-4(3H)-one hydrochloride (191 mg, 0.662 mmol) in dry t-BuOH (3.01 mL) was added sodium bicarbonate (152 mg, 1.81 mmol). The mixture was warmed to 115° C. for 24 h. The reaction mixture was diluted with water (50 mL) and extracted with EtOAc (3×20 mL). The combined organic layers were dried (MgSO$_4$), filtered and evaporated under reduced pressure. The residue was purified by Combiflash™, eluting with a gradient of 20-70% EtOAc/Hexanes to afford the title compound.

Step 2: tert-Butyl{5-[3-(5-chloro-4-oxo-3,4-dihydro-1'H-spiro[chromene-2,4'-piperidin]-1'-yl)isoxazol-5-yl]-2H-tetrazol-2-yl}acetate. To a solution of tert-butyl{5-[3-(5-chloro-4-oxo-3,4-dihydro-1'H-spiro[chromene-2,4'-piperidin]-1'-yl)-4,5-dihydroisoxazol-5-yl]-2H-tetrazol-2-yl}acetate (52 mg, 0.103 mmol) in THF (2.1 mL) was added portion wise (3×) CAN (113 mg, 0.207 mmol) over 45 minutes. 15 minutes later, the reaction mixture was diluted with water (20 mL) extracted with EtOAc (3×10 mL). The combined organic layers were dried (MgSO$_4$), filtered and evaporated under reduced pressure. The resulting residue was purified by Combiflash™, eluting with a gradient of 20-70% EtOAc/Hexanes to afford the title compound.

Step 3: {5-[3-(5-Chloro-4-oxo-3,4-dihydro-1'H-spiro [chromene-2,4'-piperidin]-1'-yl)isoxazol-5-yl]-2H-tetrazol-2-yl}acetic acid The title compound was prepared in a similar manner as that described for Example 8 Step 2 from tert-butyl{5-[3-(5-chloro-4-oxo-3,4-dihydro-1'H-spiro [chromene-2,4'-piperidin]-1'-yl)isoxazol-5-yl]-2H-tetrazol-2-yl}acetate and TFA. $^1$H NMR (500 MHz, DMSO-d$_6$): δ 7.52 (t, 1 H), 7.25 (s, 1 H), 7.11 (d, 2 H), 5.83 (s, 2 H), 3.67 (d, 2 H), 3.29 (t, 2 H), 2.92 (s, 2 H), 1.97 (d, 2 H), 185 (t, 2 H). MS (+ESI): m/z 446 (MH$^+$).

EXAMPLE 16

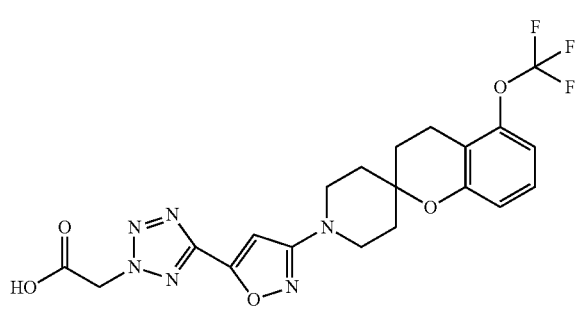 [SMILES: O=C(O)Cn1nnc(-c2cc(N3CCC4(CCc5c(OC(F)(F)F)cccc5O4)CC3)no2)n1]

(5-{3-[5-(Trifluoromethoxy)-3,4-dihydro-1H-spiro [chromene-2,4'-piperidin]-1'-yl]isoxazol-5-yl}-2H-tetrazol-2-yl)acetic acid Step 1: tert-Butyl (5-{3-[5-(trifluoromethoxy)-3,4-dihydro-1'H-spiro[chromene-2,4'-piperidin]-1'-yl]-4,5-dihydroisoxazol-5-yl}-2H-tetrazol-2-yl)acetate A suspension of dried Na$_2$CO$_3$ (694 mg, 6.55 mmol) in anhydrous t-BuOH was added 5-(trifluoromethoxy)-3,4-dihydrospiro [chromene-2,4'-piperidinium]chloride (848 mg, 2.62 mmol) (Intermediate 8) and tert-butyl[5-(3-bromo-4,5-dihydroisoxazol-5-yl)-2H-tetrazol-2-yl]acetate (725 mg, 2.183 mmol) (Intermediate 7). The mixture was directly heated to 115° C. for 24 h. The reaction mixture was diluted with MTBE, poured into aq. NH$_4$Cl and extracted with EtOAc. The organic layer was washed with water and brine. The aqueous phases were back extracted with EtOAc. The combined organic layers were dried (MgSO$_4$), filtered and evaporated under reduced pressure. The residue was purified by column chromatography on SiO$_2$ (50 g, gradient from 0 to 70% EtOAc/hexanes) to afford the title compound as a white solid. LC-MS: m/z=539.1 (MH+).

Step 2: tert-Butyl (5-{3-[5-(trifluoromethoxy)-3,4-dihydro-1'H-spiro[chromene-2,4'-piperidin]-1'-yl]isoxazol-5-yl}-2H-tetrazol-2-yl)acetate To tert-butyl (5-{3-[5-(trifluoromethoxy)-3,4-dihydro-1'H-spiro[chromene-2,4'-piperidin]-1'-yl]-4,5-dihydro isoxazol-5-yl}-2H-tetrazol-2-yl)acetate (880 mg, 1.634 mmol) in THF (10 mL) was added in one portion CAN (1344 mg, 2.451 mmol) at −78° C. The reaction was slowly warmed to 0° C. for 40 min. Then the reaction mixture was cooled to −78° C., diluted with water, and extracted with EtOAc. The organic layer was washed with brine. The aqueous phases were back extracted with EtOAc. The combined organic layers were dried (MgSO$_4$), filtered and evaporated under reduced pressure. The resulting residue was purified by column chromatography on SiO$_2$ (50 g, gradient from 0 to 50% EtOAc/hexanes) to afford the title compound as a white solid. LC-MS: m/z=537.1 (MH+).

Step 3: (5-{3-[5-(Trifluoromethoxy)-3,4-dihydro-1'H-spiro[chromene-2,4'-piperidin]-1'-yl]isoxazol-5-yl}-2H-tetrazol-2-yl)acetic acid Water (0.8 mL) and formic acid (3.2 mL, 83 mmol) were added to tert-butyl (5-{3-[5-(trifluoromethoxy)-3,4-dihydro-1'H-spiro[chromene-2,4'-piperidin]-1'-yl]isoxazol-5-yl}-2H-tetrazol-2-yl)acetate (378 mg, 0.705 mmol) and the final solution was immersed into a preheated oil bath at 100° C. for 30 min. The reaction was poured into water and extracted with EtOAc. The organic layer was washed with water (5×) and brine, dried (Na$_2$SO$_4$), filtered and concentrated. The resulting residue was triturated with Et$_2$O/heptane, filtered and dried to afford the title compound as a white solid. LC-MS: m/z=481.1 (MH+). $^1$H NMR (400 MHz, DMSO-d$_6$): δ 13.92 (br s, 1 H), 7.28-7.20 (m, 2 H), 6.93-6.88 (m, 2 H), 5.85 (s, 2 H), 3.69-3.59 (m, 2 H), 3.33-3.27 (m, 2 H), 2.74 (t, 2 H), 1.88 (t, 2 H), 1.86-1.70 (m, 4 H).

EXAMPLE 17

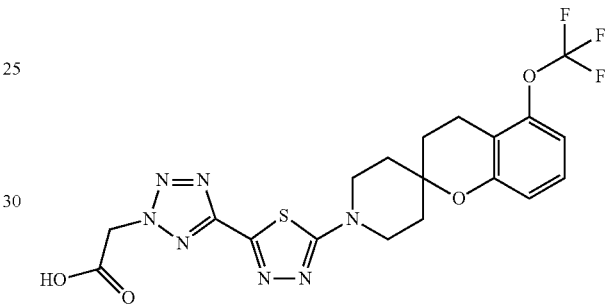

(5-{5-[5-(Trifluoromethoxy)-3,4-dihydro-1'H-spiro [chromene-2,4'-piperidin]-1'-yl]-1,3,4-thiadiazol-2-yl}-2H-tetrazol-2-yl)acetic acid Step 1: tert-Butyl (5-{5-[5-(trifluoromethoxy)-3,4-dihydro-1'H-spiro[chromene-2,4'-piperidin]-1'-yl]-1,3,4-thiadiazol-2-yl}-2H-tetrazol-2-yl)acetate A solution of tert-butyl[5-(5-bromo-1,3,4-thiadiazol-2-yl)-2H-tetrazol-2-yl]acetate (10.5 g, 30.2 mmol; Intermediate 6) and 5-(trifluoromethoxy)-3,4-dihydrospiro[chromene-2,4'-piperidinium] chloride (10.77 g, 33.3 mmol; Intermediate 8) in THF (30 mL) was treated with Hunig's base (15.85 mL, 91 mmol). The reaction mixture was heated to 80° C. for 6 h. Then the reaction was diluted with EtOAc, poured into 0.5 N HCl, and extracted with EtOAc. The organic layer was separated, washed with water (2×) and brine, dried (Na$_2$SO$_4$), filtered and concentrated. After evaporation of the solvents, the resulting residue was purified by flash chromatography on SiO$_2$ (gradient 0 to 30% MTBE/toluene) followed by multiple recrystallizations from toluene to afford the title compound as a white solid. LC-MS: m/z=554.1 (MH+). $^1$H NMR (400 MHz, acetone-d$_6$): δ 7.28 (t, 1 H), 6.97 (d, 1 H), 6.92 (d, 1 H), 5.70 (s, 2 H), 4.04-3.95 (m, 2 H), 3.77-3.67 (m, 2 H), 2.89-2.84 (m, 2 H), 2.05-1.91 (m, 6 H), 1.52 (s, 9 H).

Step 2: (5-{5-[5-(Trifluoromethoxy)-3,4-dihydro-1'H-spiro[chromene-2,4'-piperidin]-1'-yl]-1,3,4-thiadiazol-2-yl}-2H-tetrazol-2-yl)acetic acid Water (13 mL) and formic acid (52 mL, 1356 mmol) were added to tert-butyl (5-{5-[5-(trifluoromethoxy)-3,4-dihydro-1'H-spiro[chromene-2,4'-piperidin]-1'-yl]-1,3,4-thiadiazol-2-yl}-2H-tetrazol-2-yl)acetate (12.0 g, 21.68 mmol) and the final suspension was heated to 100° C. for 30 min. The reaction was poured into water (400 mL), extracted with EtOAc (300 mL), washed with water (4×400 mL) and brine (400 mL). The aqueous phases were back-extracted with EtOAc (300 mL). The organic layers were combined, dried (MgSO$_4$), filtered and concentrated. After evaporation of the solvents and co-evaporation with Et$_2$O/heptane, the residue was triturated with 5% Et$_2$O in pentane (400 mL) overnight, filtered and dried to give the title compound as a white solid. LC-MS: m/z=498.0 (MH+). $^1$H NMR (400 MHz, DMSO-d$_6$): δ 13.90 (br s, 1 H), 7.26 (t, 1 H), 6.96-6.88 (m, 2 H), 5.84 (s, 2 H), 3.92-3.82 (m, 2 H), 3.66-3.55 (m, 2 H), 2.75 (t, 2 H), 1.95-1.81 (m, 6 H).

EXAMPLE 18

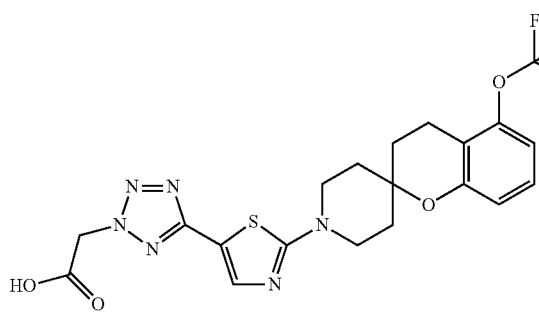

(5-{2-[5-(Trifluoromethoxy)-3,4-dihydro-1'H-spiro[chromene-2,4'-piperidin]-1'-yl]-1,3-thiazol-5-yl}-2H-tetrazol-2-yl)acetic acid Step 1: tert-Butyl (5-{2-[5-(trifluoromethoxy)-3,4-dihydro-1'H-spiro[chromene-2,4'-piperidin]-1'-yl]-1,3-thiazol-5-yl}-2H-tetrazol-2-yl)acetate A solution of tert-butyl[5-(5-bromo-1,3-thiazol-2-yl)-2H-tetrazol-2-yl]acetate (7.5 g, 21.7 mmol; Intermediate 3) and 5-(trifluoromethoxy)-3,4-dihydrospiro[chromene-2,4'-piperidinium]chloride (7.71 g, 23.8 mmol; Intermediate 8) in THF (20 mL) was treated with Hunig's base (11.4 mL, 65.0 mmol). The reaction was heated to 80° C. and stirred at this temperature under reflux overnight, then the reaction was diluted with EtOAc, and poured into 0.5 N HCl. The resulting mixture was extracted with EtOAc, washed with 0.5 N HCl (2×) and brine, dried (MgSO$_4$), filtered and concentrated. After evaporation of the solvents, the resulting residue was purified by flash chromatography on SiO$_2$ (gradient 0 to 30% EtOAc/toluene) followed by multiple successive recrystallizations from toluene/heptane (1:1) with cooling to 0° C. to afford the title compound as a white solid. LC-MS: m/z=553.1 (MH+). $^1$H NMR (400 MHz, acetone-d$_6$): δ 7.86 (s, 1 H), 7.27 (t, 1 H), 6.96 (d, 1 H), 6.91 (d, 1 H), 5.57 (s, 2 H), 4.01-3.91 (m, 2 H), 3.65-3.53 (m, 2 H), 2.89-2.82 (m, 2 H), 2.02-1.84 (m, 6 H), 1.51 (s, 9 H).

Step 2: (5-{2-[5-(Trifluoromethoxy)-3,4-dihydro-1'H-spiro[chromene-2,4'-piperidin]-1'-yl]-1,3-thiazol-5-yl}-2H-tetrazol-2-yl)acetic acid Water (7.6 mL) and formic acid (30 mL, 782 mmol) were added to tert-butyl (5-{2-[5-(trifluoromethoxy)-3,4-dihydro-1'H-spiro[chromene-2,4'-piperidin]-1'-yl]-1,3-thiazol-5-yl}-2H-tetrazol-2-yl)acetate (7.80 g, 14.1 mmol) and the final solution was heated to 100° C. for 2 h. The reaction was poured into water (400 mL), extracted with EtOAc (300 mL), washed with water (4×400 mL) and brine (400 mL). The aqueous phases were back-extracted with EtOAc (300 mL) and the organic layers were combined, dried (MgSO$_4$), filtered and concentrated. After evaporation of the solvents, the resulting residue was co-evaporated with toluene (100 mL) and dried under vacuum to give the title compound. LC-MS: m/z=497 (MH+). $^1$H NMR (500 MHz, DMSO-d$_6$): δ 13.77 (br s, 1 H), 7.88 (s, 1 H), 7.24 (t, 1 H), 6.93-6.87 (m, 2 H), 5.67 (s, 2 H), 3.88-3.80 (m, 2 H), 3.54-3.44 (m, 2 H), 2.74 (t, 2 H), 1.92-1.76 (m, 6 H).

EXAMPLE 19

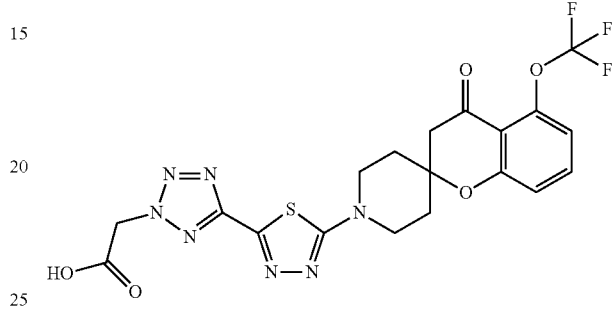

(5-{5-[4-Oxo-5-(trifluoromethoxy)-3,4-dihydro-1'H-spiro[chromene-2,4'-piperidin]-1'-yl]-1,3,4-thiadiazol-2-yl}-2H-tetrazol-2-yl)acetic acid The title compound was prepared, as a white solid, through two synthetic steps in the same manner as described for Example 17, but using 4-oxo-5-(trifluoromethoxy)-3,4-dihydrospiro[chromene-2,4'-piperidinium]chloride (Intermediate 9) in step 1. LC-MS: m/z=512 (MH+). $^1$H NMR (400 MHz, acetone-d$_6$): δ 7.70 (t, 1 H), 7.27 (dd, 1 H), 7.04 (d, 1 H), 5.70 (s, 2 H), 4.04-3.97 (m, 2 H), 3.79-3.68 (m, 2 H), 2.97 (s, 2 H), 2.25 (d, 2 H), 2.14-2.04 (m, 2 H).

EXAMPLE 20

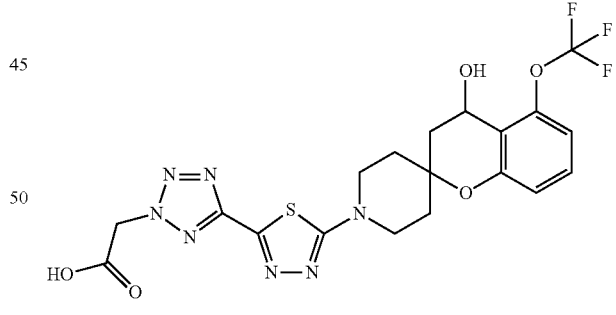

(5-{5-[4-Hydroxy-5-(trifluoromethoxy)-3,4-dihydro-1'H-spiro[chromene-2,4'-piperidin]-1'-yl]-1,3,4-thiadiazol-2-yl}-2H-tetrazol-2-yl)acetic acid A suspension of (5-{5-[4-oxo-5-(trifluoromethoxy)-3,4-dihydro-1'H-spiro[chromene-2,4'-piperidin]-1'-yl]-1,3,4-thiadiazol-2-yl}-2H-tetrazol-2-yl)acetic acid (146 mg, 0.285 mmol; Example 19) in THF (3 mL) and MeOH (3 mL) was treated with NaBH$_4$ (86 mg, 2.284 mmol) at −78° C. The suspension was warmed to 0° C. and stirred for 30 min. The suspension was then cooled to −78° C. and acetone was added to quench the excess of hydride before to be warmed to 0° C. The reaction mixture was poured into 10% aqueous AcOH and the aqueous media was extracted with EtOAc. The organic layer was washed with water (2×), and brine, dried (MgSO₄), filtered and concentrated. The resulting residue was triturated with Et₂O/heptane, filtered and dried to give the title compound as a white solid. LC-MS: m/z=514 (MH⁺). ¹H NMR (400 MHz, acetone-d₆): δ 7.36 (t, 1 H), 6.98 (d, 1 H), 6.97-6.93 (m, 1 H), 5.53 (s, 2 H), 5.12 (dd, 1 H), 4.03-3.97 (m, 1 H), 3.91-3.79 (m, 2 H), 3.64-3.57 (m, 1 H), 2.54-2.48 (m, 1 H), 2.30 (dd, 1 H), 2.12-2.06 (m, 4 H).

EXAMPLE 21

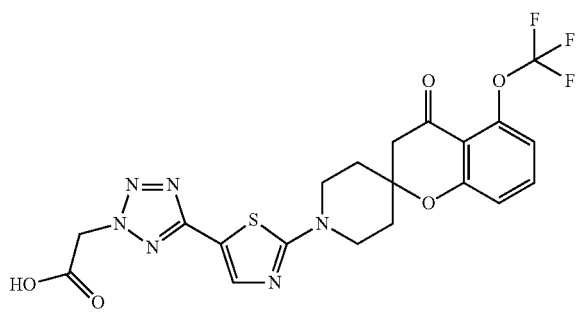 [SMILES: O=C(O)Cn1nnc(-c2cnc(N3CCC4(CC3)CC(=O)c3c(OC(F)(F)F)cccc3O4)s2)n1]

(5-{2-[4-Oxo-5-(trifluoromethoxy)-3,4-dihydro-1'H-spiro[chromene-2,4'-piperidin]-1'-yl]-1,3-thiazol-5-yl}-2H-tetrazol-2-yl)acetic acid Step 1: tert-Butyl (5-{2-[4-oxo-5-(trifluoromethoxy)-3,4-dihydro-1'H-spiro[chromene-2,4'-piperidin]-1'-yl]-1,3-thiazol-5-yl}-2H-tetrazol-2-yl)acetate To a solution of tert-butyl [5-(2-bromo-1,3-thiazol-5-yl)-2H-tetrazol-2-yl]acetate (308 mg, 0.888 mmol) (Intermediate 2) and 4-oxo-5-(trifluoromethoxy)-3,4-dihydrospiro[chromene-2,4'-piperidinium] chloride (250 mg, 0.740 mmol; Intermediate 9) in NMP (1 mL) was added DBU (0.223 mL, 1.48 mmol). The tube was sealed and immersed into a preheated oil bath at 130° C., and stirred at this temperature for 20-30 min. The reaction was diluted with EtOAc, poured into 0.5 N HCl, extracted with EtOAc, washed with water (3×) and brine, dried (MgSO4), filtered and concentrated. After evaporation of the solvents, the resulting residue was purified by flash chromatography on SiO₂ (24 g, gradient 0 to 70% EtOAc/hexanes) to give the title compound as a foamy yellow solid. LC-MS: m/z=567.1 (MH⁺).

Step 2: (5-{2-[4-Oxo-5-(trifluoromethoxy)-3,4-dihydro-1'H-spiro[chromene-2,4'-piperidin]-1'-yl]-1,3-thiazol-5-yl}-2H-tetrazol-2-yl)acetic acid Water (0.4 mL) and formic acid (1.6 mL, 41.7 mmol) were added to tert-butyl (5-{2-[4-oxo-5-(trifluoromethoxy)-3,4-dihydro-1'H-spiro[chromene-2,4'-piperidin]-1'-yl]-1,3-thiazol-5-yl}-2H-tetrazol-2-yl)acetate (328 mg, 0.579 mmol) and the final solution was immersed into a preheated oil bath at 100° C. for 45 min. The reaction was poured into water, extracted with EtOAc, washed with water (3×) and brine, dried (MgSO₄), filtered and concentrated. After evaporation of the solvents, the resulting material was triturated with Et₂O/heptane, filtered and dried to give the title compound as an off-white solid. LC-MS: m/z=511 (MH⁺). ¹H NMR (500 MHz, DMSO-d₆): δ 13.74 (br s, 1 H), 7.88 (s, 1 H), 7.68 (t, 1 H), 7.23 (d, 1 H), 7.04 (d, 1 H), 5.68 (s, 2 H), 3.89-3.83 (m, 2 H), 3.52-3.45 (m, 2 H), 2.95 (s, 2 H), 2.05 (d, 2 H), 1.94-1.89 (m, 2 H).

EXAMPLE 22

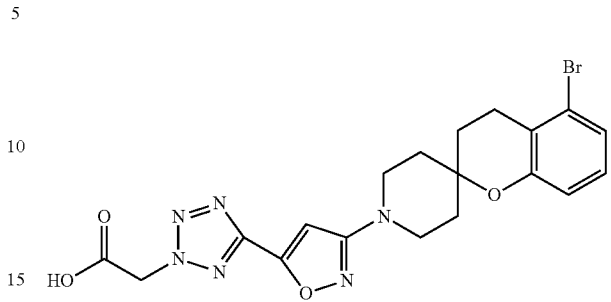

{5-[3-(5-Bromo-3,4-dihydro-1'H-spiro[chromene-2,4'-piperidin]-1'-yl)isoxazol-5-yl]-2H-tetrazol-2-yl}acetic acid The title compound was prepared, as a white solid, through three synthetic steps in the same manner as described for Example 16, but using 5-bromo-3,4-dihydrospiro[chromene-2,4'-piperidinium]chloride (Intermediate 10) in step 1. LC-MS: m/z=475.0, 477.0 (MH+). ¹H NMR (400 MHz, DMSO-d₆): δ 13.91 (br s, 1 H), 7.27 (s, 1 H), 7.18 (d, 1 H), 7.08 (t, 1 H), 6.89 (d, 1 H), 5.85 (s, 2 H), 3.67-3.58 (m, 2 H), 3.33-3.24 (m, 2 H), 2.71 (t, 2 H), 1.91 (t, 2 H), 1.80-1.74 (m, 4 H).

EXAMPLE 23

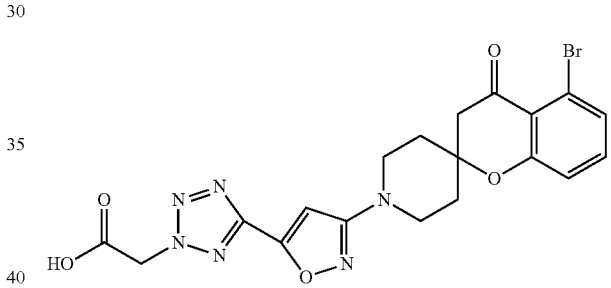

{5-[3-(5-Bromo-4-oxo-3,4-dihydro-1'H-spiro[chromene-2,4'-piperidin]-1'-yl)isoxazol-5-yl]-2H-tetrazol-2-yl}acetic acid The title compound was prepared, as a yellow solid, through three synthetic steps in the same manner as described for Example 16, but using 5-bromospiro[chromene-2,4'-piperidin]-4(3H)-one (Intermediate 11) in step 1. LC-MS: m/z=489.0, 491.0 (MH+). ¹H NMR (500 MHz, acetone-d₆): δ 7.41 (t, 1 H), 7.30 (dd, 1 H), 7.16 (dd, 1 H), 6.96 (s, 1 H), 5.68 (s, 2 H), 3.75-3.67 (m, 2 H), 3.43-3.34 (m, 2 H), 2.91 (s, 2 H), 2.13-2.04 (m, 2 H), 1.98-1.88 (m, 2 H).

EXAMPLE 24

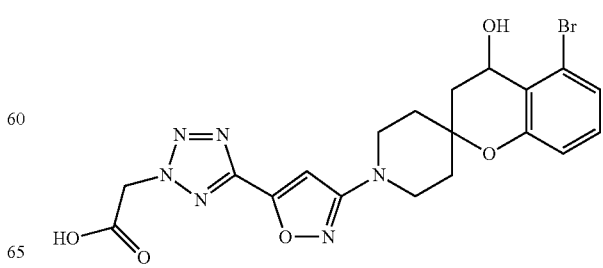

{5-[3-(5-Bromo-4-hydroxy-3,4-dihydro-1'H-spiro[chromene-2,4'-piperidin]-1'-yl)isoxazol-5-yl]-2H-tetrazol-2-yl}acetic acid The title compound was prepared, as an off-white solid, in the same manner as described for Example 20, but using {5-[3-(5-bromo-4-oxo-3,4-dihydro-1'H-spiro[chromene-2,4'-piperidin]-1'-yl)isoxazol-5-yl]-2H-tetrazol-2-yl}acetic acid (Example 23). LC-MS: m/z=491.0, 493.0 (MH+). ¹H NMR (500 MHz, DMSO-d₆): δ 13.90 (br s, 1 H), 7.25 (s, 1 H), 7.19-7.11 (m, 2 H), 6.90 (d, 1 H), 5.83 (s, 2 H), 5.33 (d, 1 H), 4.78 (br s, 1 H), 3.66-3.60 (m, 1 H), 3.56-3.50 (m, 1 H), 3.49-3.41 (m, 1 H), 3.24-3.15 (m, 1 H), 2.25-2.15 (m, 2 H), 1.95 (dd, 1 H), 1.92-1.82 (m, 2 H), 1.77 (d, 1 H).

EXAMPLE 25

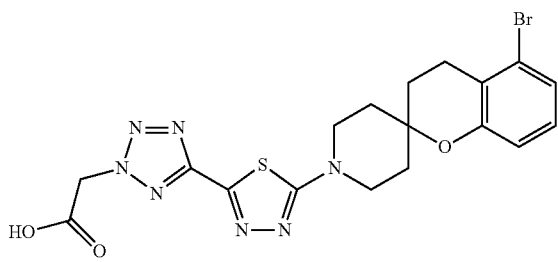

{5-[5-(5-Bromo-3,4-dihydro-1'H-spiro[chromene-2,4'-piperidin]-1'-yl)-1,3,4-thiadiazol-2-yl]-2H-tetrazol-2-yl}acetic acid The title compound was prepared, as a white solid, through two synthetic steps in the same manner as described for Example 17, but using 5-bromo-3,4-dihydrospiro[chromene-2,4'-piperidinium]chloride (Intermediate 10) in step 1. LC-MS: m/z=492.0, 494.0 (MH+). ¹HNMR (500 MHz, DMSO-d₆): δ 13.88 (br s, 1 H), 7.18 (d, 1 H), 7.09 (t, 1 H), 6.90 (d, 1 H), 5.83 (s, 2 H), 3.88-3.81 (m, 2 H), 3.63-3.55 (m, 2 H), 2.71 (t, 2 H), 1.92 (t, 2 H), 1.87-1.80 (m, 4 H).

EXAMPLE 26

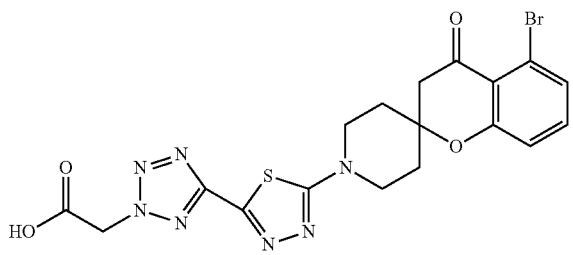 [SMILES: O=C(O)Cn1nnc(-c2nnc(N3CCC4(CC3)CC(=O)c3c(Br)cccc3O4)s2)n1]

{5-[5-(5-Bromo-4-oxo-3,4-dihydro-1'H-spiro[chromene-2,4'-piperidin]-1'-yl)-1,3,4-thiadiazol-2-yl]-2H-tetrazol-2-yl}acetic acid The title compound was prepared, as a white solid, through two synthetic steps in the same manner as described for Example 17, but using 5-bromospiro[chromene-2,4'-piperidin]-4(3H)-one (Intermediate 11) in step 1. LC-MS: m/z=505.9, 507.9 (MH+). ¹H NMR (500 MHz, DMSO-d₆): δ 13.88 (br s, 1 H), 7.45 (t, 1 H), 7.34 (dd, 1 H), 7.18 (dd, 1 H), 5.83 (s, 2 H), 3.90-3.83 (m, 2 H), 3.65-3.55 (m, 2 H), 2.97 (s, 2 H), 2.05 (d, 2 H), 1.98-1.89 (m, 2H).

EXAMPLE 27

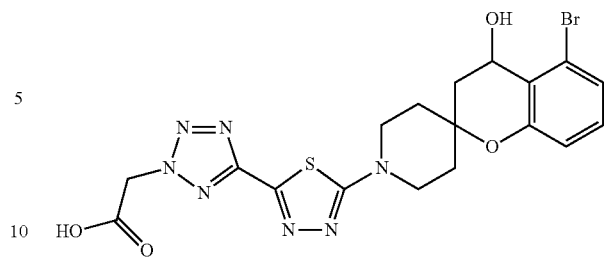

{5-[5-(5-Bromo-4-hydroxy-3,4-dihydro-1'H-spiro[chromene-2,4'-piperidin]-1'-yl)-1,3,4-thiadiazol-2-yl]-2H-tetrazol-2-yl}acetic acid The title compound was prepared, as a white solid, in the same manner as described for Example 20, but using {5-[5-(5-Bromo-4-oxo-3,4-dihydro-1'H-spiro[chromene-2,4'-piperidin]-1'-yl)-1,3,4-thiadiazol-2-yl]-2H-tetrazol-2-yl}acetic acid (Example 26). LC-MS: m/z=507.9, 509.9 (MH+). ¹H NMR (500 MHz, DMSO-d₆): δ 13.89 (br s, 1 H), 7.20 (dd, 1 H), 7.15 (t, 1 H), 6.92 (dd, 1 H), 5.82 (s, 2 H), 5.38 (d, 1 H), 4.83-4.77 (m, 1 H), 3.91-3.87 (m, 1 H), 3.79-3.70 (m, 2 H), 3.54-3.46 (m, 1 H), 2.34 (d, 1 H), 2.20 (dd, 1 H), 2.02-1.85 (m, 4 H).

EXAMPLE 28

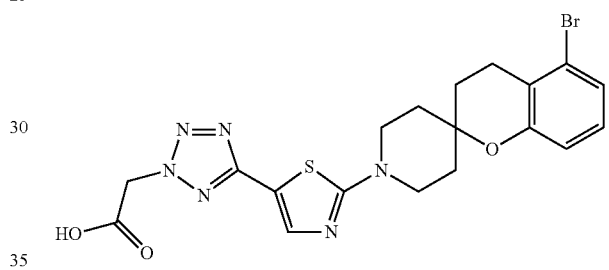

{5-[2-(5-Bromo-3,4-dihydro-1'H-spiro[chromene-2,4'-piperidin]-1'-yl)-1,3-thiazol-5-yl]-2H-tetrazol-2-yl}acetic acid The title compound was prepared, as a white solid, through two synthetic steps in the same manner as described for Example 21, but using 5-bromo-3,4-dihydrospiro[chromene-2,4'-piperidinium]chloride (Intermediate 10) in step 1. LC-MS: m/z=491, 493 (MH⁺). ¹H NMR (500 MHz, DMSO-d₆): δ 13.78 (br s, 1 H), 7.87 (s, 1 H), 7.18 (d, 1 H), 7.08 (t, 1 H), 6.90 (d, 1 H), 5.67 (s, 2 H), 3.86-3.79 (m, 2 H), 3.53-3.43 (m, 2 H), 2.71 (t, 2 H), 1.92 (t, 2 H), 1.86-1.74 (m, 4 H).

EXAMPLE 29

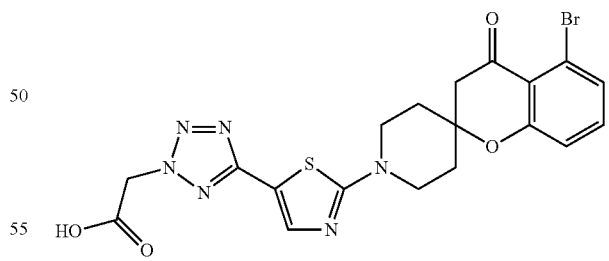

{5-[2-(5-Bromo-4-oxo-3,4-dihydro-1'H-spiro[chromene-2,4'-piperidin]-1'-yl)-1,3-thiazol-5-yl]-2H-tetrazol-2-yl}acetic acid The title compound was prepared, as a pink solid, through 2 synthetic steps in the same manner as described for Example 21, but using 5-bromospiro[chromene-2,4'-piperidin]-4(3H)-one (Intermediate 11) in step 1. LC-MS: m/z=505, 507 (MH⁺). ¹H NMR (400 MHz, DMSO-d₆): δ 13.78 (br s, 1 H), 7.89 (s, 1 H), 7.45 (t, 1 H), 7.34 (d, 1 H), 7.18 (d, 1 H), 5.70 (s, 2 H), 3.90-3.79 (m, 2 H), 3.56-3.44 (m, 2 H), 2.97 (s, 2 H), 2.04 (d, 2 H), 1.95-1.82 (m, 2 H).

EXAMPLE 30

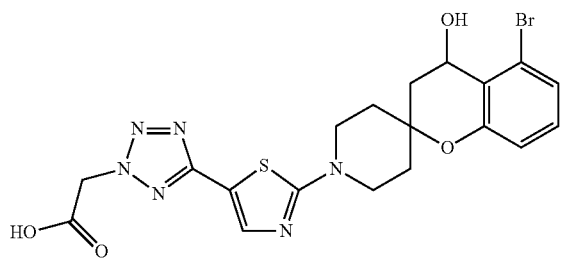

{5-[2-(5-Bromo-4-hydroxy-3,4-dihydro-1'H-spiro[chromene-2,4'-piperidin]-1'-yl)-1,3-thiazol-5-yl]-2H-tetrazol-2-yl}acetic acid The title compound was prepared, as an off-white solid, in the same manner as described for Example 20, but using {5-[2-(5-bromo-4-oxo-3,4-dihydro-1'H-spiro[chromene-2,4'-piperidin]-1'-yl)-1,3-thiazol-5-yl]-2H-tetrazol-2-yl}acetic acid (Example 29). LC-MS: m/z=507.9, 509.9 (MH+). $^1$H NMR (500 MHz, DMSO-d$_6$): δ 13.77 (br s, 1 H), 7.88 (s, 1 H), 7.19 (dd, 1 H), 7.15 (t, 1 H), 6.92 (dd, 1 H), 5.68 (s, 2 H), 5.36 (d, 1 H), 4.81-4.77 (m, 1 H), 3.87-3.82 (m, 1 H), 3.76-3.71 (m, 1 H), 3.68-3.59 (m, 1 H), 3.41-3.35 (m, 1 H) 2.33-2.30 (m, 1 H), 2.19 (dd, 1 H), 2.00-1.80 (m, 4 H).

EXAMPLE 31

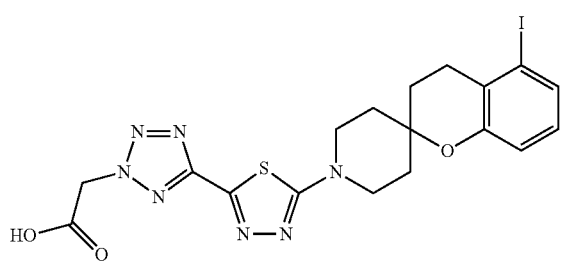

{5-[5-(5-Iodo-3,4-dihydro-1'H-spiro[chromene-2,4'-piperidin]-1'-yl)-1,3,4-thiadiazol-2-yl]-2H-tetrazol-2-yl}acetic acid The title compound was prepared, as a white solid, through two synthetic steps in the same manner as described for Example 17, but using 5-iodo-3,4-dihydrospiro[chromene-2,4'-piperidinium]chloride (Intermediate 14) in step 1. LC-MS: m/z=539.9 (MH+). $^1$H NMR (400 MHz, DMSO-d$_6$): δ 13.86 (br s, 1 H), 7.44-7.38 (m, 1 H), 6.91-6.86 (m, 2 H), 5.81 (s, 2 H), 3.88-3.78 (m, 2 H), 3.62-3.51 (m, 2 H), 2.60 (t, 2 H), 1.89 (t, 2 H), 1.85-1.74 (m, 4 H).

EXAMPLE 32

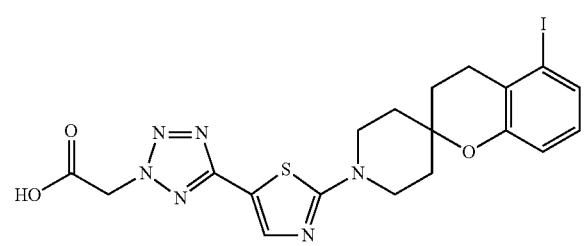 [SMILES: O=C(O)Cn1nnc(-c2cnc(N3CCC4(CCc5c(I)cccc5O4)CC3)s2)n1]

{5-[2-(5-Iodo-3,4-dihydro-1'H-spiro[chromene-2,4'-piperidin]-1'-yl)-1,3-thiazol-5-yl]-2H-tetrazol-2-yl}acetic acid The title compound was prepared, as a white solid, through 2 synthetic steps in the same manner as described for Example 21, but using 5-iodo-3,4-dihydrospiro[chromene-2,4'-piperidinium]chloride (Intermediate 14) in step 1. LC-MS: m/z=538.9 (MH+). $^1$H NMR (500 MHz, DMSO-d$_6$): δ 13.75 (br s, 1 H), 7.87 (s, 1 H), 7.45-7.40 (m, 1H), 6.92-6.90 (m, 2 H), 5.69 (s, 2 H), 3.85-3.78 (m, 2 H), 3.53-3.43 (m, 2 H), 2.62 (t, 2 H), 1.91 (t, 2 H), 1.86-1.72 (m, 4 H).

EXAMPLE 33

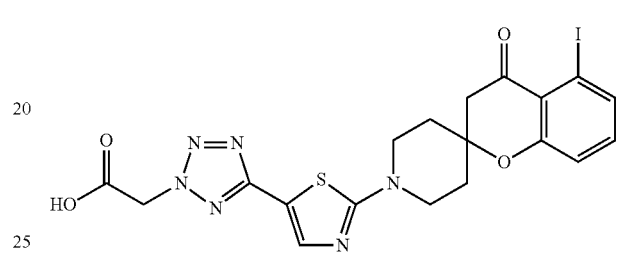

{5-[2-(5-Iodo-4-oxo-3,4-dihydro-1'H-spiro[chromene-2,4'-piperidin]-1'-yl)-1,3-thiazol-5-yl]-2H-tetrazol-2-yl}acetic acid The title compound was prepared, as a white solid, through 2 synthetic steps in the same manner as described for Example 21, but using 5-iodo-4-oxo-3,4-dihydrospiro[chromene-2,4'-piperidinium]chloride (Intermediate 15) in step 1. LC-MS: m/z=552.9 (MH+). $^1$H NMR (500 MHz, DMSO-d$_6$): δ 13.77 (br s, 1 H), 7.88 (s, 1 H), 7.67 (dd, 1 H), 7.23 (t, 1 H), 7.18 (dd, 1 H), 5.69 (s, 2 H), 3.88-3.79 (m, 2 H), 3.52-3.43 (m, 2 H), 2.97 (s, 2 H), 2.04-1.97 (m, 2 H), 1.93-1.83 (m, 2 H).

EXAMPLE 34

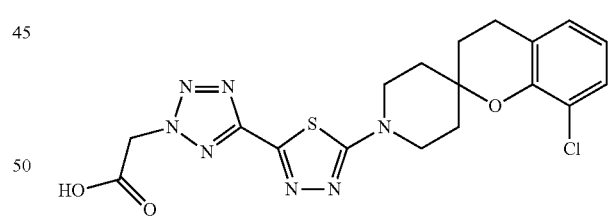

{5-[5-(8-Chloro-3,4-dihydro-1'H-spiro[chromene-2,4'-piperidin]-1'-yl)-1,3,4-thiadiazol-2-yl]-2H-tetrazol-2-yl}acetic acid The title compound was prepared, as a white solid, through 2 synthetic steps in the same manner as described for Example 17, but using 8-chloro-3,4-dihydrospiro[chromene-2,4'-piperidinium]chloride (Intermediate 12) and ethyl[5-(5-bromo-1,3,4-thiadiazol-2-yl)-2H-tetrazol-2-yl]acetate (Intermediate 5) in step 1; followed by basic hydrolysis with 1 N NaOH in step 2. LC-MS: m/z=448.0, 450.0 (MH+). $^1$H NMR (500 MHz, acetone-d$_6$): δ 7.25 (d, 1 H), 7.10 (d, 1 H), 6.88 (t, 1 H), 5.62 (s, 2 H), 4.04-3.99 (m, 2 H), 3.77-3.69 (m, 2 H), 2.92 (t, 2 H), 2.01-1.92 (m, 6 H).

EXAMPLE 35

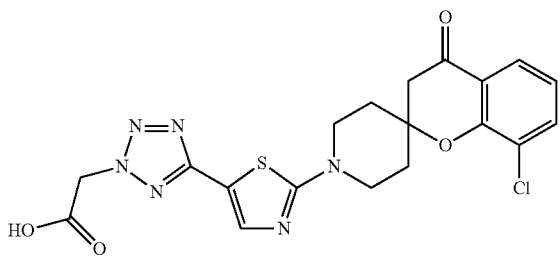 [SMILES: O=C(O)Cn1nnc(-c2cnc(N3CCC4(CC3)CC(=O)c3cccc(Cl)c3O4)s2)n1]

{5-[2-(8-Chloro-4-oxo-3,4-dihydro-1'H-spiro[chromene-2,4'-piperidin]-1'-yl)-1,3-thiazol-5-yl]-2H-tetrazol-2-yl}acetic acid The title compound was prepared, as a pink solid, through 2 synthetic steps in the same manner as described for Example 21, but using 8-chloro-4-oxo-3,4-dihydrospiro[chromene-2,4'-piperidinium]chloride (Intermediate 13) in step 1. LC-MS: m/z=461, 463 (MH+). $^1$H NMR (400 MHz, DMSO-d$_6$): δ 13.78 (br s, 1 H), 7.89 (s, 1 H), 7.81 (dd, 1 H), 7.75 (dd, 1 H), 7.14-7.09 (m, 1 H), 5.70 (s, 2 H), 3.93 (d, 2 H), 3.52-3.38 (m, 2 H), 3.01 (s, 2 H), 2.10 (d, 2 H), 1.98-1.87 (m, 2 H).

EXAMPLE 36

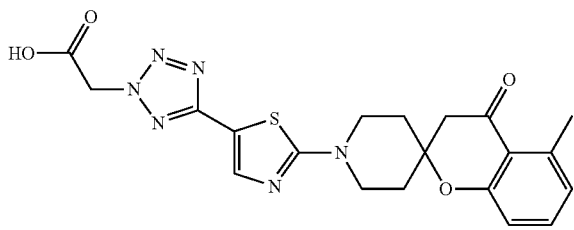 [SMILES: Cc1cccc2c1C(=O)CC1(CCN(c3ncc(-c4nnn(CC(=O)O)n4)s3)CC1)O2]

{5-[2-(5-Methyl-4-oxo-3,4-dihydro-1'H-spiro[chromene-2,4'-piperidin]-1'-yl)-1,3-thiazol-5-yl]-2H-tetrazol-2-yl}acetic acid Step 1: tert-Butyl 5-methyl-4-oxo-3,4-dihydro-1'H-spiro[chromene-2,4'-piperidine]-1'-carboxylate. To a degassed mixture of THF (1.0 mL) and water (104 µl) was added tert-butyl 5-bromo-4-oxo-3,4-dihydro-1'-spiro[chromene-2,4'-piperidine]-1'-carboxylate (50.0 mg, 0.13 mmol; Intermediate 10, Step 4), potassium methyltrifluoroborate (14 mg, 0.12 mmol), PdCl$_2$(dppf)-CH$_2$Cl$_2$ (9.38 mg, 0.011 mmol) and cesium carbonate (112 mg, 0.34 mmol). The reaction mixture was stirred at reflux for 16 h in a sealed tube. The volatiles were evaporated under reduced pressure. The resulting residue was diluted with water (10 mL)/1N HCl (10 mL) and extracted with DCM (3×5 mL) using a separation cartridge. The residue was purified by Combiflash™ chromatography (SiO$_2$, 12 g, elution with 0-60% EtOAc/hexanes over 40 min) to afford the title compound as an oil.

Step 2: 5-Methylspiro[chromene-2,4'-piperidin]-4(3H)-one. tert-Butyl 5-methyl-4-oxo-3,4-dihydro-1'H-spiro[chromene-2,4'-piperidine]-1'-carboxylate (25 mg, 0.08 mmol) was diluted in 4N HCl in dioxane (3 mL) and placed in a round bottom flask equipped with a condenser. The mixture was heated periodically (every 10 min) to reflux using a heat gun for a total of 30 min. Then the volatiles were evaporated under reduced pressure to afford the title compound as a solid.

Step 3: tert-Butyl{5-[2-(5-methyl-4-oxo-3,4-dihydro-1'H-spiro[chromene-2,4'-piperidin]-1'-yl)-1,3-thiazol-5-yl]-2H-tetrazol-2-yl}acetate. The title compound was prepared in a similar manner as that described for Example 5 (step 1) from 5-methylspiro[chromene-2,4'-piperidin]-4(3H)-one and Intermediate 3.

Step 4: {5-[2-(5-Methyl-4-oxo-3,4-dihydro-1'H-spiro[chromene-2,4'-piperidin]-1'-yl)-1,3-thiazol-5-yl]-2H-tetrazol-2-yl}acetic acid. The title compound was prepared in a similar manner as that described for Example 9 (step 2) from tert-butyl{5-[2-(5-methyl-4-oxo-3,4-dihydro-1'H-spiro[chromene-2,4'-piperidin]-1'-yl)-1,3-thiazol-5-yl]-2H-tetrazol-2-yl}acetate and LiOH. $^1$H NMR (500 MHz, DMSO-d$_6$): δ 7.87 (s, 1 H), 7.43 (t, 1 H), 6.97 (d, 1 H), 6.86 (d, 1 H), 5.70-5.66 (m, 2 H), 3.84 (d, 3 H), 3.48 (t, 2 H), 2.87 (s, 2 H), 2.56 (s, 4 H), 2.03 (d, 2 H), 1.88-1.85 (m, 2 H). MS (+ESI): m/z 441.2 (MH+).

EXAMPLE 37

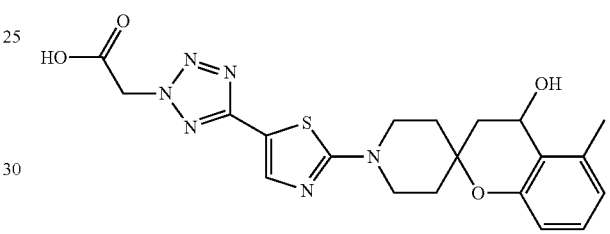

{5-[2-(4-Hydroxy-5-methyl-3,4-dihydro-1'H-spiro[chromene-2,4'-piperidin]-thiazol-5-yl]-2H-tetrazol-2-yl}acetic acid The title compound was prepared in a similar manner as that described for Intermediate 1 (step 3) from {5-[2-(5-methyl-4-oxo-3,4-dihydro-1'H-spiro[chromene-2,4'-piperidin]-1'-yl)-1,3-thiazol-5-yl]-2H-tetrazol-2-yl}acetic acid and NaBH$_4$. $^1$H NMR (500 MHz, DMSO-d$_6$): δ 7.84 (s, 2 H), 7.07 (t, 2 H), 6.74 (d, 2 H), 6.69 (d, 2 H), 5.33 (s, 2 H), 5.13 (d, 2 H), 4.79-4.76 (m, 2 H), 3.81 (d, 2 H), 3.73 (d, 2 H), 3.61-3.57 (m, 2 H), 3.45-3.31 (m, 166 H), 2.36 (s, 6 H), 2.25 (d, 2 H), 2.12 (d, 2 H), 1.97 (d, 3 H), 1.88-1.80 (m, 6 H). MS (+ESI): m/z 443.1 (MH+).

EXAMPLE 38

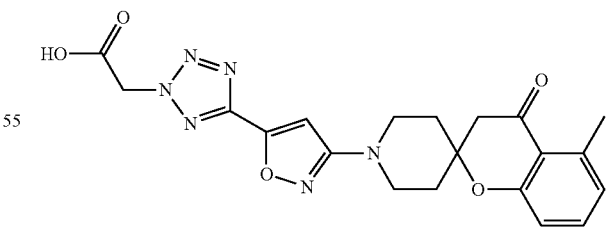

{5-[3-(5-Methyl-4-oxo-3,4-dihydro-1'H-spiro[chromene-2,4'-piperidin]-1'-yl)isoxazol-5-yl]-2H-tetrazol-2-yl}acetic acid Step 1: tert-Butyl{5-[3-(5-methyl-4-oxo-3,4-dihydro-1'H-spiro[chromene-2,4'-piperidin]-1'-yl)-4,5-dihydroisoxazol- 5-yl]-2H-tetrazol-2-yl}acetate. The title compound was prepared in a similar manner as that described for Example 15 (step 1) from 5-methylspiro[chromene-2,4'-piperidin]-4 (3H)-one and Intermediate 3.

Step 2: tert-Butyl{5-[3-(5-methyl-4-oxo-3,4-dihydro-1'H-spiro[chromene-2,4'-piperidin]-1'-yl)isoxazol-5-yl]-2H-tetrazol-2-yl}acetate. The title compound was prepared in a similar manner as that described for Example 15 (step 2) from tert-butyl{5-[3-(5-methyl-4-oxo-3,4-dihydro-1'H-spiro[chromene-2,4'-piperidin]-1'-yl)-4,5-dihydroisoxazol-5-yl]-2H-tetrazol-2-yl}acetate and CAN.

Step 3: {5-[3-(5-Methyl-4-oxo-3,4-dihydro-1'H-spiro[chromene-2,4'-piperidin]-1'-yl)isoxazol-5-yl]-2H-tetrazol-2-yl}acetic acid. The title compound was prepared in a similar manner as that described for Example 9 (step 2) from tert-butyl{5-[3-(5-methyl-4-oxo-3,4-dihydro-1'H-spiro[chromene-2,4'-piperidin]-1'-yl)isoxazol-5-yl]-2H-tetrazol-2-yl}acetate and LiOH. $^1$H NMR (500 MHz, DMSO-d$_6$): δ 7.44-7.40 (m, 1 H), 7.24 (s, 1 H), 6.95 (d, 1 H), 6.85 (d, 1 H), 5.79 (s, 2 H), 3.63 (d, 2 H), 3.29-3.26 (m, 2 H), 2.86-2.84 (m, 2 H), 2.56 (s, 3 H), 1.96 (d, 2 H), 1.85-1.78 (m, 2 H). MS (+ESI): m/z 425.1 (MH$^+$).

EXAMPLE 39

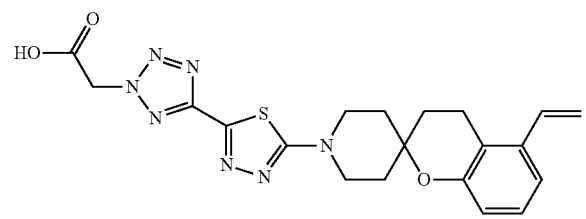 [SMILES: C=Cc1cccc2c1CCC1(CCN(c3nnc(-c4nnn(CC(=O)O)n4)s3)CC1)O2]

{5-[5-(5-Vinyl-3,4-dihydro-1'H-spiro[chromene-2,4'-piperidin]-1'-yl)-1,3,4-thiadiazol-2-yl]-2H-tetrazol-2-yl}acetic acid Step 1: tert-Butyl{5-[5-(5-vinyl-3,4-dihydro-1'H-spiro[chromene-2,4'-piperidin]-1'-yl)-1,3,4-thiadiazol-2-yl]-2H-tetrazol-2-yl}acetate. To a solution of tert-butyl{5-[5-(5-iodo-3,4-dihydro-1'H-spiro[chromene-2,4'-piperidin]-1'-yl)-1,3,4-thiadiazol-2-yl]-2H-tetrazol-2-yl}acetate (50 mg, 0.08 mmol) (Example 31, step 1) in degassed DMF (420 µl) was added Pd(Ph$_3$P)$_4$ (9.70 mg, 8.40 µmol) and tributyl(vinyl)tin (29.6 µl, 0.10 mmol). The reaction mixture was stirred at 80° C. for 16 h. The reaction mixture was diluted with EtOAc (5 mL)/water (10 mL) and then acidified with 1N HCl (10 mL). The organic layer was extracted with EtOAc (2×5 mL). The combined organic layers were washed with water (10 mL), brine (10 mL), dried on MgSO$_4$, filtered and evaporated under reduced pressure. The residue was purified by Combiflash™ chromatography (SiO$_2$, 12 g, elution with 0-40% EtOAc/hexanes over 40 min) to afford the title compound as solid.

Step 2: {5-[5-(5-Vinyl-3,4-dihydro-1'H-spiro[chromene-2,4'-piperidin]-1'-yl)-1,3,4-thiadiazol-2-yl]-2H-tetrazol-2-yl}acetic acid The title compound was prepared in a similar manner as that described for Example 9 (step 2) from tert-butyl{5-[5-(5-vinyl-3,4-dihydro-1'H-spiro[chromene-2,4'-piperidin]-1'-yl)-1,3,4-thiadiazol-2-yl]-2H-tetrazol-2-yl}acetate and LiOH. $^1$H NMR (500 MHz, DMSO-d$_6$): δ 7.11-7.08 (m, 1 H), 6.93 (dd, 1 H), 6.80 (dd, 1 H), 5.79 (s, 2 H), 5.71 (d, 1 H), 5.34 (d, 1 H), 3.88-3.82 (m, 2 H), 3.63-3.57 (m, 2 H), 2.76 (t, 2 H), 1.91-1.81 (m, 6 H). MS (+ER): m/z 440.1 (MH$^+$).

EXAMPLE 40

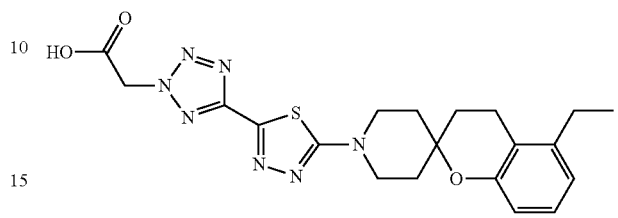

{5-[5-(5-Ethyl-3,4-dihydro-1'H-spiro[chromene-2,4'-piperidin]-1'-yl)-1,3,4-thiadiazol-2-0]-2H-tetrazol-2-yl}acetic acid Step 1: tert-Butyl{5-[5-(5-ethyl-3,4-dihydro-1'H-spiro[chromene-2,4'-piperidin]-1'-yl)-1,3,4-thiadiazol-2-yl]-2H-tetrazol-2-yl}acetate. To a solution of tert-butyl{5-[5-(5-vinyl-3,4-dihydro-1'H-spiro[chromene-2,4'-piperidin]-1'-yl)-1,3,4-thiadiazol-2-yl]-2H-tetrazol-2-yl}acetate (47 mg, 0.1 mmol; Example 39, Step 1) in degassed MeOH (474 µl) was added Pd/C (10.09 mg, 0.1 mmol). H$_2$ was bubble into solution for 2 min. The reaction mixture was stirred at room temperature for 2 h. The reaction mixture was filtered on celite an evaporated under reduced pressure. The final product was use crud for the next step.

Step 2: {5-[5-(5-Ethyl-3,4-dihydro-1'H-spiro[chromene-2,4'-piperidin]yl]-2H-tetrazol-2-yl}acetic acid. The title compound was prepared in a similar manner as that described for Example 8 (step 2) from tert-butyl{5-[5-(5-ethyl-3,4-dihydro-1'H-spiro[chromene-2,4'-piperidin]-1'-yl)-1,3,4-thiadiazol-2-yl]-2H-tetrazol-2-yl}acetate and TFA. $^1$H NMR (400 MHz, DMSO-d$_6$): δ 7.06 (t, 1 H), 6.76 (d, 1 H), 6.70 (d, 1 H), 5.84 (s, 2 H), 3.86 (dt, 2 H), 3.65-3.57 (m, 2 H), 2.70 (t, 2 H), 2.59 (q, 2 H), 1.89-1.80 (m, 6 H), 1.17 (t, 3 H). MS (+ESI): m/z 442.2 (MH$^+$).

EXAMPLE 41

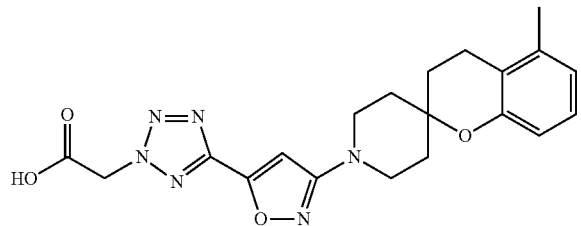 [SMILES: Cc1cccc2c1CCC1(CCN(c3cc(-c4nnn(CC(=O)O)n4)on3)CC1)O2]

{5-[3-(5-methyl-3,4-dihydro-1'H-spiro[chromene-2,4'-piperidin]-1'-yl)isoxazol-5-yl]-2H-tetrazol-2-yl}acetic acid The title compound was prepared in a similar manner as that described for Example 36 (step 1) from {5-[3-(5-bromo-3,4-dihydro-1'H-spiro[chromene-2,4'-piperidin]-1'-yl)isoxazol-5-yl]-2H-tetrazol-2-yl}acetic acid (Example 22) and potassium methyltrifluoroborate. $^1$H NMR (500 MHz, DMSO-d$_6$): δ 7.14 (s, 1 H), 6.98 (t, 1 H), 6.71 (d, 1 H), 6.67 (d, 1 H), 4.97

(s, 3 H), 3.63-3.58 (m, 3 H), 3.45-3.39 (m, 7 H), 2.62 (t, 2 H), 2.19 (s, 3 H), 1.86 (t, 2 H), 1.78-1.68 (m, 10 H). MS (+ESI): m/z 411.2 (MH⁺).

EXAMPLE 42

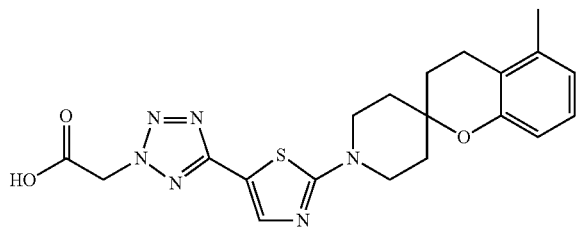 [SMILES: Cc1cccc2c1CCC1(CCN(c3ncc(-c4nnn(CC(=O)O)n4)s3)CC1)O2]

{5-[2-(5-Methyl-3,4-dihydro-1'H-spiro[chromene-2,4'-piperidin]-1'-yl)-1,3-thiazol-5-yl]-2H-tetrazol-2-yl}acetic acid The title compound was prepared in a similar manner as that described for Example 36 (step 1) from {5-[2-(5-bromo-3,4-dihydro-1'H-spiro[chromene-2,4'-piperidin]-1'-yl)-1,3-thiazol-5-yl]-2H-tetrazol-2-yl}acetic acid (Example 28) and potassium methyltrifluoroborate. $^1$H NMR (500 MHz, DMSO-$d_6$): δ 7.87-7.86 (m, 1 H), 6.99 (t, 1 H), 6.73 (d, 1 H), 6.69-6.67 (m, 1 H), 5.68 (m, 2 H), 3.84-3.79 (m, 2 H), 3.51-3.46 (m, 2 H), 2.62 (t, 2 H), 2.19 (s, 3 H), 1.89-1.75 (m, 6 H). MS (+ESI): m/z 427.2 (MH⁺).

EXAMPLE 43

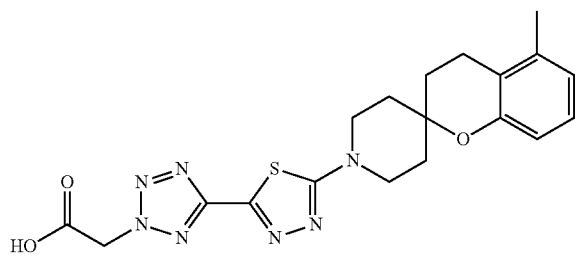 [SMILES: Cc1cccc2c1CCC1(CCN(c3nnc(-c4nnn(CC(=O)O)n4)s3)CC1)O2]

{5-[5-(5-Methyl-3,4-dihydro-1'H-spiro[chromene-2,4'-piperidin]-1'-yl)-1,3,4-thiadiazol-2-yl]-2H-tetrazol-2-yl}acetic acid The title compound was prepared in a similar manner as that described for Example 36 (step 1) from {5-[5-(5-bromo-3,4-dihydro-1'H-spiro[chromene-2,4'-piperidin]-1'-yl)-1,3,4-thiadiazol-2-yl]-2H-tetrazol-2-yl}acetic acid (Example 25) and potassium methyltrifluoroborate. $^1$H NMR (500 MHz, DMSO-$d_6$): δ 7.00 (t, 1 H), 6.73 (d, 1 H), 6.69 (d, 1 H), 5.82 (s, 2 H), 3.86-3.83 (m, 2 H), 3.59 (t, 2 H), 2.65-2.61 (m, 2 H), 2.19 (s, 3 H), 1.90-1.80 (m, 6 H). MS (+ESI): m/z 428.2 (MH⁺).

EXAMPLE 44

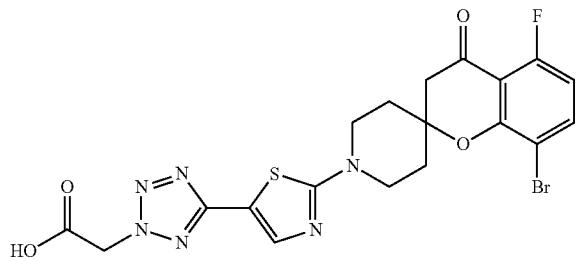 [SMILES: O=C(O)Cn1nnc(-c2cnc(N3CCC4(CC3)CC(=O)c3c(F)ccc(Br)c3O4)s2)n1]

{5-[2-(8-Bromo-5-fluoro-4-oxo-3,4-dihydro-1'H-spiro[chromene-2,4'-piperidin]-1'-yl)-1,3-thiazol-5-yl]-2H-tetrazol-2-yl}acetic acid Step 1: 8-Bromo-5-fluorospiro[chromene-2,4'-piperidin]-4(3H)-one hydrochloride The title compound was prepared in a similar manner as that described for Intermediate 1 (steps 1 and 2) and follow by the procedure detail in Example 36 (step 2), starting from 2-bromo-5-fluorophenol.

Step 2: {5-[2-(8-Bromo-5-fluoro-4-oxo-3,4-dihydro-1'H-spiro[chromene-2,4'-piperidin]-1'-yl)-1,3-thiazol-5-yl]-2H-tetrazol-2-yl}acetic acid. The title compound was prepared in a similar manner as that described for Example 14 (steps 1 and 2) from Intermediate 3 and 8-bromo-5-fluorospiro[chromene-2,4'-piperidin]-4(3H)-one hydrochloride. $^1$H NMR (500 MHz, DMSO-$d_6$): δ 7.94 (dd, 1 H), 7.88 (s, 1 H), 6.92 (dd, 1 H), 5.65 (s, 2 H), 3.96-3.91 (m, 2 H), 3.48-3.41 (m, 2 H), 2.98 (s, 2 H), 2.13-2.08 (m, 2 H), 1.95-1.88 (m, 2 H). MS (+ESI): m/z 522.9, 523.9 (MH⁺).

EXAMPLE 45

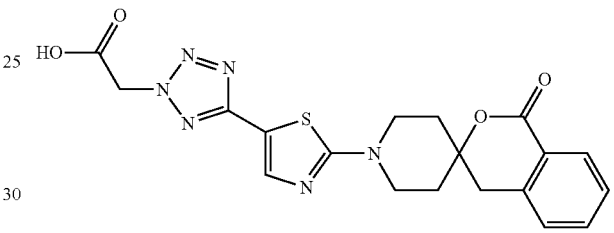

{5-[2-(1-Oxo-1,4-dihydro-1'H-spiro[isochromene-3,4'-piperidin]-1'-yl)-1,3-thiazol-5-yl]-2H-tetrazol-2-yl}acetic acid Step 1: tert-Butyl{5-[2-(1-oxo-1,4-dihydro-1'H-spiro[isochromene-3,4'-piperidin]-1'-yl)-1,3-thiazol-5-yl]-2H-tetrazol-2-yl}acetate. The title compound was prepared in a similar manner as that described for Example 5 (step 1) from Intermediate 3 and spiro[isochromene-3,4'-piperidin]-1(4H)-one hydrochloride.

Step 2: {5-[2-(1-Oxo-1,4-dihydro-1'H-spiro[isochromene-3,4'-piperidin]-1'-yl)-1,3-thiazol-5-yl]-2H-tetrazol-2-yl}acetic acid. The title compound was prepared in a similar manner as that described for Example 8 (step 2) from tert-Butyl{5-[2-(1-oxo-1,4-dihydro-1'H-spiro[isochromene-3,4'-piperidin]-1'-yl)-1,3-thiazol-5-yl]-2H-tetrazol-2-yl}acetate. and TFA. $^1$H NMR (400 MHz, DMSO-$d_6$): δ 7.97 (d, 1 H), 7.89 (s, 1 H), 7.70-7.65 (m, 1 H), 7.50-7.45 (m, 1 H), 7.41 (d, 1 H), 5.71 (s, 2 H), 3.86-3.80 (m, 2 H), 3.56-3.47 (m, 2 H), 3.23 (s, 2 H), 1.96-1.90 (m, 4 H). MS (+ESI): m/z 427.20 (MH⁺).

EXAMPLE 46

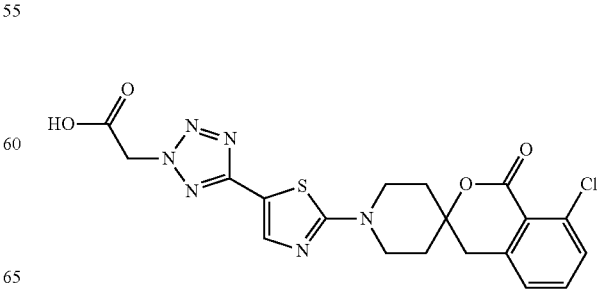

{5-[2-(8-Chloro-1-oxo-1,4-dihydro-1'H-spiro[isochromene-3,4'-piperidin]-1'-yl)-1,3-thiazol-5-yl]-2H-tetrazol-2-yl}acetic acid Step 1: tert-Butyl{5-[2-(8-chloro-1-oxo-1,4-dihydro-1'H-spiro[isochromene-3,4'-piperidin]-1'-yl)-1,3-thiazol-5-yl]-2H-tetrazol-2-yl}acetate. The title compound was prepared in a similar manner as that described for Example 5 (step 1) from Intermediate 3 and Intermediate 16.

Step 2: {5-[2-(8-Chloro-1-oxo-1,4-dihydro-1'H-spiro[isochromene-3,4'-piperidin]-1'-yl)-1,3-thiazol-5-yl]-2H-tetrazol-2-yl}acetic acid. The title compound was prepared in a similar manner as that described for Example 8 (step 2) from tert-butyl{5-[2-(8-chloro-1-oxo-1,4-dihydro-1'H-spiro[isochromene-3,4'-piperidin]-1'-yl)-1,3-thiazol-5-yl]-2H-tetrazol-2-yl}acetate and TFA. $^1$H NMR (500 MHz, DMSO-$d_6$): δ 7.88 (s, 1 H), 7.64-7.60 (m, 1 H), 7.54 (d, 1 H), 7.37 (d, 1 H), 5.69 (s, 2 H), 3.80 (d, 2 H), 3.55-3.47 (m, 2 H), 3.26 (s, 2 H), 1.94-1.84 (m, 4 H). MS (+ESI): m/z 461.10 (MH$^+$).

EXAMPLE 47

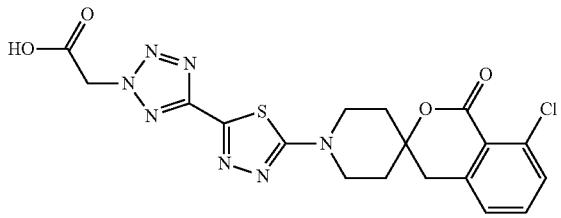 [SMILES: O=C(O)Cn1nnc(-c2nnc(N3CCC4(CC3)Cc3cccc(Cl)c3C(=O)O4)s2)n1]

{5-[5-(8-Chloro-1-oxo-1,4-dihydro-1'H-spiro[isochromene-3,4'-piperidin]-1'-yl)-1,3,4-thiadiazol-2-yl]-2H-tetrazol-2-yl}acetic acid Step 1: tert-Butyl{5-[5-(8-chloro-1-oxo-1,4-dihydro-1'H-spiro[isochromene-3,4'-piperidin]-1'-yl)-1,3,4-thiadiazol-2-yl]-2H-tetrazol-2-yl}acetate. The title compound was prepared in a similar manner as that described for Example 13 (step 1) from Intermediate 6 and Intermediate 16.

Step 2: {5-[2-(8-Chloro-1-oxo-1,4-dihydro-1'H-spiro[isochromene-3,4'-piperidin]-1'-yl)-1,3-thiazol-5-yl]-2H-tetrazol-2-yl}acetic acid. The title compound was prepared in a similar manner as that described for Example 8 (step 2) from tert-butyl{5-[5-(8-chloro-1-oxo-1,4-dihydro-1'H-spiro[isochromene-3,4'-piperidin]-1'-yl)-1,3,4-thiadiazol-2-yl]-2H-tetrazol-2-yl}acetate. and TFA. $^1$H NMR (500 MHz, DMSO-$d_6$): δ 7.62 (d, 1 H), 7.55 (d, 1 H), 7.37 (d, 1 H), 5.82 (s, 2H), 3.83 (s, 2 H), 3.60 (s, 2 H), 3.27 (s, 2 H), 1.94-1.89 (m, 4 H). MS (+ESI): m/z 462.0 (MH$^+$).

EXAMPLE 48

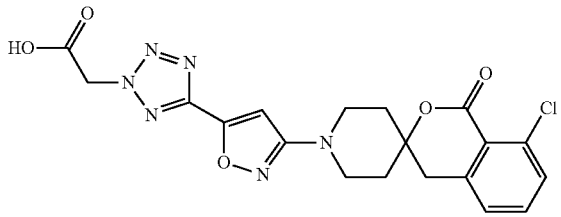

{5-[3-(8-Chloro-1-oxo-1,4-dihydro-1'H-spiro[isochromene-3,4'-piperidin]-1'-yl)isoxazol-5-yl]-2H-tetrazol-2-yl}acetic acid Step 1: tert-Butyl{5-[3-(8-chloro-1-oxo-1,4-dihydro-1'H-spiro[isochromene-3,4'-piperidin]-1'-yl)-4,5-dihydroisoxazol-5-yl]-2H-tetrazol-2-yl}acetate. The title compound was prepared in a similar manner as that described for Example 15 (step 1) from Intermediate 7 and Intermediate 16.

Step 2: tert-Butyl{5-[3-(8-chloro-1-oxo-1,4-dihydro-1'H-spiro[isochromene-3,4'-piperidin]-1'-yl)isoxazol-5-yl]-2H-tetrazol-2-yl}acetate. The title compound was prepared in a similar manner as that described for Example 15 (step 2) from tert-butyl{5-[3-(8-chloro-1-oxo-1,4-dihydro-1'H-spiro[isochromene-3,4'-piperidin]-1'-yl)-4,5-dihydroisoxazol-5-yl]-2H-tetrazol-2-yl}acetate and CAN.

Step 3: {5-[3-(8-Chloro-1-oxo-1,4-dihydro-1'H-spiro[isochromene-3,4'-piperidin]-1'-yl)isoxazol-5-yl]-2H-tetrazol-2-yl}acetic acid. The title compound was prepared in a similar manner as that described for Example 8 (step 2) from tert-Butyl{5-[3-(8-chloro-1-oxo-1,4-dihydro-1'H-spiro[isochromene-3,4'-piperidin]-1'-yl)isoxazol-5-yl]-2H-tetrazol-2-yl}acetate and TFA. $^1$H NMR (400 MHz, DMSO-$d_6$): δ 7.64-7.59 (m, 1 H), 7.55 (d, 1 H), 7.38 (d, 1 H), 7.26 (s, 1 H), 5.86 (s, 2 H), 3.59 (s, 2 H), 3.34 (d, 2 H), 3.26 (s, 2 H), 1.87-1.80 (m, 4 H). MS (+ESI): m/z 445.0 (MH$^+$).

EXAMPLE 49

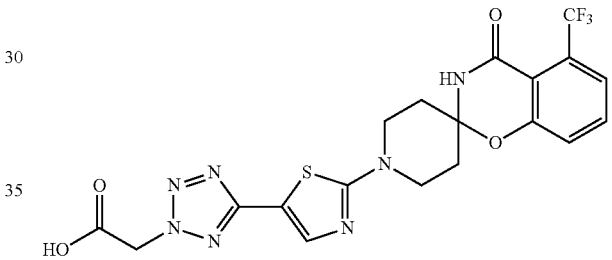

(5-{2-[4-Oxo-5-(trifluoromethyl)-3,4-dihydro-1'H-spiro[1,3-benzoxazine-2,4'-piperidin]-1'-yl]-1,3-thiazol-5-yl}-2H-tetrazol-2-yl)acetic acid Step 1: 2-Fluoro-6-(trifluoromethyl)benzamide. To a solution of 2-fluoro-6-(trifluoromethyl)benzoic acid (1 g, 4.81 mmol) in THF (24.0 mL) was added a few drops of DMF and oxalyl chloride (1.05 ml, 12.01 mmol) at 0° C. The reaction mixture was stirred at room temperature for 1.5 h. The volatiles were evaporated under reduced pressure. The residue was diluted with THF and evaporated under reduced pressure. The same process was repeated several times. The residue was dissolved in THF and ammonia gas was bubble into solution for 5 min. The reaction mixture was stirred at room temperature for 1.5 h. The solvent was evaporated under reduced pressure. The residue was triturated with DCM/hexanes (1/10), filtered, washed with hexanes and dried to afford the title compound as a solid.

Step 2: 2-Hydroxy-6-(trifluoromethyl)benzamide. To a solution of 2-fluoro-6-(trifluoromethyl)benzamide (500 mg, 2.41 mmol) in diglyme (8.05 mL) was added potassium trimethylsilanolate (1.08 g, 8.45 mmol). The reaction mixture was stirred at 120° C. overnight. The reaction mixture was acidified with 1N HCl (30 mL) and extracted with EtOAc (3×10 mL). The combined organic layers were washed with 10% solution of LiCl in water, dried with MgSO$_4$, filtered and evaporated under reduced pressure. The resulting residue was purified by Combiflash™ chromatography (SiO$_2$, 12 g, elution with 20-40% EtOAc/hexanes over 40 min) to afford the title compound as solid.

Step 3: (5-{2-[4-Oxo-5-(trifluoromethyl)-3,4-dihydro-1'H-spiro[1,3-benzoxazine-2,4'-piperidin]-1'-yl]-1,3-thiazol-5-yl}-2H-tetrazol-2-yl)acetic acid. To a solution of Intermediate 17 (42 mg, 0.13 mmol) and 2-hydroxy-6-(trifluoromethyl)benzamide (28.2 mg, 0.14 mmol) in toluene (624 μL) was added p-toluenesulfonic acid monohydrate (9.50 mg, 0.05 mmol). The reaction mixture was stirred at 140° C. for 30 min. The solvent was evaporated under reduced pressure. The resulting residue was purified by Combiflash™ chromatography (SiO$_2$, 12 g, elution with 0-5% MeOH/DCM over 40 min) to afford the title compound as solid. $^1$H NMR (500 MHz, DMSO-d$_6$): δ 9.14 (s, 2 H), 7.85 (s, 1 H), 7.73 (s, 1 H), 7.56 (s, 1 H), 7.49 (s, 1 H), 5.33 (s, 2 H), 3.88 (d, 4 H), 3.48 (s, 2 H), 2.15 (s, 3 H), 2.00-1.97 (m, 3 H). MS (+ESI): m/z 496.2 (MH$^+$).

EXAMPLE 50

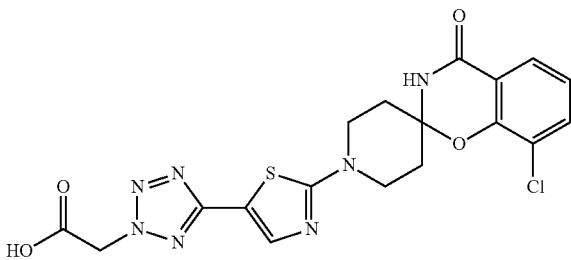 [SMILES: O=C(O)Cn1nnc(-c2cnc(N3CCC4(CC3)NC(=O)c3cccc(Cl)c3O4)s2)n1]

{5-[2-(8-Chloro-4-oxo-3,4-dihydro-1'H-spiro[1,3-benzoxazine-2,4'-piperidin]-1'-yl)-1,3-thiazol-5-yl]-2H-tetrazol-2-yl}acetic acid Step 1: 3-Chloro-2-hydroxybenzamide. A mixture of 3-chloro-2-hydroxybenzoic acid (335 mg, 1.94 mmol), DIPEA (2.98 mL, 17.08 mmol), HATU (849 mg, 2.232 mmol) was dissolved in DMF (1.94 mL)/THF (7.77 mL). The reaction was stirred for 15 min, then ammonium chloride (457 mg, 8.54 mmol) was added. The reaction mixture was stirred at room temperature overnight. The volatiles were evaporated under reduced pressure. The residue was diluted with saturated 1N HCl (20 mL) and extracted with EtOAc (3×5 mL). The combined organic fractions were washed with water (30 mL), sat. NaHCO$_3$ (20 mL), brine (20 mL), dried over MgSO$_4$ and evaporated under reduced pressure. The resulting residue was purified by Combiflash™ chromatography (SiO$_2$, 12 g, elution with 10-70% EtOAc/hexanes over 40 min) to afford the title compound as solid.
Step 2: {Ethyl{5-[2-(8-chloro-4-oxo-3,4-dihydro-1'H-spiro[1,3-benzoxazine-2,4'-piperidin]-1'-yl)-1,3-thiazol-5-yl]-2H-tetrazol-2-yl}acetate. The title compound was prepared in a similar manner as that described for Example 49 (step 3) from Intermediate 17 and 3-chloro-2-hydroxybenzamide.
Step 3: {5-[2-(8-Chloro-4-oxo-3,4-dihydro-1'H-spiro[1,3-benzoxazine-2,4'-piperidin]-1'-yl)-1,3-thiazol-5-yl]-2H-tetrazol-2-yl}acetic acid. The title compound was prepared in a similar manner as that described for Example 9 (step 2) from {ethyl{5-[2-(8-chloro-4-oxo-3,4-dihydro-1'H-spiro[1,3-benzoxazine-2,4'-piperidin]-1'-yl)-1,3-thiazol-5-yl]-2H-tetrazol-2-yl}acetate and LiOH. $^1$H NMR (500 MHz, DMSO-d$_6$): δ 9.04 (s, 1 H), 7.90 (s, 1 H), 7.76 (dd, 1 H), 7.73 (dd, 1 H), 7.17 (t, 1 H), 5.70 (s, 2 H), 4.01-3.97 (m, 2 H), 3.46-3.41 (m, 2 H), 2.24-2.20 (m, 2 H), 1.98-1.96 (m, 2 H). MS (+ESI): m/z 462.1 (MH$^+$).

EXAMPLE 51

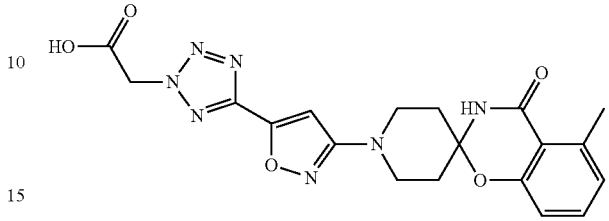

{5-[3-(5-Methyl-4-oxo-3,4-dihydro-1'H-spiro[1,3-benzoxazine-2,4'-piperidin]-1'-yl)isoxazol-5-yl]-2H-tetrazol-2-yl}acetic acid Step 1: 2-Hydroxy-6-methylbenzamide. A solution of ethyl 2-hydroxy-6-methylbenzoate (600 mg, 3.33 mmol) was dissolved in methanol (10 mL) and cooled to 0° C. Ammonia gas was bubble into solution for 5 min. A catalytic amount of KCN was added and the reaction was allowed to warm to room temperature. After 30 min, the reaction mixture was stirred at 60° C. overnight. The volatiles were evaporated under reduced pressure. The resulting residue was triturated with DCM/hexanes (1:10), filtered, washed with hexanes and dried.
Step 2: Benzyl 5-methyl-4-oxo-3,4-dihydro-1'H-spiro[1,3-benzoxazine-2,4'-piperidine]-1'-carboxylate. The title compound was prepared in a similar manner as that described for Example 49 (step 3) from 2-hydroxy-6-methylbenzamide and benzyl 4-oxopiperidine-1-carboxylate.
Step 3: 5-Methylspiro[1,3-benzoxazine-2,4'-piperidin]-4(3)-one. To a solution of benzyl 5-methyl-4-oxo-3,4-dihydro-1'H-spiro[1,3-benzoxazine-2,4'-piperidine]-1'-carboxylate (293 mg, 0.80 mmol) in degassed MeOH (4.00 mL) was added Pd/C (85 mg, 0.80 mmol), then H$_2$ (1.61 mg, 0.80 mmol) was bubbled into the solution for 5 min. The reaction was stirred at room temperature for 1.5 h. The reaction mixture was filtered on Celite™ and the solvent was evaporated under reduced pressure to afford the title compound as a solid.
Step 4: tert-Butyl{5-[3-(5-methyl-4-oxo-3,4-dihydro-1'H-spiro[1,3-benzoxazine-2,4'-piperidin]-1'-yl)-4,5-dihydroisoxazol-5-yl]-2H-tetrazol-2-yl}acetate. The title compound was prepared in a similar manner as that described for Example 15 (step 1) from Intermediate 7 and 5-methylspiro[1,3-benzoxazine-2,4'-piperidin]-4(3)-one.
Step 5: tert-Butyl{5-[3-(5-methyl-4-oxo-3,4-dihydro-1'H-spiro[1,3-benzoxazine-2,4'-piperidin]-1'-yl)isoxazol-5-yl]-2H-tetrazol-2-yl}acetate. The title compound was prepared in a similar manner as that described for Example 15 (step 2) from tert-butyl{5-[3-(5-methyl-4-oxo-3,4-dihydro-1'H-spiro[1,3-benzoxazine-2,4'-piperidin]-1'-yl)-4,5-dihydroisoxazol-5-yl]-2H-tetrazol-2-yl}acetate and CAN.
Step 6: {5-[3-(5-Methyl-4-oxo-3,4-dihydro-1'H-spiro[1,3-benzoxazine-2,4'-piperidin]-1'-yl)isoxazol-5-yl]-2H-tetrazol-2-yl}acetic acid. The title compound was prepared in a similar manner as that described for Example 9 (step 2) from tert-butyl{5-[3-(5-methyl-4-oxo-3,4-dihydro-1'H-spiro[1,3-benzoxazine-2,4'-piperidin]-1'-yl)isoxazol-5-yl]-2H-tetrazol-2-yl}acetate and LiOH. $^1$H NMR (500 MHz, DMSO-d$_6$): δ 8.67-8.66 (m, 1 H), 7.36 (d, 1 H), 7.26 (s, 1 H), 6.93-6.90 (m, 2 H), 5.78 (s, 2 H), 3.69-3.66 (m, 2 H), 3.31-3.27 (m, 2 H), 2.61 (s, 3 H), 2.06-2.03 (m, 2 H), 1.92-1.88 (m, 2 H) MS (+ESI): m/z 426.1 (MH$^+$).

The Examples listed in Table 1 were prepared essentially following the procedures outlined for Examples 49-51.

TABLE 1

| Example | Structure | Characterisation by Mass Spectrometry |
|---|---|---|
| 52 | 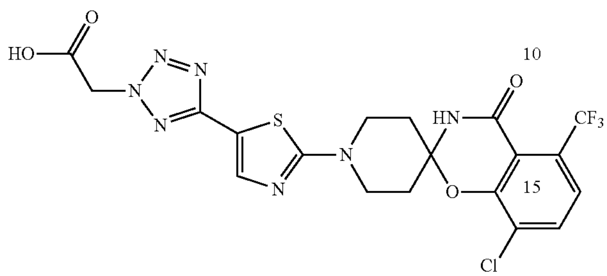 [SMILES: O=C(O)Cn1nnc(-c2cnc(N3CCC4(CC3)NC(=O)c3c(C(F)(F)F)ccc(Cl)c3O4)s2)n1] | MS: m/z 530.0 (MH$^+$) |
| 53 | 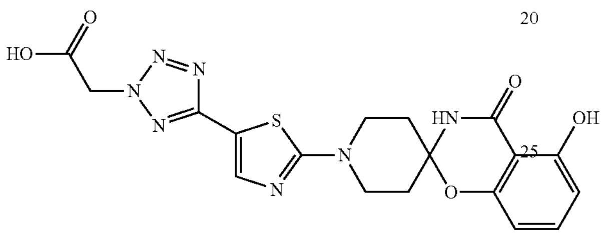 [SMILES: O=C(O)Cn1nnc(-c2cnc(N3CCC4(CC3)NC(=O)c3c(O)cccc3O4)s2)n1] | MS: m/z 444.2 (MH$^+$) |
| 54 | 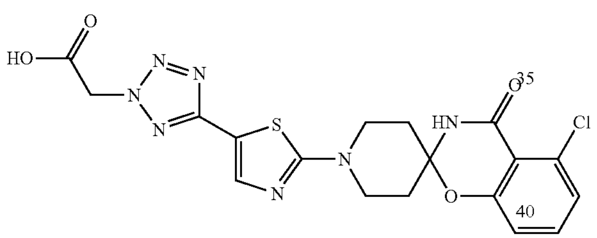 | MS: m/z 462.0 (MH$^+$) |
| 55 | 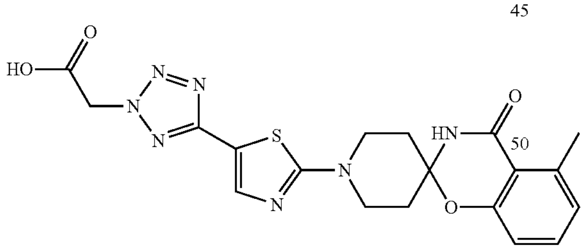 | MS: m/z 442.2 (MH$^+$) |
| 56 | 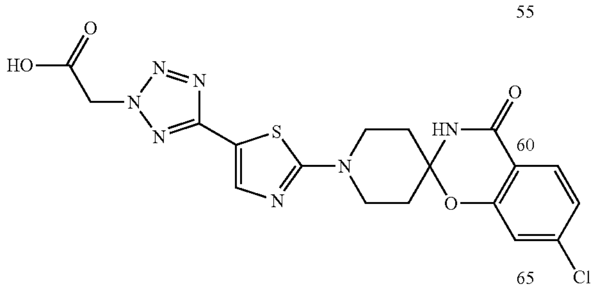 | MS: m/z 462.1 (MH$^+$) |

EXAMPLE 57

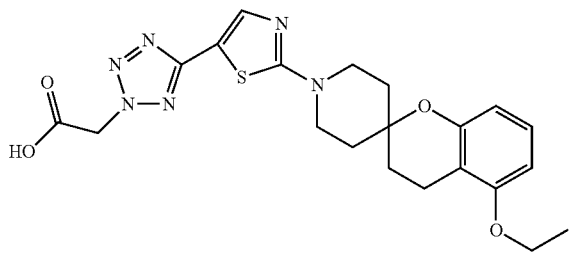 [SMILES: CCOc1cccc2c1CCC1(CCN(c3ncc(-c4nnn(CC(=O)O)n4)s3)CC1)O2]

{5-[2-(5-Ethoxy-3,4-dihydro-1'H-spiro[chromene-2,4'-piperidin]-1'-yl)-1,3-thiazol-5-yl]-2H-tetrazol-2-yl}acetic acid Step 1. Benzyl 5-hydroxy-4-oxo-3,4-dihydro-1'H-spiro[chromene-2,4'-piperidine]-1'-carboxylate To a solution of benzyl 4-oxopiperidine-1-carboxylate (2.67 g, 11.45 mmol) in methanol (25 ml) was added freshly distilled pyrrolidine (1.2 ml, 14.51 mmol), followed by hydroxyphenone (2.07 g, 13.61 mmol). The mixture was stirred at an external temperature of 75° C. for 90 min, then cooled to room temperature and concentrated. The resulting oily residue was purified by flash chromatography on silica gel (eluting with 20% to 80% EtOAc in hexane) to give the title compound as a pale yellow oil.

Step 2. Benzyl 4,5-dihydroxy-3,4-dihydro-1'H-spiro[chromene-2,4'-piperidine]-1'-carboxylate To a solution of benzyl 5-hydroxy-4-oxo-3,4-dihydro-1'H-spiro[chromene-2,4'-piperidine]-1'-carboxylate (3.96 g, 10.78 mmol) in THF (15 ml) and MeOH (35 ml), stirred at 0° C., was added portion wise solid sodium borohydride (588 mg, 15.54 mmol). The reaction was stirred at 0° C. for 1 h, then quenched at 0° C. by the addition of acetone. The reaction was diluted with DCM, washed with 5% $KHSO_4$, dried over $MgSO_4$, filtered and concentrated to give the title compound as a white foam.

Step 3: Benzyl 5-ethoxy-4-hydroxy-3,4-dihydro-1'H-spiro[chromene-2,4'-piperidine]-1'-carboxylate and Benzyl 5-ethoxy-1'H-spiro[chromene-2,4'-piperidine]-1'-carboxylate A solution of benzyl 4,5-dihydroxy-3,4-dihydro-1'H-spiro[chromene-2,4'-piperidine]-1'-carboxylate (570 mg, 1.54 mmol) in DME (5 ml) was treated with potassium carbonate (639 mg, 4.62 mmol), followed by neat ethyl bromide (1700 mg, 15.6 mmol). The mixture was stirred at room temperature for 68 h, then diluted with DCM, washed with 1M NaOH, dried over $MgSO_4$ filtered and concentrated. The resulting crude mixture was used in the next step without further purification.

Step 4: 5-Ethoxy-3,4-dihydrospiro[chromene-2,4'-piperidine] To a mixture of benzyl 5-ethoxy-4-hydroxy-3,4-dihydro-1'H-spiro[chromene-2,4'-piperidine]-1'-carboxylate, and benzyl 5-ethoxy-1'H-spiro[chromene-2,4'-piperidine]-1'-carboxylate (1.54 mmol) was added solid 10% Pd on carbon (350 mg, 21 mol %), followed by the addition of MeOH (60 ml) via a cannula. The reaction was stirred under vacuum for 3 min. A balloon filled with $H_2$ was attached to the reaction vessel and the reaction mixture was stirred under a hydrogen atmosphere at room temperature for 1 h. Then 10 M HCl (0.4 mL, 4 mmol) was added, and the reaction was stirred under a $H_2$ atmosphere overnight. The reaction mixture was then filtered through a pad of Celite™ and concentrated. The resulting mixture was dissolved in DCM and washed with 1M NaOH in water, dried over $MgSO_4$, filtered and concentrated to give the title compound.

Step 5: tert-butyl[5-({[(5-ethoxy-3,4-dihydro-1'H-spiro[chromene-2,4'-piperidin]-1'-yl)(imino) methyl]sulfanyl}methyl)-2-H-tetrazol-2-yl]acetate A mixture of 5-ethoxy-3,4-dihydrospiro[chromene-2,4'-piperidine] (78 mg, 0.315 mmol), tert-butyl[5-(2-bromo-1,3-thiazol-5-yl)-2H-tetrazol-2-yl]acetate (96 mg, 0.277 mmol), and $K_2CO_3$ (127 mg, 0.919 mmol) was suspended in dry diglyme (1.5 ml). The reaction vial was sealed and the reaction was stirred under $N_2$ at external temperature of 110° C. for 2.5 h. The reaction was then cooled, diluted with EtOAc, washed with sat. $NaHCO_3$ and water, dried over $MgSO_4$, filtered and concentrated. The resulting brown oily residue was purified by flash chromatography on silica gel (eluting with 5% to 50% EtOAc in hexane) to give the title compound as a pale yellow solid.

Step 6: {5-[2-(5-ethoxy-3,4-dihydro-1'H-spiro[chromene-2,4'-piperidin]-1'-yl)-1,3-thiazol-5-yl]-2H-tetrazol-2-yl}acetic acid To a solution of tert-butyl[5-({[(5-ethoxy-3,4-dihydro-1'H-spiro[chromene-2,4'-piperidin]-1'-yl)(imino)methyl]sulfanyl}methyl)-2H-tetrazol-2-yl]acetate (5.1 mg, 9.95 μmol) in THF (1 ml) and ethanol (0.5 ml) was added a solution of NaOH (10 mg, 0.250 mmol) in water (0.25 ml). The resulting suspension was stirred at 0° C. for 2 h, then diluted with DCM, washed with 5% $KHSO_4$ in water (final pH=1.5), dried over $MgSO_4$, filtered and concentrated. The resulting residue was purified by flash chromatography on silica gel (eluting with 1% to 40% MeOH in DCM) to give the title compound as an off white solid. $^1$H NMR (MeOH-$d_4$): δ 7.82 (1 H, s), 7.05 (1 H, t), 6.49 (2 H, m), 5.27 (2 H, s), 4.05 (2 H, q), 3.88 (2 H, d), 3.59 (2 H, t), 2.72 (2 H, t), 1.95 (2 H, d), 1.90-1.83 (4 H, m), 1.45 (3 H, t). MS: m/z 457 (MH$^+$).

EXAMPLE 58

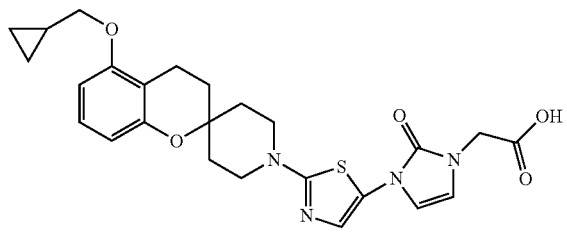 [SMILES: O=C(O)Cn1ccn(-c2cnc(N3CCC4(CCc5c(OCC6CC6)cccc5O4)CC3)s2)c1=O]

(3-{2-[5-(Cyclopropylmethoxy)-3,4-dihydro-1'H-spiro[chromene-2,4'-piperidin]-1'-yl]-1,3-thiazol-5-yl}-2-oxo-2,3-dihydro-1H-imidazol-1-yl)acetic acid Step 1: 3,4-Dihydrospiro[chromene-2,4'-piperidin]-5-ol To a solution of benzyl 4,5-dihydroxy-3,4-dihydro-1'H-spiro[chromene-2,4'-piperidine]-1'-carboxylate (853 mg, 2.31 mmol) in ethanol (20 ml) was added solid 10% Pd on carbon (361 mg, 15 mol %), followed by 10 M HCl in water (2 mL, 20 mmol). After stirring under vacuum for 5 min, a balloon filled with $H_2$ was attached to the reaction vessel and the reaction was stirred under a hydrogen atmosphere at room temperature for 48 h. The reaction mixture was then filtered through a pad of Celite™ and concentrated three times in the presence of dry EtOH (co-distillation) to give the title compound as a pale beige foam.

Step 2: 1'-(5-Bromo-1,3-thiazol-2-yl)-3,4-dihydrospiro[chromene-2,4'-piperidin]-5-ol A mixture of 3,4-dihydrospiro[chromene-2,4'-piperidin]-5-ol (504 mg, 2.30 mmol), 2,5-dibromothiazole (583 mg, 2.400 mmol), and K₂CO₃ (795 mg, 5.75 mmol) was suspended in dry DMSO (5 ml), and stirred under N₂ at an external temperature of 110° C. for 2 h. The reaction mixture was then cooled down to room temperature, and poured on 5% KHSO₄ in water. After stirring for 10 min, the precipitate was collected to give the title compound as a brown solid residue, which was stored under vacuum for 5 h prior to use.

Step 3: 1'-(5-bromo-1,3-thiazol-2-yl)-5-(cyclopropylmethoxy)-3,4-dihydrospiro[chromene-2,4'-piperidine] hromene-2,4'-piperidine] A solution of 1'-(5-bromo-1,3-thiazol-2-yl)-3,4-dihydrospiro[chromene-2,4'-piperidin]-5-ol (227 mg, 0.595 mmol) and triphenylphosphine (356 mg, 1.357 mmol) in dry THF (2 ml), stirred under N₂ at 0° C., was treated with neat cyclopropyl methanol (135 mg, 1.87 mmol), followed by DEAD (0.165 ml, 1.04 mmol). The reaction mixture was stirred at the same temperature for 30 min and then at room temperature overnight. The reaction mixture was then concentrated and purified by flash chromatography on silica gel (eluting with 3% to 10% EtOAc in hexane) to give the title compound as a white solid.

Step 4: Ethyl (3-{2-[5-(cyclopropylmethoxy)-3,4-dihydro-1'H-spiro[chromene-2,4'-piperidin]-1'-yl]-1,3-thiazol-5-yl}-2-oxo-2,3-dihydro-1H-imidazol-1-yl)acetate A mixture 1'-(5-bromo-1,3-thiazol-2-yl)-5-(cyclopropylmethoxy)-3,4-dihydrospiro[chromene-2,4'-piperidine]hromene-2,4'-piperidine] (61.5 mg, 0.141 mmol), 2-imidazolone (41 mg, 0.241 mmol), copper(I) iodide (25 mg, 0.131 mmol) and potassium phosphate tribasic (104 mg, 0.490 mmol) was suspended in dry dioxane (1.5 ml), stirred under vacuum for 3 min, and then backfilled with N₂. The reaction mixture was treated with neat dimethyl ethylenediamine (24.68 mg, 0.28 mmol) in a sealed vial, which was covered with aluminum foil and placed in an oil bath preheated to 95° C. The mixture was stirred at 95° C. for 3.5 h, then diluted with DCM, washed with sat. NH₄Cl plus some 5% KHSO₄, dried over MgSO₄, filtered and concentrated. The resulting oily residue was purified by flash chromatography on silica gel (eluting with 10% to 100% EtOAc in hexane) to give the title compound as a white solid.

Step 5: (3-{2-[5-(cyclopropylmethoxy)-3,4-dihydro-1'H-spiro[chromene-2,4'-piperidin]-1'-yl]-1,3-thiazol-5-yl}-2-oxo-2,3-dihydro-1H-imidazol-1-yl)acetic acid A solution of ethyl (3-{2-[5-(cyclopropylmethoxy)-3,4-dihydro-1'H-spiro[chromene-2,4'-piperidin]-1'-yl]-1,3-thiazol-5-yl}-2-oxo-2,3-dihydro-1H-imidazol-1-yl)acetate (38 mg, 0.072 mmol) in THF (1.5 ml) and ethanol (1 ml), stirred at 0° C., was treated with a solution of sodium hydroxide (51 mg, 1.275 mmol) in water (1 mL). The reaction was stirred at 0° C. for 1.5 h. The reaction mixture was then diluted with DCM, washed with a solution of 5% KHSO₄ in water, dried over MgSO₄, filtered and concentrated to provide a residue, which was further triturated with ether-hexane, filtered and dried to give the title compound as a white solid. ¹H NMR (DMSO-d₆): δ7.25 (1 H, s), 7.07 (1H, t), 6.94 (1 H, s), 6.77 (1 H, s), 6.45 (2 H, m), 4.33 (2 H, s), 3.82 (2 H, d), 3.67 (2 H, d), 2.61 (2 H, s), 1.81 (4 H, d), 1.73 (2 H, d), 1.24 (1 H, m), 0.58 (2 H, d), 0.35 (2 H, d). (two protons are missing because their signals overlap with that of the solvent). MS: m/z 497 (MH⁺).

The following Examples were prepared in the manner previously described for similar analogs. Example 59 was prepared according to the synthesis described in Example 16. Examples 60 and 61 were prepared according to the synthesis described in Example 57. Examples 63, 64 and 65 were prepared according to the synthesis described in Example 21. Example 62 was prepared by the alkylation of the compound of Example 63 with 3,4-difluorobenzyl bromide.

TABLE 2

| Example | Structure | Characterisation by Mass Spectrometry |
|---------|-----------|----------------------------------------|
| 59 | 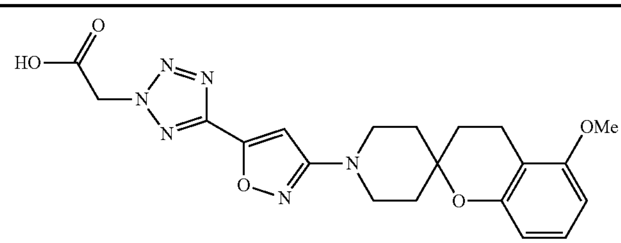 | MS: m/z 427 (MH⁺) |
| 60 | 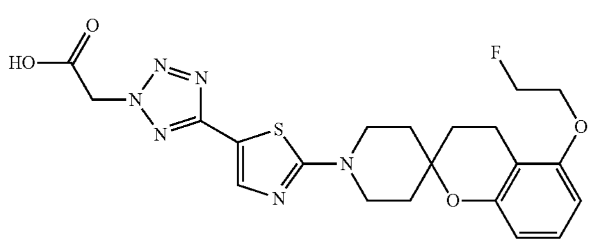 [SMILES: O=C(O)Cn1nnc(-c2cnc(N3CCC4(CCc5c(OCCF)cccc5O4)CC3)s2)n1] | MS: m/z 475 (MH⁺) |
| 61 | 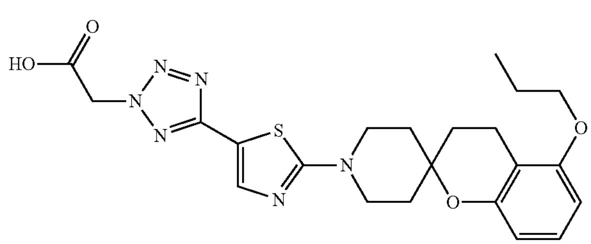 | MS: m/z 471 (MH⁺) |

TABLE 2-continued

| Example | Structure | Characterisation by Mass Spectrometry |
|---|---|---|
| 62 | 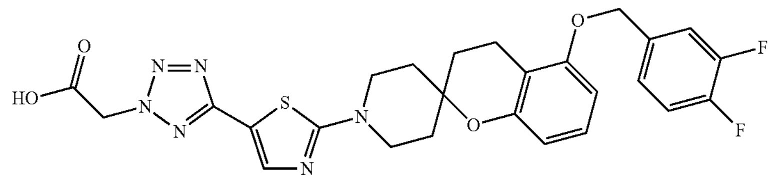 [SMILES: O=C(O)Cn1nnc(-c2cnc(N3CCC4(CCc5c(OCc6ccc(F)c(F)c6)cccc5O4)CC3)s2)n1] | MS: m/z 555 (MH+) |
| 63 | 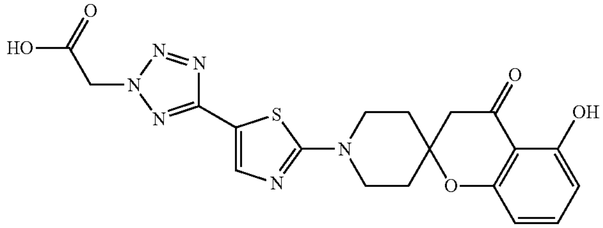 [SMILES: O=C(O)Cn1nnc(-c2cnc(N3CCC4(CC3)CC(=O)c3c(O)cccc3O4)s2)n1] | MS: m/z 443 (MH+) |
| 64 | 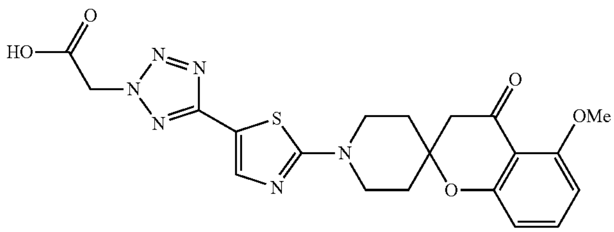 [SMILES: COc1cccc2c1C(=O)CC1(CCN(c3ncc(-c4nnn(CC(=O)O)n4)s3)CC1)O2] | MS: m/z 457 (MH+) |
| 65 | 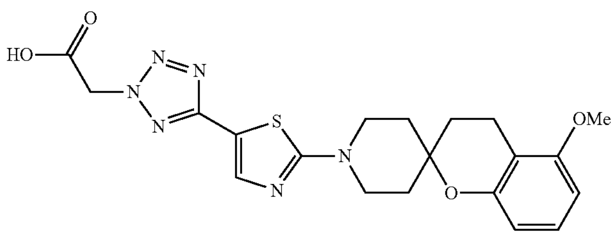 [SMILES: COc1cccc2c1CCC1(CCN(c3ncc(-c4nnn(CC(=O)O)n4)s3)CC1)O2] | MS: m/z 443 (MH+) |

EXAMPLE 66

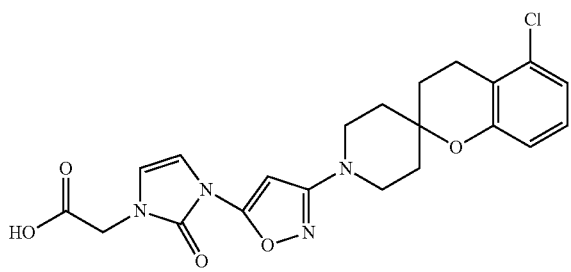 [SMILES: O=C(O)Cn1ccn(-c2cc(N3CCC4(CCc5c(Cl)cccc5O4)CC3)no2)c1=O]

{3-[3-(5-Chloro-3,4-dihydro-1'H-spiro[chromene-2,4'-piperidin]-1'-yl)isoxazol-5-yl]-2-oxo-2,3-dihydro-1H-imidazol-1-yl}acetic acid Step 1: Ethyl 3-(5-chloro-3,4-dihydro-1'H-spiro[chromene-2,4'-piperidin]-1'-yl)-4,5-dihydroisoxazole-5-carboxylate A mixture of 3-bromo-4,5-dihydroisoxazole-5-carboxylate from Example 2, step 1 (3.37 g, 15 mmol), 5-chloro-3,4-dihydrospiro[chromene-2,4'-piperidine] (3.8 g, 16 mmol) and DIPEA (5.8 g, 45 mmol) in EtOH (30 mL) was refluxed overnight. The resulting mixture was cooled to room temperature, adjusted to pH 5 with 1 M HCl, and then extracted with EtOAc (20 mL×2). The combined organic layers were washed with brine (10 mL), dried over $Na_2SO_4$ and concentrated. The resulting residue was purified by column chromatography on silica gel (PE/EA=5/1) to afford the title compound. $^1$H NMR (CDCl$_3$ 400 MHz) δ 7.04 (t, 1H), 6.93 (d, 1H), 6.75 (d, 1H), 4.95-4.99 (m, 1H), 4.25 (q, 2H), 3.41-3.44 (m, 2H), 3.23-3.36 (m, 4H), 2.77 (t, 2H), 1.80-1.85 (m, 4H), 1.61-1.68 (m, 2H), 1.34 (t, 3H).

Step 2: 3-(5-Chloro-3,4-dihydro-1'H-spiro[chromene-2,4'-piperidin]-1'-yl)isoxazole-5-carboxylic acid To a mixture of ethyl 3-(5-chloro-3,4-dihydro-1'H-spiro[chromene-2,4'-piperidin]-1'-yl)-4,5-dihydroisoxazole-5-carboxylate (2.53 g, 6.7 mmol), NaOAc (1.43 g, 17.4 mmol) in chlorobenzene (20 mL) was added I$_2$ (2.2 g, 8.7 mmol). The mixture was stirred at 110° C. overnight. After cooling, the resulting mixture was quenched with 10% $Na_2S_2O_3$ (50 mL), and extracted with EtOAc (60 mL×2). The combined organic layers were washed with brine (30 mL), dried over $Na_2SO_4$ and concentrated under vacuum. The crude residue was purified by column chromatography on silica gel (PE/EA=20/1) to afford ethyl 3-(5-chloro-3,4-dihydro-1'H-spiro[chromene-2,4'-piperidin]-1'-yl)isoxazole-5-carboxylate.

To a stirred solution of ethyl 3-(5-chloro-3,4-dihydro-1'H-spiro[chromene-2,4'-piperidin]-1'-yl)isoxazole-5-carboxylate (2.05 g, 5.4 mmol) in THF (20 mL) was added 1 M LiOH (21.8 mL). The mixture was stirred at room temperature for 1 hour, then the solvent was evaporated under vacuum. The resulting residue was diluted with water (5 mL), adjusted to pH 3 with 1 M HCl, and then extracted with Et$_2$O (10 mL×3). The combined organic layers were washed with brine (5 mL), dried over Na$_2$SO$_4$ and concentrated under vacuum. The resulting crude product was washed with n-hexane (30 mL) and filtered to afford the title compound. $^1$H NMR (CD$_3$OD 400 MHz) δ 7.07 (t, 1H), 6.93 (d, 1H), 6.80 (d, 1H), 6.94 (s, 1H), 3.52-3.57 (m, 2H), 3.27-3.32 (m, 2H), 2.81 (t, 2H), 1.77-1.92 (m, 6H).

Step 3: 3-(5-Chloro-3,4-dihydro-1'H-spiro[chromene-2,4'-piperidin]-1'-yl)isoxazol-5-amine To a mixture of 3-(5-chloro-3,4-dihydro-1'H-spiro[chromene-2,4'-piperidin]-1'-yl)isoxazole-5-carboxylic acid (1.9 g, 5.5 mmol) and TEA (1.5 mL, 11 mmol) in 2-methylpropan-2-ol (20.2 g, 273 mmol) was added DPPA (7.5 g, 27.3 mmol). The mixture was stirred at 90° C. overnight under N$_2$. Solvent was removed under vacuum. The resulting residue was purified by column chromatography on silica gel (PE/EA=10/1) to afford crude tert-butyl[3-(5-chloro-3,4-dihydro-1'H-spiro[chromene-2,4'-piperidin]-1'-yl)isoxazol-5-yl]carbamate.

A mixture of crude tert-butyl[3-(5-chloro-3,4-dihydro-1'H-spiro-[chromene-2,4'-piperidin]-1'-yl)isoxazol-5-yl]carbamate and 4M HCl in dioxane (50 mL) was stirred at room temperature overnight. The volatile materials were removed under vacuum. The resulting residue was diluted with water (10 mL), treated with NaOH (0.32 g, 8 mmol), then stirred for 1 hour and extracted with EtOAc (10 mL×3). The combined organic layers were washed with brine, dried over Na$_2$SO$_4$, and concentrated to afford the title compound. $^1$H NMR (CDCl$_3$ 400 MHz) δ 7.08 (t, 1H), 6.95 (d, 1H), 6.81 (d, 1H), 3.66 (s, 1H), 3.52-3.56 (m, 4H), 2.82 (t, 2H), 1.90-1.94 (m, 4H), 1.76-1.84 (m, 2H).

Step 4: 1-[3-(5-Chloro-3,4-dihydro-1'H-spiro[chromene-2,4'-piperidin]-1'-yl)isoxazol-5-yl]-1,3-dihydro-2H-imidazol-2-one To a solution of 3-(5-chloro-3,4-dihydro-1'H-spiro[chromene-2,4'-piperidin]-1'-yl)isoxazol-5-amine (790 mg, 2.47 mmol), DMAP (30 mg, 0.247 mmol) and pyridine (215 mg, 2.72 mmol) in anhydrous DCM (10 mL) was added phenyl carbonochloridate (464 mg, 2.97 mmol) in portions at 0° C. Then the mixture was stirred at room temperature overnight, washed successively with saturated citric acid solution (3 mL), sat. NaHCO$_3$ (3 mL) and brine, dried over Na$_2$SO$_4$ and concentrated. The resulting crude product was purified on silic gel (PE/EA=5/1) to afford phenyl[3-(5-chloro-3,4-dihydro-1'H-spiro[chromene-2,4'-piperidin]-1'-yl)isoxazol-5-yl]carbamate.

To a solution of phenyl[3-(5-chloro-3,4-dihydro-1'H-spiro [chromene-2,4'-piperidin]-1'-yl)isoxazol-5-yl]carbamate (410 mg, 0.93 mmol) in DMSO (5 mL) was added 2,2-dimethoxyethanamine (117 mg, 1.12 mmol). The mixture was stirred at 60° C. for 3 hours, then diluted with water (20 mL), and extracted with EtOAc (7 mL×2). The combined organic layers were washed with brine (5 mL), dried over Na$_2$SO$_4$ and concentrated to afford crude N-[3-(5-chloro-3,4-dihydro-1'H-spiro[chromene-2,4'-piperidin]-1'-yl)isoxazol-5-yl]-N'-(2,2-dimethoxyethyl)urea.

A mixture of N-[3-(5-chloro-3,4-dihydro-1'H-spiro [chromene-2,4'-piperidin]-1'-yl)isoxazol-5-yl]-N'-(2,2-dimethoxyethyl)urea (515 mg, 1 mmol) in HCOOH (6 mL) was stirred at 75° C. for 2 hours. The volatile materials were removed in vacuo. The resulting residue was diluted with water (3 mL), adjusted to pH 8 with sat. NaHCO$_3$, and extracted with EtOAc (4 mL×3). The combined organic layers were washed with brine (10 mL), dried over Na$_2$SO$_4$ and concentrated. The resulting residue was purified on silica gel (PE/EA=1/1) to afford the title compound. $^1$H NMR (CDCl$_3$ 400 MHz) δ 8.87 (s, 1H), 7.05 (t, 1H), 6.95 (t, 1H), 6.77-6.83 (m, 2H), 6.43-6.45 (m, 1H), 6.23 (s, 1H), 3.54-3.58 (m, 2H), 3.32-3.39 (m, 2H), 2.79 (t, 2H), 1.84-1.87 (m, 4H), 1.67-1.75 (m, 2H).

Step 5: {3-[3-(5-Chloro-3,4-dihydro-1'H-spiro[chromene-2,4'-piperidin]-1'-yl)isoxazol-5-yl]-2-oxo-2,3-dihydro-1H-imidazol-1-yl}acetic acid To a solution of 1-[3-(5-chloro-3,4-dihydro-1'H-spiro[chromene-2,4'-piperidin]-1'-yl) isoxazol-5-yl]-1,3-dihydro-2H-imidazol-2-one (230 mg, 0.596 mmol) in MeCN (5 mL) was added K$_2$CO$_3$ (164 mg, 1.192 mmol) and ethyl 2-bromoacetate (148 mg, 0.89 mmol). The mixture was stirred at 80° C. over 8 hours and filtered. The filtrate was concentrated and purified on silica gel with PE/EtOAc to afford ethyl{3-[3-(5-chloro-3,4-dihydro-1'H-spiro[chromene-2,4'-piperidin]-1'-yl)isoxazol-5-yl]-2-oxo-2,3-dihydro-1H-imidazol-1-yl}acetate.

To a solution of ethyl{3-[3-(5-chloro-3,4-dihydro-1'H-spiro[chromene-2,4'-piperidin]-1'-yl)isoxazol-5-yl]-2-oxo-2,3-dihydro-1H-imidazol-1-yl}acetate (180 mg, 0.38 mmol) in THF (5 mL) was added 1 M LiOH (1.5 mL). The mixture was stirred at room temperature for 2 hours. The solvent was evaporated under vacuum. The resulting residue was diluted with water (4 mL), adjusted to pH 3 with 1 M HCl, and filtered to afford the title compound. $^1$H NMR (CD$_3$OD 400 MHz) δ7.07 (t, 1H), 6.92-6.96 (m, 2H), 6.78-6.81 (m, 1H), 6.73 (d, 1H), 6.27 (s, 1H), 4.45 (s, 2H), 3.53-3.56 (m, 2H), 3.29-3.35 (m, 2H), 2.80 (t, J=7 Hz, 2H), 1.73-1.91 (m, 6H).

EXAMPLE 67

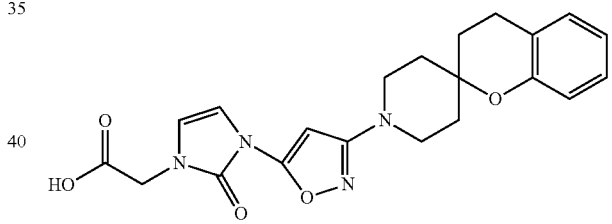

{3-[3-(3,4-Dihydro-1'H-spiro[chromene-2,4'-piperidin]-1'-yl)isoxazol-5-yl]-2-oxo-2,3-dihydro-1H-imidazol-1-yl}acetic acid Step 1: 3,4-Dihydrospiro[chromene-2,4'-piperidine] TFA salt A mixture of tert-butyl 4-oxopiperidine-1-carboxylate (29.27 g, 0.147 mol), pyrrolidine (14.6 g, 0.2 mol) and 2'-hydroxyacetophenone (20 g, 0.147 mol) in MeOH (300 mL) was refluxed for 1 hour. After cooling to room temperature, the solvent was removed in vacuo. The residue was diluted with EtOAc (500 mL) and washed with water (2×500 mL). The organic phase was dried over anhydrous sodium sulfate and concentrated under vacuum. The resulting residue was purified by silica gel chromatography with PE/EtOAc to give tert-butyl 4-oxo-3,4-dihydro-1'H-spiro[chromene-2,4'-piperidine]-1'-carboxylate as a white solid.

To a solution of tert-butyl 4-oxo-3,4-dihydro-1'H-spiro [chromene-2,4'-piperidine]-1'-carboxylate (15 g, 47 mmol) in MeOH (150 mL) was added NaBH$_4$ (1.88 g, 49 mmol) portionwise at 25° C. over 30 min. The resulting mixture was stirred for 2 hours at room temperature, then quenched by the addition of 50 mL of water. The resulting mixture was extracted with ethyl acetate (100 mL×2). The combined organic layers were washed with water (100 mL×2), dried over anhydrous sodium sulfate, and concentrated under vacuum to give tert-butyl 4-hydroxy-3,4-dihydro-1'H-spiro [chromene-2,4'-piperidine]-1'-carboxylate as a white solid.

To a mixture of tert-butyl 4-hydroxy-3,4-dihydro-1'H-spiro[chromene-2,4'-piperidine]-1'-carboxylate (11.4 g, 43.8 mmol) in TFA (140 mL) was added triethylsilane (21 g, 180 mmol). The resulting mixture was stirred at 80° C. for 5 hours, and then concentrated in vacuo. The resulting residue was swished with Et$_2$O, filtered and dried to give the title compound as a white solid. $^1$H NMR (DMSO-d6 400 MHz) δ 7.05-7.07 (m, 2H), 6.77-6.83 (m, 2H), 3.15-3.19 (m, 2H), 3.01-3.07 (m, 2H), 2.70-2.73 (m, 2H), 1.73-1.86 (m, 6H).

Step 2: {3-[3-(3,4-Dihydro-1'H-spiro[chromene-2,4'-piperidin]-1'-yl)isoxazol-5-yl]-2-oxo-2,3-dihydro-1H-imidazol-1-yl}acetic acid The title compound was prepared in a similar manner as described for Example 66 from 3,4-dihydrospiro[chromene-2,4'-piperidine] TFA salt and 3-bromo-4,5-dihydroisoxazole-5-carboxylate. $^1$H NMR (CD$_3$OD 400 MHz) δ 6.94-6.96 (m, 2H), 6.82 (d, 1H), 6.70 (t, 2H), 6.61 (d, 1H), 6.17 (s, 1H), 4.25 (s, 2H), 3.44 (d. 2H), 3.21-3.28 (m, 2H), 2.71 (t, 2H), 1.73-1.78 (m, 4H), 1.61-1.68 (m, 2H).

EXAMPLE 68

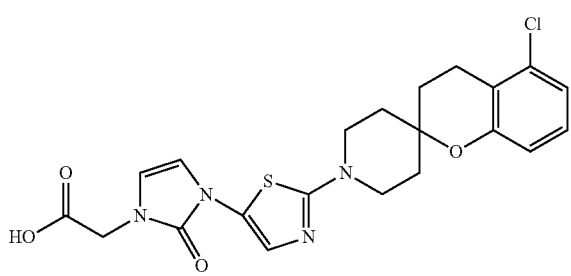 [SMILES: O=C(O)Cn1ccn(-c2cnc(N3CCC4(CCc5c(Cl)cccc5O4)CC3)s2)c1=O]

{3-[2-(5-Chloro-3,4-dihydro-1'H-spiro[chromene-2,4'-piperidin]-1'-yl)-1,3-thiazol-5-yl]-2-oxo-2,3-dihydro-1H-imidazol-1-yl}acetic acid Step 1: 1'-(5-Bromo-1,3-thiazol-2-yl)-5-chloro-3,4-dihydrospiro[chromene-2,4'-piperidine] A mixture of 2,5-dibromothiazole (0.975 g, 4.01 mmol), 5-chloro-3,4-dihydrospiro[chromene-2,4'-piperidine] HCl salt (1 g, 3.65 mmol) and DBU (1.3 mL, 8.62 mmol) in DMF (15 mL) was heated at 120° C. for 16 h. After cooling, the mixture was diluted with water and extracted with CH$_2$Cl$_2$. The CH$_2$Cl$_2$ extract was washed with water (3×), dried (Na$_2$SO$_4$) and concentrated. The resulting residue was dissolved in CH$_2$Cl$_2$ and passed through a short silica pad (eluting with CH$_2$Cl$_2$/EtOAc (1:1). After evaporation of the filtrate, the resulting residue was swished with Et$_2$O, filtered and dried to give the title compound as a beige powder.

Step 2: Ethyl{3-[2-(5-chloro-3,4-dihydro-1'H-spiro[chromene-2,4'-piperidin]-1'-yl)-1,3-thiazol-5-yl]-2-oxo-2,3-dihydro-1H-imidazol-1-yl}acetate To a 2-dram vial was added 1'-(5-bromo-1,3-thiazol-2-yl)-5-chloro-3,4-dihydrospiro[chromene-2,4'-piperidine] (250 mg, 0.625 mmol), ethyl (2-oxo-2,3-dihydro-1H-imidazol-1-yl)acetate (117 mg, 0.67 mmol), potassium phosphate tribasic (266 mg, 1.25 mmol) and copper(i) iodide (40 mg, 0.21 mmol) in dioxane (3 mL), followed by N,N'-dimethylethylenediamine (45 µL, 0.422 mmol). The mixture was stirred at 90° C. for 4 h. After cooling, the mixture was diluted with water (~2 mL) and EtOAc, filtered through Celite™ and the filter cake was washed with EtOAc. The combined EtOAc filtrates were concentrated in vacuo. The resulting residue was purified by Combi-Flash™ (10 g, 30-80% EtOAc in hexanes for 20 min, 30 mL/min, 20 mL/fraction) to give the title compound as a white solid.

Step 3: {3-[2-(5-Chloro-3,4-dihydro-1'H-spiro[chromene-2,4'-piperidin]-1'-yl)-1,3-thiazol-5-yl]-2-oxo-2,3-dihydro-1H-imidazol-1-yl}acetic acid To a solution of ethyl 13-[2-(5-chloro-3,4-dihydro-1'H-spiro[chromene-2,4'-piperidin]-1'-yl)-1,3-thiazol-5-yl]-2-oxo-2,3-dihydro-1H-imidazol-1-yl}acetate (140 mg, 0.29 mmol) in THF (4 mL) and MeOH (1 mL) was added 1N NaOH (0.6 mL, 0.60 mmol). The mixture was stirred for 15 min, then diluted with water and acidified with 1N HCl. The resulting white precipitate was collected, and washed with water and Et$_2$O to give the title compound as a white powder. $^1$H NMR (500 MHz, acetone-d$_6$): δ 7.20 (s, 1 H), 7.15 (t, 1 H), 6.99 (d, 1 H), 6.89-6.84 (m, 2 H), 6.75 (d, 1 H), 4.49 (s, 2 H), 3.81 (d, 2 H), 3.48-3.39 (m, 2 H), 2.80 (m, 2H), 2.01-1.78 (m, 6 H). MS: m/z 461 (MH$^+$).

EXAMPLE 69

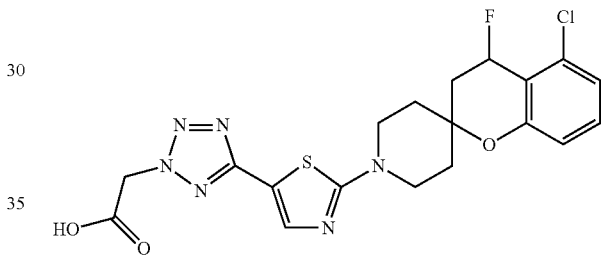

{5-[2-(5-Chloro-4-fluoro-3,4-dihydro-1'H-spiro [chromene-2,4'-piperidin]-1'-yl)-1,3-thiazol-5-yl]-2H-tetrazol-2-yl}acetic acid Step 1: Ethyl{5-[2-(5-chloro-4-fluoro-3,4-dihydro-1'H-spiro[chromene-2,4'-piperidin]-1'-yl)-1,3-thiazol-5-yl]-2H-tetrazol-2-yl}acetate To a solution of tert-butyl{5-[2-(5-chloro-4-oxo-3,4-dihydro-1'H-spiro[chromene-2,4'-piperidin]-1'-yl)-1,3-thiazol-5-yl]-2H-tetrazol-2-yl}acetate from Example 14, step 1 (200 mg, 0.4 mmol) in THF (8 mL) was added NaBH$_4$ (5.7 mg, 0.149 mmol). The mixture was stirred at room temperature for 2 hours, quenched with water (10 mL), and extracted with EtOAc (10 mL×2). The combined organic layers were washed with 10 mL of brine, dried over Na$_2$SO$_4$, concentrated and purified by PRE-TLC to afford ethyl{5-[2-(5-chloro-4-hydroxy-3,4-dihydro-1'H-spiro[chromene-2,4'-piperidin]-1'-yl)-1,3-thiazol-5-yl]-2H-tetrazol-2-yl}acetate as white solid.

To a solution of ethyl{5-[2-(5-chloro-4-hydroxy-3,4-dihydro-1'H-spiro[chromene-2,4'-piperidin]-1'-yl)-1,3-thiazol-5-yl]-2H-tetrazol-2-yl}acetate from above (88 mg, 0.179 mmol) in anhydrous DCM (2 mL) was added DAST (116 mg, 0.718 mmol) at −78° C. The mixture was stirred at −78° C. for 1 hour, then at room temperature overnight. The volatile materials were removed, and the resulting residue was purified by preparative TLC (PE/EA=1/1) to afford the title compound as a colorless oil. $^1$H NMR (CDCl$_3$ 400 MHz) δ 7.92 (s, 1H), 7.23 (s, 1H), 7.05 (d, 1H), 6.87 (d, 1H), 5.74-5.87 (m, 1H), 5.38 (s, 2H), 4.28 (q, 2H), 4.00 (d, 1H), 3.69-3.79 (m, 2H), 3.36-3.43 (m, 1H), 2.34-2.46 (m, 2H), 2.02-2.17 (m, 4H), 1.38 (t, 3H).

Step 2: {5-[2-(5-Chloro-4-fluoro-3,4-dihydro-1'H-spiro [chromene-2,4'-piperidin]-1'-yl)-1,3-thiazol-5-yl]-2H-tetrazol-2-yl}acetic acid The title compound was prepared in a similar manner as that described for Example 9 Step 2 from ethyl{5-[2-(5-chloro-4-fluoro-3,4-dihydro-1'H-spiro [chromene-2,4'-piperidin]-1'-yl)-1,3-thiazol-5-yl]-2H-tetrazol-2-yl}acetate. $^1$H NMR (CD$_3$OD 400 MHz) δ 7.86 (s, 1H), 7.28-7.32 (m, 1H), 7.06 (d, 1H), 6.93 (d, 1H), 5.82 (dd, 1H), 5.58 (s, 2H), 3.95-3.99 (m, 1H), 3.72-3.81 (m, 2H), 3.41-3.48 (m, 1H), 2.48 (t, 1H), 2.31 (d, 1H), 2.23-2.29 (m, 1H), 2.07-2.13 (m, 2H), 1.86-1.98 (m, 1H).

EXAMPLE 70

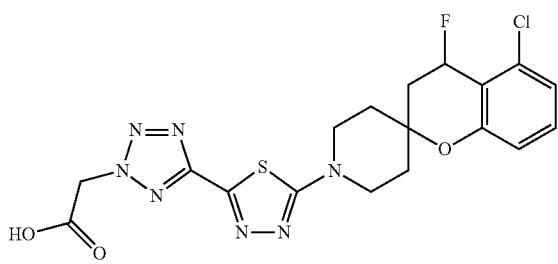 [SMILES: O=C(O)Cn1nnc(-c2nnc(N3CCC4(CC3)CC(F)c3c(Cl)cccc3O4)s2)n1]

{5-[5-(5-Chloro-4-fluoro-3,4-dihydro-1'H-spiro [chromene-2,4'-piperidin]-1'-yl)-1,3,4-thiadiazol-2-yl]-2H-tetrazol-2-yl}acetic acid The title compound was prepared in a similar as described for Example 69 from {5-[5-(5-chloro-4-oxo-3,4-dihydro-1'H-spiro[chromene-2,4'-piperidin]-1'-yl)-1,3,4-thiadiazol-2-yl]-2H-tetrazol-2-yl}acetic acid (Example 13). $^1$H NMR (CD$_3$OD 400 MHz) δ 7.28 (t, 1H), 7.04 (d, 1H), 6.92 (d, 1H), 5.80 (d, 1H), 5.58 (s, 2H), 3.97 (d, 1H), 3.77-3.86 (m, 2H), 3.52-3.55 (m, 1H), 2.44-2.52 (m, 1H), 1.97-2.21 (m, 5H).

EXAMPLE 71

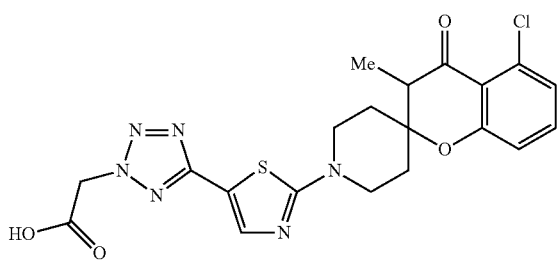 [SMILES: CC1C(=O)c2c(Cl)cccc2OC12CCN(c1ncc(-c3nnn(CC(=O)O)n3)s1)CC2]

{5-[2-(5-Chloro-3-methyl-4-oxo-3,4-dihydro-1'H-spiro[chromene-2,4'-piperidin]-1'-yl)-1,3-thiazol-5-yl]-2H-tetrazol-2-yl}acetic acid Step 1: tert-Butyl 5-chloro-3-methyl-4-oxo-3,4-dihydro-1'H-spiro[chromene-2,4'-piperidine]-1'-carboxylate To a solution of LiHMDS (0.37 mL, 0.37 mmol, 1.0 M/THF) in THF (0.3 mL) at −78° C. was added tert-butyl 5-chloro-4-oxo-3,4-dihydro-1'H-spiro[chromene-2,4'-piperidine]-1'-carboxylate (Intermediate 1, step 2), and (100 mg, 0.29 mmol) in THF (0.8 mL) under Argon. After stirring for 30 min at −78° C., the solution was warmed to −20° C., and stirred for 1 h. A cooled solution of methyl iodide (122 mg, 0.86 mmol) and HMPA (0.15 mL, 0.86 mmol) in THF (0.6 mL) was added dropwise via cannula, and the reaction mixture was stirred at −20° C. After 2 h, the reaction was quenched with saturated aqueous ammonium chloride (30 mL), warmed to room temperature, stirred for 30 min, and then extracted with EtOAc (20 mL×3). The combined organic extracts were washed with saturated aqueous ammonium chloride (20 mL) and saturated aqueous sodium chloride (20 mL), dried over Na$_2$SO$_4$, filtered and concentrated under reduced pressure. The resulting residue was purified by preparative TLC (PE/EtOAc) to give the title compound.

Step 2: 5-Chloro-3-methylspiro[chromene-2,4'-piperidin]-4(3H)-one hydrochloride A mixture of tert-butyl 5-chloro-3-methyl-4-oxo-3,4-dihydro-1'H-spiro[chromene-2,4'-piperidine]-1'-carboxylate (600 mg, 1.64 mmol) in HCl/dioxane (10 mL, 8 M) was stirred at room temperature for 2 h, and then Et$_2$O (10 mL) was added to the mixture. The resulting precipitate was collected by filtration, washed with 10 mL Et$_2$O, and dried in vacuo to give title compound. $^1$H NMR (CDCl$_3$ 400 MHz): δ 9.74 (br, 2H), 7.38 (t, 1H), 7.08 (d, 1H), 6.93 (d, 1H), 3.27-3.41 (m, 4H), 2.73-2.79 (m, 1H), 2.27-2.34 (m, 1H), 2.03-2.17 (m, 3H), 1.22 (d, 3H).

Step 3: tert-Butyl{5-[2-(5-chloro-3-methyl-4-oxo-3,4-dihydro-1'H-spiro[chromene-2,4'-piperidin]-1'-yl)-1,3-thiazol-5-yl]-2H-tetrazol-2-yl}acetate To a solution of 5-chloro-3-methylspiro[chromene-2,4'-piperidin]-4(3H)-one hydrochloride (0.2 g, 0.664 mmol) and tert-butyl[5-(2-bromo-1,3-thiazol-5-yl)-2H-tetrazol-2-yl]acetate, Intermediate 3, (0.23 g, 0.664 mmol) in DMF (4 mL) was added K$_2$CO$_3$ (0.366 g, 2.56 mmol) under a nitrogen atmosphere. The mixture was stirred at 65° C. for 5 h. After cooling, the resulting precipitate was removed by filtration and the filtrate was concentrated in vacuo. The resulting residue was extracted with EtOAc (10 mL×3). The combined organic layers were washed with brine (5 mL), dried over anhydrous Na$_2$SO$_4$, filtered and purified by silica gel chromatography (PE/EtOAc) to give title compound.

Step 4: {5-[2-(5-Chloro-3-methyl-4-oxo-3,4-dihydro-1'H-spiro[chromene-2,4'-piperidin]-1'-yl)-1,3-thiazol-5-yl]-2H-tetrazol-2-yl}acetic acid The title compound was prepared in a similar manner as described above for step 2 of this example from tert-butyl{5-[2-(5-chloro-3-methyl-4-oxo-3,4-dihydro-1'H-spiro[chromene-2,4'-piperidin]-1'-yl)-1,3-thiazol-5-yl]-2H-tetrazol-2-yl}acetate with HCl in dioxane. $^1$H NMR (CD$_3$OD 400 MHz): δ 7.75 (s, 1H), 7.34-7.38 (m, 1H), 6.96-7.00 (m, 2H), 5.46 (s, 2H), 3.83-3.87 (m, 2H), 3.39-3.49 (m, 2H), 2.70-2.76 (m, 1H), 1.90-2.03 (m, 3H), 1.72-1.88 (m, 1H), 1.12 (d, 3H).

EXAMPLE 72

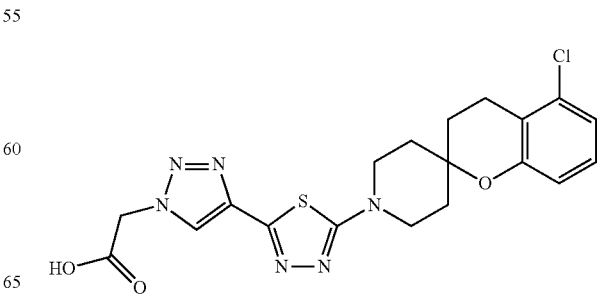

{4-[5-(5-Chloro-3,4-dihydro-1'H-spiro[chromene-2,4'-piperidin]-1'-yl)-1,3,4-thiadiazol-2-yl]-1H-1,2,3-triazol-1-yl}acetic acid Step 1: Ethyl[4-(tributylstannyl)-1H-1,2,3-triazol-1-yl]acetate A mixture of ethyl azidoacetate (1.72 g, 13.3 mmol) and tributyl(ethynyl)stannane (4.20 g, 13.3 mmol) in 30 mL of anhydrous toluene was refluxed for 24 hours. After removing the solvent, the residual was purified by silica gel column chromatography (PE/EA=15:1) to afford the title compound. $^1$HNMR (CDCl3 400 MHz) δ 7.53 (s, 1H), 5.13 (s, 2H), 4.17 (q, 2H), 1.56 (m, 6H), 1.20-1.28 (m, 9H), 1.03-1.07 (m, 6H), 0.75-0.82 (m, 9H). M+1: 444 and 446.

Step 2: 5-(5-Chloro-3,4-dihydro-1'H-spiro[chromene-2,4'-piperidin]-1'-yl)-1,3,4-thiadiazol-2-amine To a solution of the 5-chloro-3,4-dihydrospiro[chromene-2,4'-piperidine], TFA salt of Intermediate 1, (0.6 g, 1.8 mmol), and 5-bromo-1,3,4-thiadiazol-2-amine (0.32 g, 1.8 mmol) in DMF (12 mL) was added $K_2CO_3$ (0.75 g, 5.4 mmol) under a nitrogen atmosphere. The mixture was stirred at 65° C. for 2 hours. After cooling, the resulting precipitate was removed by filtration and the filtrate was concentrated in vacuo. Then the residue was extracted with EtOAc. The combined organic layers were washed with brine, dried over anhydrous $Na_2SO_4$, filtered and purified by silica gel chromatography PE/EtOAc to give the title compound.

Step 3: 1'-(5-Bromo-1,3,4-thiadiazol-2-yl)-5-chloro-3,4-dihydrospiro[chromene-2,4'-piperidine] A mixture of $CuBr_2$ (0.34 g, 1.54 mmol) and anhydrous $CH_3CN$ (10 ml) was purged with argon and cooled to 0° C. with an ice bath, then t-BuONO (0.207 g, 2 mmol) was added dropwise. The resulting mixture was stirred at 0° C. for 15 min, and then treated with 5-(5-chloro-3,4-dihydro-1'H-spiro[chromene-2,4'-piperidin]-1'-yl)-1,3,4-thiadiazol-2-amine (0.45 g, 1.339 mmol). The cooling bath was removed and the mixture was stirred at room temperature for 3 h. The mixture was diluted with aqueous HCl (10 mL, 1N) and extracted with EtOAc (20 mL×3). The combined organic layers were washed with brine and dried over $Na_2SO_4$, and concentrated in vacuo to afford the title compound.

Step 4: Ethyl{4-[5-(5-chloro-3,4-dihydro-1'H-spiro[chromene-2,4'-piperidin]-1'-yl)-1,3,4-thiadiazol-2-yl]-1H-1,2,3-triazol-1-yl}acetate A mixture of 1'-(5-bromo-1,3,4-thiadiazol-2-yl)-5-chloro-3,4-dihydrospiro[chromene-2,4'-piperidine] (400 mg, 1 mmol), ethyl[4-(tributylstannyl)-1H-1,2,3-triazol-1-yl]acetate (625 mg, 1.4 mmol), $Pd(PPh_3)_4$ (115 mg, 0.1 mmol) in DMF (10 ml) was stirred at 80° C. for 8 h under Argon. After cooling, the mixture was diluted with water and extracted with EtOAc (20 mL×2). The combined organic layers were concentrated in vacuo, and the resulting residue was purified by preparative TLC to give the title compound. $^1$H NMR (CDCl$_3$ 400 MHz) δ 8.23 (s, 1H), 7.06 (t, 1H), 6.96 (d, 1H), 6.76 (d, 1H), 5.22 (s, 2H), 4.26-4.32 (m, 2H), 3.84-3.88 (m, 2H), 3.59-3.66 (m, 2H), 2.79-2.83 (m, 2H), 1.96-1.97 (m, 2H), 1.89-1.92 (m, 2H), 1.78-1.83 (m, 2H), 1.36 (t, 3H).

Step 5: {4-[5-(5-Chloro-3,4-dihydro-1'H-spiro[chromene-2,4'-piperidin]-1'-yl)-1,3,4-thiadiazol-2-yl]-1H-1,2,3-triazol-1-yl}acetic acid The title compound was prepared in a similar manner as that described for Example 9 Step 2 from ethyl{4-[5-(5-chloro-3,4-dihydro-1'H-spiro[chromene-2,4'-piperidin]-1'-yl)-1,3,4-thiadiazol-2-yl]-1H-1,2,3-triazol-1-yl}acetate. $^1$H NMR (DMSO-d$_6$, 400 MHz) δ 8.60 (s, 1H), 7.15 (t, 1H), 7.01 (d, 1H), 6.85 (d, 1H), 5.13 (s, 2H), 3.76-3.80 (m, 2H), 3.49-3.55 (m, 2H), 2.72-2.76 (m, 2H), 1.89-1.92 (m, 2H), 1.81-1.84 (m, 4H).

EXAMPLE 73

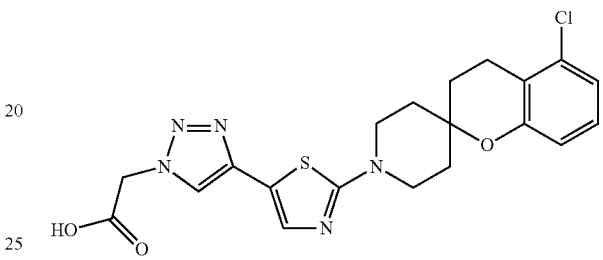

{4-[2-(5-Chloro-3,4-dihydro-1'H-spiro[chromene-2,4'-piperidin]-1'-yl)-1,3-thiazol-5-yl]-1H-1,2,3-triazol-1-yl}acetic acid The title compound was prepared in a similar manner as described for Example 72 (steps 4 and 5) from 1'-(5-bromo-1,3-thiazol-2-yl)-5-chloro-3,4-dihydrospiro[chromene-2,4'-piperidine] (from Example 68, step 1), and ethyl[4-(tributylstannyl)-1H-1,2,3-triazol-1-yl]acetate (from Example 72, step 1). $^1$H NMR (DMSO-d$_6$, 400 MHz). δ8.37 (s, 1H), 7.58 (s, 1H), 7.20 (t, 1H), 7.06 (d, 1H), 6.91 (d, 1H), 5.30 (s, 2H), 3.79-3.83 (m, 2H), 2.77-2.81 (m, 2H), 1.95-1.98 (m, 2H), 1.83-1.90 (m, 4H).

EXAMPLE 74

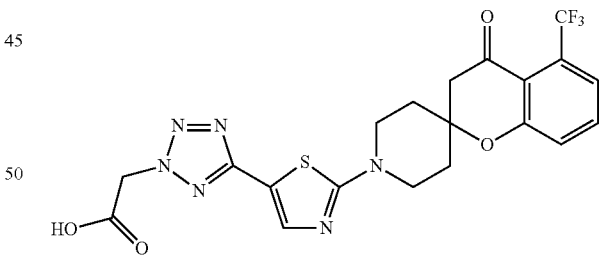

(5-{2-[4-Oxo-5-(trifluoromethyl)-3,4-dihydro-1'H-spiro[chromene-2,4'-piperidin]-1'-yl]-1,3-thiazol-5-yl}-2H-tetrazol-2-yl)acetic acid Step 1: 5-(Trifluoromethyl)spiro[chromene-2,4'-piperidin]-4(3H)-one hydrochloride The title compound was obtained by the treatment of tert-butyl 4-oxo-5-(trifluoromethyl)-3,4-dihydro-1'H-spiro[chromene-2,4'-piperidine]-1'-carboxylate (which was prepared in a similar fashion from 3-trifluoromethyl phenol as described for steps 1 and 3 of Intermediate 1) with 4M HCl in dioxane.

Step 2: tert-Butyl (5-{2-[4-oxo-5-(trifluoromethyl)-3,4-dihydro-1'H-spiro[chromene-2,4'-piperidin]-1'-yl]-1,3-thiazol-5-yl}-2H-tetrazol-2-yl)acetate To a suspension of 5-(trifluoromethyl)spiro[chromene-2,4'-piperidin]-4(3H)-one hydrochloride (310 mg, 0.96 mmol) and tert-butyl[5-(2-bromo-1,3-thiazol-5-yl)-2H-tetrazol-2-yl]acetate (346 mg, 1 mmol) in NMP (3 mL) was added DBU (0.45 mL, 2.99 mmol). The mixture was stirred at 120° C. for 20 min. After cooling, the mixture was diluted with water, acidified with 1M HCl and extracted with EtOAc. The EtOAc extract was washed with water (2×), dried (Na$_2$SO$_4$) and concentrated in vacuo. The resulting residue was purified via Combi-Flash™ (40 g, 20-60% EtOAc in hexanes for 15 min, 35 mL/min, 20 mL/fraction) to afford the title compound as a foam. $^1$H NMR (500 MHz, acetone-d$_6$): δ 7.85 (s, 1 H), 7.80-7.73 (m, 1 H), 7.52 (d, 2 H), 5.57 (s, 2 H), 3.99 (d, 2 H), 3.65-3.56 (m, 2 H), 3.02 (s, 2 H), 2.21 (d, 2 H), 2.06-1.98 (m, 2 H), 1.50 (s, 9 H).

Step 3: (5-{2-[4-Oxo-5-(trifluoromethyl)-3,4-dihydro-1'H-spiro[chromene-2,4'-piperidin]-1'-yl]-1,3-thiazol-5-yl}-2H-tetrazol-2-yl)acetic acid To a solution of tert-butyl (5-{2-[4-oxo-5-(trifluoromethyl)-3,4-dihydro-1'H-spiro[chromene-2,4'-piperidin]-1'-yl]-1,3-thiazol-5-yl}-2H-tetrazol-2-yl)acetate (300 mg, 0.55 mmol) in THF (5 mL) and MeOH (1 mL) was added a solution of 1M aqueous NaOH (1.1 mL, 1.1 mmol). After stirring for 10 min, the mixture was acidified with 1M HCl, and extracted with EtOAc. The EtOAc extract was washed with water, dried (Na$_2$SO$_4$) and concentrated in vacuo. The resulting residue was purified by LC/MS using Max-RP™ (50×21 mm column and a gradient of CH$_3$CN:0.6% formic acid 30-55% in 8.3 min, flow rate 25 mL/min) to give the title compound. $^1$H NMR (500 MHz, DMSO-d$_6$): δ 7.87 (s, 1 H), 7.79-7.72 (m, 1 H), 7.50 (d, 2 H), 5.62 (s, 2 H), 3.86 (d, 2 H), 3.53-3.44 (m, 2 H), 2.10-2.01 (m, 2 H), 1.95-1.86 (m, 2 H). MS; m/z 495 (MH$^+$).

EXAMPLE 75

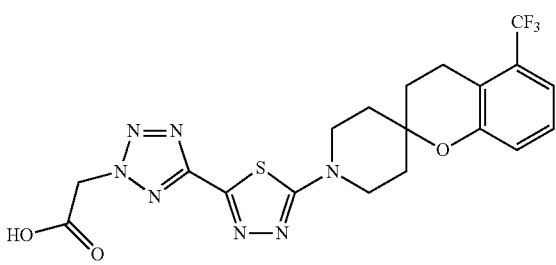 [SMILES: O=C(O)Cn1cc(-c2nnc(N3CCC4(CCc5c(Cl)cccc5O4)CC3)s2)nn1]

(5-{5-[5-(Trifluoromethyl)-3,4-dihydro-1'H-spiro[chromene-2,4'-piperidin]-1'-yl]-1,3,4-thiadiazol-2-yl}-2H-tetrazol-2-yl)acetic acid The title compound was prepared in a similar manner as described for Example 13, step 1 and followed by Example 74, step 3 starting from 5-(trifluoromethyl)-3,4-dihydrospiro[chromene-2,4'-piperidine]hydrochloride, and tert-butyl[5-(5-bromo-1,3,4-thiadiazol-2-yl)-2H-tetrazol-2-yl]acetate, Intermediate 6. $^1$H NMR (500 MHz, acetone-d$_6$): δ 7.37-7.26 (m, 2 H), 7.20 (d, 1H), 5.79 (s, 2 H), 3.98 (d, 2 H), 3.76-3.67 (m, 2 H), 3.02 (s, 2 H), 2.04-1.93 (m, 6 H). MS: m/z 482 (MH$^+$).

EXAMPLE 76

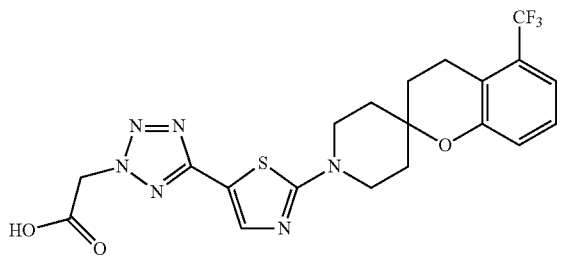

(5-{2-[5-(Trifluoromethyl)-3,4-dihydro-1'H-spiro[chromene-2,4'-piperidin]-1'-yl]-1,3-thiazol-5-yl}-2H-tetrazol-2-yl)acetic acid The title compound was prepared in a similar manner as described for Example 74, steps 2 and 3 from 5-(trifluoromethyl)-3,4-dihydrospiro[chromene-2,4'-piperidine]hydrochloride, and tert-butyl[5-(2-bromo-1,3-thiazol-5-yl)-2H-tetrazol-2-yl]acetate, Intermediate 3. $^1$H NMR (500 MHz, acetone-d$_6$): δ 7.85 (d, 1 H), 7.37-7.27 (m, 2 H), 7.20 (d, 1 H), 5.66 (s, 2 H), 3.96 (d, 2 H), 3.64-3.54 (m, 2 H), 3.01 (s, 3 H), 2.05-1.95 (m, 4 H), 1.95-1.86 (m, 2 H). MS: m/z 481 (MH$^+$).

EXAMPLE 77

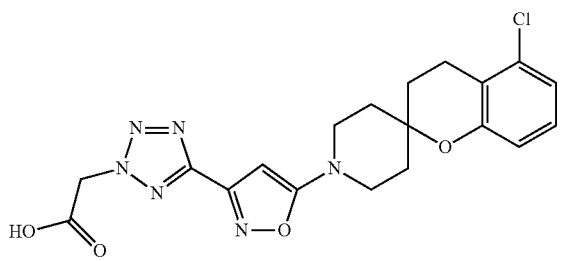 [SMILES: O=C(O)Cn1nnc(-c2cc(N3CCC4(CCc5c(Cl)cccc5O4)CC3)on2)n1]

{5-[5-(5-Chloro-3,4-dihydro-1'H-spiro[chromene-2,4'-piperidin]-1'-yl)isoxazol-3-yl]-2H-tetrazol-2-yl}acetic acid Step 1: 5-Chloro-1'-ethanethioyl-3,4-dihydrospiro[chromene-2,4'-piperidine] To a suspension of 5-chloro-3,4-dihydrospiro[chromene-2,4'-piperidine] HCl salt (2 g, 7.3 mmol) and Et$_3$N (3 mL, 21.5 mmol) in CH$_2$Cl$_2$ (25 mL) was added acetyl chloride (0.7 mL, 9.8 mmol). After stirring for 1 h, the mixture was diluted with water and extracted with CH$_2$Cl$_2$. The CH$_2$Cl$_2$ extract was washed with diluted brine, dried (MgSO$_4$) and concentrated. The resulting residue was purified by Combi-Flash™ (40 g, 50-100% EtOAc in hexanes for 20 min, 40 mL/min, 18 mL/fraction) to give 1'-acetyl-5-chloro-3,4-dihydrospiro[chromene-2,4'-piperidine] as an oil, which solidified on standing.

A mixture of 1'-acetyl-5-chloro-3,4-dihydrospiro[chromene-2,4'-piperidine] (1.9 g, 6.8 mmol) and Lawesson's reagent (3.6 g, 8.9 mmol) in CH$_3$CN (30 mL) was heated at 65° C. overnight. After cooling, the mixture was diluted with hexanes:Et₂O (1:1), and filtered through Celite™. The filtrate was concentrated and purified by Combi-Flash™ (40 g, 20-50% EtOAc in hexanes for 20 min, 40 mL/min, 18 mL/fraction) to give the title compound.

Step 2: Ethyl 4-(5-chloro-3,4-dihydro-1'H-spiro[chromene-2,4'-piperidin]-1'-yl)-2-oxo-4-thioxobutanoate To a suspension of NaH (1.5 g, 36.5 mmol) in THF (20 mL) was added diethyl oxalate (1 mL, 7.3 mmol), followed by a solution of 5-chloro-P-ethanethioyl-3,4-dihydrospiro[chromene-2,4'-piperidine] (1.8 g, 6.1 mmol) and dibenzo-18-C-6 (110 mg, 0.3 mmol) in THF (30 mL). The mixture was refluxed for 1 h and then poured into a 1:1 mixture of Et₂O/1N HCl (200 mL) at −10° C. The reaction mixture was extracted with EtOAc. The organic layer was separated, dried (Na₂SO₄) and concentrated. The resulting residue was purified by chromatography on silica gel (hexanes:EtOAc, 5-40% over 15 min) to give the title compound as a yellow powder.

Step 3: Ethyl 5-(5-chloro-3,4-dihydro-1'H-spiro[chromene-2,4'-piperidin]-1'-yl)isoxazole-3-carboxylate A mixture of ethyl 4-(5-chloro-3,4-dihydro-1'H-spiro[chromene-2,4'-piperidin]-1'-yl)-2-oxo-4-thioxobutanoate (1 g, 2.5 mmol), hydroxylamine hydrochloride (211 mg, 2.5 mmol), and NaHCO₃ (276 mg, 3.3 mmol) in EtOH (20 mL) was refluxed for 2 h. After cooling, the mixture was diluted with water and extracted with EtOAc (3×). The combined EtOAc extracts were washed with brine, dried over Na₂SO₄, and concentrated. The resulting residue was purified by chromatography on silica gel (hexanes/EtOAc 5-40% in 15 min) to give the title compound as a yellow solid. ¹H NMR (400 MHz, acetone-d₆): δ 7.16-7.08 (m, 1 H), 6.99-6.92 (m, 1 H), 6.85 (d, 1 H), 5.57 (s, 1 H), 4.30 (q, 2 H), 3.70-3.63 (m, 2 H), 3.46-3.37 (m, 2 H), 2.80 (m, 2 H), 1.99-1.75 (m, 6 H), 1.35 (t, 3 H).

Step 4: 5-(5-Chloro-3,4-dihydro-1'H-spiro[chromene-2,4'-piperidin]-1'-yl)isoxazole-3-carboxamide To a solution of ethyl 5-(5-chloro-3,4-dihydro-1'H-spiro[chromene-2,4'-piperidin]-1'-yl)isoxazole-3-carboxylate (500 mg, 1.3 mmol) in THF (2 mL) and MeOH (1 mL) was added ammonium hydroxide (1.5 mL, 38.5 mmol). The mixture was stirred at room temperature overnight. The volatile materials were removed in vacuo. The resulting residue was diluted with water, acidified with 1M HCl and extracted with EtOAc. The EtOAc layer was washed with water, dried (MgSO₄) and concentrated. The resulting residue was swished with Et₂O, filtered and dried to give the title compound as a white solid. ¹H NMR (500 MHz, acetone-d₆): δ 7.15 (m, 2 H), 6.99 (d, 1 H), 6.88 (d, 1 H), 6.80 (s, 1 H), 5.53 (s, 1 H), 3.68 (d, 2 H), 3.43 (t, 2 H), 1.98 (t, 2 H), 1.95-1.78 (m, 4 H).

Step 5: {5-[5-(5-Chloro-3,4-dihydro-1'H-spiro[chromene-2,4'-piperidin]-1'-yl)isoxazol-3-yl]-2H-tetrazol-2-yl}acetic acid The title compound was prepared in a similar manner as described for Example 2, steps 5 and 6, from 5-(5-chloro-3,4-dihydro-1'H-spiro[chromene-2,4'-piperidin]-1'-yl)isoxazole-3-carboxamide. ¹H NMR (500 MHz, acetone-d₆): δ 7.19-7.12 (m, 1 H), 7.00 (d, 1 H), 6.89 (d, 1 H), 5.80 (s, 1 H), 5.76 (s, 2 H), 3.77 (d, 2 H), 3.55-3.45 (m, 2 H), 2.04-1.86 (m, 6 H). MS: m/z 431 (MH⁺).

EXAMPLE 78

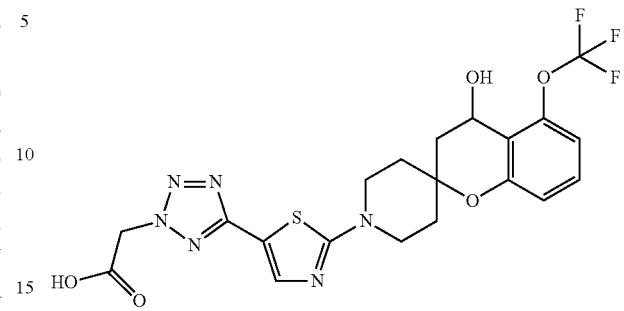

(5-{2-[4-Hydroxy-5-(trifluoromethoxy)-3,4-dihydro-1'H-spiro[chromene-2,4'-piperidin]-1'-yl]-1,3-thiazol-5-yl}-2H-tetrazol-2-yl)acetic acid The title compound was prepared, as a white solid, in the same manner as described for Example 20, but using (5-{2-[4-oxo-5-(trifluoromethoxy)-3,4-dihydro-1'H-spiro[chromene-2,4'-piperidin]-1'-yl]-1,3-thiazol-5-yl}-2H-tetrazol-2-yl)acetic acid (Example 21). LC-MS: m/z=513 (MH⁺). ¹H NMR (400 MHz, DMSO-d₆): δ 13.80 (br s, 1 H), 7.89 (s, 1 H), 7.33 (t, 1 H), 6.95-6.88 (m, 2 H), 5.70 (s, 2 H), 5.41 (d, 1 H), 4.93-4.87 (m, 1 H), 3.89-3.80 (m, 1 H), 3.80-3.72 (m, 1 H), 3.66-3.54 (m, 1 H), 3.56-3.30 (m, 1 H), 2.28 (d, 1 H), 2.13 (dd, 1 H), 2.03-1.94 (m, 1 H), 1.97-1.80 (m, 3 H).

EXAMPLE 79

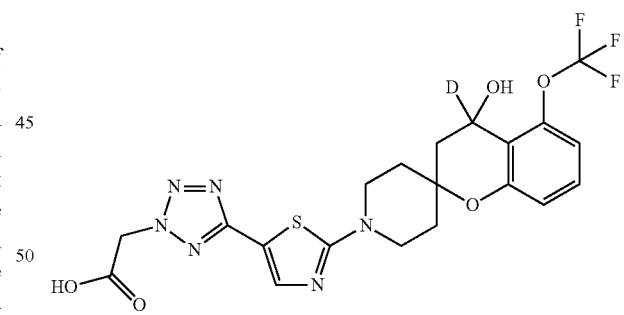

(5-{2-[4-Hydroxy-5-(trifluoromethoxy)-3,4-dihydro-1'H-spiro[chromene-2,4'-piperidin]-1'-yl]-1,3-thiazol-5-yl}-2H-tetrazol-2-yl)acetic acid-d₁ The title compound was prepared, as a white solid, in the same manner as described for Example 20, but using (5-{2-[4-oxo-5-(trifluoromethoxy)-3,4-dihydro-1'H-spiro[chromene-2,4'-piperidin]-1'-yl]-1,3-thiazol-5-yl}-2H-tetrazol-2-yl)acetic acid (Example 21) and NaBD₄. LC-MS: m/z=514 (MH⁺). ¹H NMR (400 MHz, DMSO-d₆): δ 13.82 (br s, 1 H), 7.89 (s, 1 H), 7.33 (t, 1 H), 6.94-6.87 (m, 2 H), 5.70 (s, 2 H), 5.39 (s, 1 H), 3.89-3.81 (m, 1 H), 3.80-3.72

(m, 1 H), 3.66-3.53 (m, 1 H), 3.53-3.28 (m, 1 H), 2.28 (d, 1 H), 2.12 (d, 1 H), 1.99 (d, 1 H), 1.94-1.80 (m, 3 H).

EXAMPLE 80

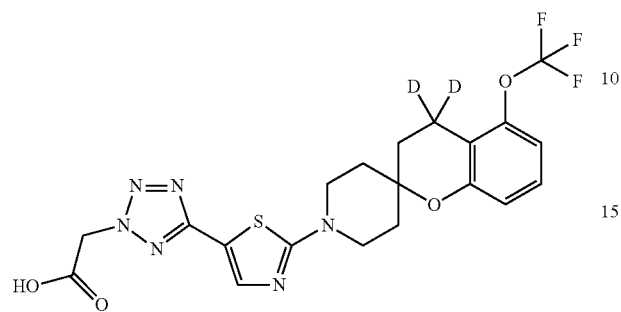

(5-{2-[5-(Trifluoromethoxy)-3,4-dihydro-1'H-spiro [chromene-2,4'-piperidin]-1'-yl]-1,3-thiazol-5-yl}-2H-tetrazol-2-yl)acetic acid-d$_2$ The title compound was prepared, as a white solid, through 2 synthetic steps in the same manner as described for Example 21, but using 5-(trifluoromethoxy)-3,4-dihydrospiro[chromene-2,4'-piperidinium]chloride-d$_2$ (Intermediate 20) in step 1. LC-MS: m/z=499 (MH$^+$). $^1$H NMR (400 MHz, DMSO-d$_6$): δ 13.81 (br s, 1H), 7.89 (s, 1 H), 7.25 (t, 1 H), 6.94-6.87 (m, 2 H), 5.70 (s, 2 H), 3.89-3.78 (m, 2 H), 3.56-3.44 (m, 2 H), 1.91-1.74 (m, 6 H).

EXAMPLE 81

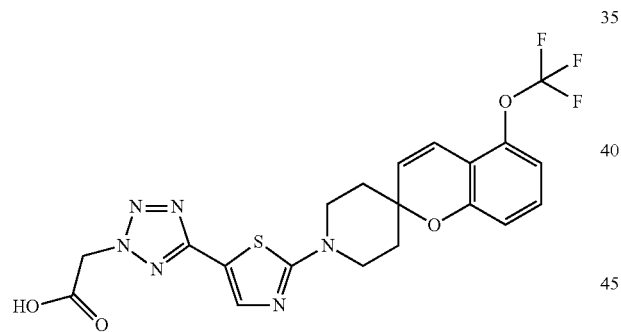

(5-{2-[5-(Trifluoromethoxy)-1'H-spiro[chromene-2,4'-piperidin]-1'-yl]-1,3-thiazol-5-yl}-2H-tetrazol-2-yl)acetic acid The title compound was prepared, as a white solid, through 2 synthetic steps in the same manner as described for Example 21, but using 5-(trifluoromethoxy)spiro[chromene-2,4'-piperidinium]chloride (Intermediate 19) in step 1. LC-MS: m/z=495.0 (MH$^+$). $^1$H NMR (400 MHz, DMSO-d$_6$): δ 13.78 (br s, 1 H), 7.89 (s, 1 H), 7.30 (t, 1 H), 7.01 (d, 1 H), 6.96 (d, 1 H), 6.66 (d, 1 H), 6.02 (d, 1 H), 5.71 (s, 2 H), 3.91-3.80 (m, 2 H), 3.62-3.51 (m, 2 H), 2.07-1.96 (m, 2 H), 1.98-1.85 (m, 2 H).

Example of a Pharmaceutical Formulation

As a specific embodiment of an oral composition of a compound of the present invention, 50 mg of the compound of any of the Examples is formulated with sufficient finely divided lactose to provide a total amount of 580 to 590 mg to fill a size O hard gelatin capsule.

While the invention has been described and illustrated in reference to specific embodiments thereof, those skilled in the art will appreciate that various changes, modifications, and substitutions can be made therein without departing from the spirit and scope of the invention. For example, effective dosages other than the preferred doses as set forth hereinabove may be applicable as a consequence of variations in the responsiveness of the human being treated for a particular condition. Likewise, the pharmacologic response observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended therefore that the invention be limited only by the scope of the claims which follow and that such claims be interpreted as broadly as is reasonable.

What is claimed is:

1. A compound of structural formula I:

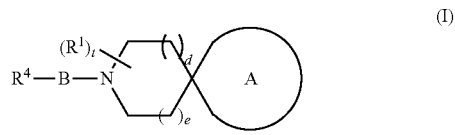

or a pharmaceutically acceptable salt thereof; wherein

A is selected from the group consisting of:

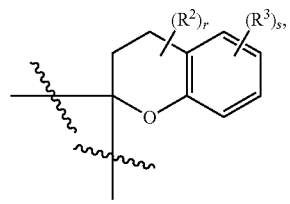

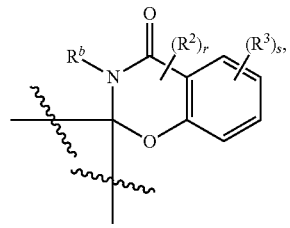

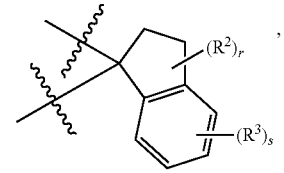

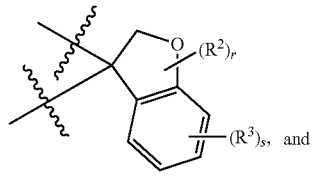

and

-continued

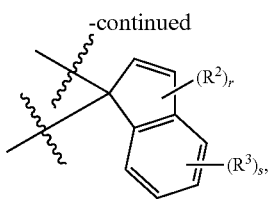

wherein r is 0 or 1; and s is 0 or 1;
B is selected from the group consisting of:

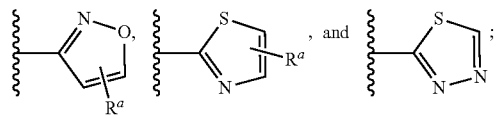

each $R^1$ is independently selected from the group consisting of: hydrogen, halogen, and $C_{1-3}$ alkyl, wherein alkyl is unsubstituted or substituted with one to three substituents independently selected from halogen and hydroxy;

each R2 is independently selected from the group consisting of:
(1) hydrogen,
(2) halogen,
(3) C1-6 alkyl,
(4) $(CH_2)_nOR^e$,
(5) $(CH_2)_nN(R^e)2$,
(6) $(CH_2)_nCN$,
(7) $(CH_2)_nCOR^e$, and
(8) $(CH_2)_nS(O)_qR^e$,
wherein alkyl is unsubstituted or substituted with hydroxy or one to three halogens, and
wherein any $CH_2$ in $R^2$ is unsubstituted or substituted with one to two groups independently selected from halogen, hydroxy, and $C_{1-4}$ alkyl unsubstituted or substituted with one to five fluorines;

each $R^3$ is independently selected from the group consisting of:
(1) hydrogen,
(2) halogen,
(3) —$C_{1-6}$ alkyl,
(4) —$C_{1-6}$ alkenyl,
(5) —$OC_{1-6}$ alkyl,
(6) $(CH_2)_nOR^e$,
(7) $(CH_2)_nN(R^e)_2$,
(8) $(CH_2)_nC\equiv N$,
(9) $(CH_2)_nCOR^e$, and
(10) $(CH_2)_nS(O)_qR^e$,
wherein alkyl is unsubstituted or substituted with one to three substituents selected from: hydroxy, halogen, and $C_{1-4}$ alkyl wherein alkyl are unsubstituted or substituted with one to three substituents selected from: halogen, hydroxy, and $C_{1-4}$ alkyl unsubstituted or substituted with one to five fluorines, and wherein any $CH_2$ in $R^3$ is unsubstituted or substituted with one to two groups independently selected from halogen, hydroxy, and $C_{1-4}$ alkyl unsubstituted or substituted with one to five fluorines;

$R^4$ is

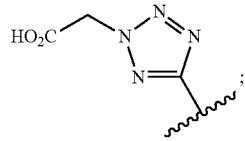

each $R^a$ is independently selected from the group consisting of:
(1) hydrogen,
(2) halogen,
(3) cyano,
(4) $C_{1-4}$ alkyl, unsubstituted or substituted with one to five fluorines,
(5) $C_{1-4}$ alkoxy, unsubstituted or substituted with one to five fluorines,
(6) $C_{1-4}$ alkylthio, unsubstituted or substituted with one to five fluorines,
(7) $C_{1-4}$ alkylsulfonyl,
(8) —$CO_2H$,
(9) $C_{1-4}$ alkyloxycarbonyl, and
(10) $C_{1-4}$ alkylcarbonyl;

each $R^e$ is independently selected from the group consisting of:
(1) hydrogen, and
(2) $C_{1-6}$ alkyl,
wherein alkyl is unsubstituted or substituted with one to three substituents independently selected from the group consisting of: halogen, cyano, —$C_{1-4}$ alkoxy, —$C_{1-4}$ alkylthio, —$C_{1-4}$ alkylsulfonyl, —$C_2H$, and —$CO_2C_{1-4}$ alkyl;

n is an integer from 0 to 3;
q is an integer from 1 to 2;
t is an integer from 0 to 8;
d is an integer from 0 to 2; and
e is an integer from 0 to 2,
provided that d+e is 2.

2. The compound of claim 1 wherein t is 0, d is 1, and e is 1; or a pharmaceutically acceptable salt thereof.

3. The compound of claim 1 wherein r is 1 or 0; s is 0 or 1; R2 is hydrogen; and $R^3$ is independently selected from the group consisting of: hydrogen, halogen, and —$OCH_3$; or a pharmaceutically acceptable salt thereof.

4. The compound of claim 1 wherein:
A is selected from the group consisting of:

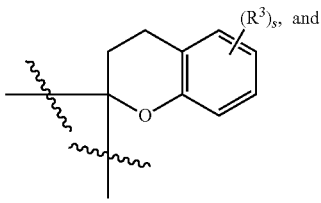

133
-continued
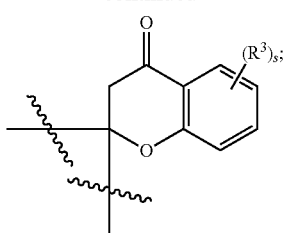
B is selected from the group consisting of:
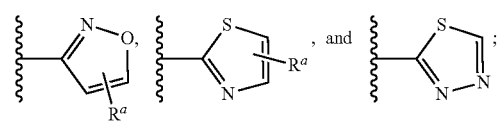
$R^4$ is
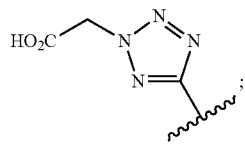
$R^3$ is independently selected from the group consisting of: hydrogen, halogen, —OH, and —OC$_{1-6}$ alkyl; and
s is 0 or 1;
or a pharmaceutically acceptable salt thereof.
5. The compound of claim 3 selected from the group consisting of:
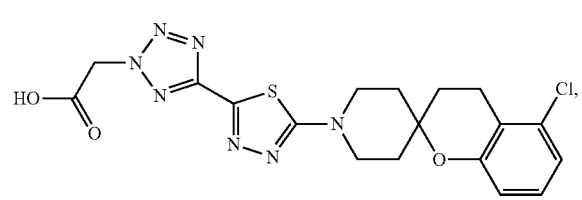
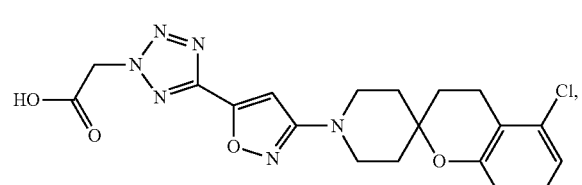
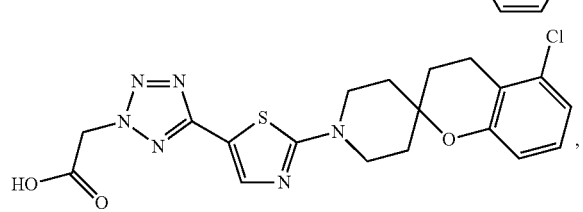
134
-continued
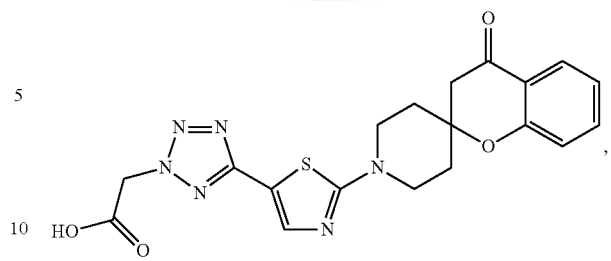
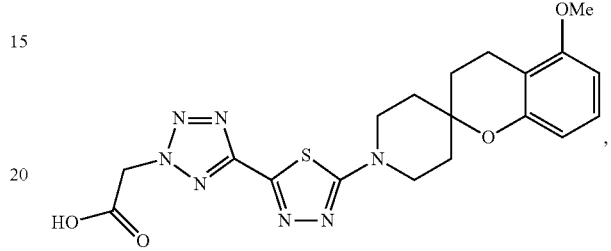
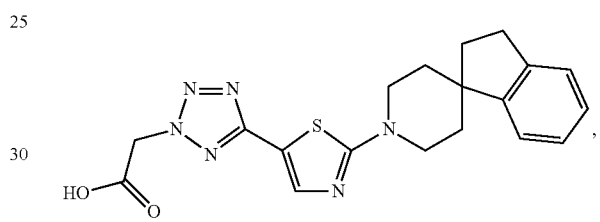
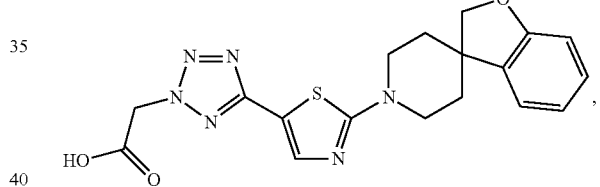
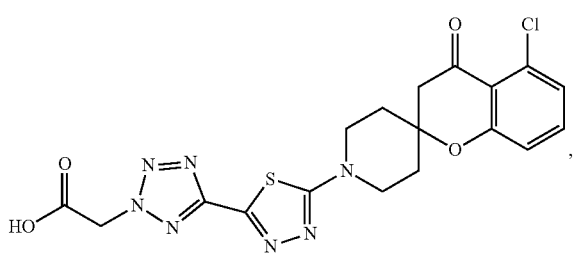
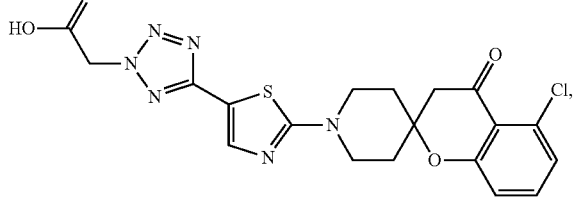
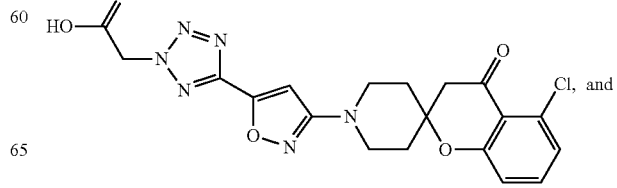

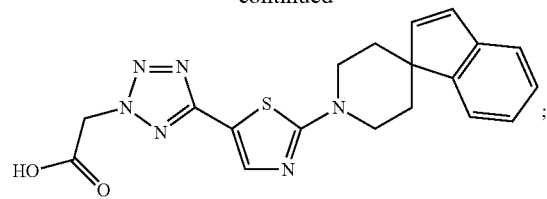
or a pharmaceutically acceptable salt thereof.
6. The compound of claim 1 wherein:
A is:
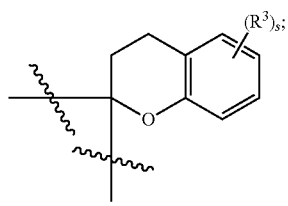
B—$R^4$ is selected from the group consisting of:
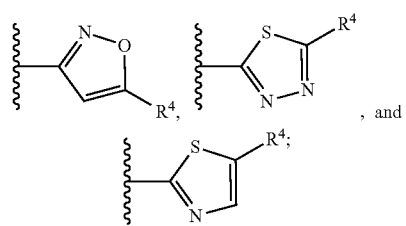
each $R^3$ is independently selected from the group consisting of: Cl, Br, —$CH_3$, —$CF_3$, and —$OCF_3$;
$R^4$ is:
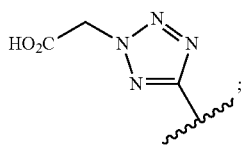 [SMILES: *c1nnn(CC(=O)O)n1 ; ";"]
and
s is 1; or a pharmaceutically acceptable salt thereof.
7. The compound of claim 1 selected from the group consisting of:
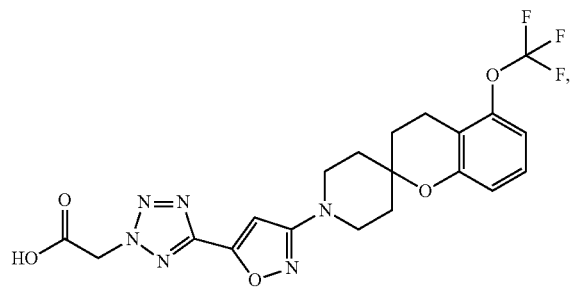
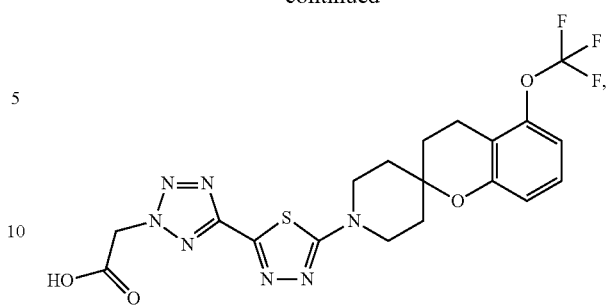
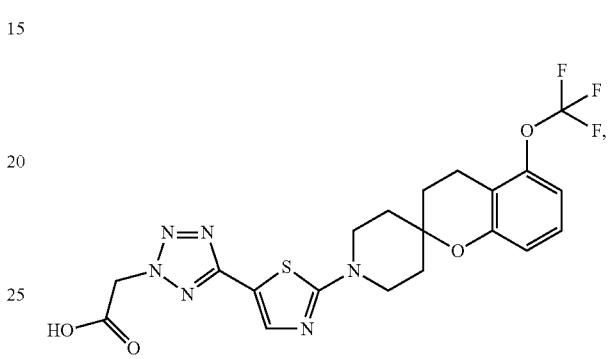
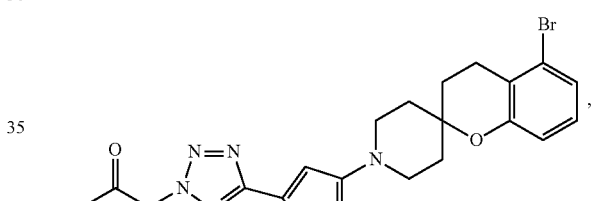
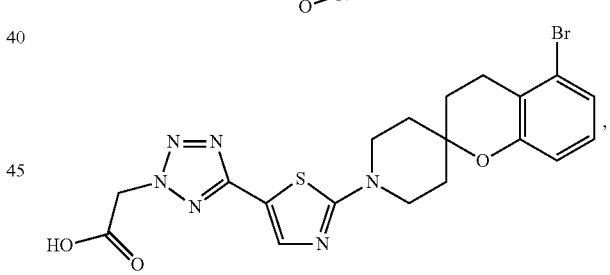
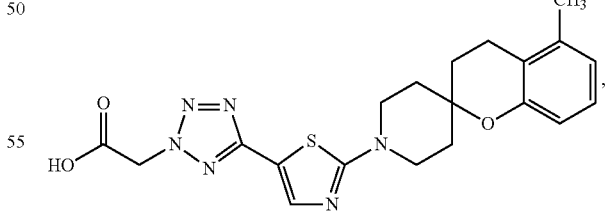
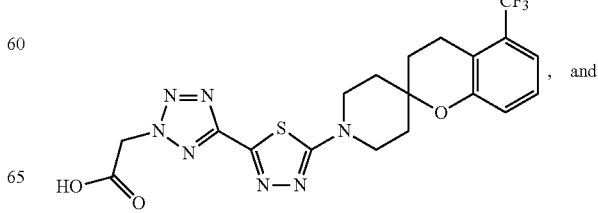

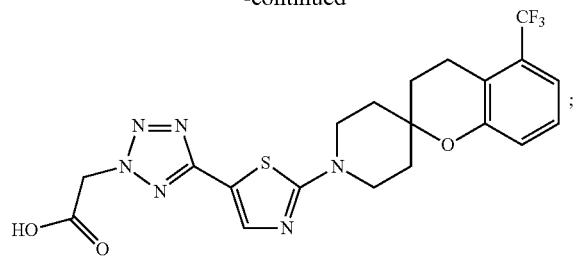

or a pharmaceutically acceptable salt thereof.

8. A pharmaceutical composition comprising a compound of claim 1 in combination with a pharmaceutically acceptable carrier.

9. The compound of claim 6 or a pharmaceutically acceptable salt thereof wherein B—R$^4$ is

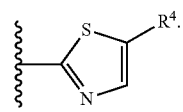

10. The compound of claim 9 selected from the group consisting of:

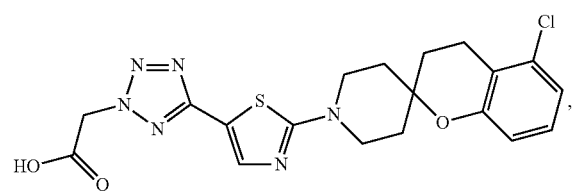

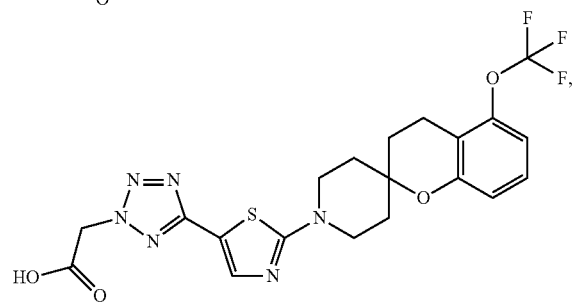

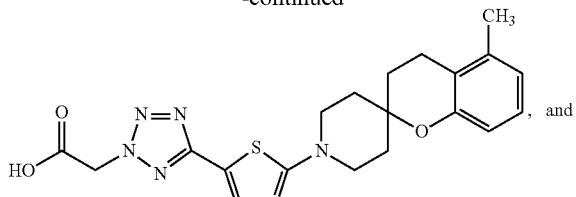

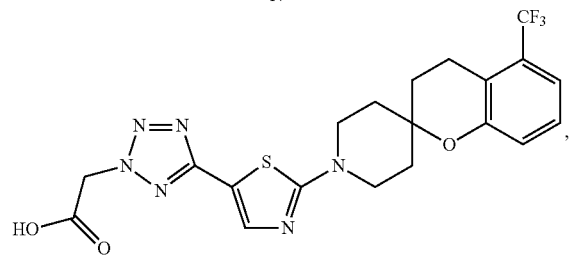

or a pharmaceutically acceptable salt thereof.

11. A compound that is

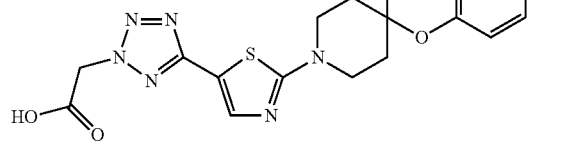

or a pharmaceutically acceptable salt thereof.

12. A compound that is

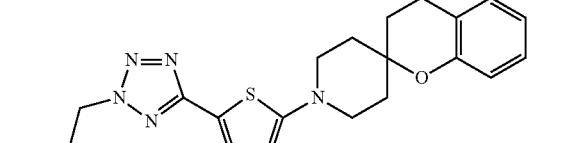

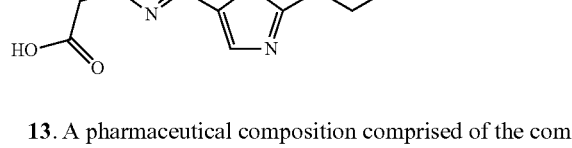

13. A pharmaceutical composition comprised of the compound of claim 11 in combination with a pharmaceutically acceptable carrier.

* * * * *